(12) United States Patent
Schumacher et al.

(10) Patent No.: US 11,540,928 B2
(45) Date of Patent: Jan. 3, 2023

(54) UNICOMPARTMENTAL KNEE ARTHROPLASTY

(71) Applicant: ENGAGE UNI LLC, Orlando, FL (US)

(72) Inventors: Brian S. Schumacher, Orlando, FL (US); Nicholas Slater, Chandler, AZ (US); Daniel F. Justin, Orlando, FL (US)

(73) Assignee: ENGAGE UNI LLC, Orlando, FL (US)

( * ) Notice: Subject to any disclaimer, the term of this patent is extended or adjusted under 35 U.S.C. 154(b) by 357 days.

(21) Appl. No.: 17/024,669

(22) Filed: Sep. 17, 2020

(65) Prior Publication Data

US 2021/0000613 A1    Jan. 7, 2021

Related U.S. Application Data

(63) Continuation-in-part of application No. 16/664,154, filed on Oct. 25, 2019, now Pat. No. 11,369,488, (Continued)

(51) Int. Cl.
*A61F 2/38* (2006.01)
*A61B 17/15* (2006.01)
(Continued)

(52) U.S. Cl.
CPC .......... *A61F 2/461* (2013.01); *A61B 17/1615* (2013.01); *A61B 17/1659* (2013.01); (Continued)

(58) Field of Classification Search
CPC .. A61F 2002/3895; A61F 2/38; A61F 2/4603; A61F 2/461; A61B 17/15;
(Continued)

(56) References Cited

U.S. PATENT DOCUMENTS 3,486,505 A    12/1969 Morrison
3,641,590 A    2/1972 Michele
(Continued)

FOREIGN PATENT DOCUMENTS

EP    0179695    3/1989
FR    2935092 A1   12/2011
(Continued)

OTHER PUBLICATIONS

DePuy Synthes, Sigma High Performance Partial Knee Unicondylar Surgical Technique, Jan. 2017 (36 pp).
(Continued)

*Primary Examiner* — Alvin J Stewart
(74) *Attorney, Agent, or Firm* — KDB Firm PLLC

(57) ABSTRACT

Implants include fixation features which slidingly receive fixation elements. The fixation features may be negative or positive features, such as undercut channels or posts. Examples include unicompartmental tibial trays having a ridge protruding from the bone-facing side, an undercut channel formed within the ridge. Instruments are disclosed for preparing a ridge-receiving feature in bone. Implants and fixation elements are configured for implantation without penetrating a cortical wall of a bone. Instruments and surgical methods are disclosed.

20 Claims, 96 Drawing Sheets

Related U.S. Application Data which is a continuation of application No. 15/910,962, filed on Mar. 2, 2018, now Pat. No. 10,456,272.

(60) Provisional application No. 62/902,875, filed on Sep. 19, 2019, provisional application No. 62/902,873, filed on Sep. 19, 2019, provisional application No. 62/467,083, filed on Mar. 3, 2017.

(51) Int. Cl.
*A61F 2/46* (2006.01)
*A61B 17/17* (2006.01)
*A61B 17/16* (2006.01)
*A61F 2/30* (2006.01)
*A61B 90/00* (2016.01)

(52) U.S. Cl.
CPC .......... *A61B 17/1764* (2013.01); *A61F 2/389* (2013.01); *A61B 17/1675* (2013.01); *A61B 2090/033* (2016.02); *A61F 2/30749* (2013.01); *A61F 2002/3071* (2013.01); *A61F 2002/30387* (2013.01); *A61F 2002/30878* (2013.01); *A61F 2002/30884* (2013.01); *A61F 2002/30894* (2013.01); *A61F 2002/3895* (2013.01); *A61F 2002/4687* (2013.01)

(58) Field of Classification Search
CPC ... A61B 17/154; A61B 17/155; A61B 17/157; A61B 17/025; A61B 2017/0268; A61B 17/17; A61B 17/1764
See application file for complete search history.

(56) References Cited

U.S. PATENT DOCUMENTS

| | | | | |
|---|---|---|---|---|
| 3,650,309 | A | 3/1972 | Neuschotz | |
| 3,842,825 | A | 10/1974 | Wagner | |
| 3,848,276 | A | 11/1974 | Martinez | |
| 3,882,917 | A | 5/1975 | Orlomoski | |
| 3,896,504 | A | 7/1975 | Fischer | |
| 3,907,017 | A | 9/1975 | Stanwick | |
| 3,927,503 | A | 12/1975 | Wilson | |
| 4,011,602 | A | 3/1977 | Rybicki | |
| 4,047,524 | A | 9/1977 | Hall | |
| 4,260,005 | A | 4/1981 | Stencel | |
| 4,349,955 | A | 9/1982 | Keen | |
| 4,355,429 | A | 10/1982 | Mittelmeier | |
| 4,454,875 | A | 6/1984 | Pratt | |
| 4,484,570 | A | 11/1984 | Sutter | |
| 4,501,269 | A | 2/1985 | Bagby | |
| D281,814 | S | 12/1985 | Pratt | |
| 4,570,623 | A | 2/1986 | Ellison | |
| 4,611,581 | A | 9/1986 | Steffee | |
| 4,642,869 | A | 2/1987 | Muller | |
| 4,681,589 | A | 7/1987 | Tronzo | |
| 4,716,893 | A | 1/1988 | Fischer | |
| 4,743,256 | A | 5/1988 | Brantigan | |
| 4,743,262 | A | 5/1988 | Tronzo | |
| 4,764,067 | A | 8/1988 | Kawashima | |
| 4,820,305 | A | 4/1989 | Harms | |
| 4,834,757 | A | 5/1989 | Brantigan | |
| 4,838,891 | A | 6/1989 | Branemark | |
| 4,848,328 | A | 7/1989 | Laboureau | |
| 4,865,607 | A | 9/1989 | Witzel | |
| 4,874,389 | A | 10/1989 | Downey | |
| 4,930,962 | A | 6/1990 | Reynolds | |
| 4,946,378 | A | 8/1990 | Hirayama | |
| 4,957,496 | A | 9/1990 | Schmidt | |
| 5,002,576 | A | 3/1991 | Fuhrmann | |
| 5,019,103 | A | 5/1991 | Van Zile | |
| 5,053,038 | A | 10/1991 | Sheehan | |
| 5,074,880 | A | 12/1991 | Mansat | |
| 5,147,361 | A | 9/1992 | Ojima | |
| 5,163,960 | A | 11/1992 | Bonutti | |
| 5,192,324 | A | 3/1993 | Kenna | |
| 5,192,327 | A | 3/1993 | Brantigan | |
| 5,234,433 | A * | 8/1993 | Bert | A61B 17/8847 606/88 |
| 5,306,309 | A | 4/1994 | Wagner | |
| 5,314,477 | A | 5/1994 | Marnay | |
| 5,352,229 | A | 10/1994 | Goble | |
| 5,366,479 | A | 11/1994 | McGarry | |
| 5,431,658 | A | 7/1995 | Moskovich | |
| 5,443,515 | A | 8/1995 | Cohen | |
| 5,449,359 | A | 9/1995 | Groiso | |
| 5,454,814 | A | 10/1995 | Comte | |
| D364,462 | S | 11/1995 | Michelson | |
| 5,507,816 | A | 4/1996 | Bullivant | |
| 5,514,180 | A | 5/1996 | Heggeness | |
| 5,520,695 | A * | 5/1996 | Luckman | A61B 17/154 606/88 |
| 5,540,696 | A * | 7/1996 | Booth, Jr. | A61B 17/025 606/88 |
| 5,593,411 | A * | 1/1997 | Stalcup | A61B 17/1764 606/88 |
| D378,409 | S | 3/1997 | Michelson | |
| 5,609,635 | A | 3/1997 | Michelson | |
| 5,649,928 | A * | 7/1997 | Grundei | A61B 17/154 606/88 |
| 5,658,337 | A | 8/1997 | Kohrs | |
| 5,660,188 | A | 8/1997 | Groiso | |
| 5,683,394 | A | 11/1997 | Rinner | |
| 5,702,449 | A | 12/1997 | McKay | |
| 5,709,683 | A | 1/1998 | Bagby | |
| 5,713,899 | A | 2/1998 | Marnay | |
| 5,735,904 | A * | 4/1998 | Pappas | A61F 2/4684 623/908 |
| 5,769,852 | A | 6/1998 | Brånemark | |
| 5,772,661 | A | 6/1998 | Michelson | |
| 5,776,199 | A | 7/1998 | Michelson | |
| 5,776,202 | A | 7/1998 | Copf | |
| 5,788,701 | A | 8/1998 | McCue | |
| 5,800,550 | A | 9/1998 | Sertich | |
| 5,853,414 | A | 12/1998 | Groiso | |
| 5,860,973 | A | 1/1999 | Michelson | |
| 5,860,980 | A * | 1/1999 | Axelson, Jr. | A61B 17/1764 606/88 |
| 5,885,287 | A | 3/1999 | Bagby | |
| 5,893,889 | A | 4/1999 | Harrington | |
| 5,893,890 | A | 4/1999 | Pisharodi | |
| 5,911,723 | A * | 6/1999 | Ashby | A61B 17/154 606/88 |
| 5,947,999 | A | 9/1999 | Groiso | |
| 5,993,476 | A | 11/1999 | Groiso | |
| 6,039,762 | A | 3/2000 | McKay | |
| 6,059,787 | A | 5/2000 | Allen | |
| 6,059,831 | A * | 5/2000 | Braslow | A61F 2/38 623/908 |
| 6,063,121 | A | 5/2000 | Xavier | |
| 6,080,155 | A | 6/2000 | Michelson | |
| 6,096,080 | A | 8/2000 | Nicholson | |
| 6,102,949 | A | 8/2000 | Biedermann | |
| 6,102,954 | A | 8/2000 | Albrektsson | |
| 6,113,638 | A | 9/2000 | Williams | |
| 6,120,503 | A | 9/2000 | Michelson | |
| 6,136,001 | A | 10/2000 | Michelson | |
| 6,159,214 | A | 12/2000 | Michelson | |
| 6,224,607 | B1 | 5/2001 | Michelson | |
| 6,235,059 | B1 | 5/2001 | Benezech | |
| 6,241,769 | B1 | 6/2001 | Nicholson | |
| 6,241,770 | B1 | 6/2001 | Michelson | |
| 6,270,498 | B1 | 8/2001 | Michelson | |
| 6,299,613 | B1 | 10/2001 | Ogilvie | |
| 6,302,914 | B1 | 10/2001 | Michelson | |
| 6,309,421 | B1 | 10/2001 | Pisharodi | |
| 6,325,805 | B1 | 12/2001 | Ogilvie | |
| 6,336,928 | B1 | 1/2002 | Guerin | |
| 6,364,880 | B1 | 4/2002 | Michelson | |
| 6,402,785 | B1 | 6/2002 | Zdeblick | |
| 6,413,278 | B1 | 7/2002 | Marchosky | |
| 6,432,107 | B1 | 8/2002 | Ferree | |
| 6,436,098 | B1 | 8/2002 | Michelson | |

(56) References Cited

U.S. PATENT DOCUMENTS

| | | |
|---|---|---|
| 6,447,524 B1 | 9/2002 | Knodel |
| 6,447,544 B1 | 9/2002 | Michelson |
| 6,447,546 B1 | 9/2002 | Bramlet |
| 6,458,159 B1 | 10/2002 | Thalgott |
| 6,478,800 B1 | 11/2002 | Fraser |
| 6,485,517 B1 | 11/2002 | Michelson |
| 6,506,216 B1 | 1/2003 | McCue |
| 6,537,320 B1 | 3/2003 | Michelson |
| 6,558,423 B1 | 5/2003 | Michelson |
| 6,558,424 B2 | 5/2003 | Thalgott |
| 6,582,468 B1 | 6/2003 | Gauchet |
| 6,599,294 B2 | 7/2003 | Fuss |
| 6,610,093 B1 | 8/2003 | Pisharodi |
| 6,620,198 B2 | 9/2003 | Burstein |
| 6,652,533 B2 | 11/2003 | O'Neil |
| 6,679,887 B2 | 1/2004 | Nicholson |
| 6,716,245 B2 | 4/2004 | Pasquet |
| 6,726,720 B2 | 4/2004 | Ross |
| 6,740,118 B2 | 5/2004 | Eisermann |
| 6,743,256 B2 | 6/2004 | Mason |
| 6,746,450 B1 | 6/2004 | Wall |
| 6,755,841 B2 | 6/2004 | Fraser |
| 6,767,356 B2 | 7/2004 | Kanner |
| 6,767,367 B1 | 7/2004 | Michelson |
| 6,770,074 B2 | 8/2004 | Michelson |
| 6,770,096 B2 | 8/2004 | Bolger |
| 6,773,437 B2 | 8/2004 | Ogilvie |
| 6,800,093 B2 | 10/2004 | Nicholson |
| 6,802,863 B2 | 10/2004 | Lawson |
| 6,827,740 B1 | 12/2004 | Michelson |
| 6,835,208 B2 | 12/2004 | Marchosky |
| 6,849,093 B2 | 2/2005 | Michelson |
| 6,875,213 B2 | 4/2005 | Michelson |
| 6,916,324 B2 * | 7/2005 | Sanford ............... A61F 2/4684 606/88 |
| 6,923,810 B1 | 8/2005 | Michelson |
| 6,923,830 B2 | 8/2005 | Michelson |
| 6,926,718 B1 | 8/2005 | Michelson |
| 6,942,698 B1 | 9/2005 | Jackson |
| 6,969,390 B2 | 11/2005 | Michelson |
| 6,969,393 B2 * | 11/2005 | Pinczewski ........ A61B 17/1659 606/88 |
| 6,972,035 B2 | 12/2005 | Michelson |
| 6,981,975 B2 | 1/2006 | Michelson |
| 6,989,031 B2 | 1/2006 | Michelson |
| 7,033,394 B2 | 4/2006 | Michelson |
| 7,041,135 B2 | 5/2006 | Michelson |
| 7,044,972 B2 | 5/2006 | Mathys, Jr. |
| 7,048,766 B2 | 5/2006 | Ferree |
| 7,056,344 B2 | 6/2006 | Huppert |
| 7,056,345 B2 | 6/2006 | Kuslich |
| 7,060,097 B2 | 6/2006 | Fraser |
| 7,066,961 B2 | 6/2006 | Michelson |
| 7,083,623 B2 | 8/2006 | Michelson |
| 7,083,652 B2 | 8/2006 | McCue |
| 7,087,082 B2 | 8/2006 | Paul |
| 7,112,206 B2 | 9/2006 | Michelson |
| 7,115,146 B2 | 10/2006 | Boyer, II |
| 7,118,580 B1 | 10/2006 | Beyersdorff |
| 7,128,761 B2 | 10/2006 | Kuras |
| 7,141,053 B2 * | 11/2006 | Rosa ................ A61B 17/157 606/88 |
| 7,163,560 B2 | 1/2007 | Mason |
| 7,166,110 B2 | 1/2007 | Yundt |
| 7,166,129 B2 | 1/2007 | Michelson |
| 7,169,182 B2 | 1/2007 | Errico |
| 7,204,852 B2 | 4/2007 | Marnay |
| 7,235,101 B2 | 6/2007 | Berry |
| 7,235,105 B2 | 6/2007 | Jackson |
| 7,238,203 B2 | 7/2007 | Bagga |
| 7,255,698 B2 | 8/2007 | Michelson |
| 7,320,707 B2 | 1/2008 | Zucherman |
| 7,326,248 B2 | 2/2008 | Michelson |
| 7,331,995 B2 | 2/2008 | Eisermann |
| 7,357,817 B2 | 4/2008 | D'Alessio, II |
| 7,364,589 B2 | 4/2008 | Eisermann |
| 7,396,365 B2 | 7/2008 | Michelson |
| 7,442,196 B2 * | 10/2008 | Fisher ................ A61F 2/4657 606/88 |
| 7,462,196 B2 | 12/2008 | Fraser |
| 7,481,830 B2 | 1/2009 | Wall |
| 7,481,832 B1 | 1/2009 | Meridew |
| D586,915 S | 2/2009 | Grim |
| 7,488,324 B1 * | 2/2009 | Metzger ............... A61F 2/4657 600/587 |
| 7,491,205 B1 | 2/2009 | Michelson |
| 7,503,933 B2 | 3/2009 | Michelson |
| 7,503,934 B2 | 3/2009 | Eisermann |
| 7,503,935 B2 | 3/2009 | Zucherman |
| D594,986 S | 6/2009 | Miles |
| 7,540,882 B2 | 6/2009 | Michelson |
| 7,556,650 B2 | 7/2009 | Collins |
| 7,572,293 B2 | 8/2009 | Rhodes |
| 7,588,600 B2 | 9/2009 | Benzel |
| 7,594,931 B2 | 9/2009 | Louis |
| 7,601,154 B2 * | 10/2009 | Kuczynski ........... A61B 17/157 606/88 |
| 7,611,538 B2 | 11/2009 | Belliard |
| 7,658,766 B2 | 2/2010 | Melkent |
| 7,678,115 B2 * | 3/2010 | D'Alessio, II ....... A61B 17/157 606/88 |
| 7,695,516 B2 | 4/2010 | Zeegers |
| 7,749,271 B2 | 7/2010 | Fischer |
| 7,763,076 B2 | 7/2010 | Navarro |
| 7,780,676 B2 | 8/2010 | Lakin |
| 7,789,885 B2 * | 9/2010 | Metzger ............... A61B 17/157 606/88 |
| 7,837,732 B2 | 11/2010 | Zucherman |
| 7,850,791 B2 | 12/2010 | Quadakkers |
| 7,883,510 B2 | 2/2011 | Kim |
| 7,887,563 B2 | 2/2011 | Cummins |
| 7,896,919 B2 | 3/2011 | Belliard |
| 7,909,871 B2 | 3/2011 | Abdou |
| 7,918,891 B1 | 4/2011 | Curran |
| 7,966,799 B2 | 6/2011 | Morgan |
| 8,021,403 B2 | 9/2011 | Wall |
| 8,034,076 B2 | 10/2011 | Criscuolo |
| 8,062,297 B2 | 11/2011 | Faillace |
| 8,100,972 B1 | 1/2012 | Bruffey |
| 8,100,974 B2 | 1/2012 | Duggal |
| 8,105,389 B2 | 1/2012 | Berelsman |
| 8,123,757 B2 | 2/2012 | Zalenski |
| 8,133,283 B2 | 3/2012 | Wilson |
| 8,157,865 B2 | 4/2012 | Hochschuler |
| 8,167,888 B2 * | 5/2012 | Steffensmeier .... A61B 17/1764 606/88 |
| 8,287,572 B2 | 10/2012 | Bae |
| 8,323,288 B2 * | 12/2012 | Zajac ................ A61B 17/155 606/88 |
| 8,491,598 B2 | 7/2013 | Crook |
| 8,500,747 B2 | 8/2013 | DeRidder |
| 8,636,191 B2 | 1/2014 | Meagher |
| 8,672,946 B2 * | 3/2014 | Fox .................. A61B 17/1764 606/88 |
| 8,747,412 B2 | 6/2014 | Bae |
| 8,808,294 B2 | 8/2014 | Fox |
| 9,220,519 B2 * | 12/2015 | Kaneyama ........... A61F 2/4684 |
| 9,254,130 B2 | 2/2016 | Hollis |
| 9,480,511 B2 | 11/2016 | Butters |
| 9,592,131 B2 | 3/2017 | Sandstrom |
| 9,615,856 B2 | 4/2017 | Arnett |
| 9,788,968 B2 | 10/2017 | Bae |
| 9,925,051 B2 | 3/2018 | Bae |
| 9,968,464 B2 | 5/2018 | Tanaka |
| 10,105,242 B2 * | 10/2018 | Rock ................ A61B 17/157 |
| 10,201,356 B2 * | 2/2019 | Wilkinson ............. A61B 17/17 |
| 10,238,382 B2 | 3/2019 | Terrill |
| 10,238,426 B2 | 3/2019 | Butters |
| 10,245,090 B2 | 4/2019 | Hollis |
| 10,342,667 B2 | 7/2019 | Bae |
| 10,349,955 B2 * | 7/2019 | Fox ................ A61B 17/72 |
| 10,390,955 B2 | 8/2019 | Bae |
| 10,456,272 B2 | 10/2019 | Su |

(56) References Cited

U.S. PATENT DOCUMENTS

| | | | |
|---|---|---|---|
| 10,716,581 B2* | 7/2020 | Fritzinger | A61B 17/1764 |
| 11,344,421 B2* | 5/2022 | Manuel | A61F 2/4684 |
| 2001/0000532 A1 | 4/2001 | Michelson | |
| 2001/0010001 A1 | 7/2001 | Michelson | |
| 2001/0010002 A1 | 7/2001 | Michelson | |
| 2001/0010020 A1 | 7/2001 | Michelson | |
| 2001/0037154 A1 | 11/2001 | Martin | |
| 2001/0047207 A1 | 11/2001 | Michelson | |
| 2001/0047208 A1 | 11/2001 | Michelson | |
| 2002/0004683 A1 | 1/2002 | Michelson | |
| 2002/0035400 A1 | 3/2002 | Bryan | |
| 2002/0049447 A1 | 4/2002 | Li | |
| 2002/0091390 A1 | 7/2002 | Michelson | |
| 2002/0095155 A1 | 7/2002 | Michelson | |
| 2002/0099376 A1 | 7/2002 | Michelson | |
| 2002/0099378 A1 | 7/2002 | Michelson | |
| 2002/0116065 A1 | 8/2002 | Jackson | |
| 2002/0116165 A1 | 8/2002 | El Ghoroury | |
| 2002/0147454 A1 | 10/2002 | Neto | |
| 2002/0147499 A1 | 10/2002 | Shea | |
| 2002/0161443 A1 | 10/2002 | Michelson | |
| 2002/0165613 A1 | 11/2002 | Lin | |
| 2003/0023307 A1 | 1/2003 | Michelson | |
| 2003/0045940 A1 | 3/2003 | Eberlein | |
| 2003/0060884 A1 | 3/2003 | Fell | |
| 2003/0120344 A1 | 6/2003 | Michelson | |
| 2003/0130665 A1* | 7/2003 | Pinczewski | A61B 17/154 |
| | | | 606/88 |
| 2003/0149483 A1 | 8/2003 | Michelson | |
| 2003/0158553 A1 | 8/2003 | Michelson | |
| 2003/0195517 A1 | 10/2003 | Michelson | |
| 2003/0195561 A1 | 10/2003 | Carley | |
| 2003/0195632 A1 | 10/2003 | Foley | |
| 2004/0030336 A1 | 2/2004 | Khanna | |
| 2004/0030339 A1 | 2/2004 | Wack | |
| 2004/0064185 A1 | 4/2004 | Michelson | |
| 2004/0073315 A1 | 4/2004 | Justin | |
| 2004/0083005 A1 | 4/2004 | Jacobsson | |
| 2004/0117018 A1 | 6/2004 | Michelson | |
| 2004/0122518 A1 | 6/2004 | Rhoda | |
| 2004/0133203 A1 | 7/2004 | Young | |
| 2004/0148028 A1 | 7/2004 | Ferree | |
| 2004/0153084 A1* | 8/2004 | Haney | A61B 17/155 |
| | | | 606/87 |
| 2004/0176853 A1 | 9/2004 | Sennett | |
| 2004/0210313 A1 | 10/2004 | Michelson | |
| 2004/0210314 A1 | 10/2004 | Michelson | |
| 2004/0215203 A1 | 10/2004 | Michelson | |
| 2004/0220668 A1 | 11/2004 | Eisermann | |
| 2004/0220670 A1 | 11/2004 | Eisermann | |
| 2004/0225295 A1 | 11/2004 | Zubok | |
| 2004/0230308 A1 | 11/2004 | Michelson | |
| 2004/0249386 A1* | 12/2004 | Faoro | A61B 17/155 |
| | | | 606/88 |
| 2004/0249388 A1 | 12/2004 | Michelson | |
| 2004/0254581 A1 | 12/2004 | Leclair | |
| 2004/0254644 A1 | 12/2004 | Taylor | |
| 2004/0260286 A1 | 12/2004 | Ferree | |
| 2005/0004672 A1 | 1/2005 | Pafford | |
| 2005/0014919 A1 | 1/2005 | Hatakeyama | |
| 2005/0027300 A1 | 2/2005 | Hawkins | |
| 2005/0038512 A1 | 2/2005 | Michelson | |
| 2005/0038513 A1 | 2/2005 | Michelson | |
| 2005/0043802 A1 | 2/2005 | Eisermann | |
| 2005/0049600 A1 | 3/2005 | Groiso | |
| 2005/0055031 A1 | 3/2005 | Lim | |
| 2005/0113842 A1 | 5/2005 | Bertagnoli | |
| 2005/0125065 A1 | 6/2005 | Zucherman | |
| 2005/0131545 A1 | 6/2005 | Chervitz | |
| 2005/0143747 A1 | 6/2005 | Zubok | |
| 2005/0149192 A1 | 7/2005 | Zucherman | |
| 2005/0165408 A1 | 7/2005 | Puno | |
| 2005/0171550 A1 | 8/2005 | Marik | |
| 2005/0171606 A1 | 8/2005 | Michelson | |
| 2005/0171607 A1 | 8/2005 | Michelson | |
| 2005/0177239 A1 | 8/2005 | Steinberg | |
| 2005/0187629 A1 | 8/2005 | Michelson | |
| 2005/0192586 A1 | 9/2005 | Zucherman | |
| 2005/0216089 A1 | 9/2005 | Michelson | |
| 2005/0234555 A1 | 10/2005 | Sutton | |
| 2005/0273108 A1 | 12/2005 | Groiso | |
| 2006/0004453 A1 | 1/2006 | Bartish | |
| 2006/0036257 A1* | 2/2006 | Steffensmeier | A61B 17/155 |
| | | | 606/90 |
| 2006/0058802 A1 | 3/2006 | Kofoed | |
| 2006/0074421 A1 | 4/2006 | Bickley | |
| 2006/0079961 A1 | 4/2006 | Michelson | |
| 2006/0085071 A1 | 4/2006 | Lechmann | |
| 2006/0095136 A1 | 5/2006 | McLuen | |
| 2006/0111787 A1 | 5/2006 | Bailie | |
| 2006/0116769 A1 | 6/2006 | Marnay | |
| 2006/0122702 A1 | 6/2006 | Michelson | |
| 2006/0129238 A1 | 6/2006 | Paltzer | |
| 2006/0136061 A1 | 6/2006 | Navarro | |
| 2006/0142860 A1 | 6/2006 | Navarro | |
| 2006/0149377 A1 | 7/2006 | Navarro | |
| 2006/0149384 A1 | 7/2006 | Navarro | |
| 2006/0167461 A1 | 7/2006 | Hawkins | |
| 2006/0178745 A1 | 8/2006 | Bartish | |
| 2006/0195097 A1 | 8/2006 | Evans | |
| 2006/0195191 A1 | 8/2006 | Sweeney | |
| 2006/0212123 A1 | 9/2006 | Lechmann | |
| 2006/0241641 A1 | 10/2006 | Albans | |
| 2006/0259143 A1 | 11/2006 | Navarro | |
| 2006/0259145 A1 | 11/2006 | Navarro | |
| 2007/0010822 A1 | 1/2007 | Zalenski | |
| 2007/0010890 A1 | 1/2007 | Collazo | |
| 2007/0050032 A1 | 3/2007 | Gittings | |
| 2007/0050033 A1 | 3/2007 | Reo | |
| 2007/0055376 A1 | 3/2007 | Michelson | |
| 2007/0055381 A1 | 3/2007 | Berelsman | |
| 2007/0073404 A1 | 3/2007 | Rashbaum | |
| 2007/0093839 A1 | 4/2007 | Beckendorf | |
| 2007/0106388 A1 | 5/2007 | Michelson | |
| 2007/0118132 A1 | 5/2007 | Culbert | |
| 2007/0123903 A1 | 5/2007 | Raymond | |
| 2007/0142922 A1 | 6/2007 | Lewis | |
| 2007/0179621 A1 | 8/2007 | McClellan | |
| 2007/0185375 A1 | 8/2007 | Stad | |
| 2007/0225812 A1 | 9/2007 | Gill | |
| 2007/0233244 A1 | 10/2007 | Lopez | |
| 2007/0239278 A1 | 10/2007 | Heinz | |
| 2007/0288005 A1 | 12/2007 | Arnin | |
| 2007/0288021 A1 | 12/2007 | Rickels | |
| 2007/0299529 A1 | 12/2007 | Rhodes | |
| 2008/0051901 A1 | 2/2008 | de Villiers | |
| 2008/0051902 A1 | 2/2008 | Dwyer | |
| 2008/0103598 A1 | 5/2008 | Trudeau | |
| 2008/0108997 A1 | 5/2008 | Berrevoets | |
| 2008/0132949 A1 | 6/2008 | Aferzon | |
| 2008/0133017 A1 | 6/2008 | Beyar | |
| 2008/0140208 A1 | 6/2008 | Zucherman | |
| 2008/0147203 A1 | 6/2008 | Cronin | |
| 2008/0154377 A1 | 6/2008 | Voellmicke | |
| 2008/0167721 A1 | 7/2008 | Bao | |
| 2008/0177275 A1 | 7/2008 | Wing | |
| 2008/0208345 A1 | 8/2008 | Hurlbert | |
| 2008/0249575 A1 | 10/2008 | Waugh | |
| 2008/0249623 A1 | 10/2008 | Bao | |
| 2008/0269764 A1 | 10/2008 | Blain | |
| 2008/0275455 A1 | 11/2008 | Berry | |
| 2008/0287957 A1 | 11/2008 | Hester | |
| 2009/0005784 A1 | 1/2009 | Blain | |
| 2009/0005870 A1 | 1/2009 | Hawkins | |
| 2009/0018560 A1 | 1/2009 | Mayer | |
| 2009/0048604 A1 | 2/2009 | Milz | |
| 2009/0062921 A1 | 3/2009 | Michelson | |
| 2009/0088849 A1 | 4/2009 | Armstrong | |
| 2009/0099601 A1 | 4/2009 | Aferzon | |
| 2009/0099602 A1 | 4/2009 | Aflatoon | |
| 2009/0164020 A1 | 6/2009 | Janowski | |
| 2009/0209967 A1 | 8/2009 | Evans | |
| 2009/0240333 A1 | 9/2009 | Trudeau | |
| 2010/0004747 A1 | 1/2010 | Lin | |

(56) References Cited

U.S. PATENT DOCUMENTS

| | | |
|---|---|---|
| 2010/0069958 A1 | 3/2010 | Sullivan |
| 2010/0076441 A1 | 3/2010 | May |
| 2010/0185287 A1 | 7/2010 | Allard |
| 2010/0201739 A1 | 8/2010 | Yamaguchi |
| 2010/0204739 A1 | 8/2010 | Bae |
| 2010/0217395 A1 | 8/2010 | Bertagnoli |
| 2010/0268238 A1 | 10/2010 | Sikora |
| 2011/0022176 A1 | 1/2011 | Zucherman |
| 2011/0054620 A1 | 3/2011 | Reo |
| 2011/0098819 A1 | 4/2011 | Eisermann |
| 2011/0106260 A1 | 5/2011 | Laurence |
| 2011/0160766 A1 | 6/2011 | Hendren |
| 2011/0160866 A1 | 6/2011 | Laurence |
| 2011/0166608 A1 | 7/2011 | Duggal |
| 2012/0083788 A1 | 4/2012 | Blakemore |
| 2012/0215315 A1 | 8/2012 | Hochschuler |
| 2012/0253406 A1 | 10/2012 | Bae |
| 2012/0259335 A1 | 10/2012 | Scifert |
| 2012/0265259 A1 | 10/2012 | LaPosta |
| 2012/0283837 A1 | 11/2012 | Bae |
| 2013/0013006 A1 | 1/2013 | Rashbaum |
| 2014/0039632 A1 | 2/2014 | Hollis |
| 2014/0171952 A1 | 6/2014 | Maxson |
| 2016/0008012 A1 | 1/2016 | Balzarini |
| 2017/0367837 A1 | 12/2017 | Harris, Jr. |
| 2019/0038298 A1 | 2/2019 | Bojarski |
| 2019/0150948 A1* | 5/2019 | Haddock ............ A61B 17/1764 |
| 2019/0321187 A1 | 10/2019 | Bae |
| 2020/0197023 A1* | 6/2020 | Chafez ................. A61B 17/155 |
| 2021/0000484 A1* | 1/2021 | Goble ................. A61B 17/164 |
| 2021/0290252 A1* | 9/2021 | Oh ........................ A61F 2/4657 |
| 2022/0054145 A1* | 2/2022 | Zaima ................. A61B 17/155 |
| 2022/0287724 A1* | 9/2022 | Yeager ................. A61B 17/155 |

FOREIGN PATENT DOCUMENTS

| | | |
|---|---|---|
| WO | WO2010039026 | 4/2010 |
| WO | WO2011044879 | 4/2011 |
| WO | 2012156806 A1 | 11/2012 |
| WO | 2018169980 A1 | 9/2018 |
| WO | 2021055684 A1 | 3/2021 |

OTHER PUBLICATIONS

European Patent Office, Extended Search Report, dated Aug. 11, 2022.

* cited by examiner

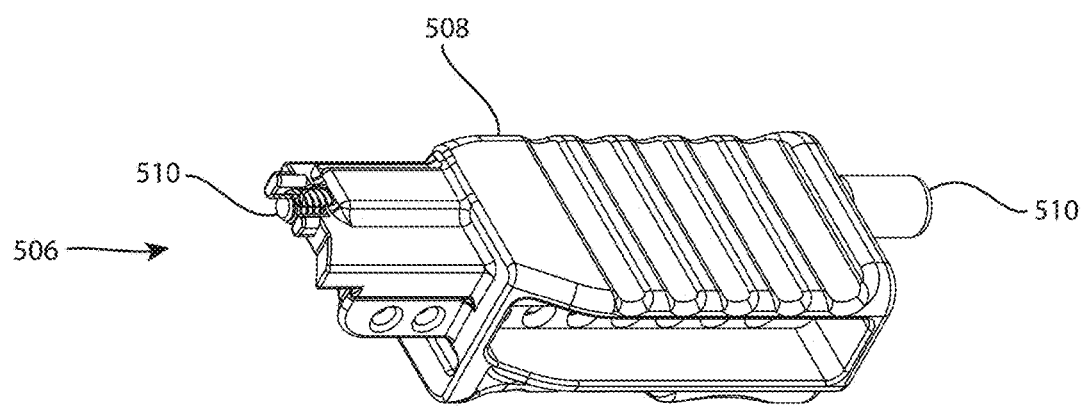
FIG. 101
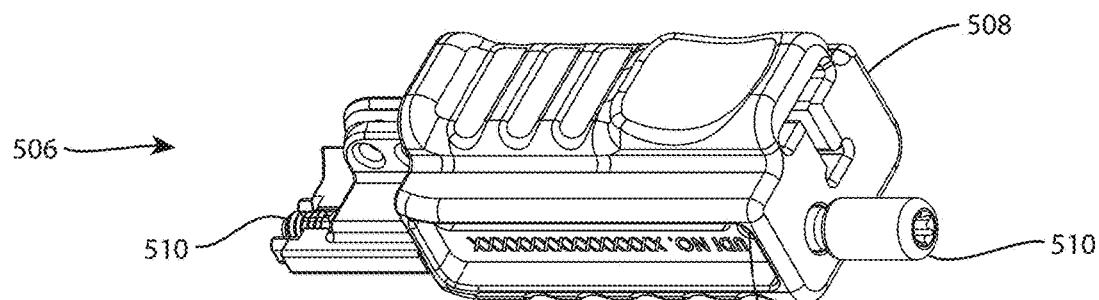
FIG. 102
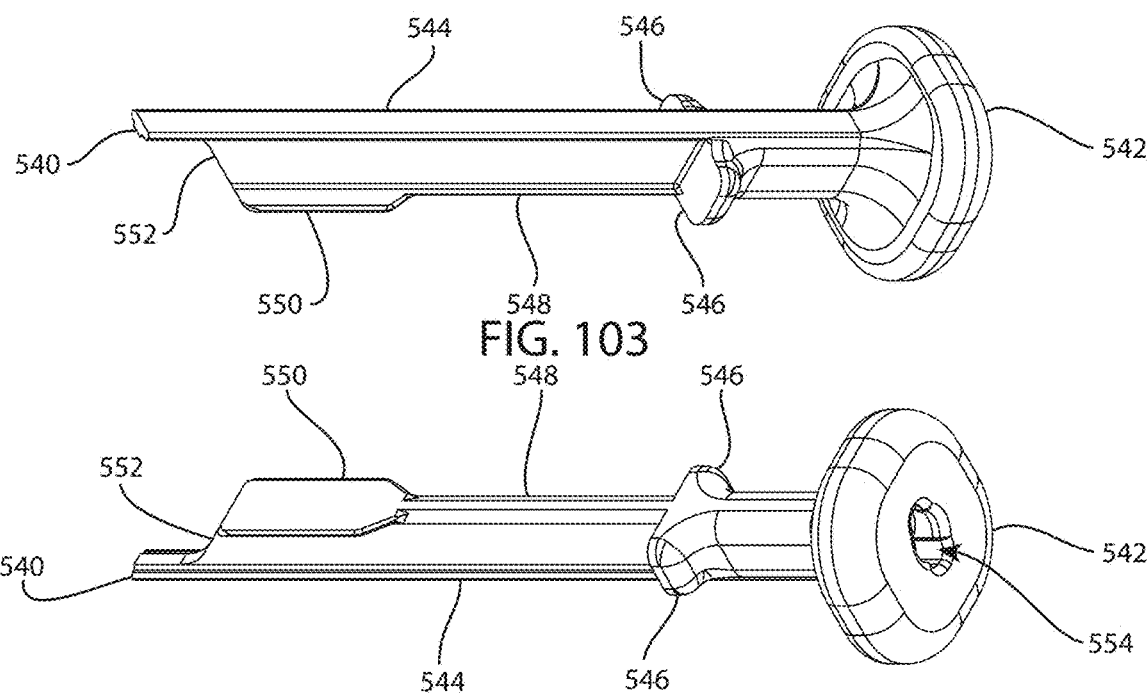
FIG. 103
FIG. 104

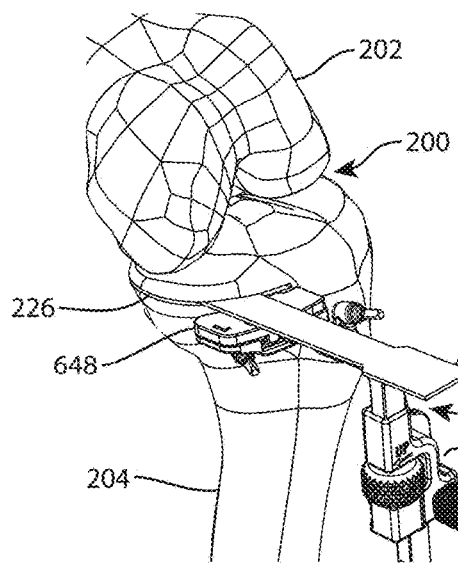
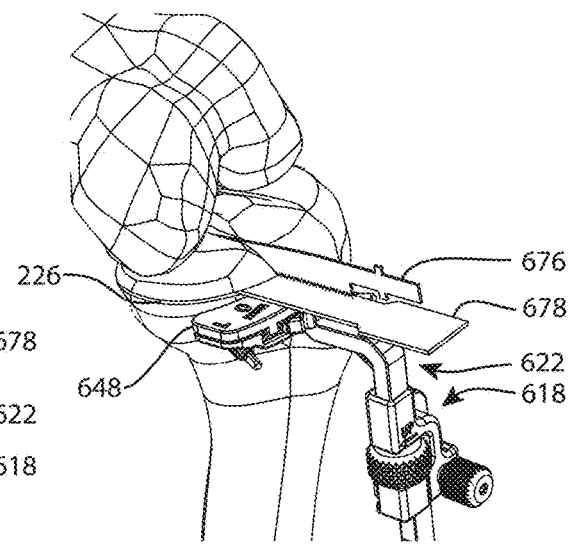
FIG. 162      FIG. 163
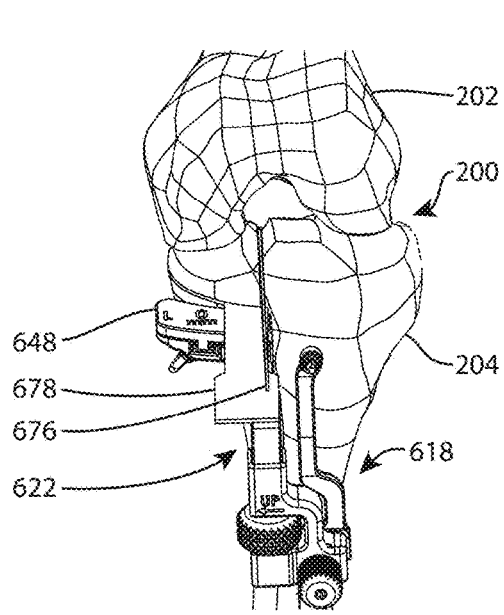
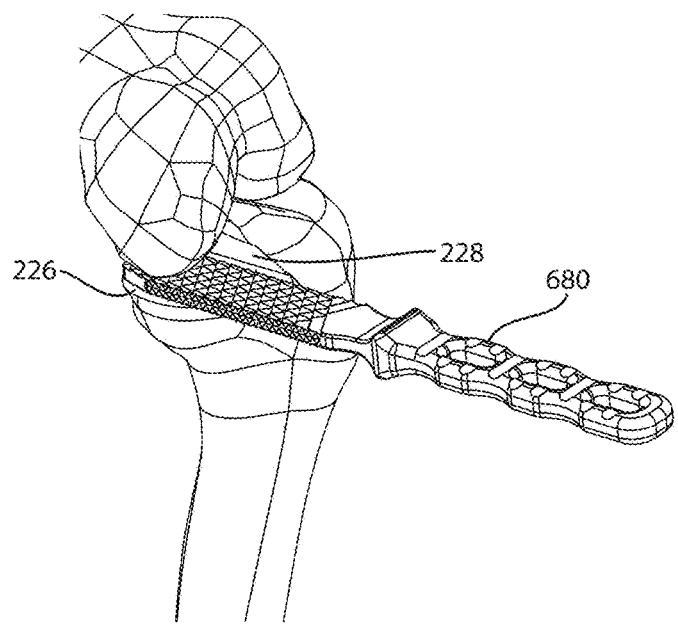
FIG. 164      FIG. 165

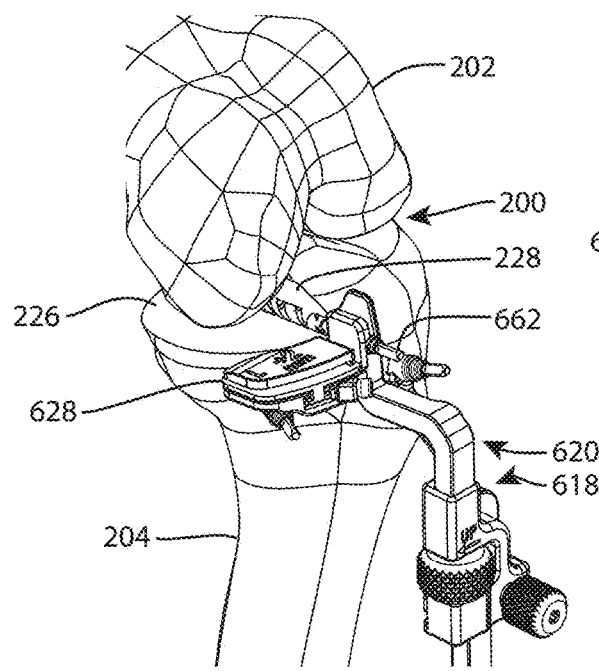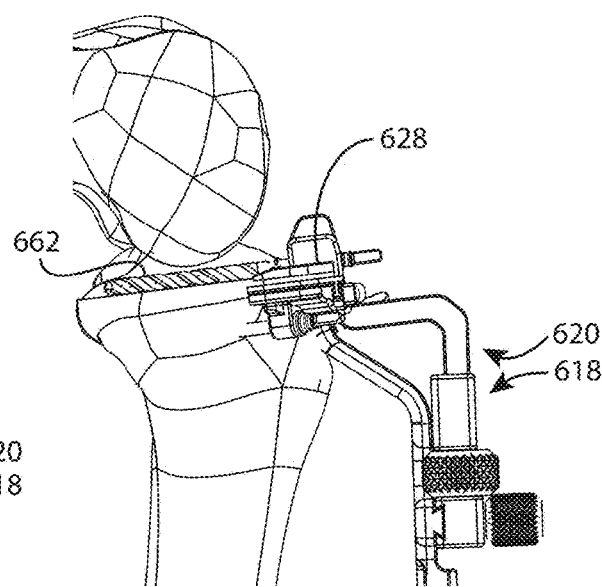
FIG. 169  FIG. 170
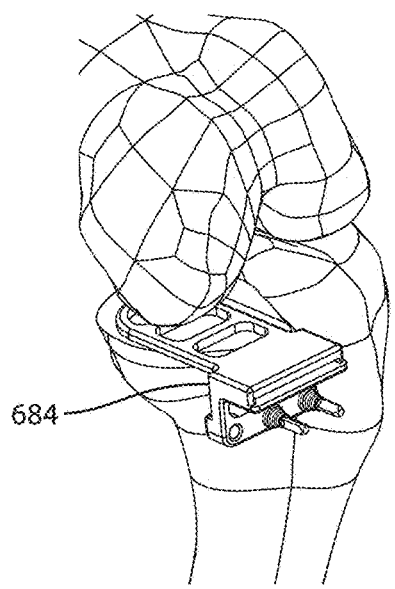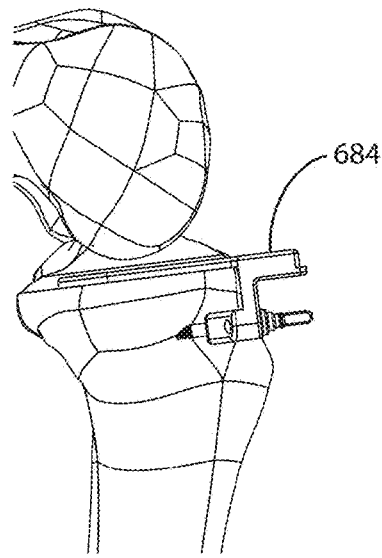
FIG. 171  FIG. 172

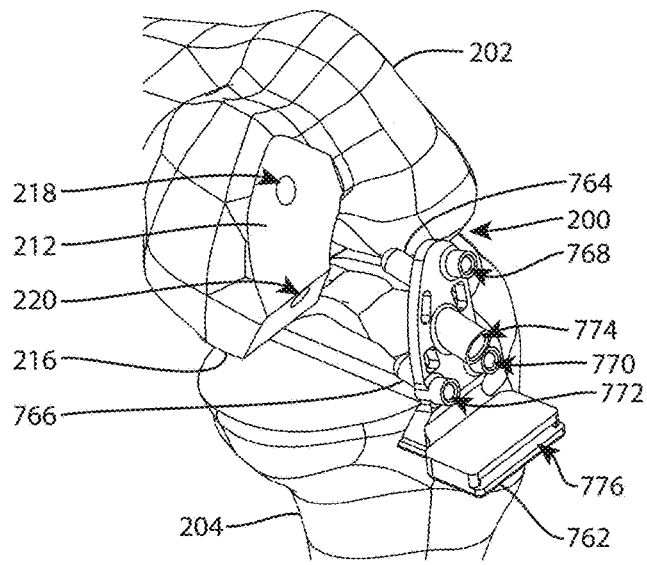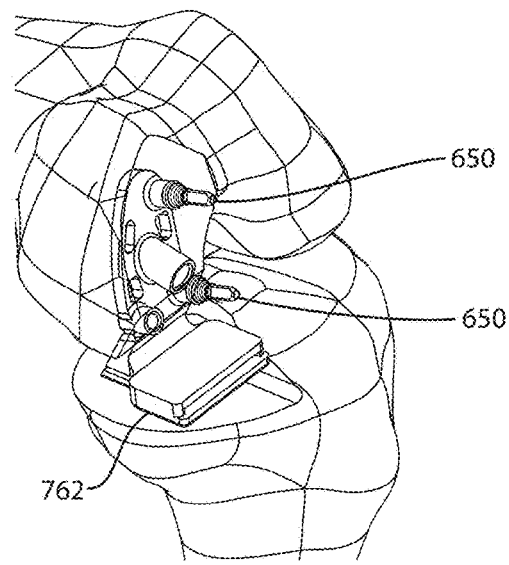
FIG. 226  FIG. 227
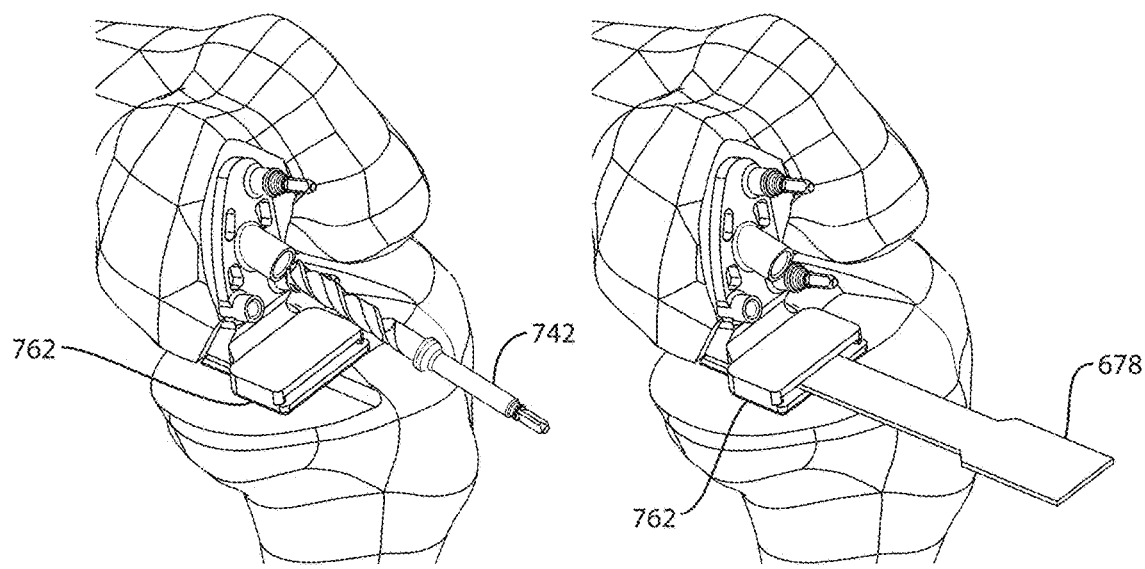
FIG. 228  FIG. 229

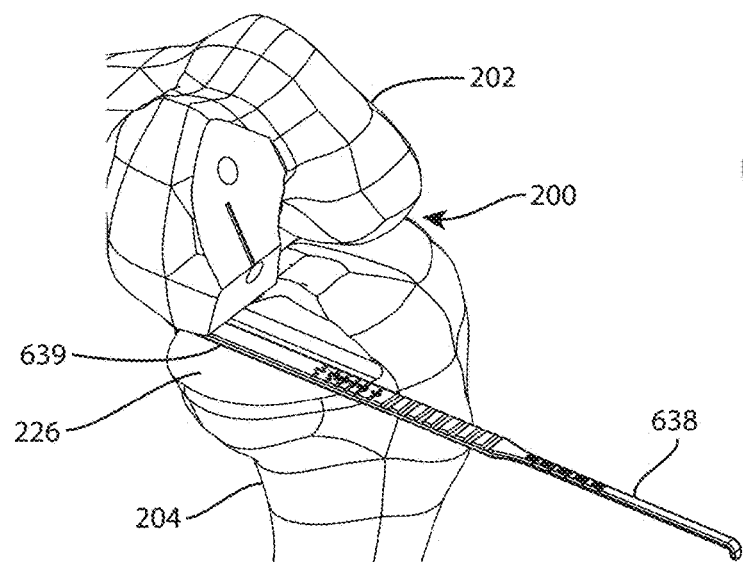 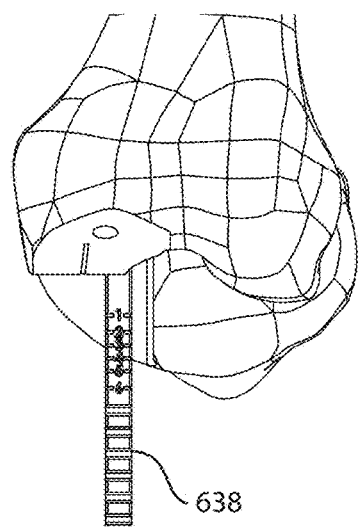
FIG. 230  FIG. 231
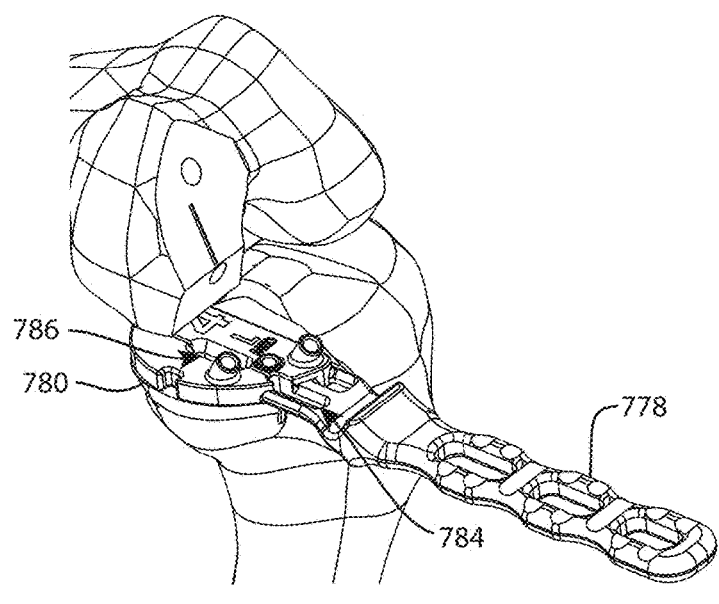 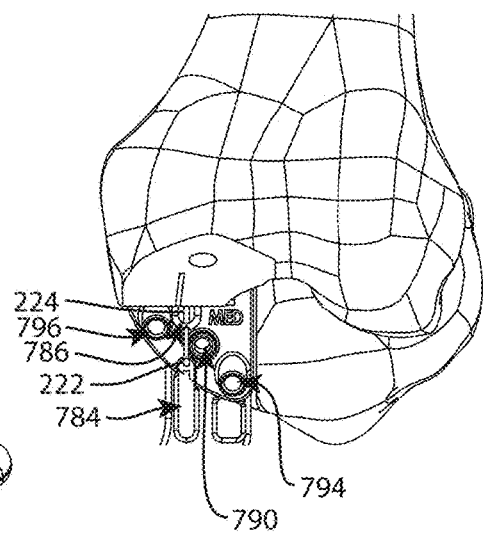
FIG. 232  FIG. 233

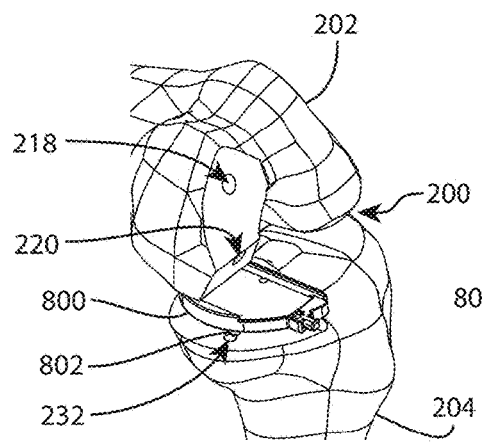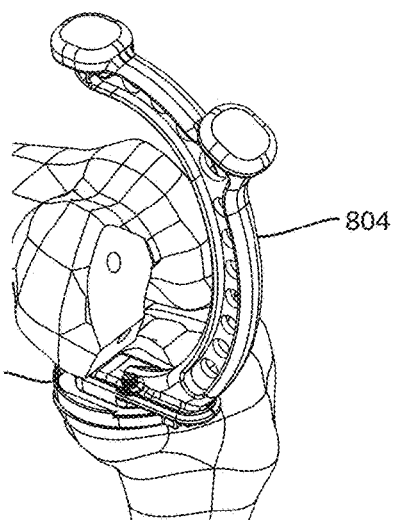
FIG. 237    FIG. 238
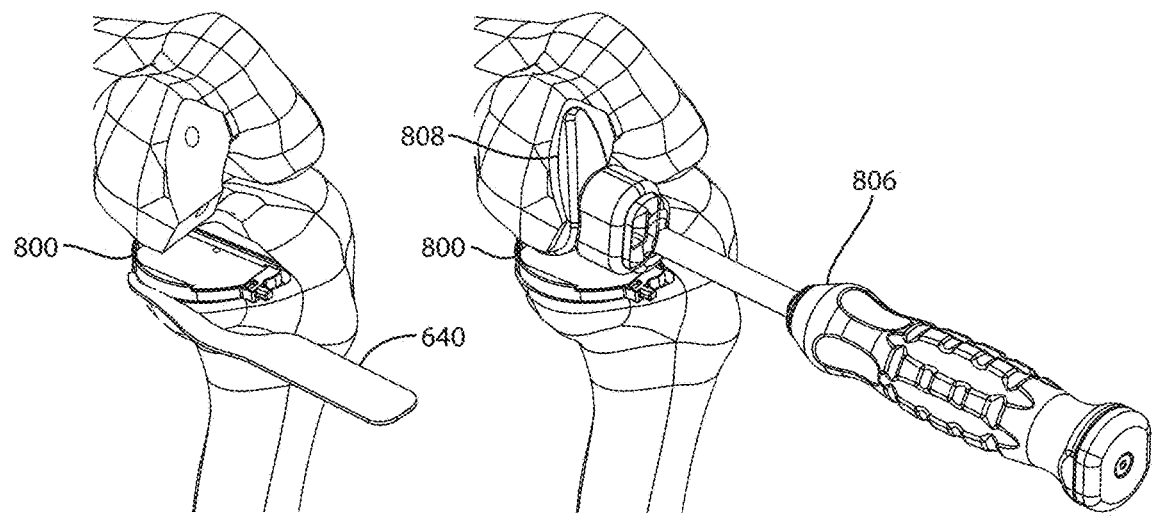
FIG. 239    FIG. 240

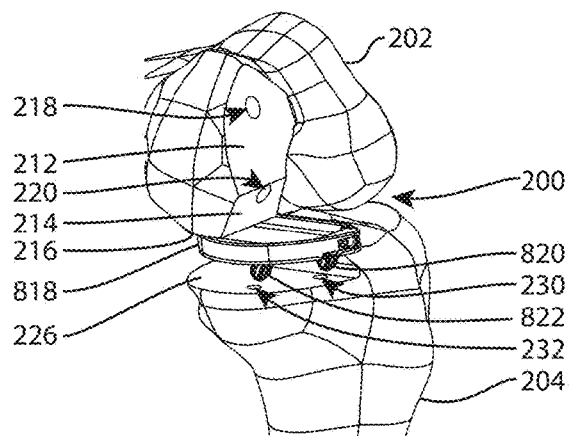
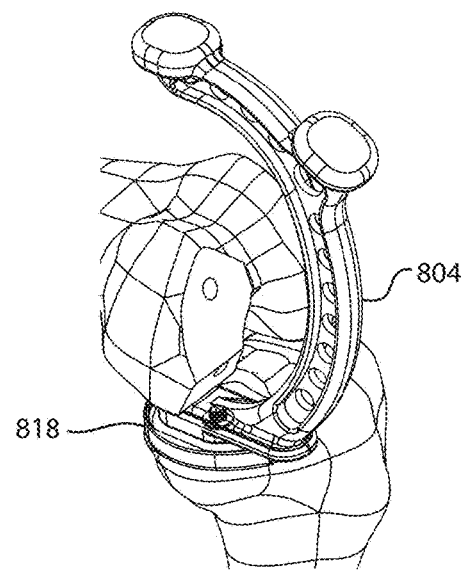
FIG. 249  FIG. 250
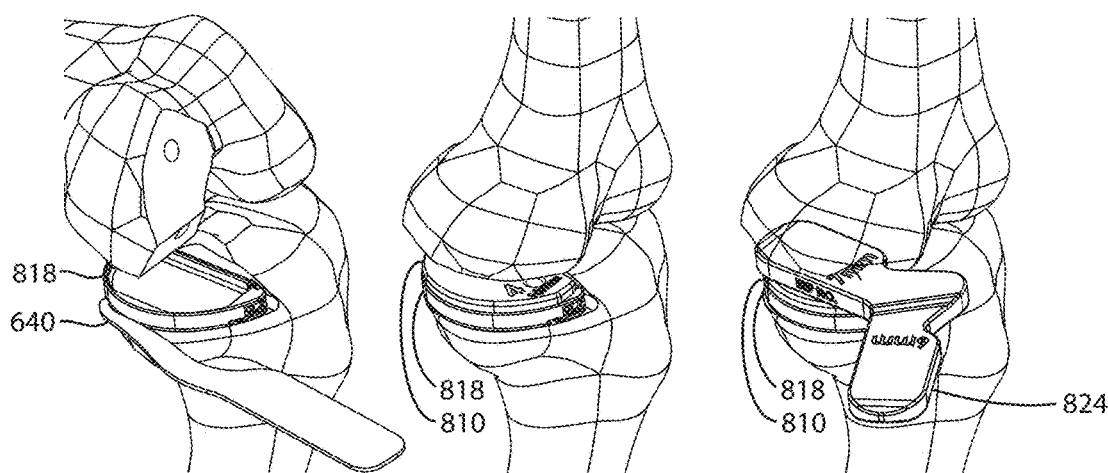
FIG. 251  FIG. 252  FIG. 253

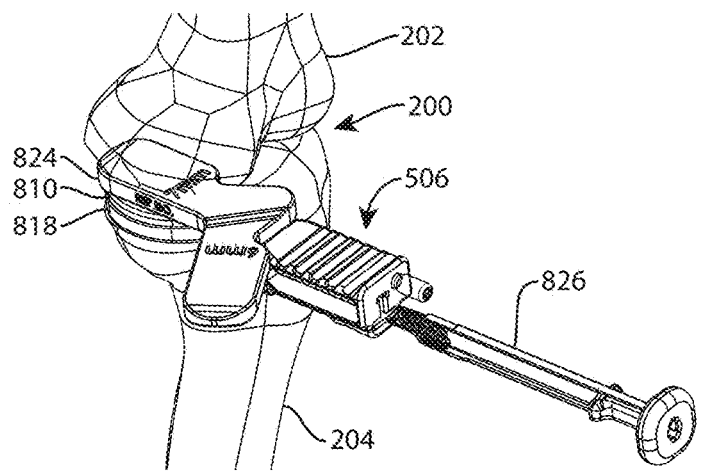
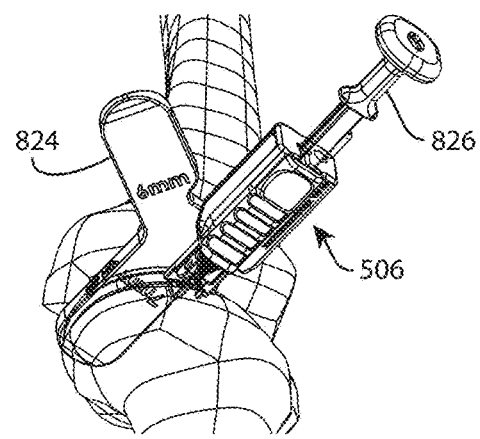
FIG. 258
FIG. 259
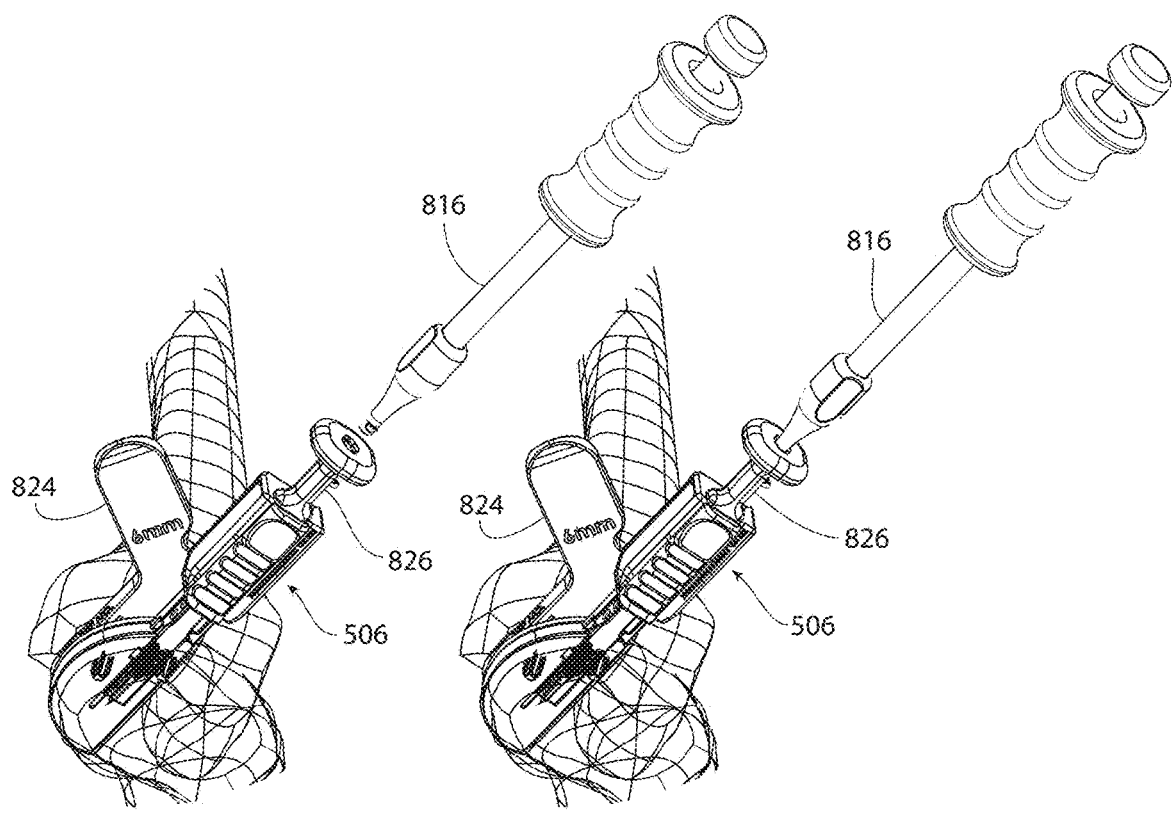
FIG. 260
FIG. 261

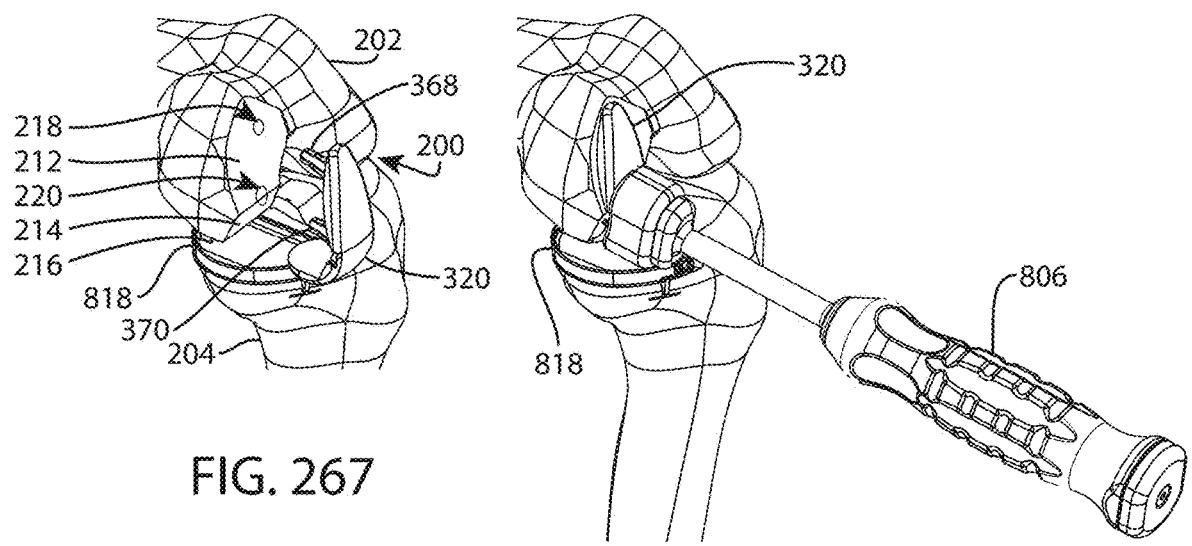
FIG. 267
FIG. 268
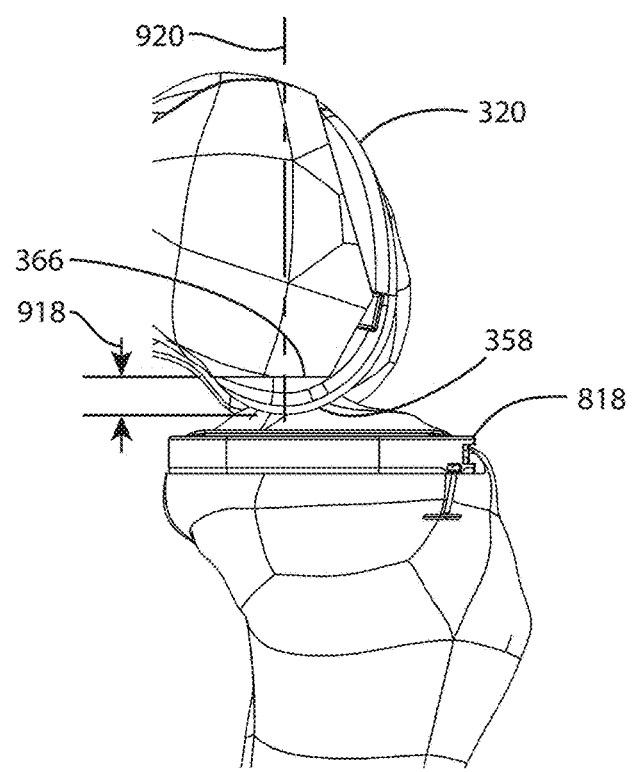
FIG. 269

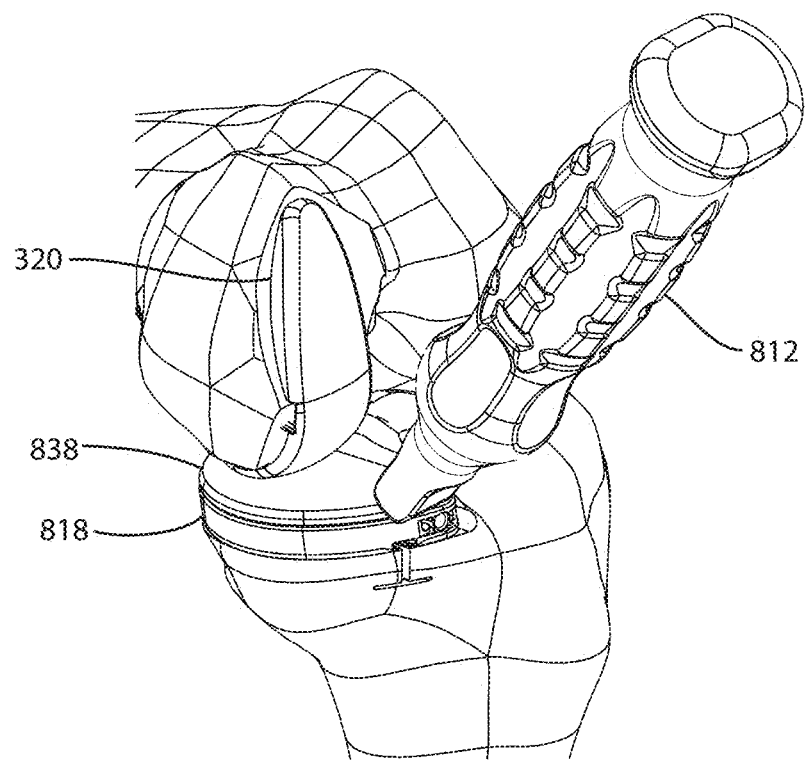
FIG. 270
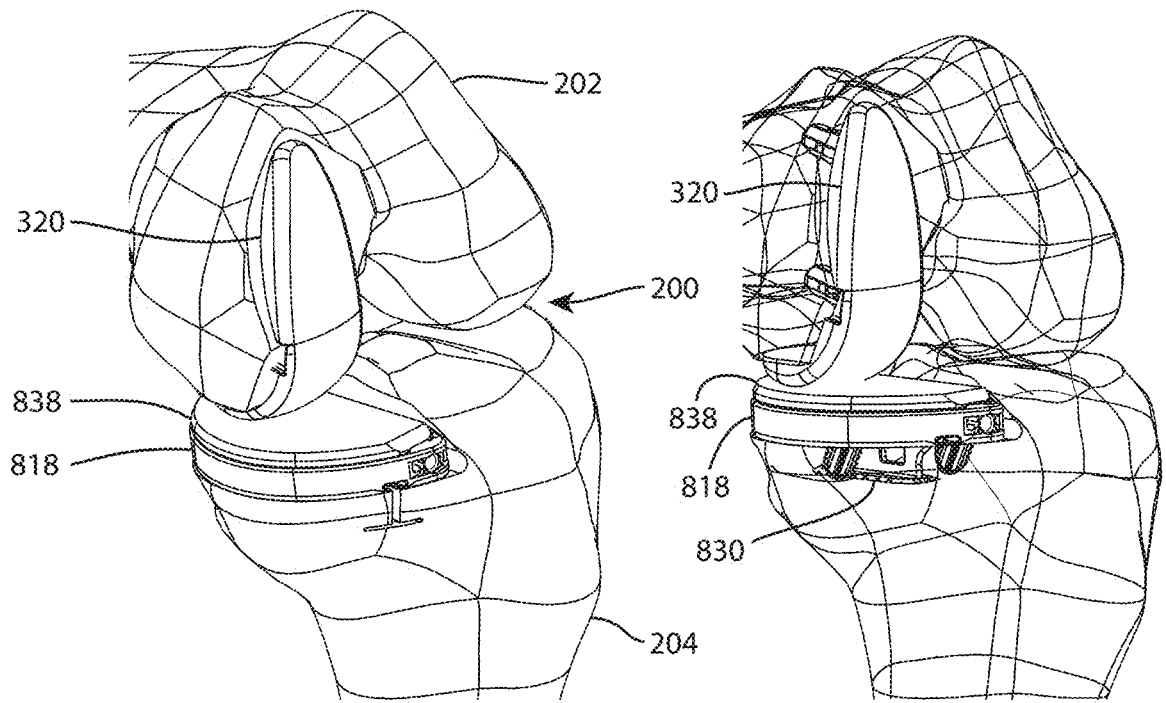
FIG. 271
FIG. 272

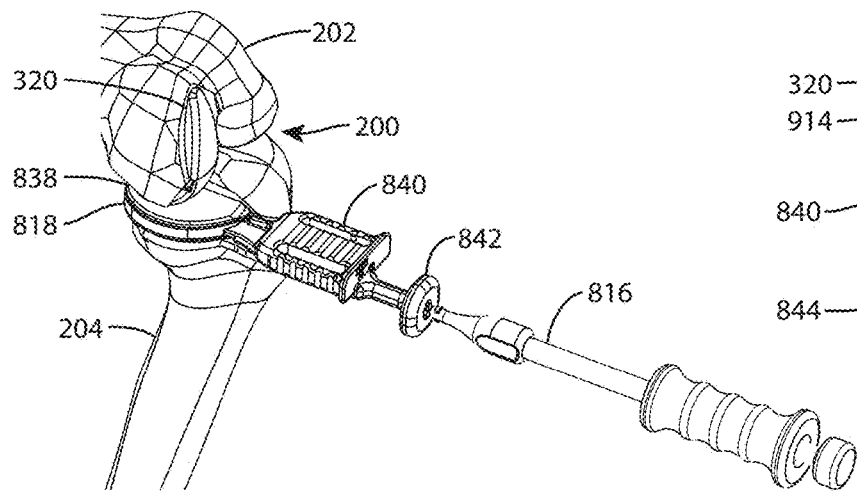
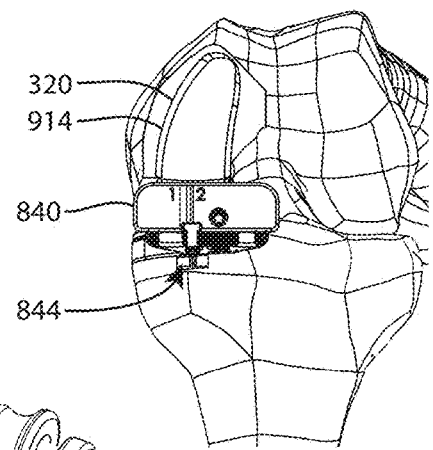
FIG. 280  FIG. 281
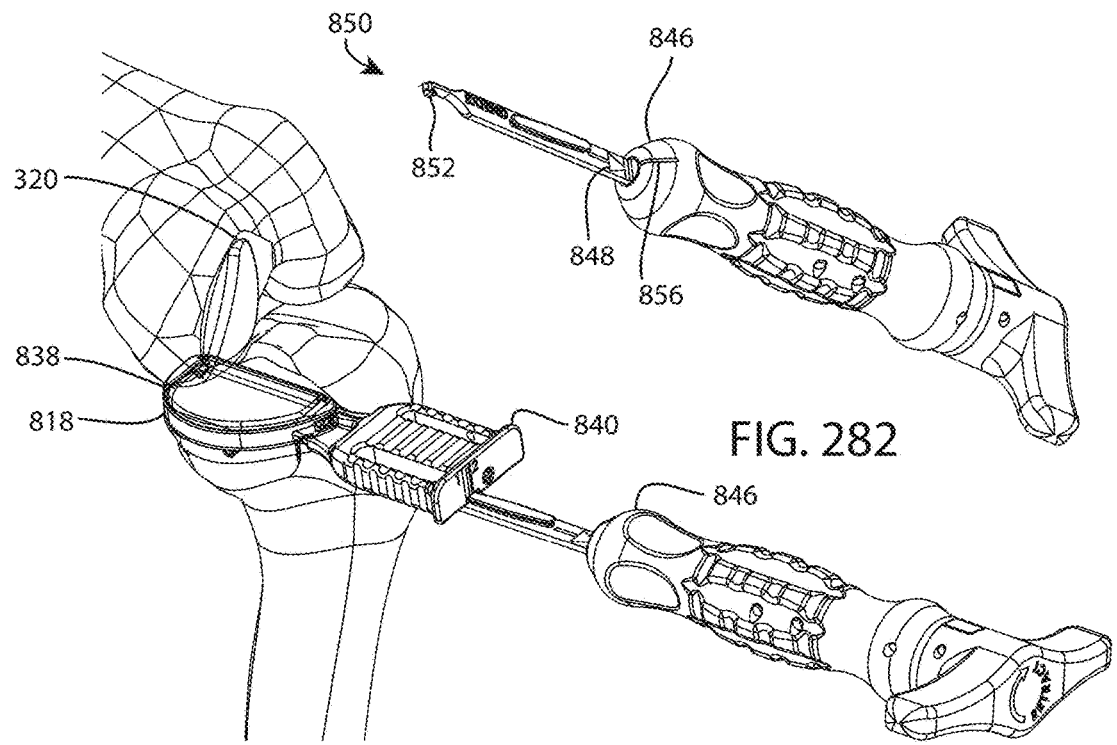
FIG. 282
FIG. 283

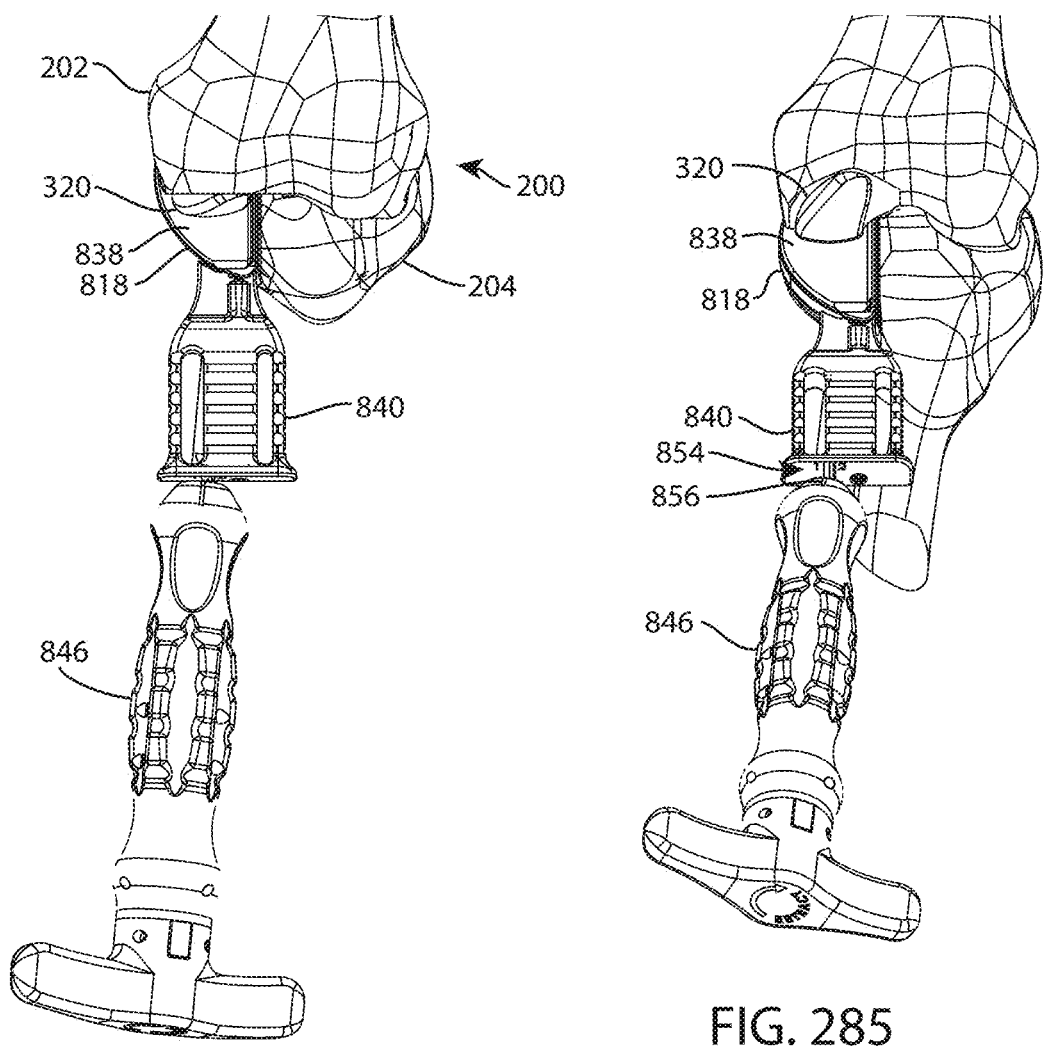
FIG. 284
FIG. 285
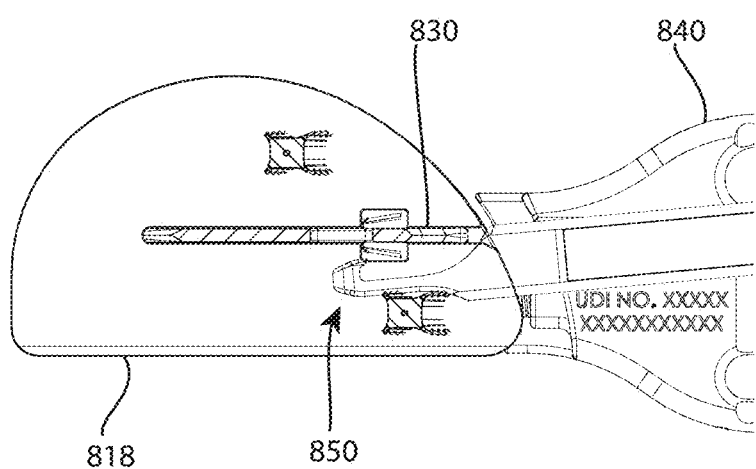
FIG. 286

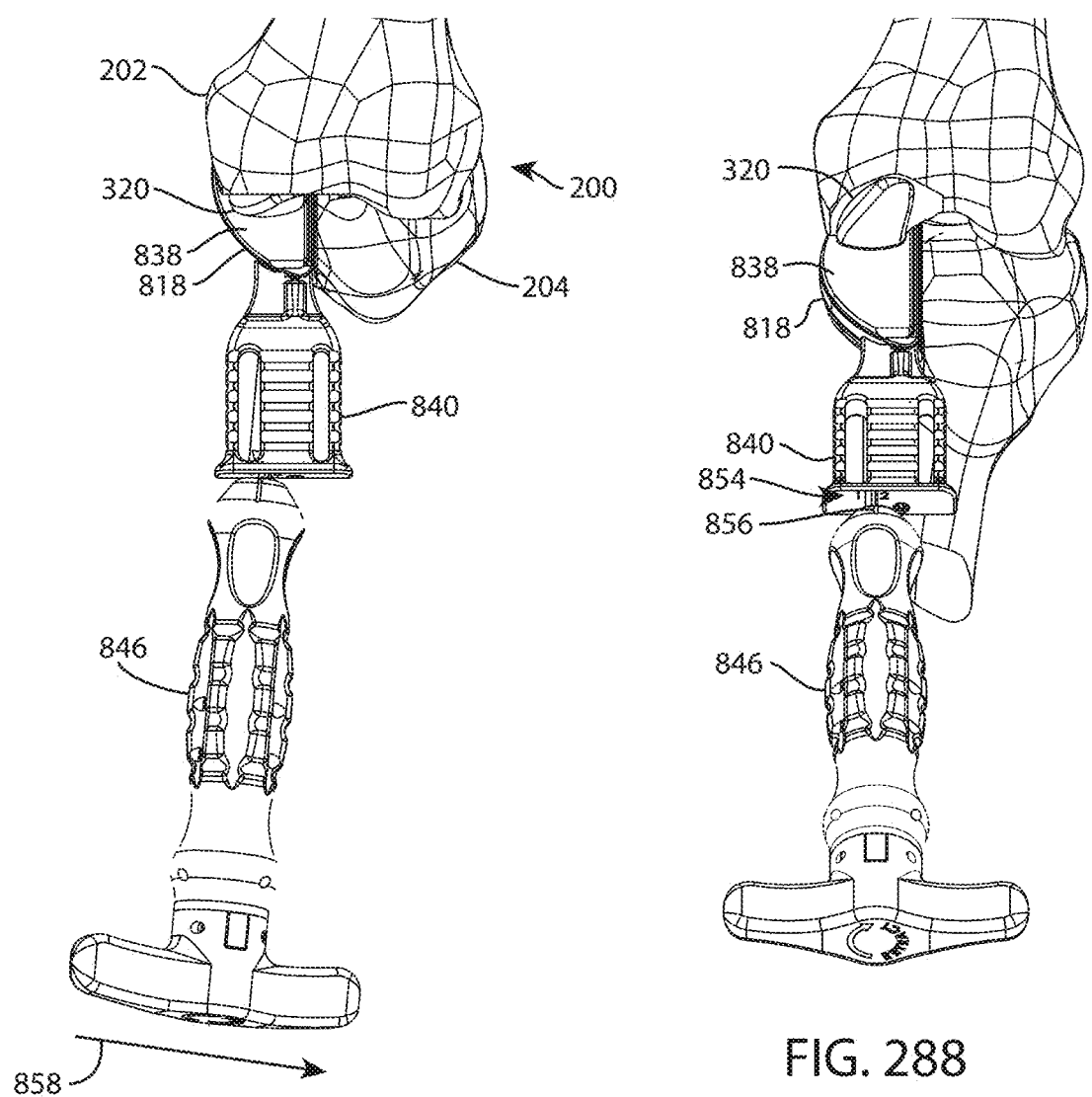
FIG. 287
FIG. 288
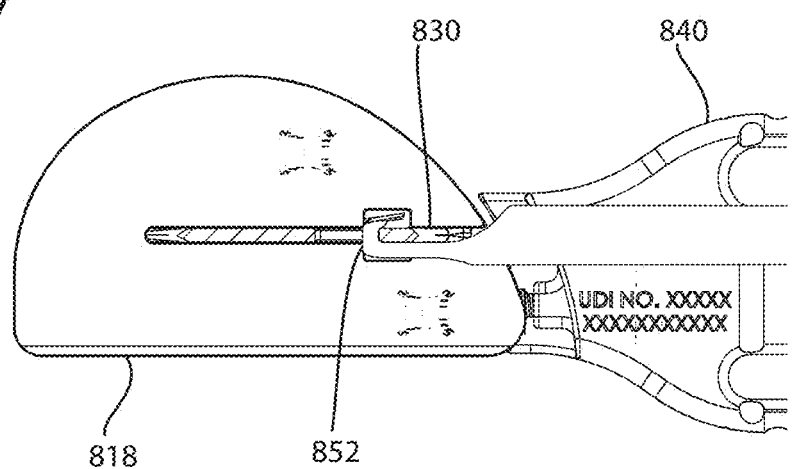
FIG. 289

UNICOMPARTMENTAL KNEE ARTHROPLASTY

CROSS-REFERENCE TO RELATED APPLICATIONS

The present application claims the benefit of:

U.S. Provisional Patent Application No. 62/902873, entitled KNEE IMPLANTS, filed Sep. 19, 2019; and U.S. Provisional Patent Application No. 62/902875, entitled SHOULDER AND KNEE IMPLANTS, filed Sep. 19, 2019.

The present application is a continuation-in-part of:

U.S. patent application Ser. No. 16/664,154, entitled UNICOMPARTMENTAL KNEE ARTHROPLASTY, filed Oct. 25, 2019.

U.S. patent application Ser. No. 16/664,154 is a continuation of:

U.S. patent application Ser. No. 15/910,962, entitled UNICOMPARTMENTAL KNEE ARTHROPLASTY, filed Mar. 2, 2018, which issued on Oct. 29, 2019 as U.S. Pat. No. 10,456,272.

U.S. patent application Ser. No. 15/910,962 claims the benefit of:

U.S. Provisional Patent Application No. 62/467083, entitled UNICOMPARTMENTAL KNEE ARTHROPLASTY, filed Mar. 3, 2017.

The foregoing are incorporated by reference as though set forth herein in their entirety.

TECHNICAL FIELD

The present disclosure relates to arthroplasty. More specifically, the present disclosure is made in the context of unicompartmental knee arthroplasty. Those of skill in the art will appreciate that the disclosed technology is applicable to other types of arthroplasty.

BACKGROUND

Arthroplasty procedures seek to replace a natural joint that has deteriorated in its functionality. Joint resurfacing typically involves removal of at least a portion of a natural articular surface of a bone in order to replace the removed tissue with a prosthesis having an articular surface that replicates at least the removed portion of the natural articular surface. Joint replacement may involve more extensive bone removal and subsequent replacement with a more substantial prosthesis. In this disclosure, remarks about resurfacing are to be considered equally relevant to replacement, and vice versa.

Arthroplasty procedures may involve one or more articular surfaces of a joint. In the knee, for example, the medial femoral condyle, the lateral femoral condyle, the medial tibial condyle, the lateral tibial condyle, the trochlear groove, and/or the patella may be resurfaced or replaced. A procedure may be described as unicondylar if one condyle of the joint is treated, such as the medial tibial condyle. Bicondylar procedures may treat two condyles of a bone, such as the medial and lateral tibial condyles. A procedure may be described as unicompartmental if one compartment of the joint is treated, such as the medial compartment of the knee. Bicompartmental procedures may treat two compartments, such as the medial and lateral compartments of the knee. A procedure may be described as a total joint procedure if most or all opposing articular surfaces of the joint are resurfaced or replaced. A procedure may be described as a hemiarthroplasty procedure if the prosthetic component articulates against an opposing natural articular surface, such as the prosthetic medial tibial component articulating against the natural medial femoral condyle.

SUMMARY

The various systems and methods of the present technology have been developed in response to the present state of the art, and in particular, in response to the problems and needs in the art that have not yet been fully solved by currently available arthroplasty systems. The systems and methods of the present technology may provide enhanced implant fixation and/or more accurate and adaptive surgical methods.

To achieve the foregoing, and in accordance with the technology as embodied and broadly described herein, in an aspect of the technology, a system for unicompartmental knee arthroplasty of a knee joint including a femur and a tibia includes: a femoral implant including an articular surface and an opposite bone-facing side including a distal surface for contacting a distal resection of a condyle of the femur, and a posterior surface for contacting a posterior resection of the femoral condyle; an articular insert implant including an articular surface for articulation with the femoral implant articular surface and an opposite tray-facing side including a tray connection feature; a tibial tray implant including an insert-facing side and an opposite bone-facing side, wherein the insert-facing side includes an insert connection feature for connection to the tray connection feature, wherein the bone-facing side is adapted for contacting a proximal resection of a proximal end of the tibia; a posterior cutting block including a bone-facing surface for contacting the distal resection, a first cutting slot for making the posterior resection, and a cylindrical first interface surface; and a rotation tensor block, including a first bone-facing side for contacting the proximal resection, an opposite second bone-facing side for contacting an unresected posterior surface of the femoral condyle, and a cylindrical second interface surface; wherein when the posterior cutting block is coupled to the rotation tensor block, the first interface surface articulates with the second interface surface so that the posterior cutting block rotates relative to the rotation tensor block around a center longitudinal axis that is common to the first and second interface surfaces, and the first cutting slot is separated from the first bone-facing side of the rotation tensor block by a distance that is substantially equal to the sum of a thickness of the femoral implant measured perpendicular to the posterior surface between the posterior surface and the articular surface of the femoral implant and a combined thickness of the articular insert implant and the tibial tray implant measured between the articular surface of the articular insert implant and the bone-facing side of the tibial tray implant.

Embodiments of this aspect may have one or more of the following attributes. In a medial-lateral plane that is perpendicular to the posterior surface, the articular surface of the femoral implant includes a medial-lateral curvature that is an arc of a circle, wherein the circle has a center point; wherein the center longitudinal axis that is common to the first and second interface surfaces is coincident with the center point of the femoral implant. The femoral implant includes an outer perimeter extending around the distal surface, wherein the posterior cutting block includes an outer perimeter extending around the bone-facing surface of the posterior cutting block, wherein the outer perimeter of the posterior cutting block matches the outer perimeter of the femoral implant. The posterior cutting block includes a window that extends through the bone-facing surface of the posterior cutting block and is centered in a medial-lateral width of the posterior cutting block. At least one of the posterior cutting block and the rotation tensor block includes a rotation limiting feature, wherein when the posterior cutting block is coupled to the rotation tensor block, the rotation limiting feature limits a rotational range of motion of the posterior cutting block relative to the rotation tensor block around the center longitudinal axis of the first and second interface surfaces. The bone-facing side of the femoral implant includes a posterior chamfer surface for contacting a posterior chamfer resection of the femoral condyle, wherein the posterior cutting block includes a second cutting slot for making the posterior chamfer resection. The femoral implant includes a peg protruding outwardly from the bone-facing side of the femoral implant, wherein the posterior cutting block includes a drill guide hole for making a peg hole in the femoral condyle to receive the peg of the femoral implant.

In another aspect of the technology, a system for unicompartmental knee arthroplasty of a knee joint including a femur and a tibia includes: a femoral implant including an articular surface and an opposite bone-facing side including a distal surface for contacting a distal resection of a condyle of the femur, and a posterior surface for contacting a posterior resection of the femoral condyle, wherein the femoral implant includes a posterior thickness measured perpendicular to the posterior surface between the posterior surface and the articular surface of the femoral implant; an articular insert implant including an articular surface for articulation with the femoral implant articular surface and an opposite tray-facing side including a tray connection feature; a tibial tray implant including an insert-facing side and an opposite bone-facing side, wherein the insert-facing side includes an insert connection feature for connection to the tray connection feature, wherein the bone-facing side is adapted for contacting a proximal resection of a proximal end of the tibia, wherein when the articular insert implant and the tibial tray implant are connected together, the connected articular insert implant and tibial tray implant include a combined thickness measured between the articular surface of the articular insert implant and the bone-facing side of the tibial tray implant; a posterior cutting block including a bone-facing surface for contacting the distal resection, a first cutting slot for making the posterior resection, and a first interface feature; and a rotation tensor block, including a first bone-facing side for contacting the proximal resection, an opposite second bone-facing side for contacting an unresected posterior surface of the femoral condyle, and a second interface feature; wherein when the posterior cutting block is coupled to the rotation tensor block, the first interface feature articulates with the second interface feature so that the posterior cutting block rotates relative to the rotation tensor block around a center longitudinal axis of the first and second interface features, and the first cutting slot is separated from the first bone-facing side of the rotation tensor block by a distance that is substantially equal to the sum of the posterior thickness of the femoral implant and the combined thickness of the articular insert implant and the tibial tray implant.

Embodiments of this aspect may have one or more of the following attributes. In a medial-lateral plane that is perpendicular to the posterior surface, the articular surface of the femoral implant includes a medial-lateral curvature that is an arc of a circle, wherein the circle includes a center point; wherein the center longitudinal axis of the first and second interface features is coincident with the center point of the femoral implant. The femoral implant includes an outer perimeter extending around the distal surface, wherein the posterior cutting block includes an outer perimeter extending around the bone-facing surface of the posterior cutting block, wherein the outer perimeter of the posterior cutting block matches the outer perimeter of the femoral implant. The posterior cutting block includes a window that extends through the bone-facing surface of the posterior cutting block and is centered in a medial-lateral width of the posterior cutting block. At least one of the posterior cutting block and the rotation tensor block includes a rotation limiting feature, wherein when the posterior cutting block is coupled to the rotation tensor block, the rotation limiting feature limits a rotational range of motion of the posterior cutting block relative to the rotation tensor block around the center longitudinal axis of the first and second interface features. The bone-facing side of the femoral implant includes a posterior chamfer surface for contacting a posterior chamfer resection of the femoral condyle, wherein the posterior cutting block includes a second cutting slot for making the posterior chamfer resection. The femoral implant includes a peg protruding outwardly from the bone-facing side of the femoral implant, wherein the posterior cutting block includes a drill guide hole for making a peg hole in the femoral condyle to receive the peg of the femoral implant.

In yet another aspect of the technology, a system for unicompartmental knee arthroplasty of a knee joint including a femur and a tibia includes: a femoral implant including an articular surface and an opposite bone-facing side including a distal surface for contacting a distal resection of a condyle of the femur, and a posterior surface for contacting a posterior resection of the femoral condyle, wherein the femoral implant includes a posterior thickness measured perpendicular to the posterior surface between the posterior surface and the articular surface of the femoral implant, wherein in a medial-lateral plane that is perpendicular to the posterior surface, the articular surface includes a medial-lateral curvature that is an arc of a circle that has a center point; an articular insert implant including an articular surface for articulation with the femoral implant articular surface and an opposite tray-facing side including a tray connection feature; a tibial tray implant including an insert-facing side and an opposite bone-facing side, wherein the insert-facing side includes an insert connection feature for connection to the tray connection feature, wherein the bone-facing side is adapted for contacting a proximal resection of a proximal end of the tibia, wherein when the articular insert implant and the tibial tray implant are connected together, the connected articular insert implant and tibial tray implant include a combined thickness measured between the articular surface of the articular insert implant and the bone-facing side of the tibial tray implant; a posterior cutting block including a bone-facing surface for contacting the distal resection and a first cutting slot for making the posterior resection; and a rotation tensor block, including a first bone-facing side for contacting the proximal resection and an opposite second bone-facing side for contacting an unresected posterior surface of the femoral condyle; wherein the posterior cutting block rotates around an axis that is coincident with the center point of the femoral implant.

Embodiments of this aspect may have one or more of the following attributes. The femoral implant includes an outer perimeter extending around the distal surface, wherein the posterior cutting block includes an outer perimeter extending around the bone-facing surface of the posterior cutting block, wherein the outer perimeter of the posterior cutting block matches the outer perimeter of the femoral implant. The posterior cutting block includes a window that extends through the bone-facing surface of the posterior cutting block and is centered in a medial-lateral width of the posterior cutting block. When the posterior cutting block is coupled to the rotation tensor block, the posterior cutting block rotates relative to the rotation tensor block around the axis, and the first cutting slot is separated from the first bone-facing side of the rotation tensor block by a distance that is substantially equal to the sum of the posterior thickness of the femoral implant and the combined thickness of the articular insert implant and the tibial tray implant. The bone-facing side of the femoral implant includes a posterior chamfer surface for contacting a posterior chamfer resection of the femoral condyle, wherein the posterior cutting block includes a second cutting slot for making the posterior chamfer resection. The femoral implant includes a peg protruding outwardly from the bone-facing side of the femoral implant, wherein the posterior cutting block includes a drill guide hole for making a peg hole in the femoral condyle to receive the peg of the femoral implant.

These and other features and advantages of the present technology will become more fully apparent from the following description and appended claims, or may be learned by the practice of the technology as set forth hereinafter.

BRIEF DESCRIPTION OF THE DRAWINGS

Exemplary embodiments of the technology will become more fully apparent from the following description and appended claims, taken in conjunction with the accompanying drawings. Understanding that these drawings depict only exemplary embodiments and are, therefore, not to be considered limiting of the scope of the technology, the exemplary embodiments will be described with additional specificity and detail through use of the accompanying drawings in which:

FIG. 101 is an oblique view of an anchor guide;

FIG. 102 is another oblique view of the anchor guide of FIG. 101 from a different direction;

FIG. 103 is an oblique view of a tamp;

FIG. 104 is another oblique view of the tamp of FIG. 103;

FIG. 119 is an oblique view of the fixation element of FIG. 116;

FIG. 120 is another oblique view of the fixation element of FIG. 119 from a different direction;

FIG. 121 is a side view of the fixation element of FIG. 119;

FIG. 122 is a top view of the fixation element of FIG. 119;

FIG. 123 is an oblique view of yet another fixation element;

FIG. 124 is another oblique view of the fixation element of FIG. 123 from a different direction;

FIG. 125 is a side view of the fixation element of FIG. 123;

FIG. 126 is a top view of the fixation element of FIG. 123;

FIG. 127 is an oblique view of yet another fixation element;

FIG. 128 is another oblique view of the fixation element of FIG. 127 from a different direction;

FIG. 129 is a side view of the fixation element of FIG. 127;

FIG. 130 is a top view of the fixation element of FIG. 127;

Figure 131:
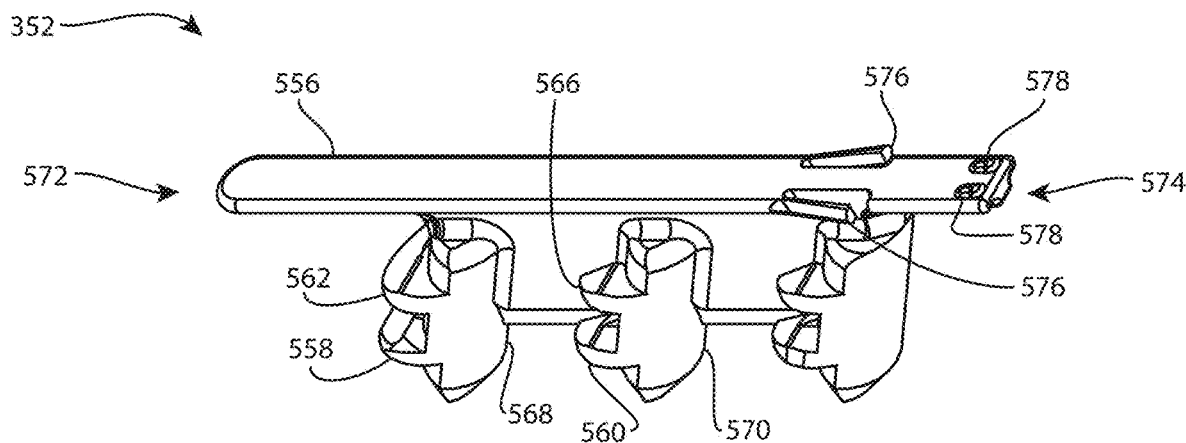
Figure 132:
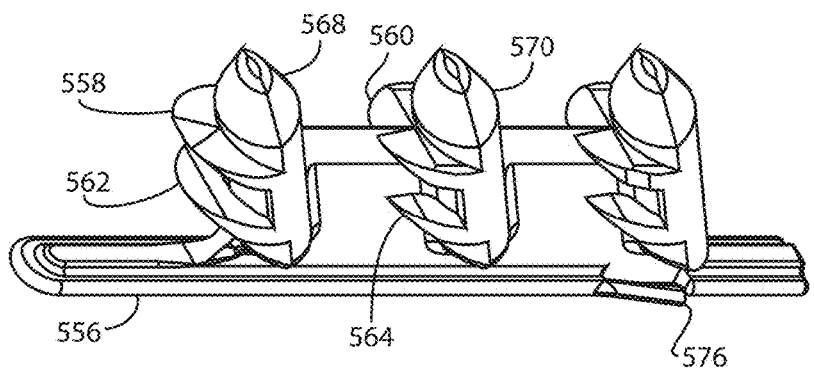
Figure 133:
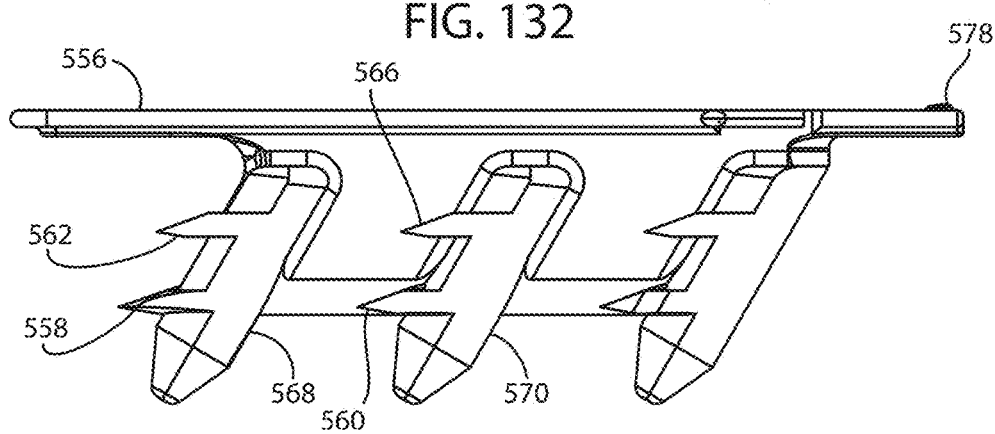
Figure 134:
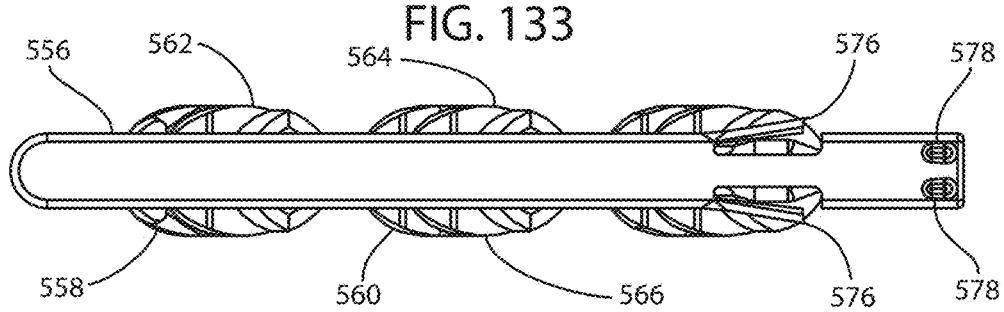
Figure 135:
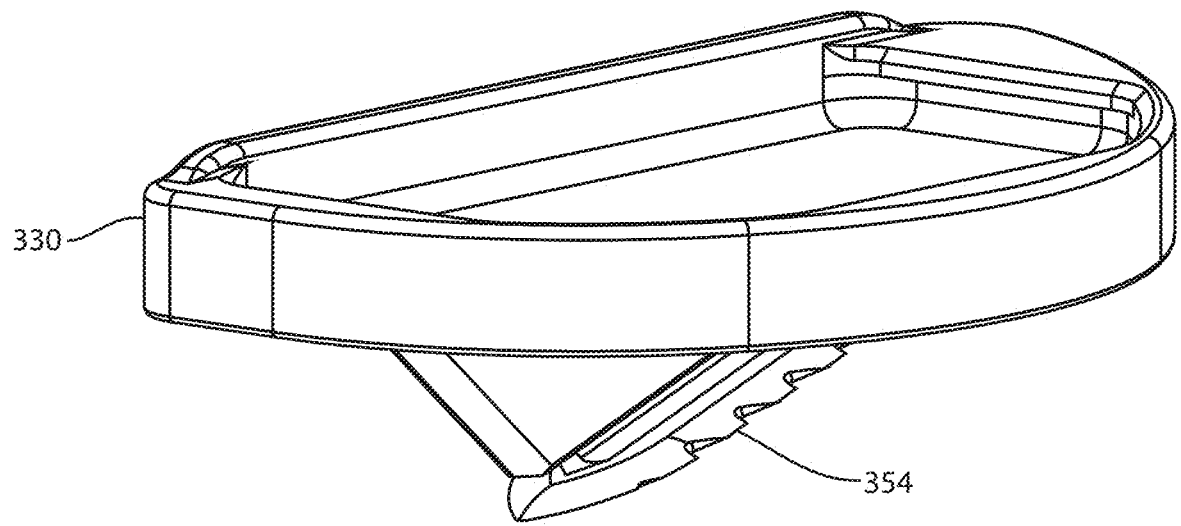
Figure 136:
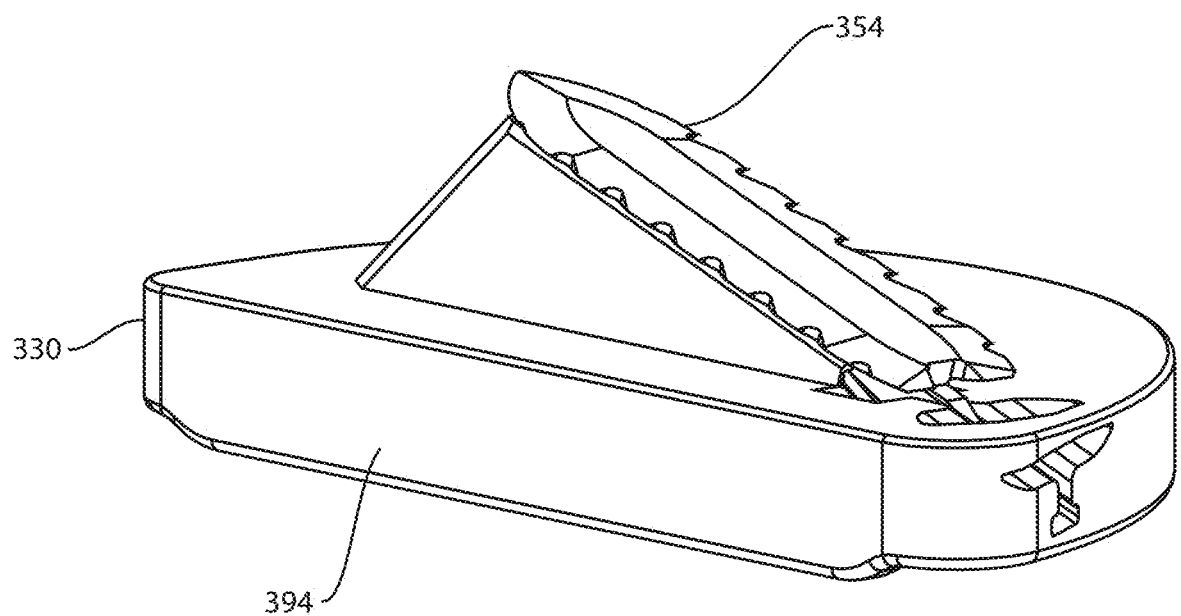
Figure 137:
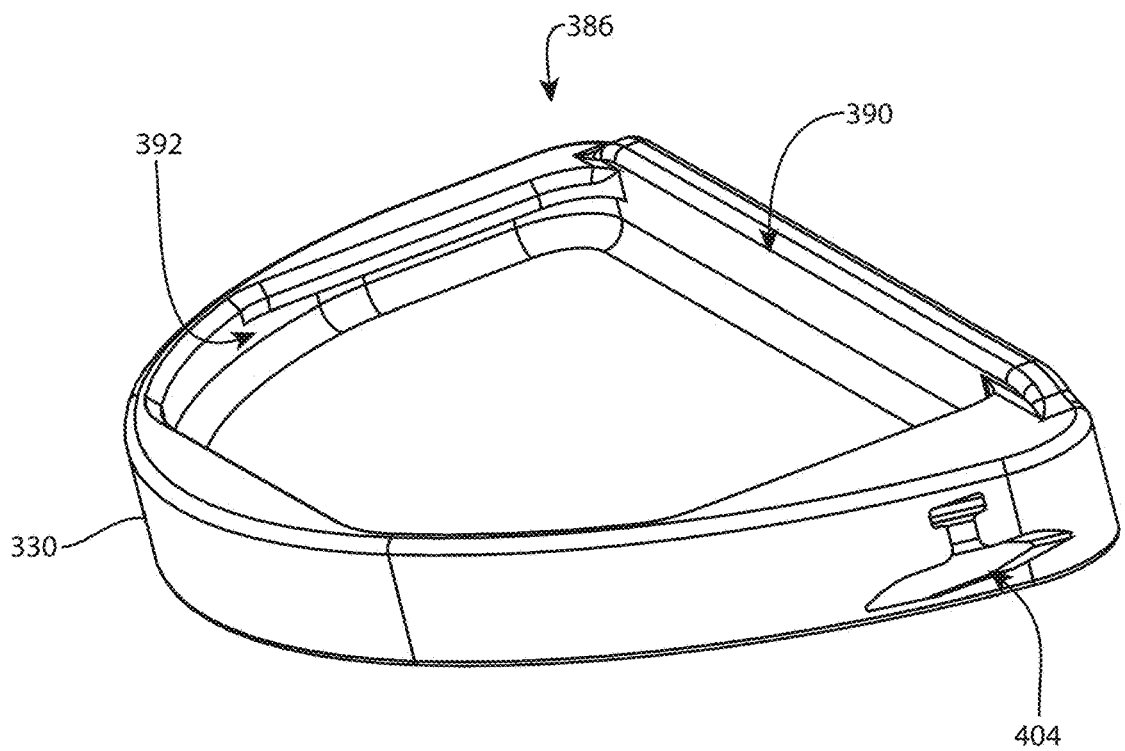
Figure 138:
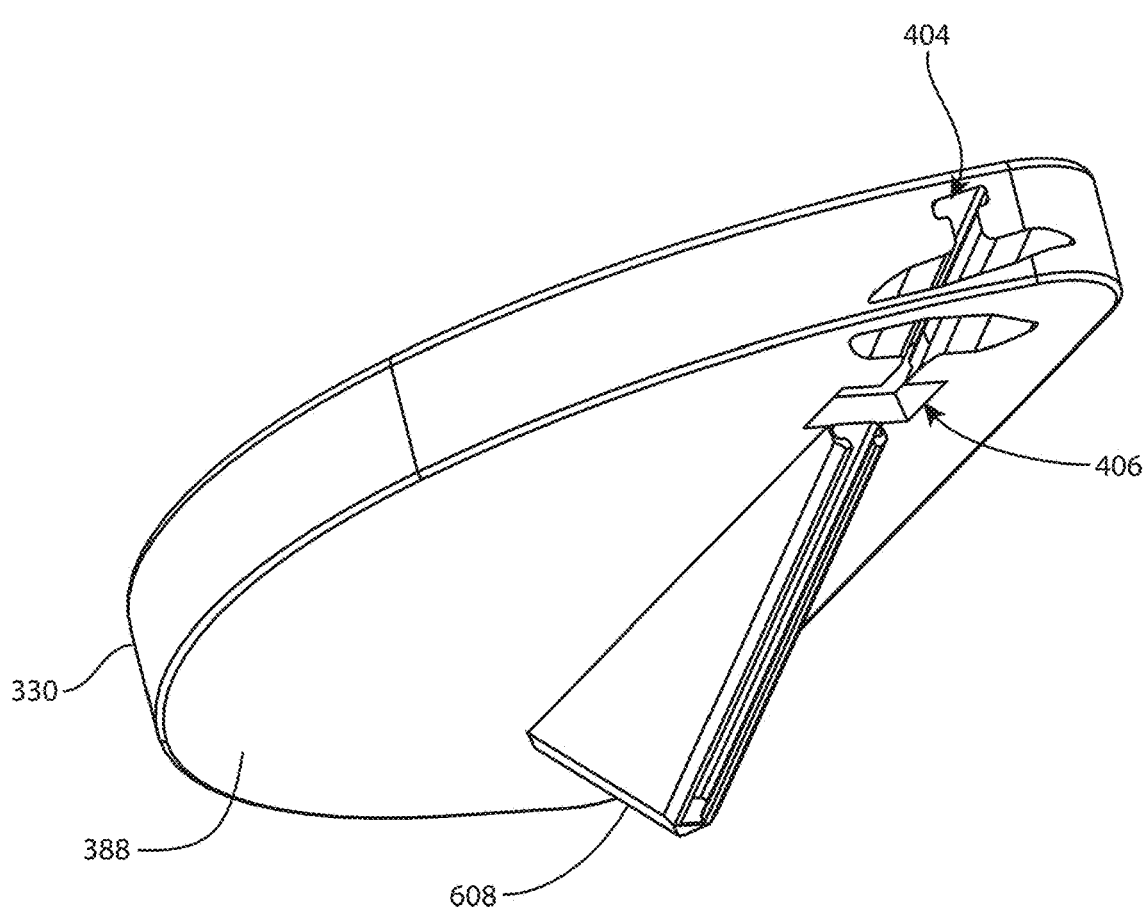
Figure 139:
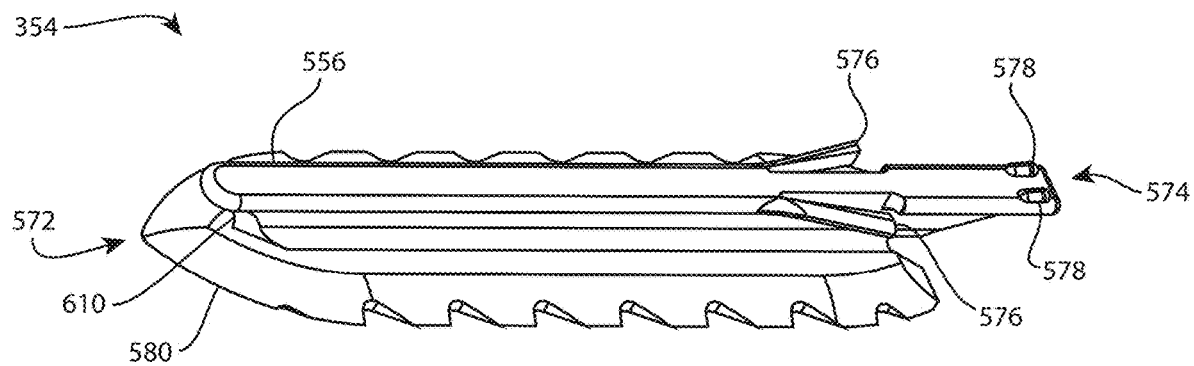
Figure 140:
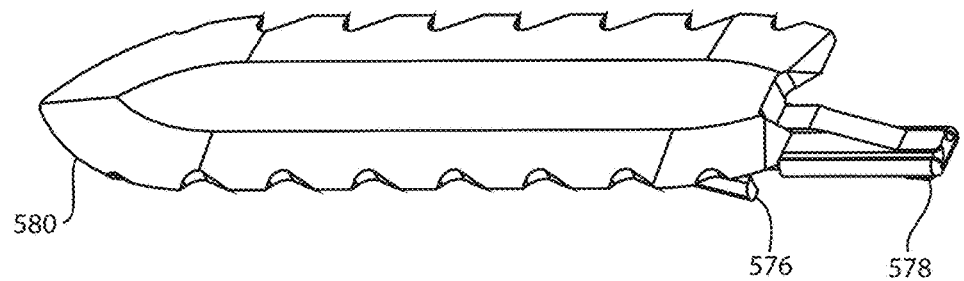
Figure 141:
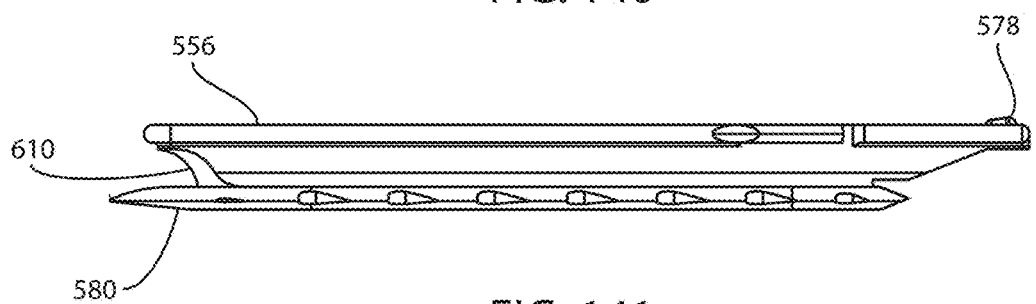
Figure 142:
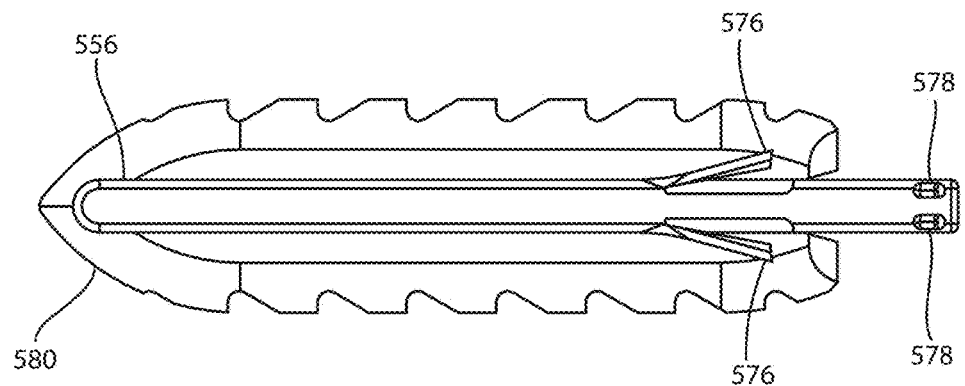
Figure 143:
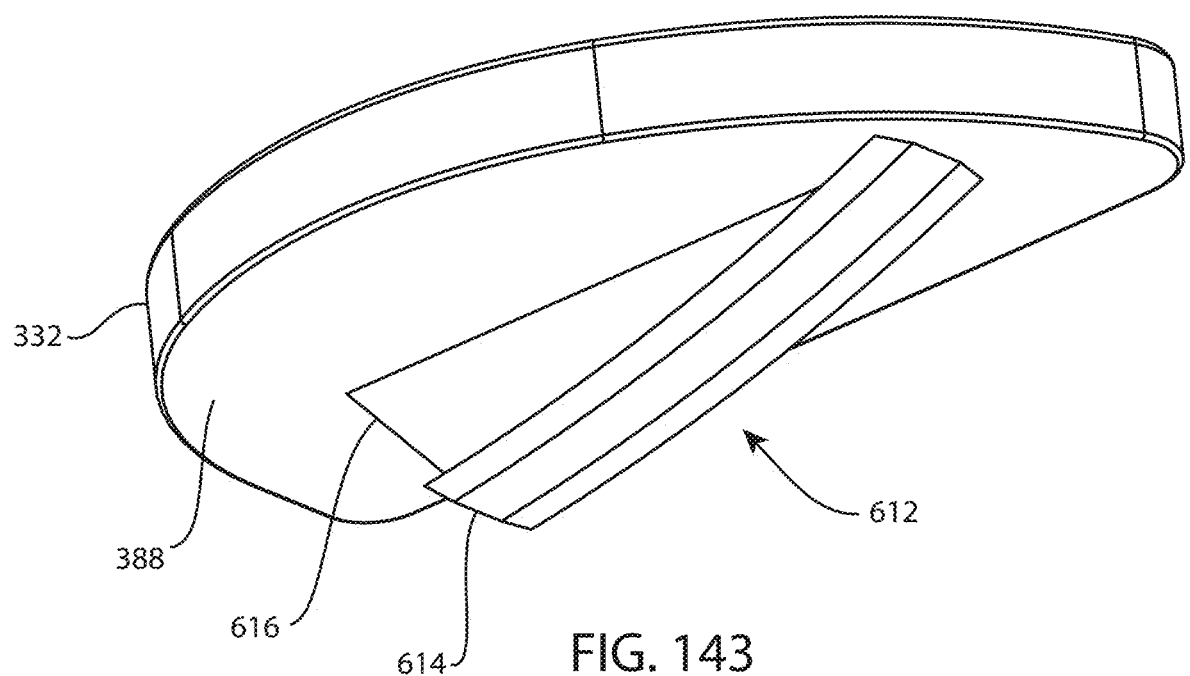
Figure 144:
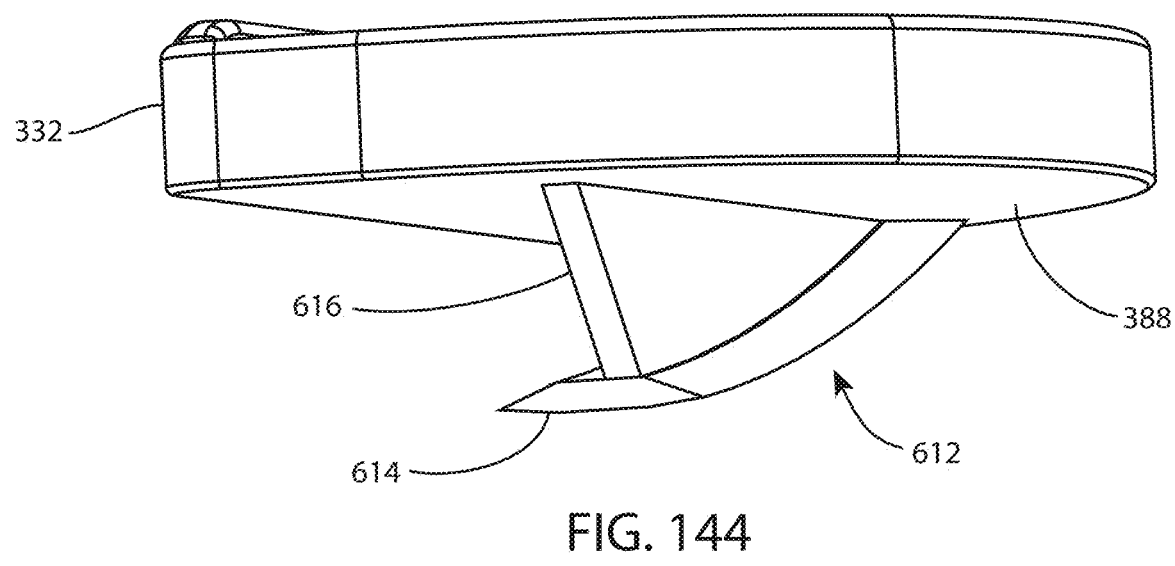
Figure 145:
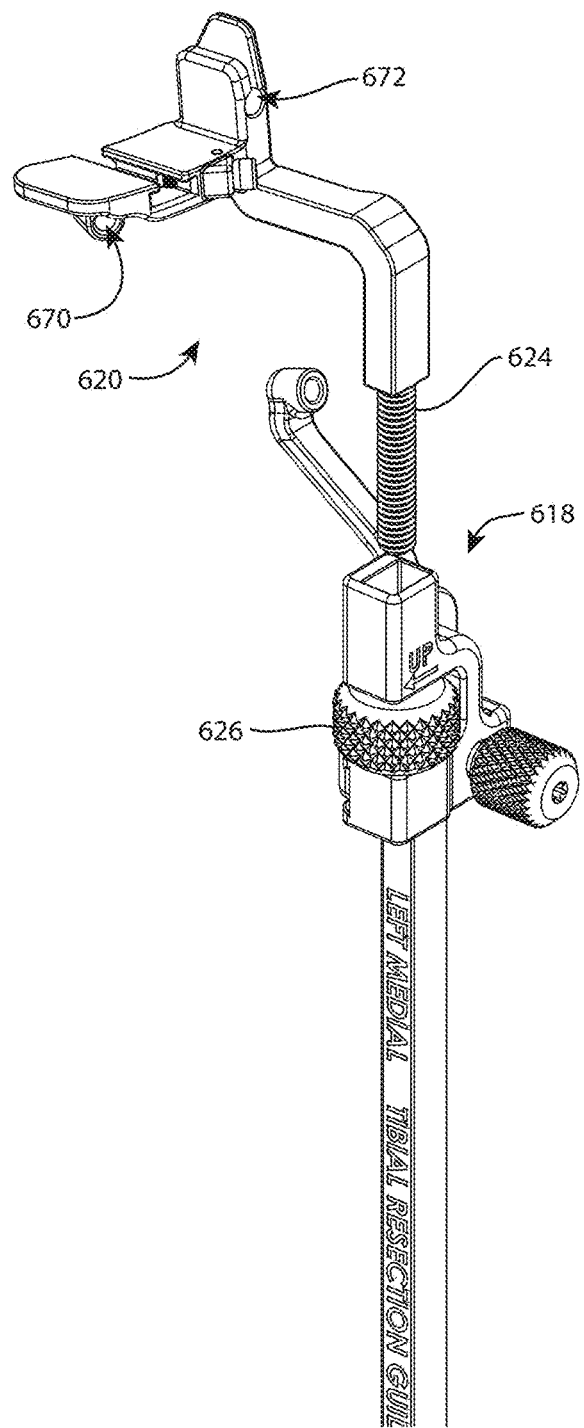
Figure 146:
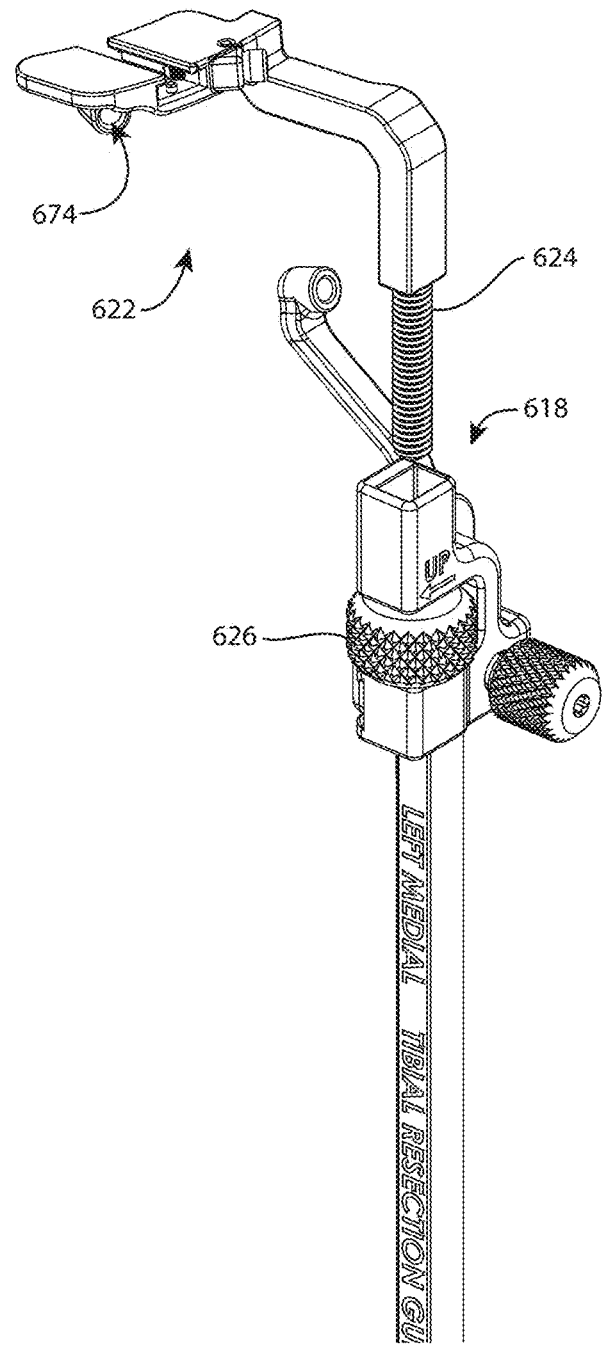
Figure 147:
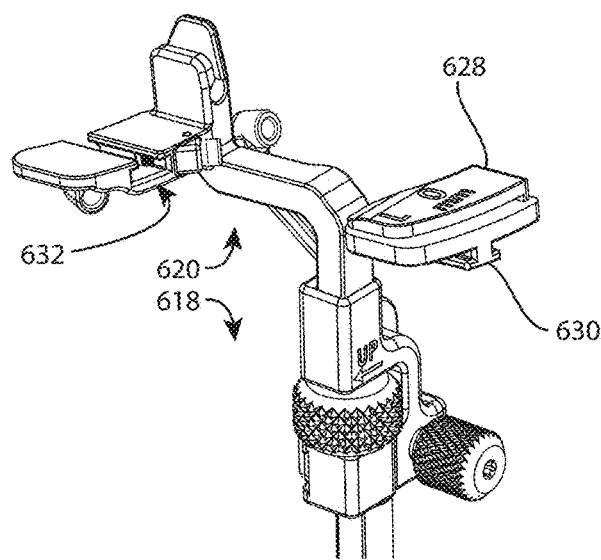
Figure 148:
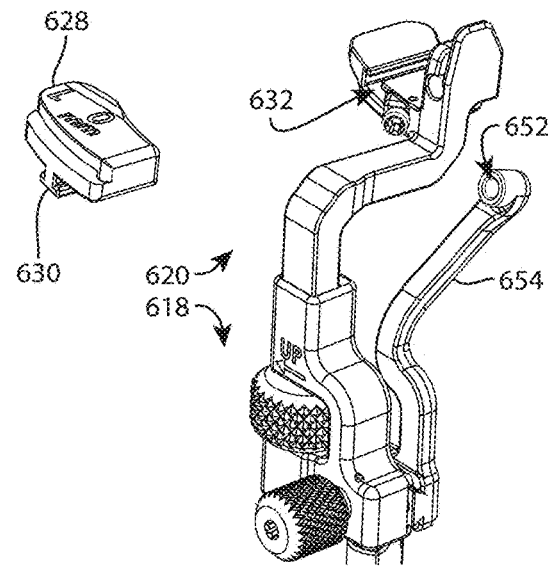
Figure 149:
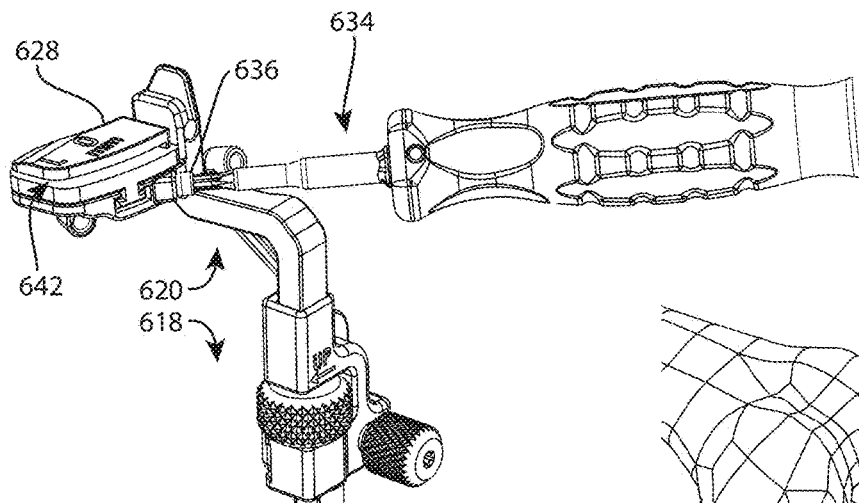
Figure 150:
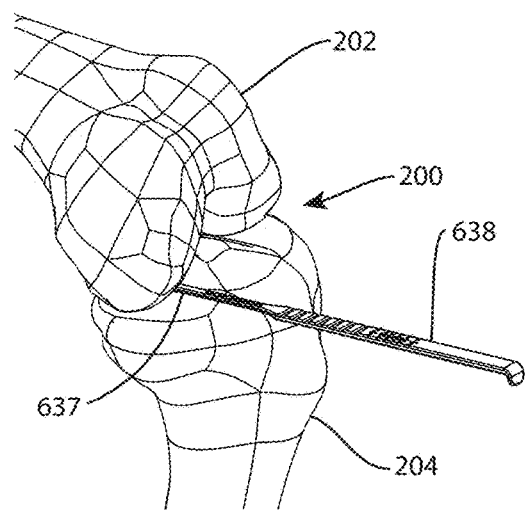
Figure 151:
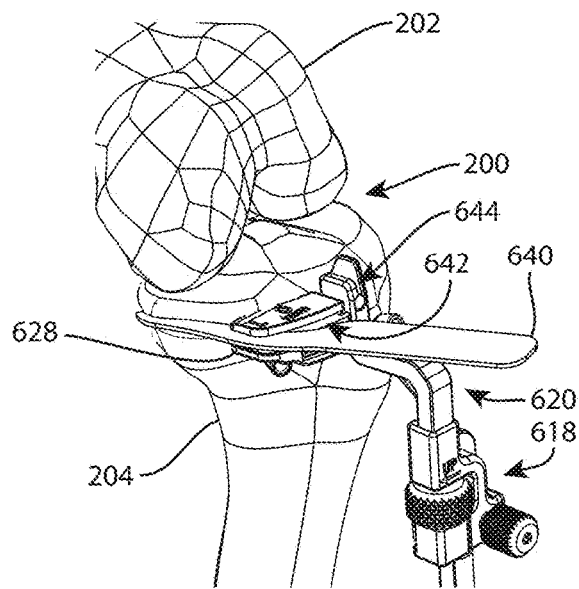
Figure 152:
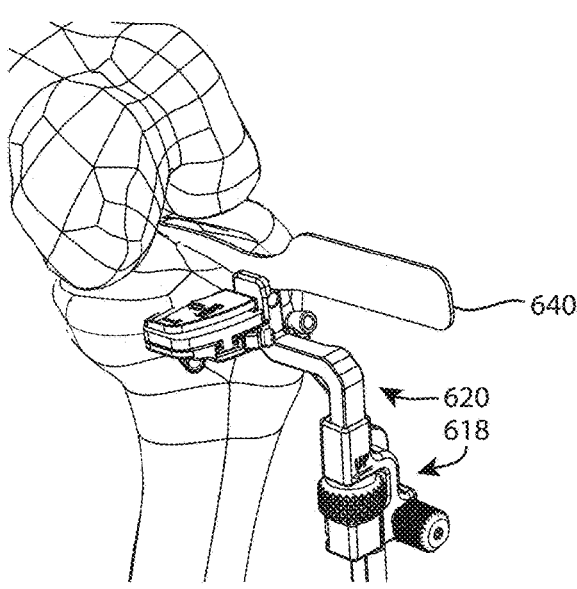
Figure 153:
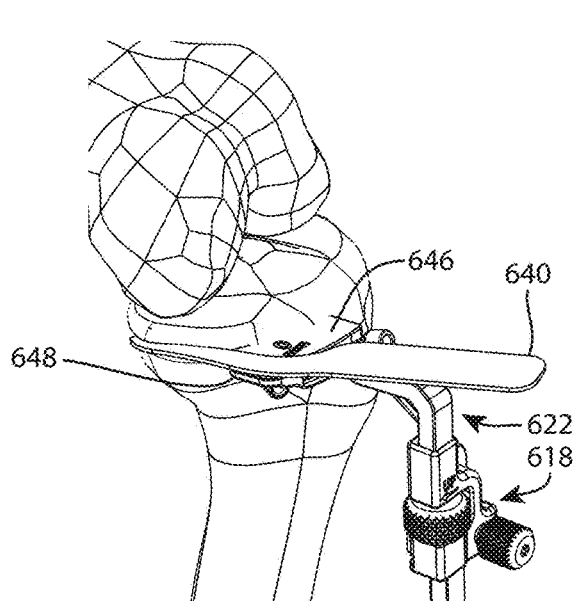
Figure 154:
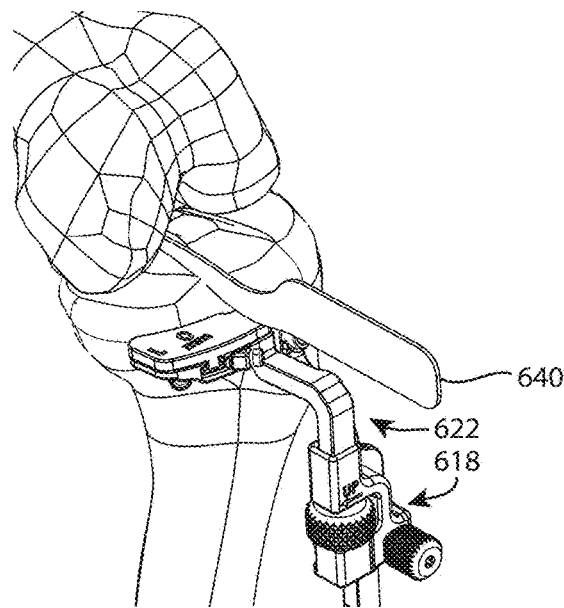
Figure 155:
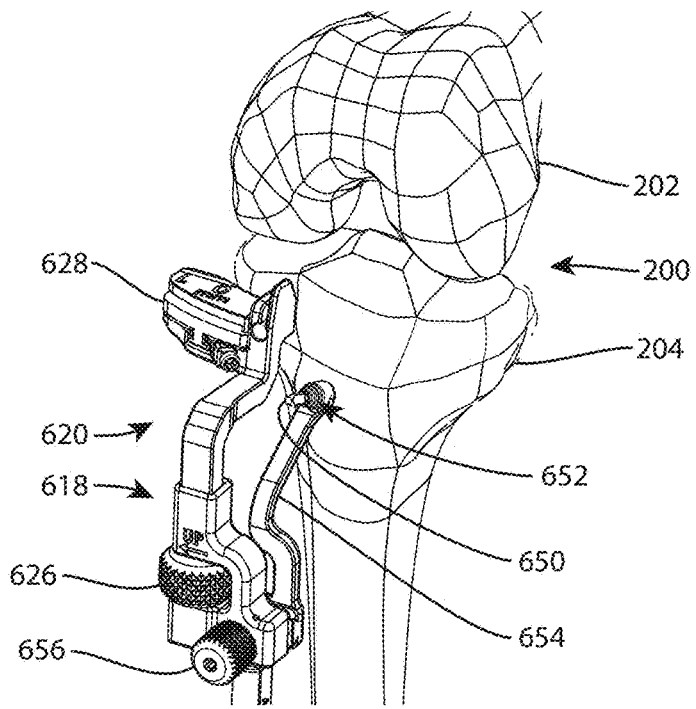
Figures 156, 157:
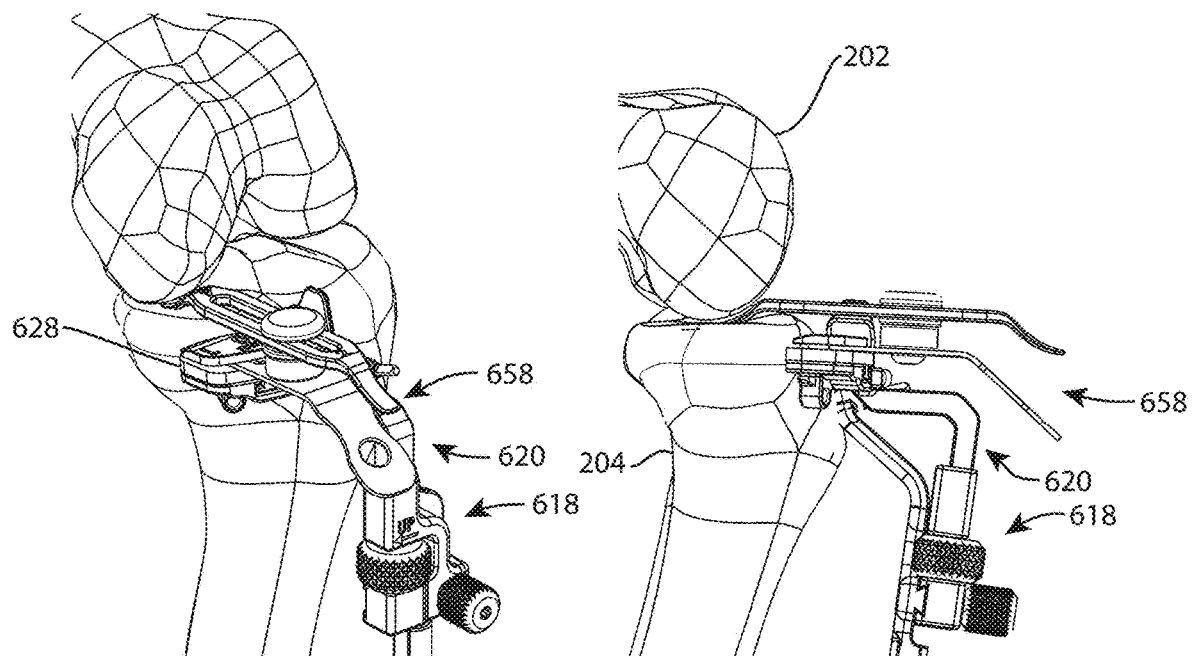
Figure 158:
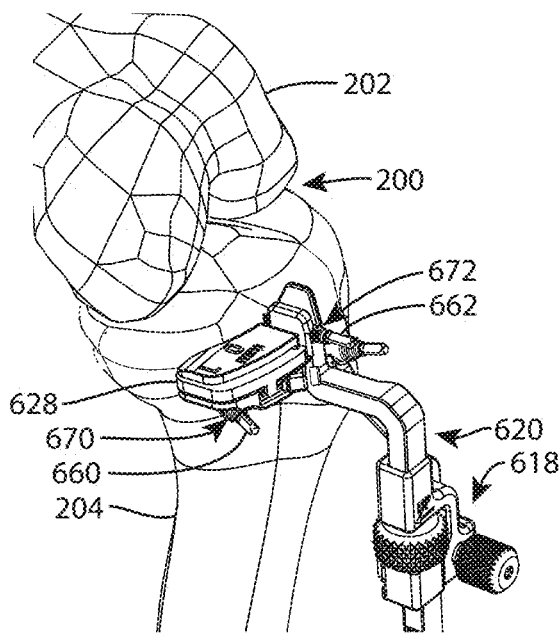
Figure 159:
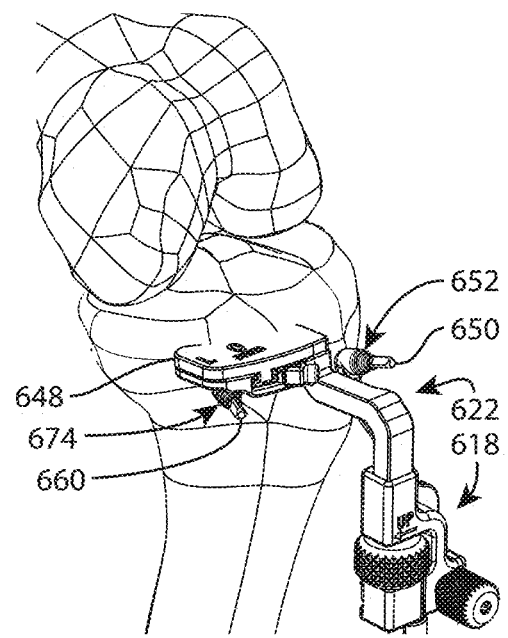
Figure 160:
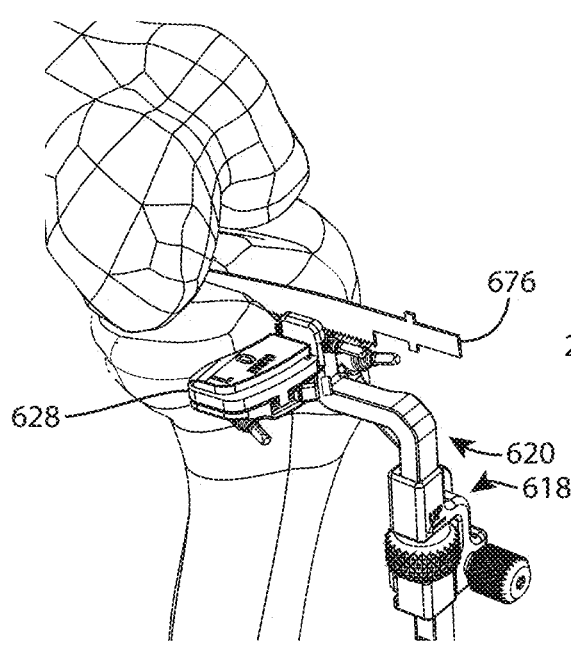
Figure 161:
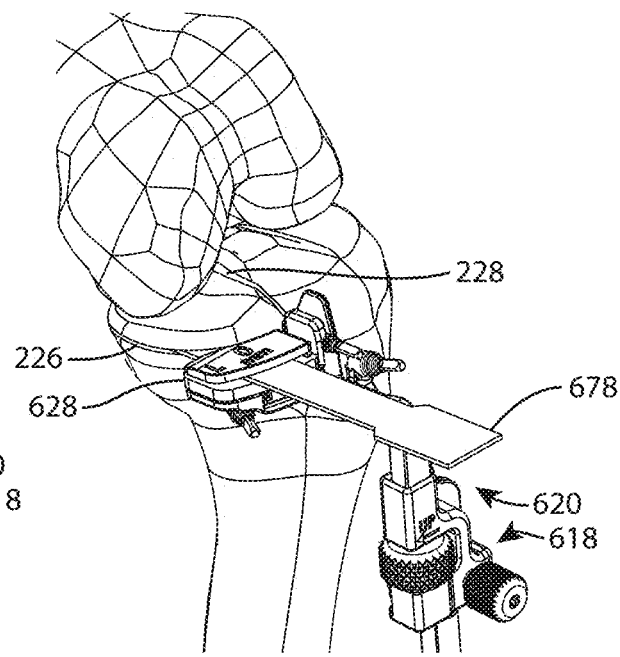
Figure 166:
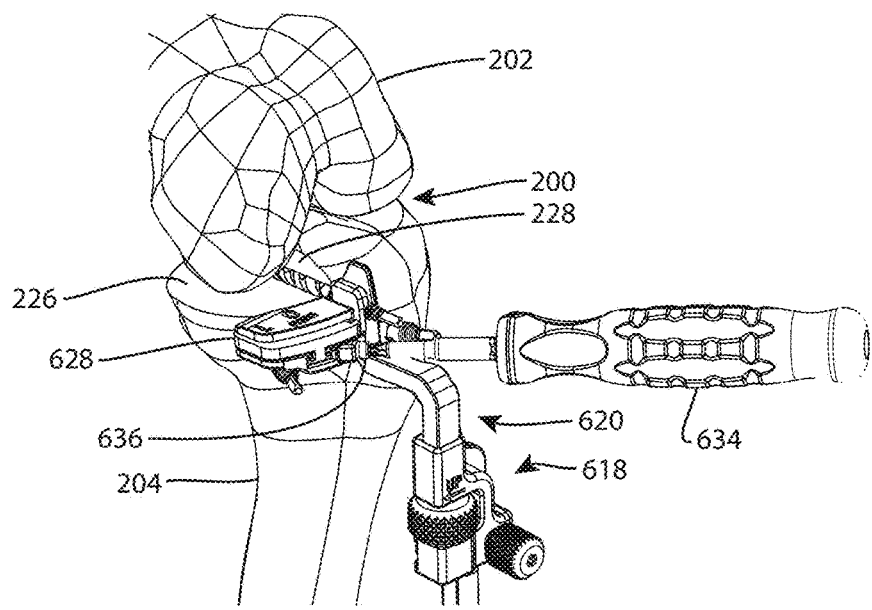
Figures 167, 168:
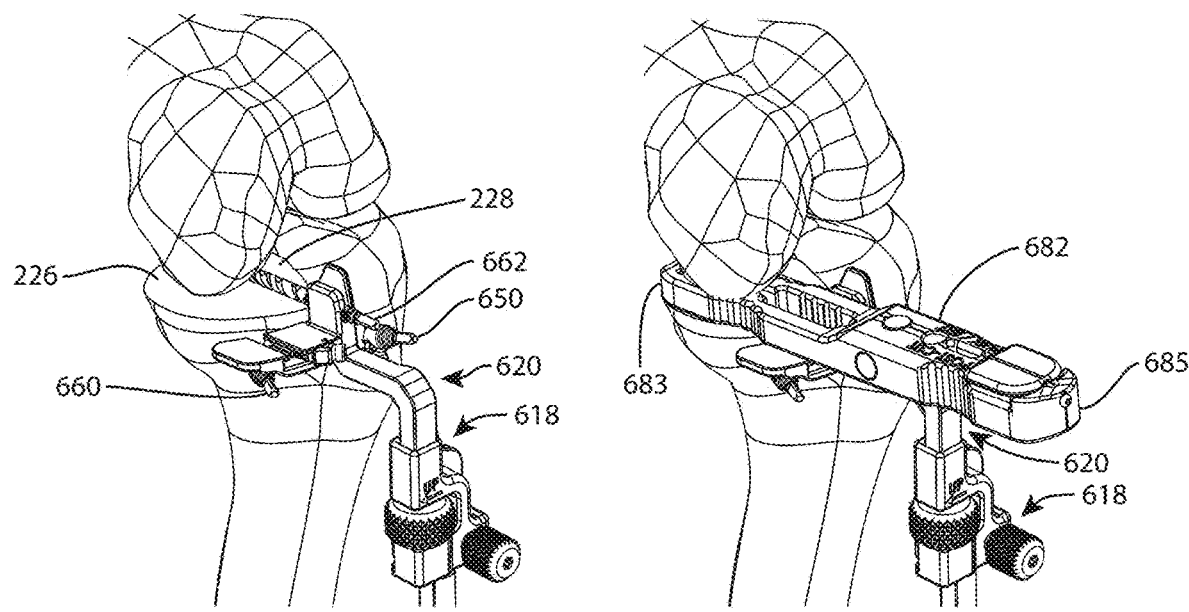
Figures 173, 174:
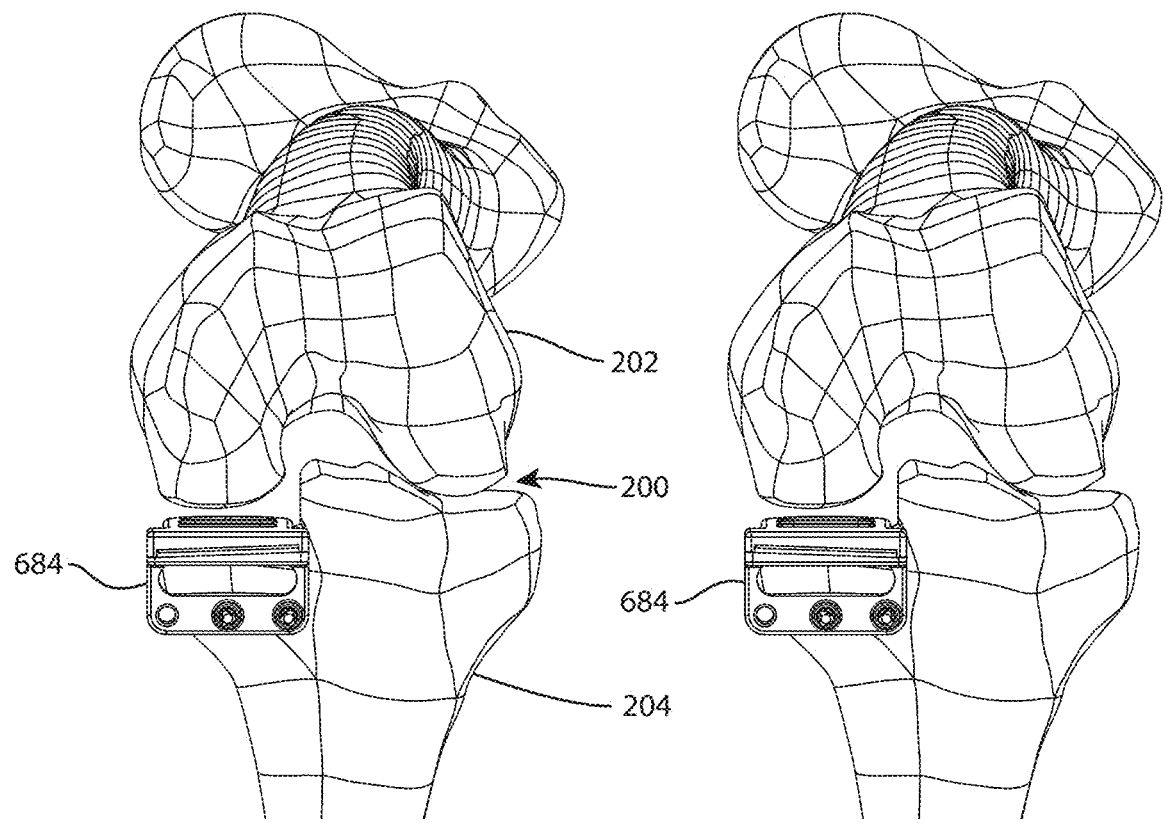
Figure 175:
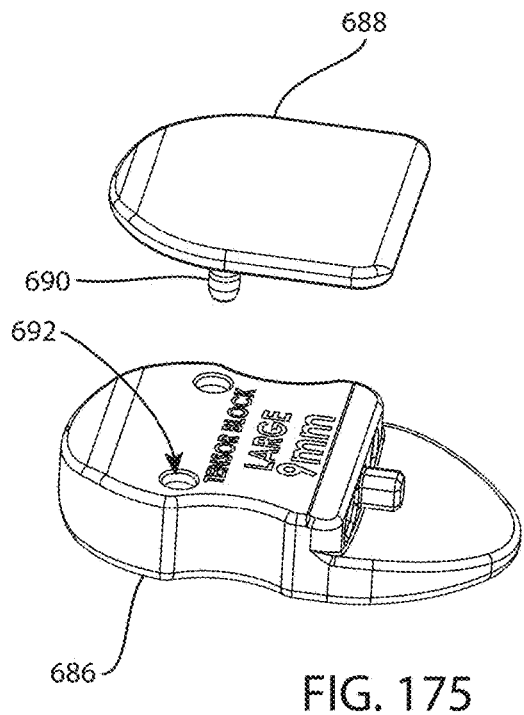
Figure 176:
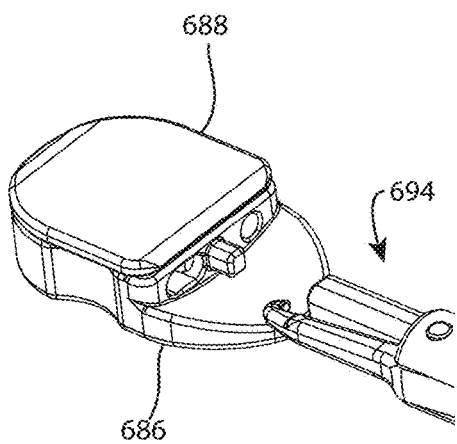
Figure 177:
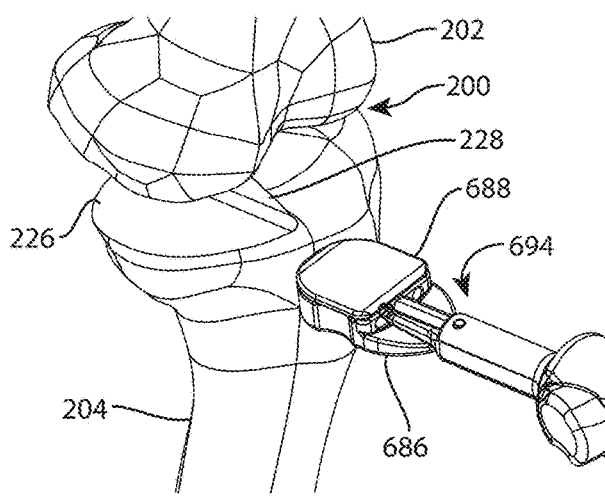
Figure 178:
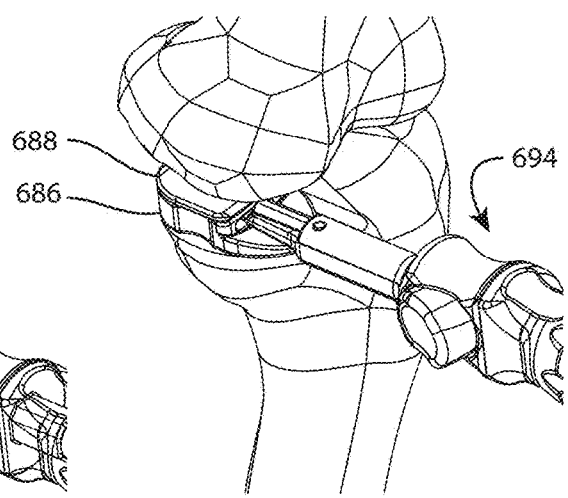
Figure 179:
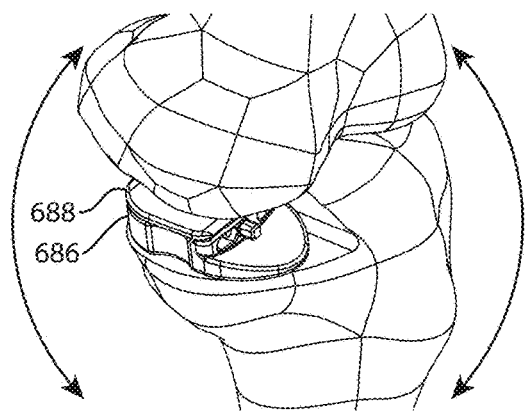
Figure 181:
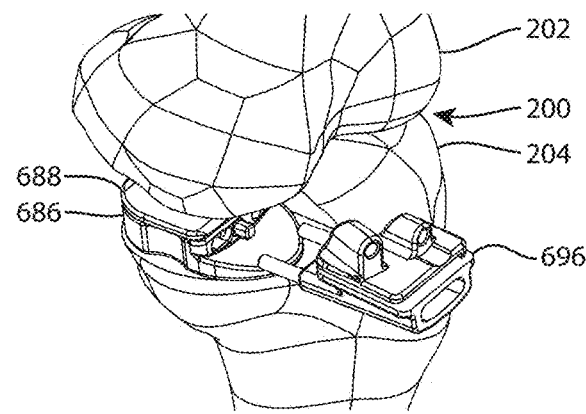
Figure 180:
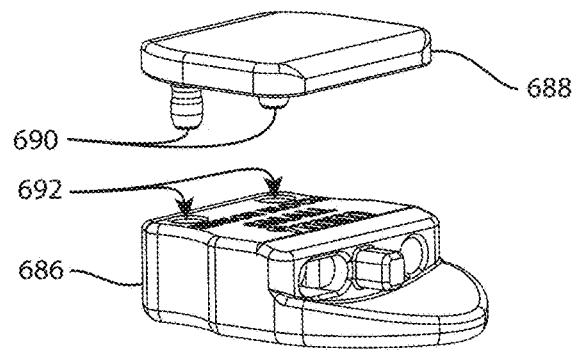
Figure 182:
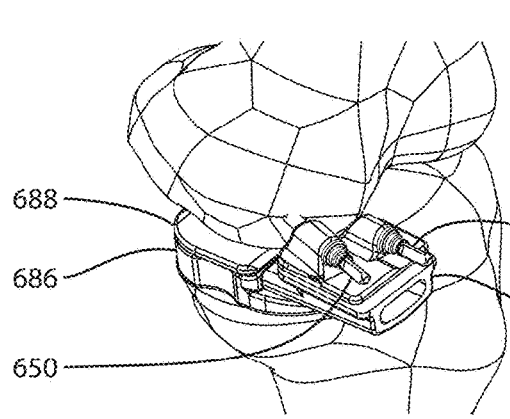
Figure 183:
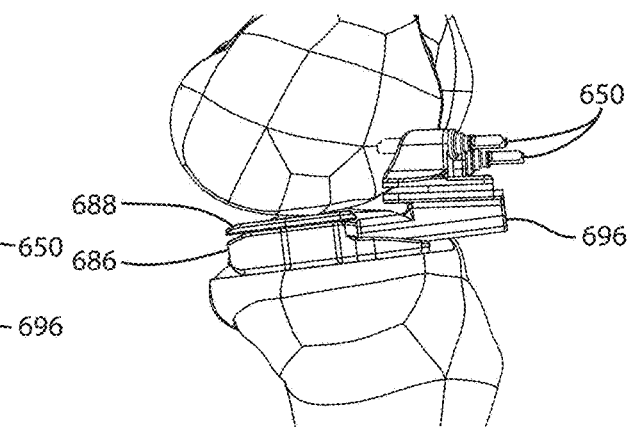
Figure 185:
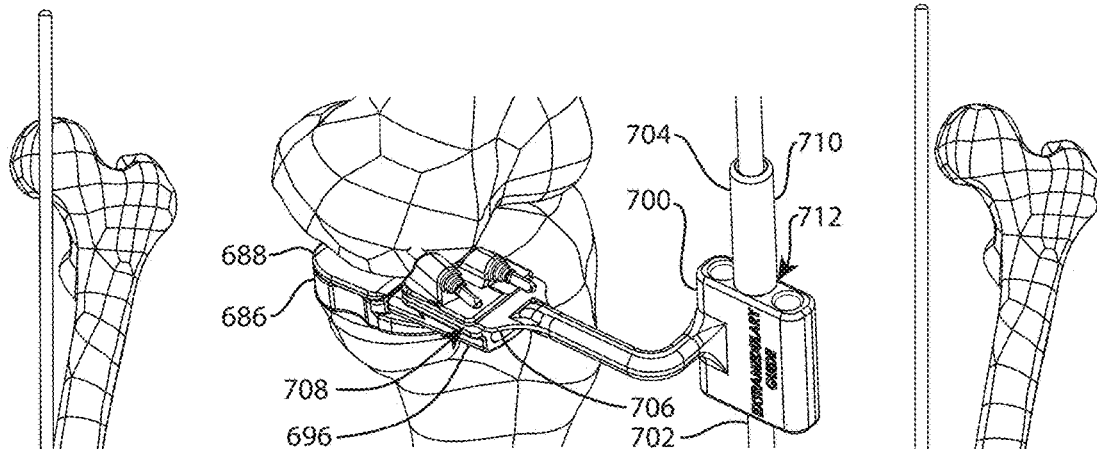
Figure 186:
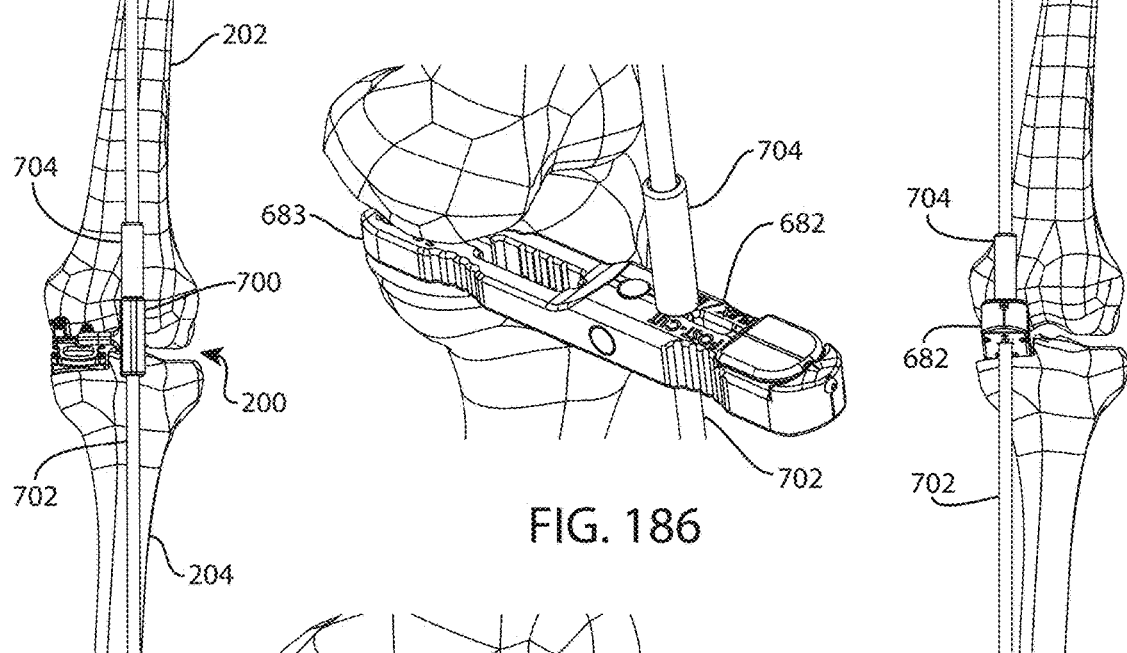
Figures 184, 187, 188:
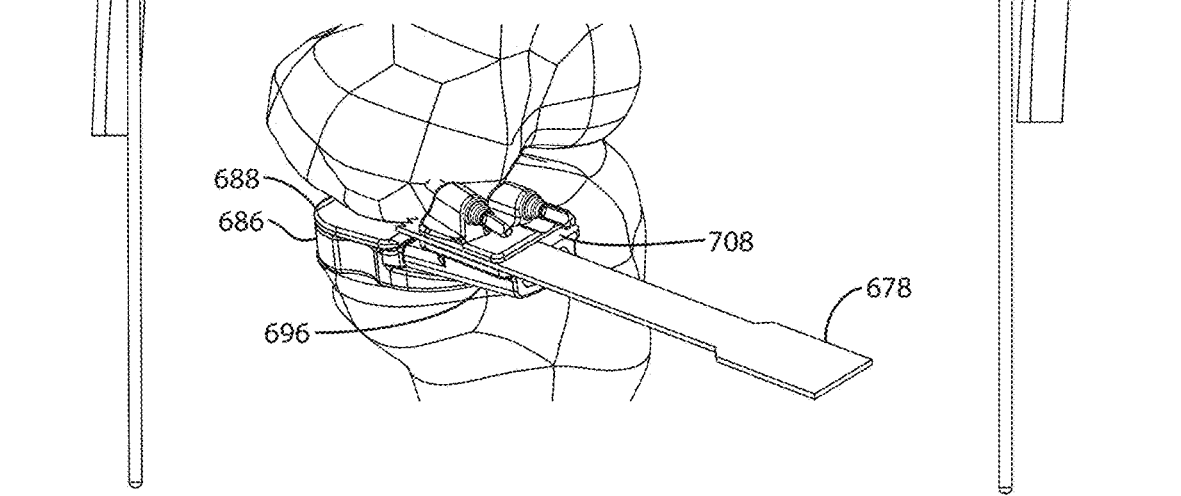
Figure 189:
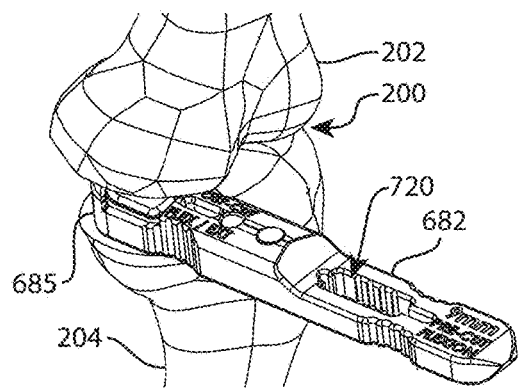
Figure 190:
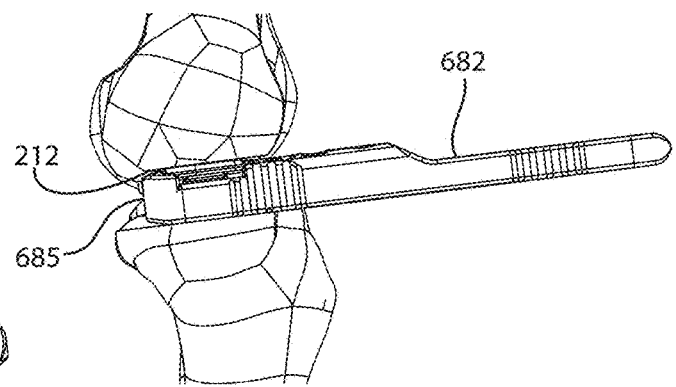
Figure 191:
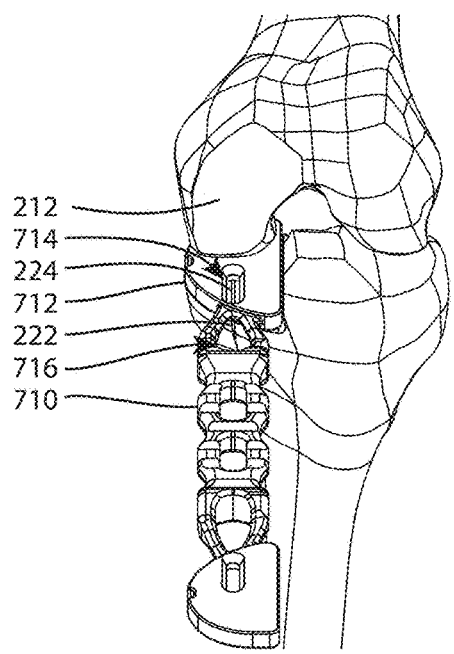
Figure 192:
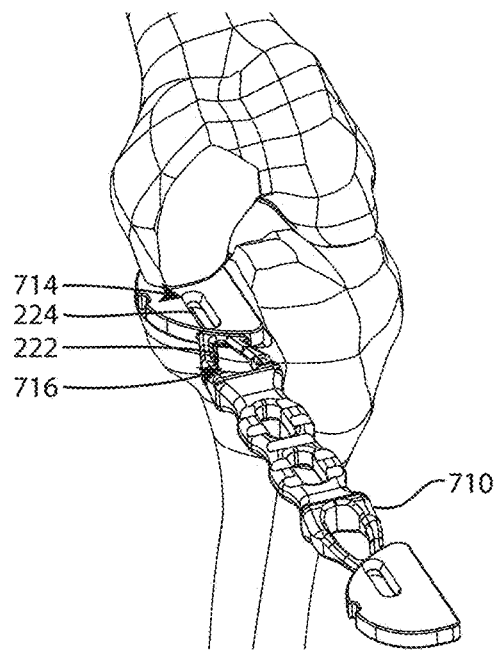
Figure 193:
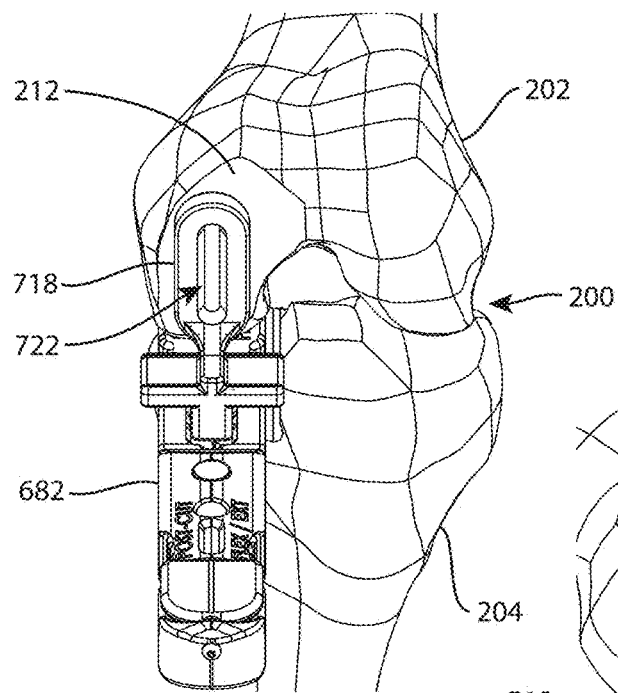
Figure 194:
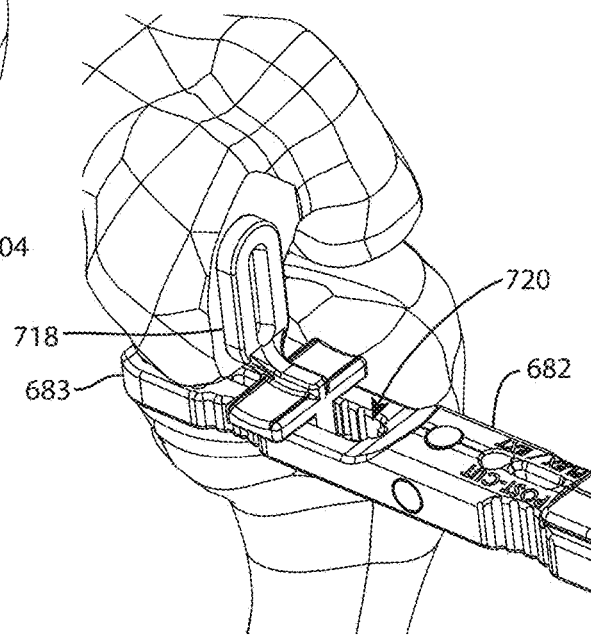
Figure 195:
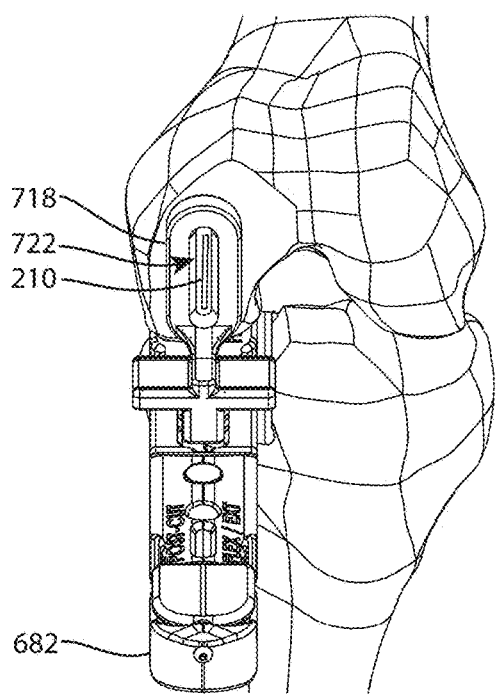
Figure 196:
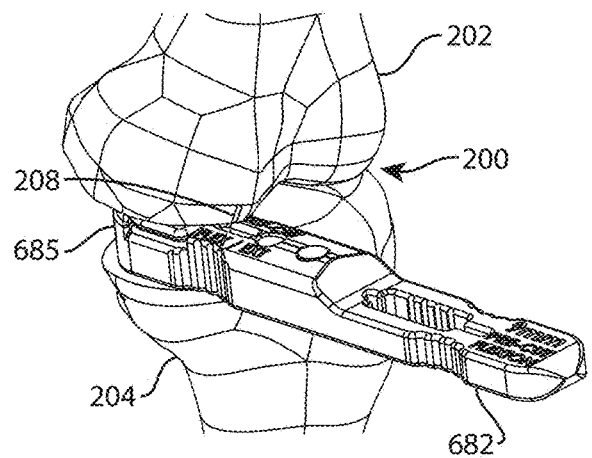
Figure 197:
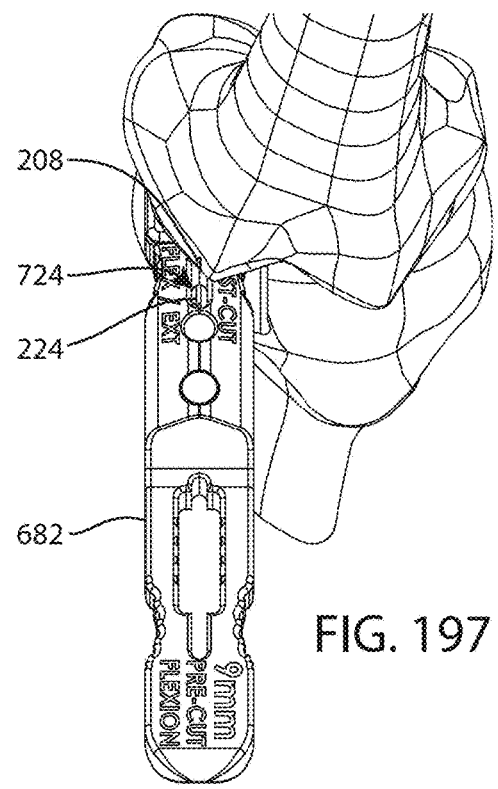
Figure 198:
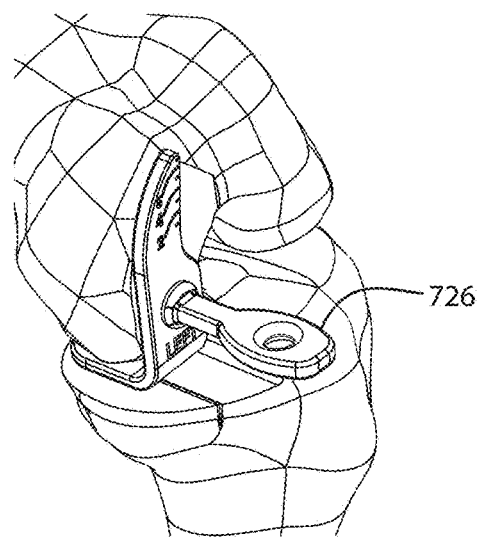
Figure 199:
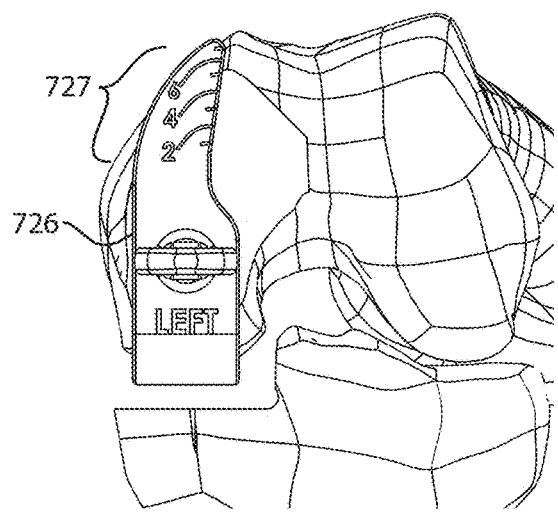
Figure 200:
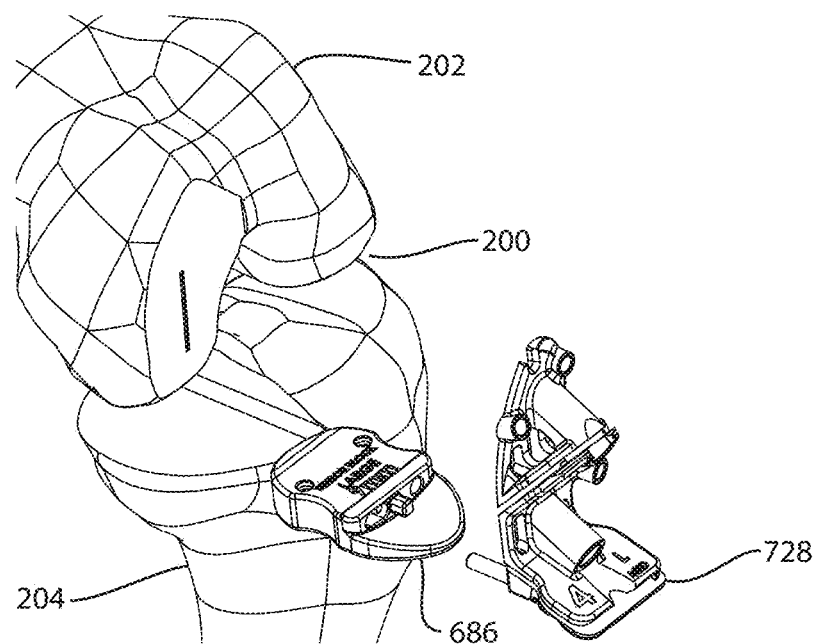
Figures 201, 202:
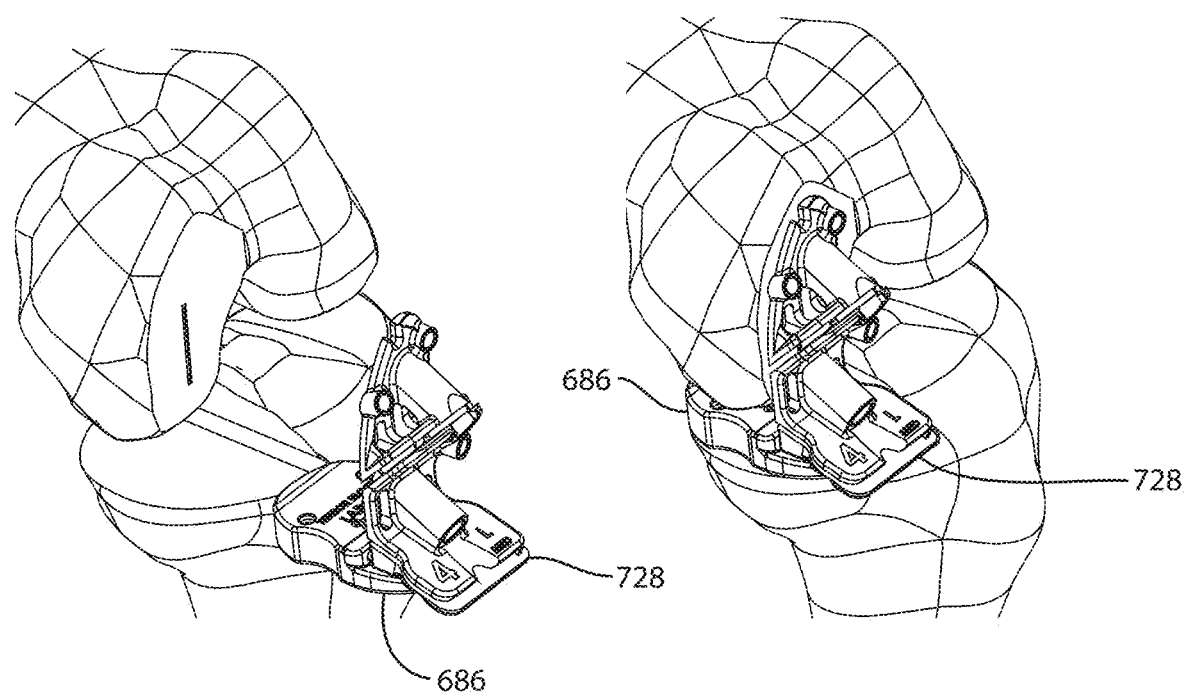
Figure 203:
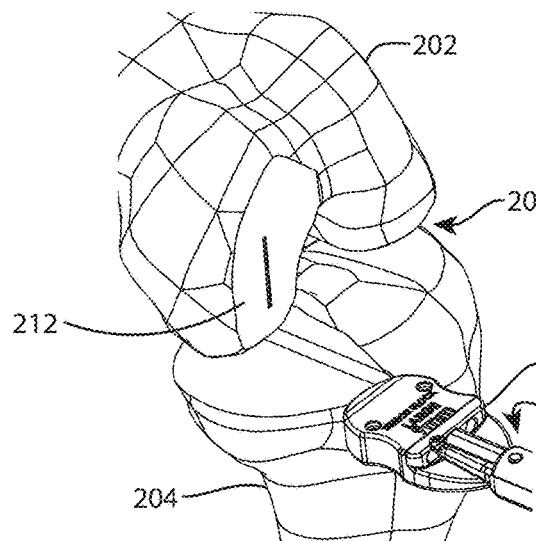
Figure 204:
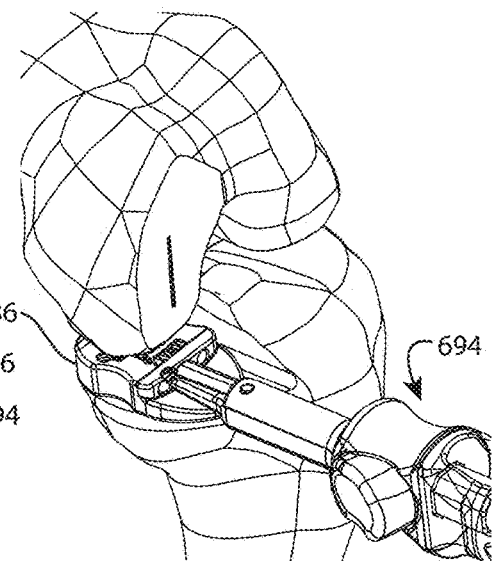
Figure 205:
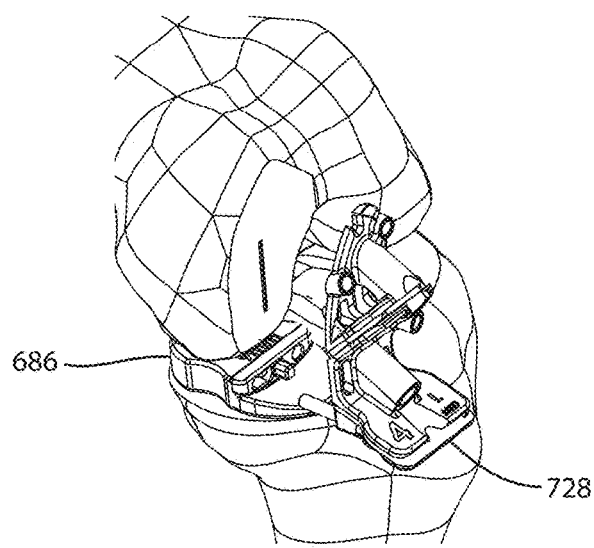
Figure 206:
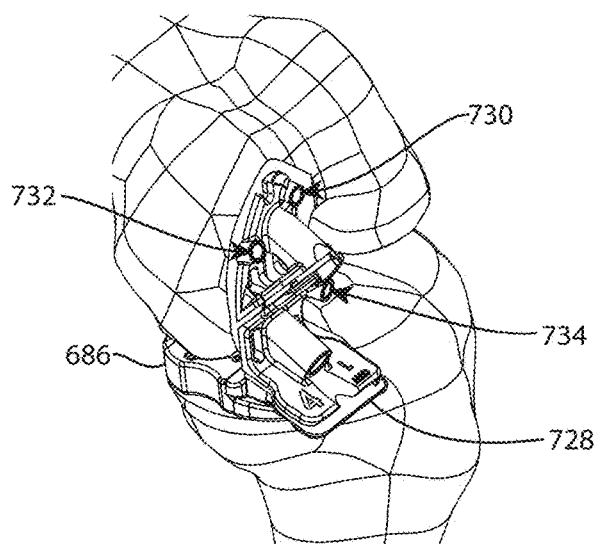
Figures 207, 208:
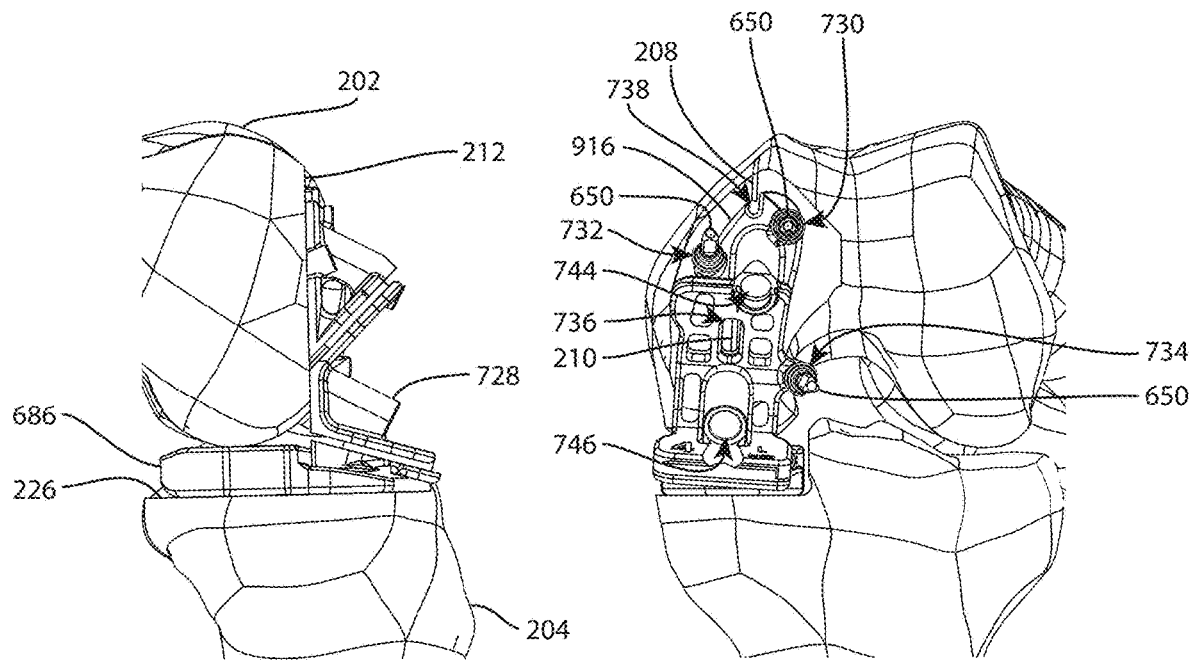
Figure 209:
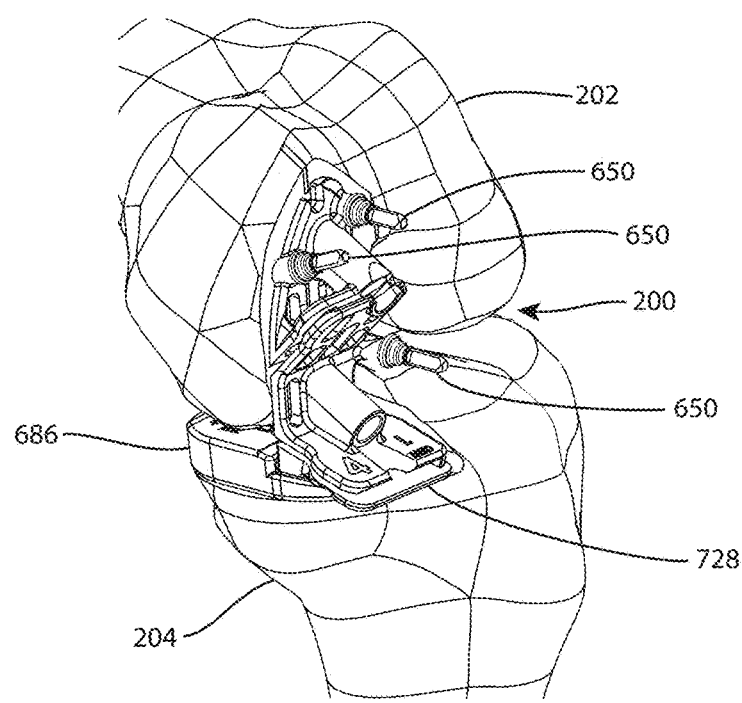
Figure 210:
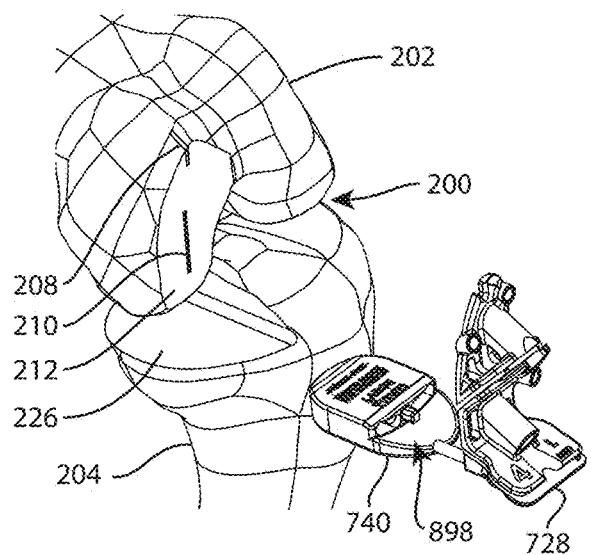
Figure 211:
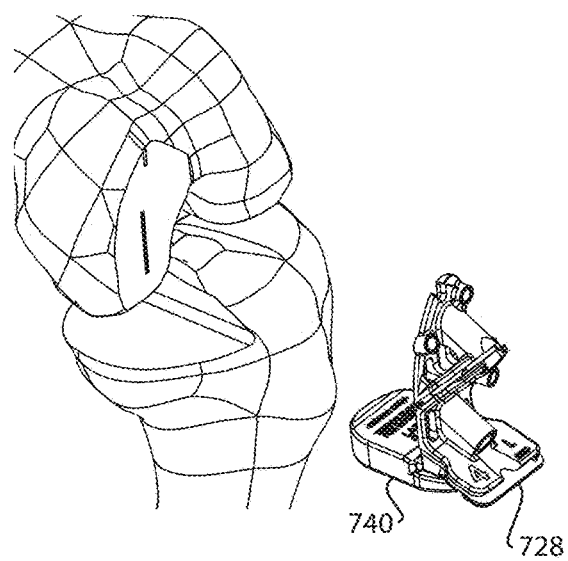
Figure 212:
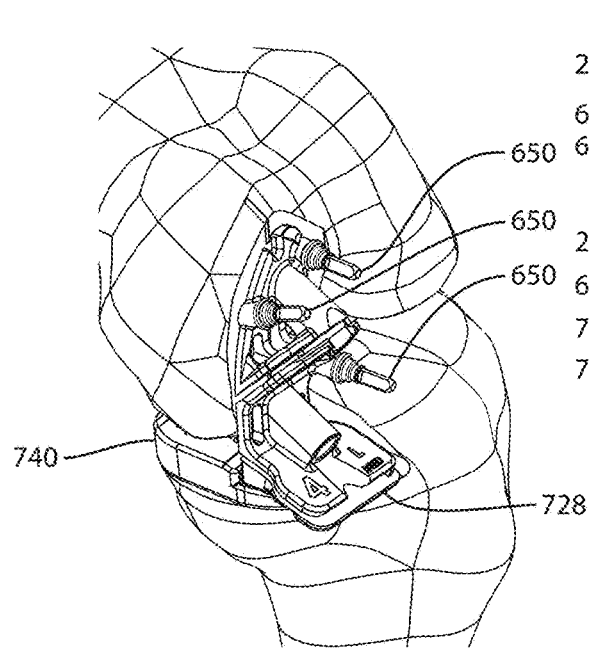
Figure 213:
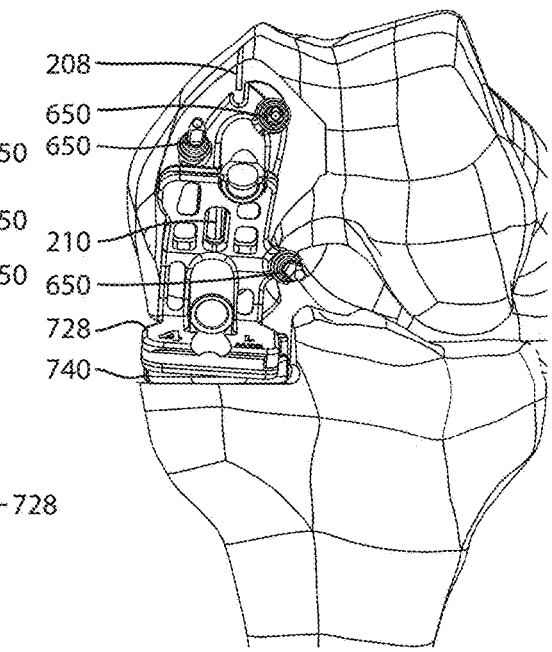
Figure 214:
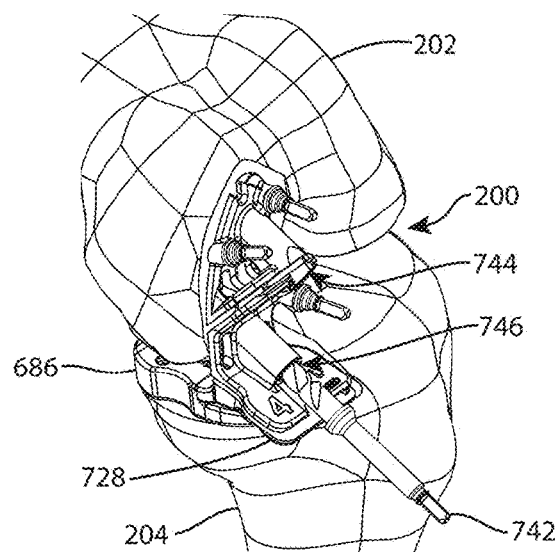
Figure 215:
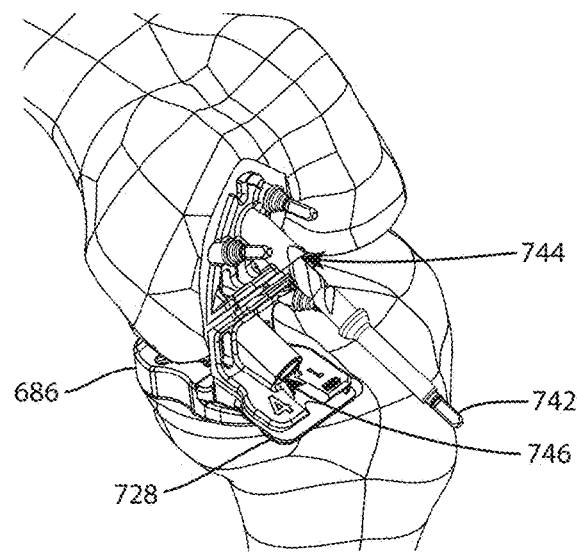
Figure 216:
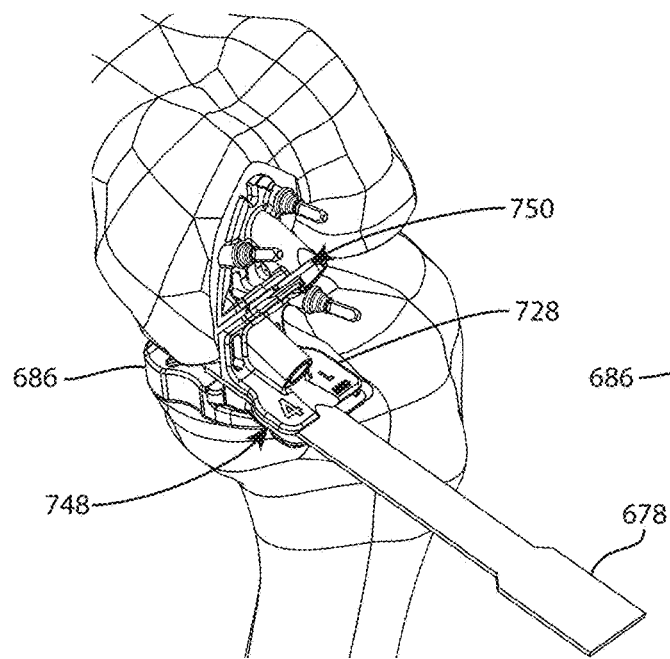
Figure 217:
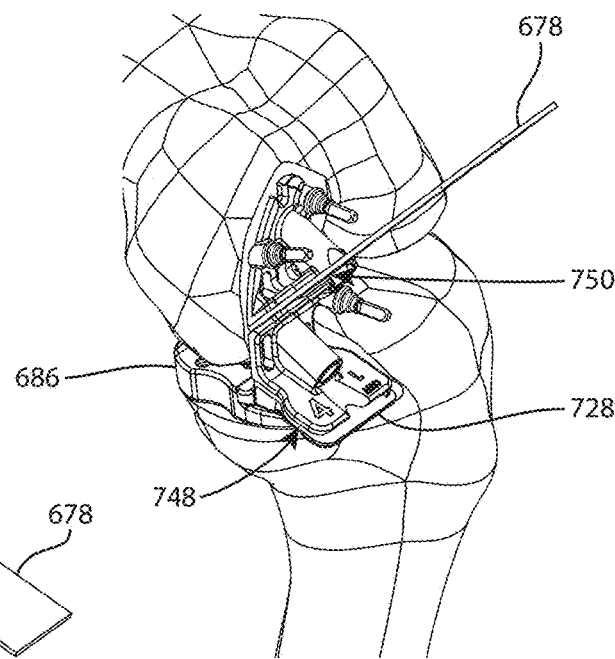
Figure 218:
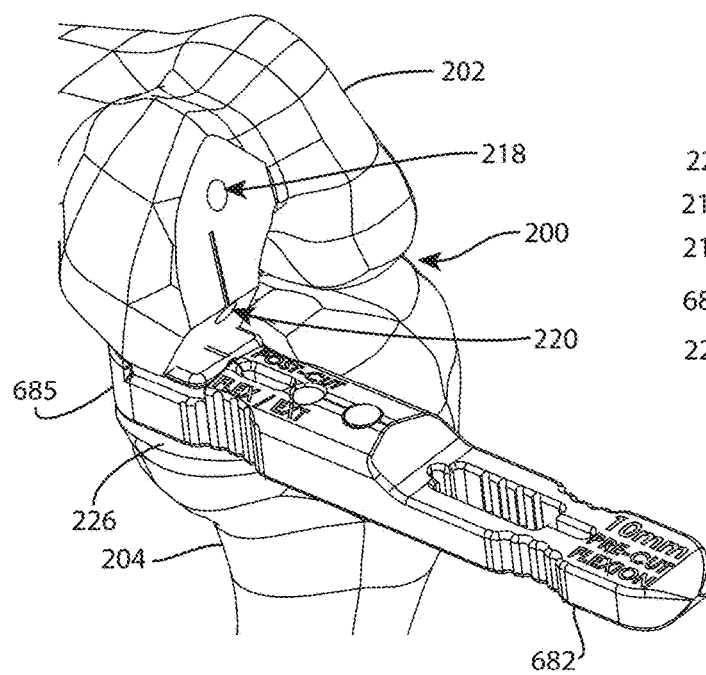
Figure 219:
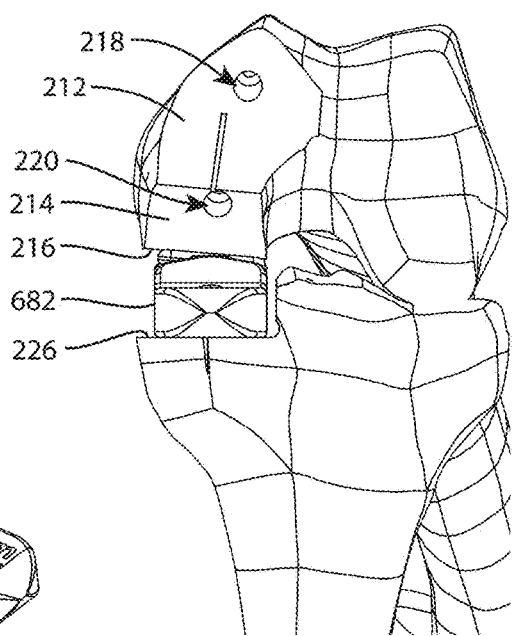
Figure 220:
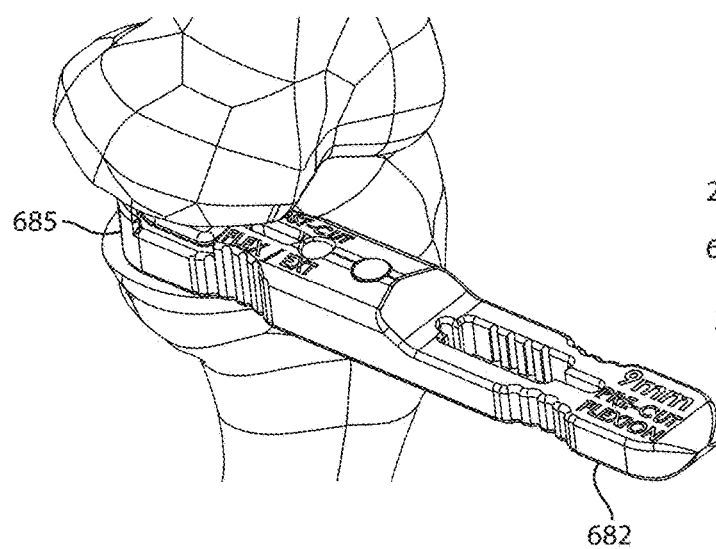
Figure 221:
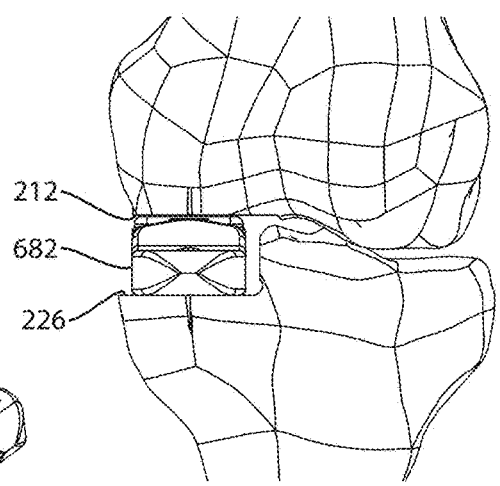
Figure 222:
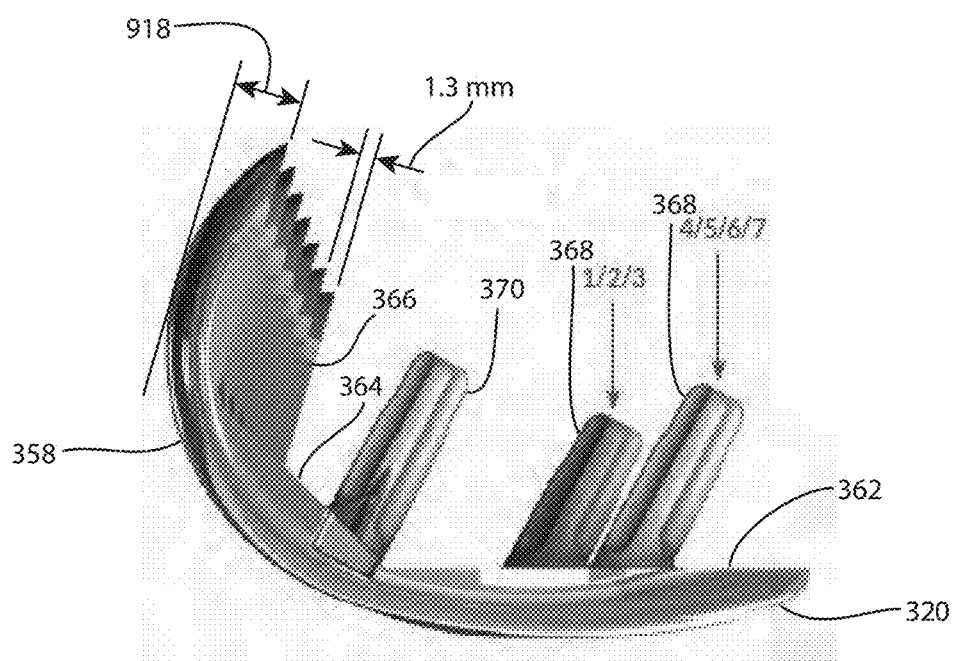
Figures 223, 224, 225:
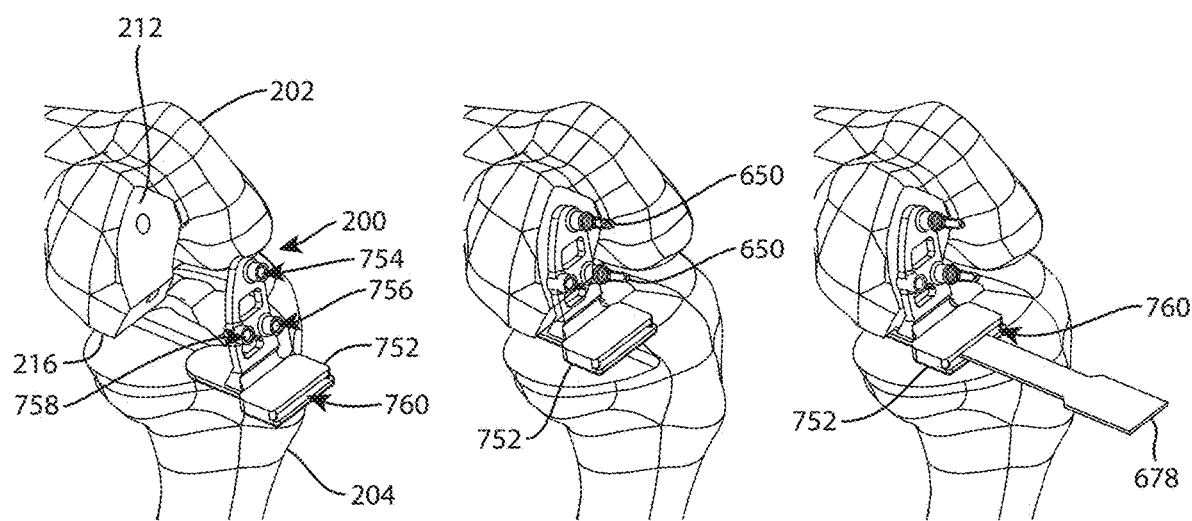
Figure 234:
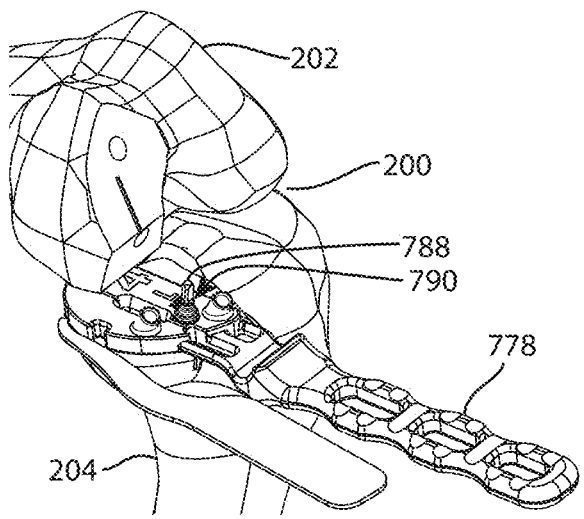
Figure 235:
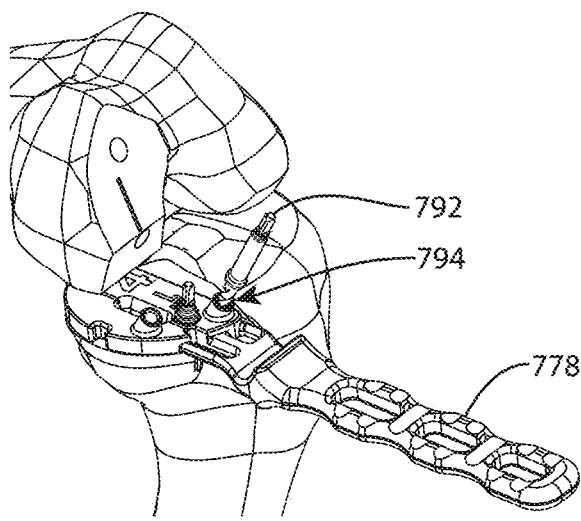
Figure 236:
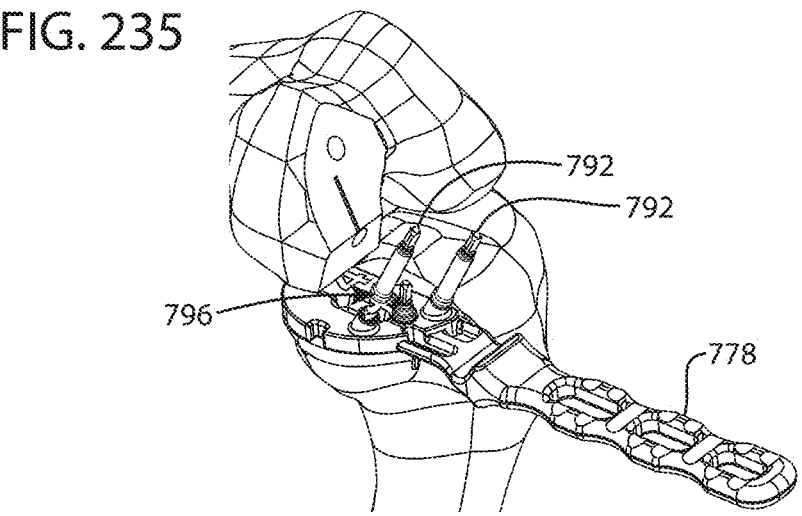
Figure 241:
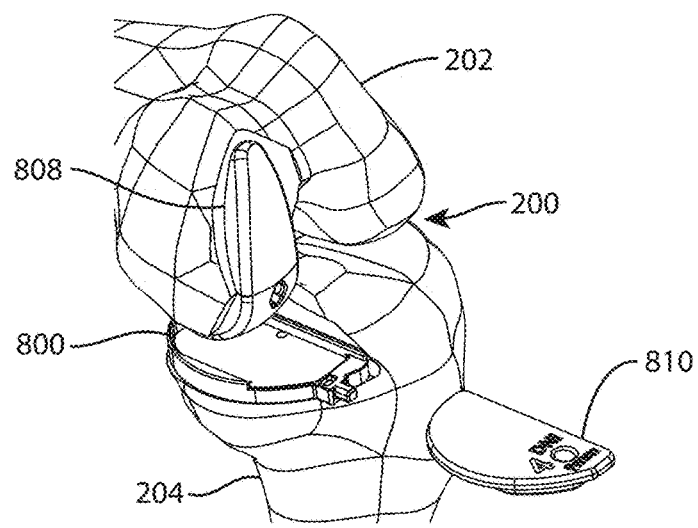
Figure 242:
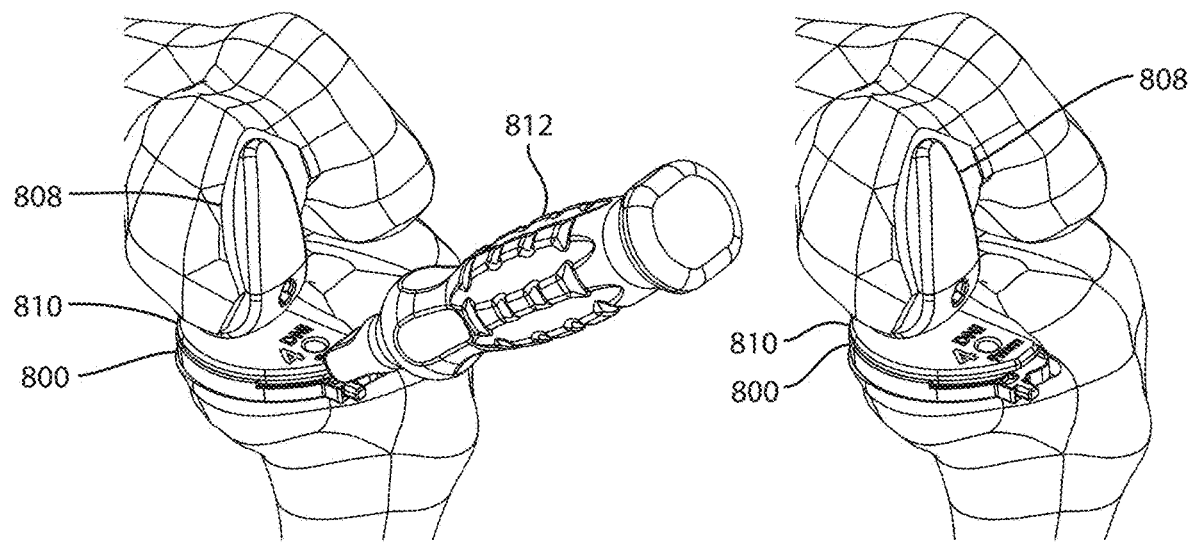
Figure 243:
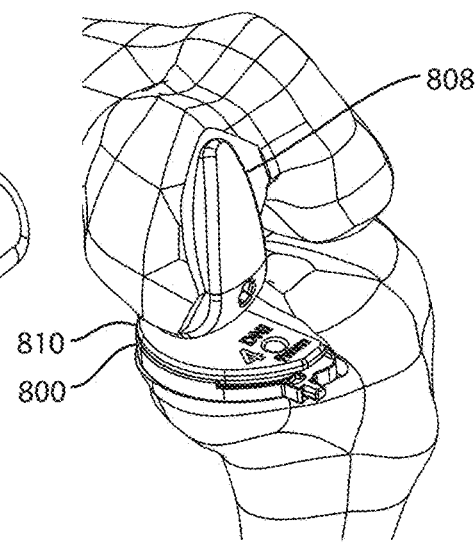
Figure 244:
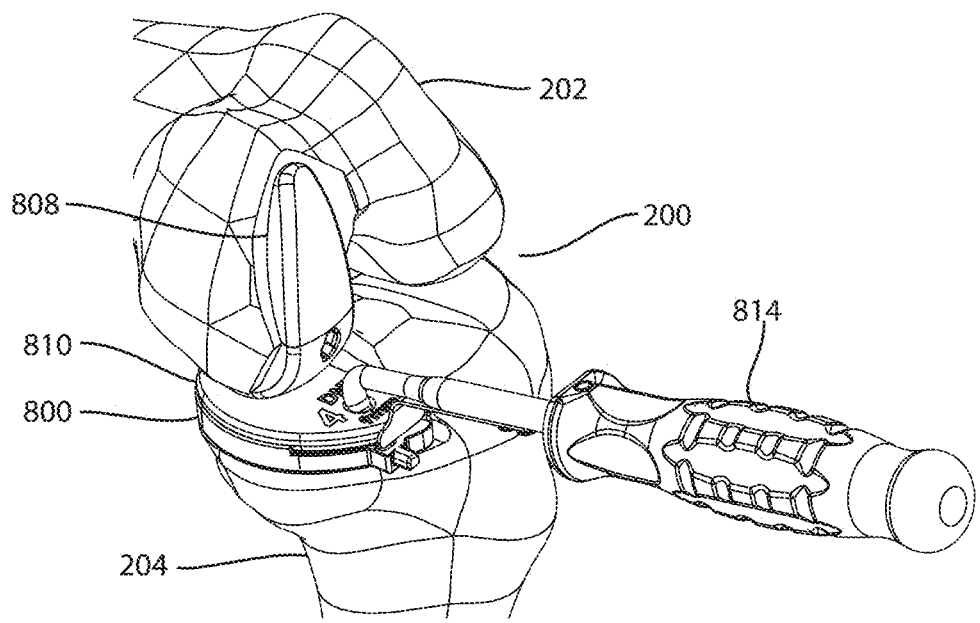
Figure 245:
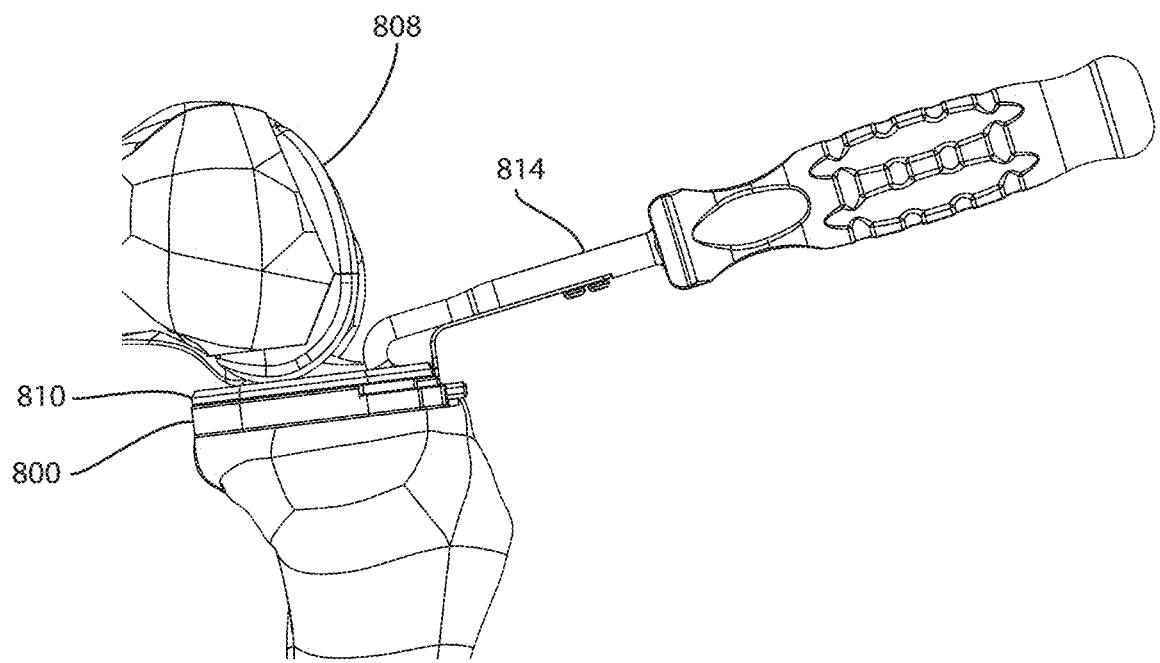
Figure 246:
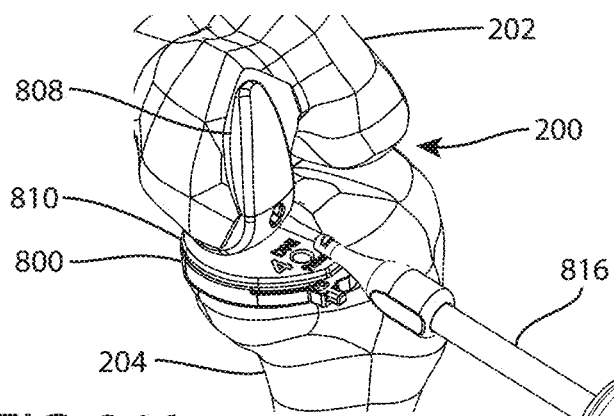
Figure 247:
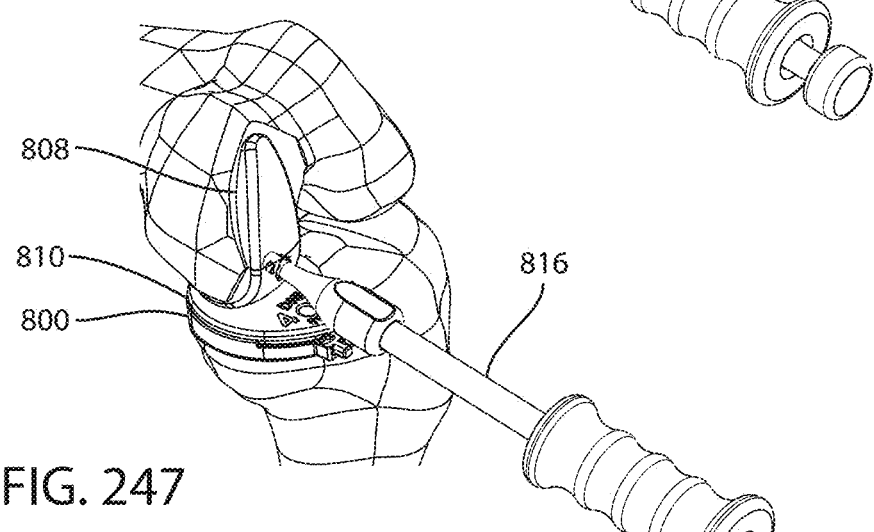
Figure 248:
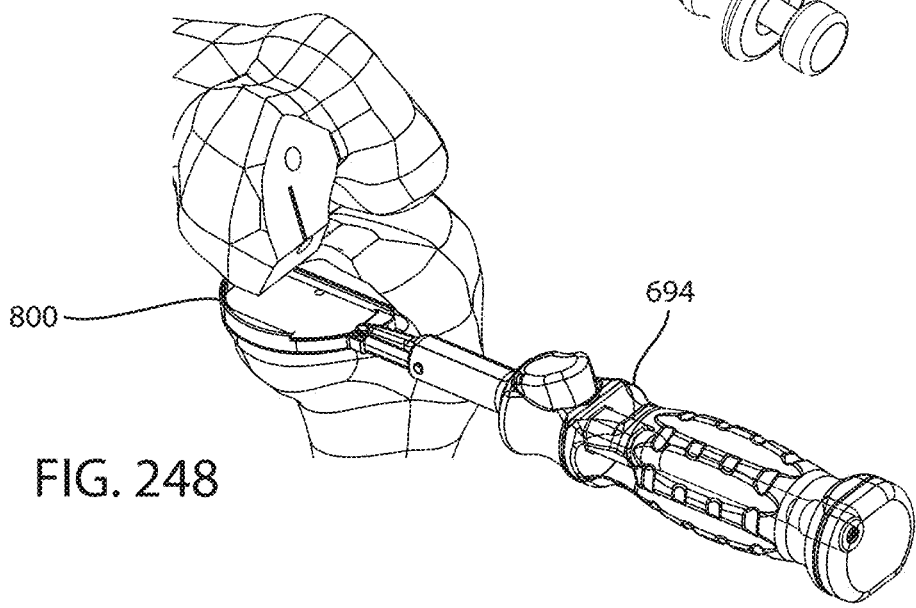
Figure 254:
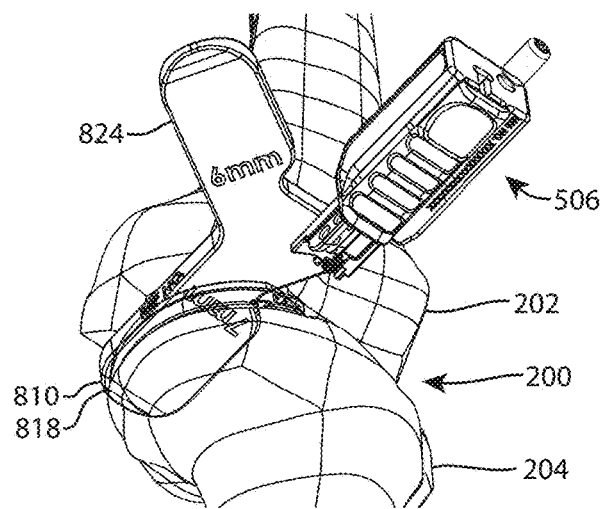
Figure 255:
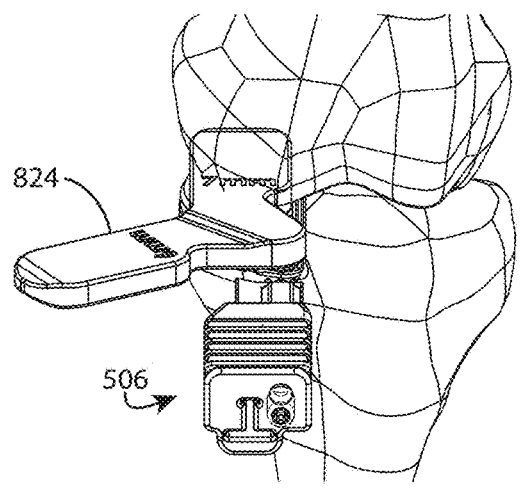
Figure 256:
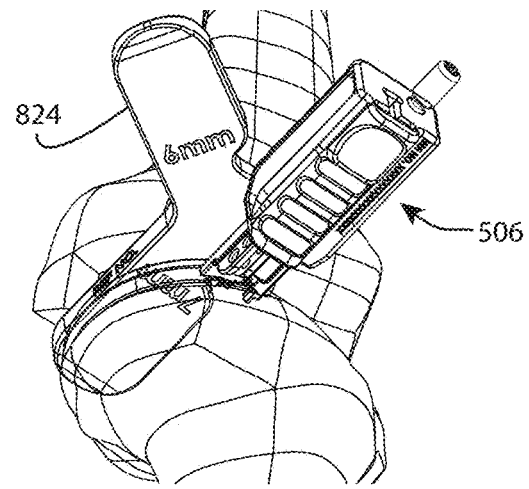
Figure 257:
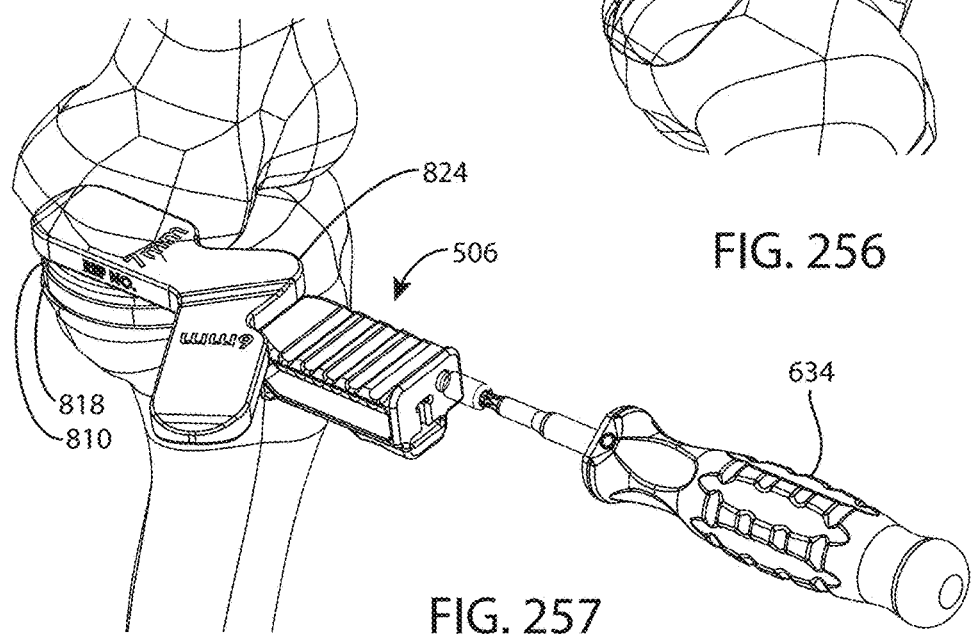
Figure 262:
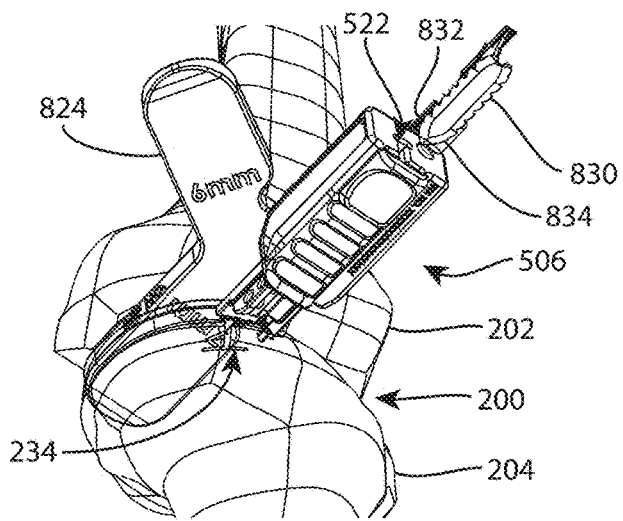
Figures 263, 264:
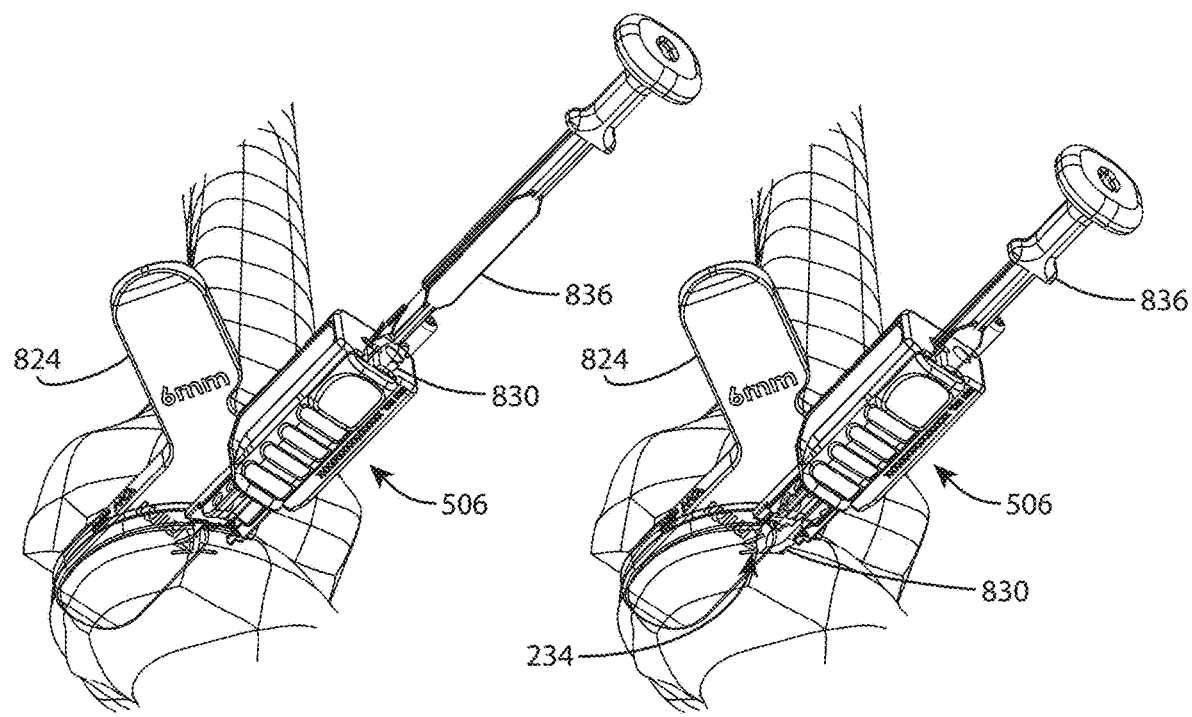
Figure 265:
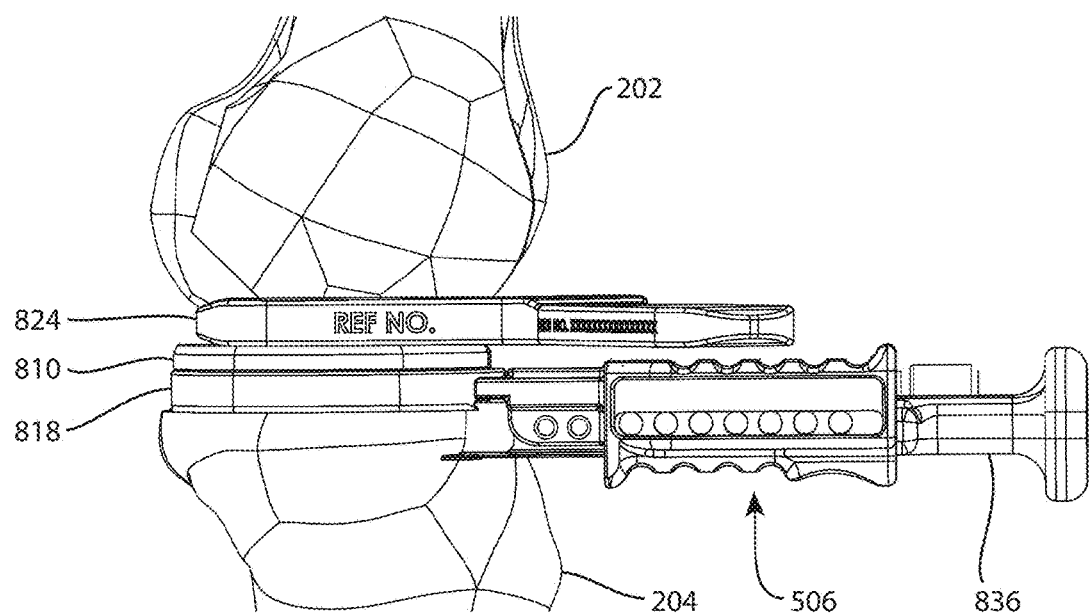
Figure 266:
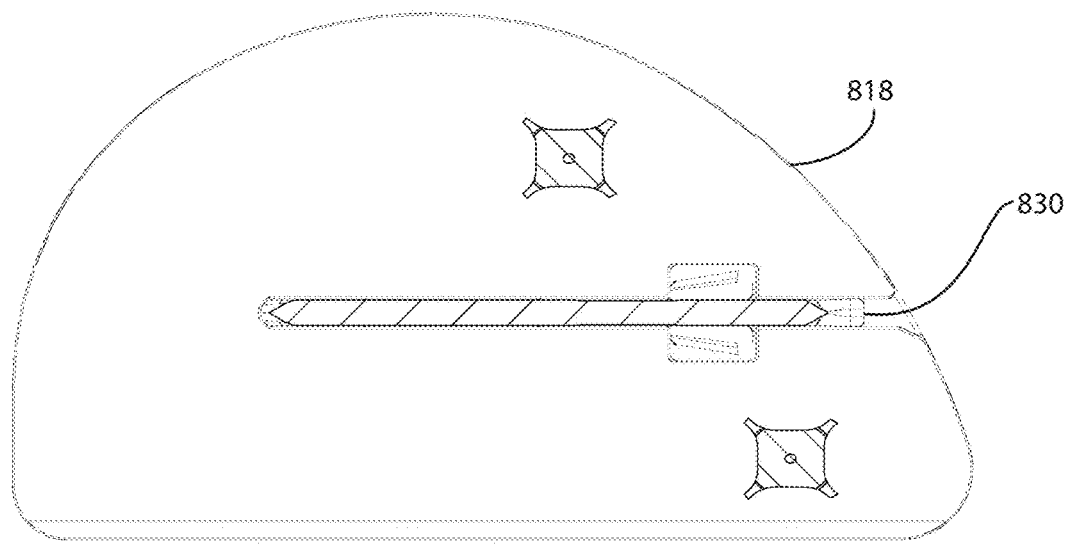
Figures 273, 274:
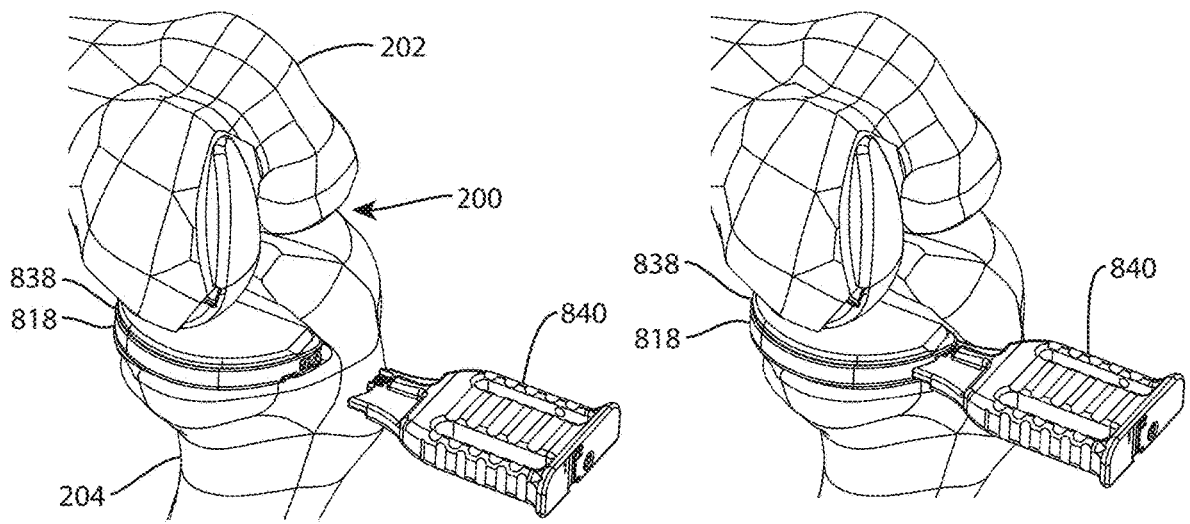
Figure 275:
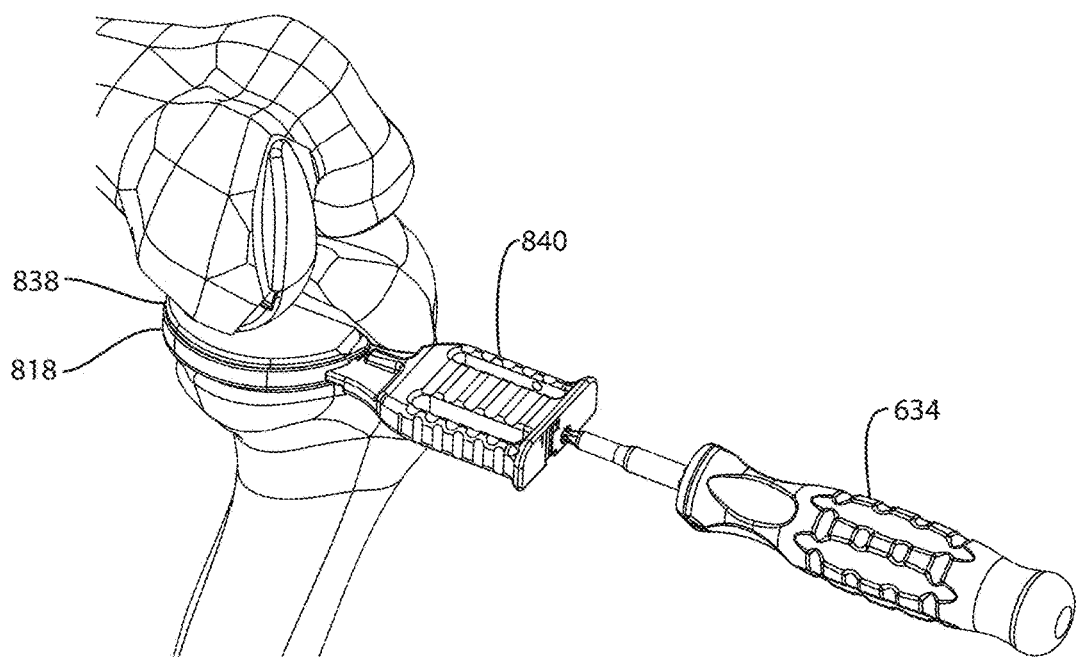
Figure 276:
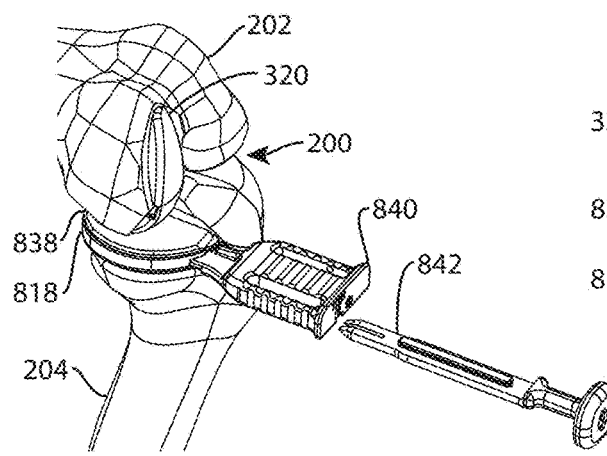
Figure 277:
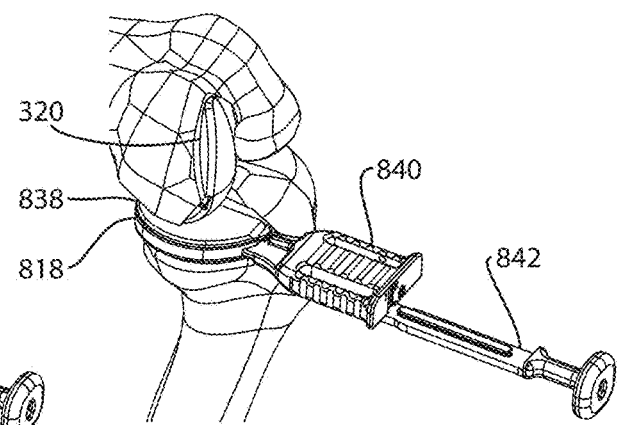
Figure 278:
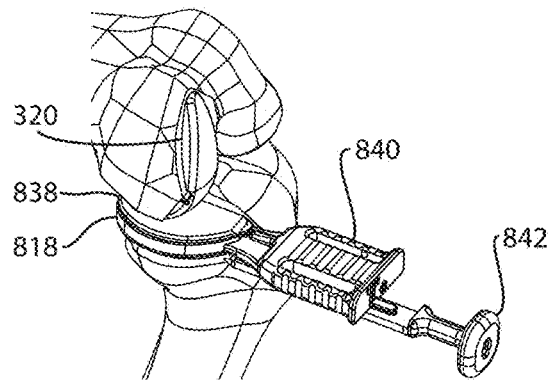
Figure 279:
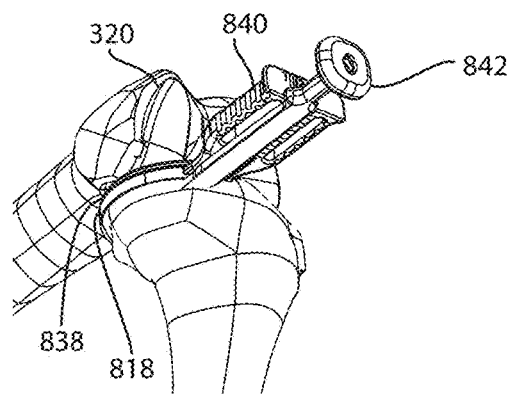
Figure 290:
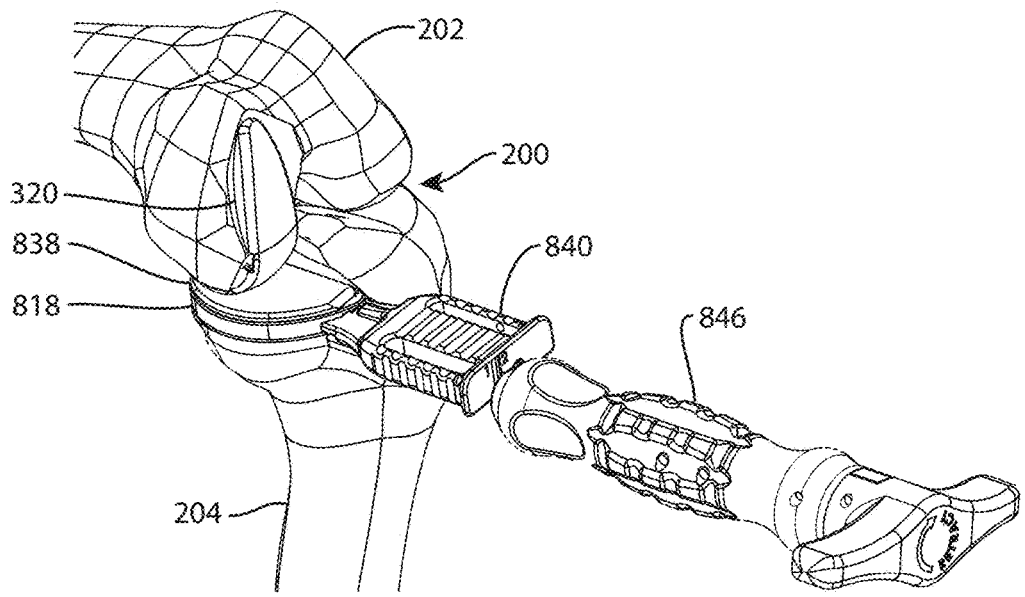
Figure 291:
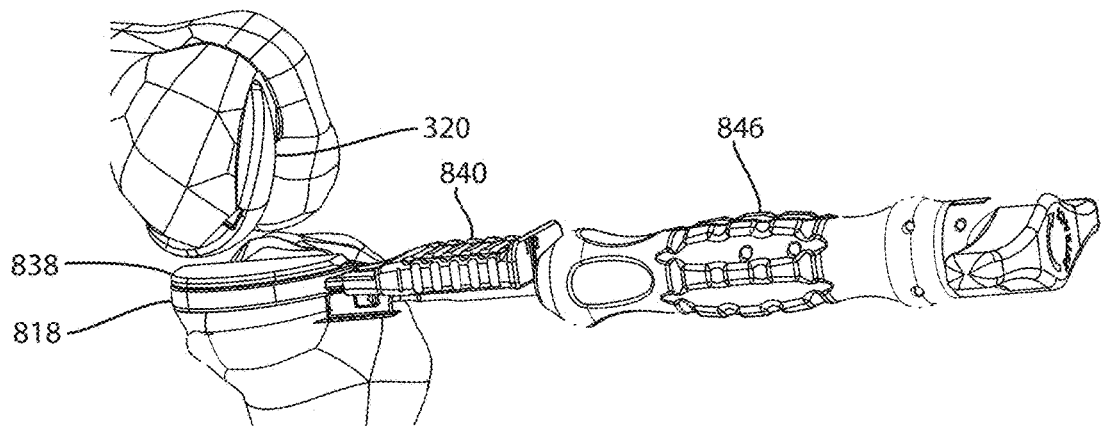
Figure 292:
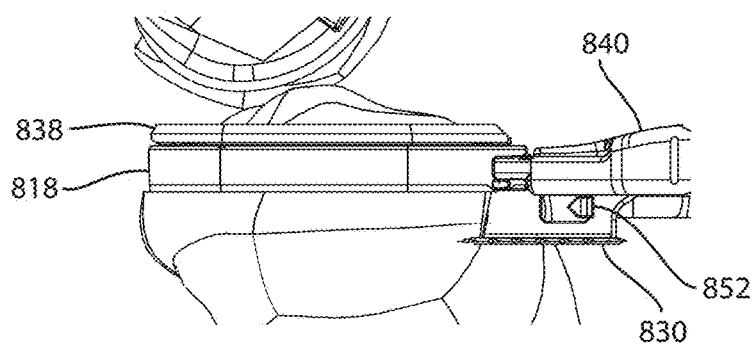
Figure 293:
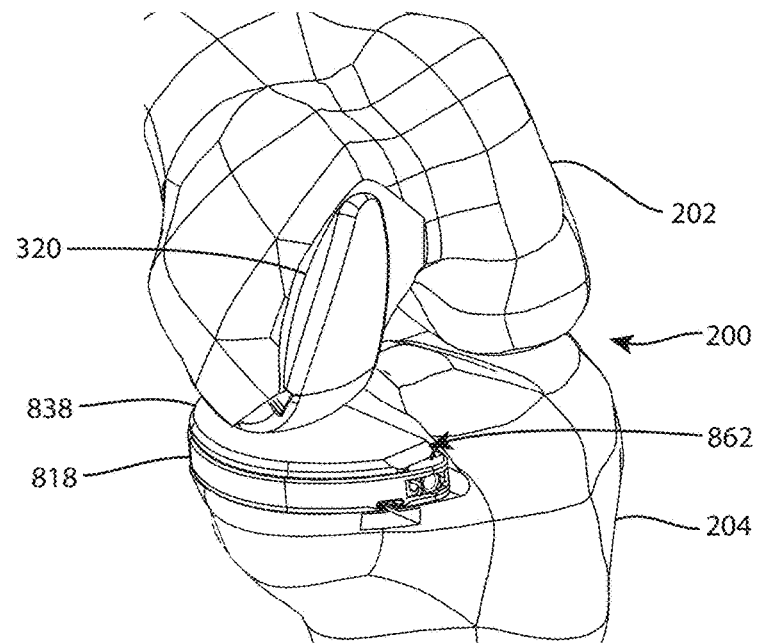
Figure 294:
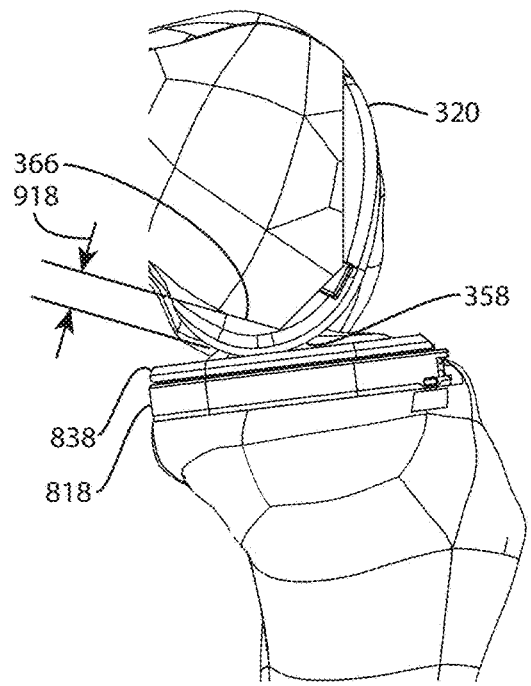
Figure 295:
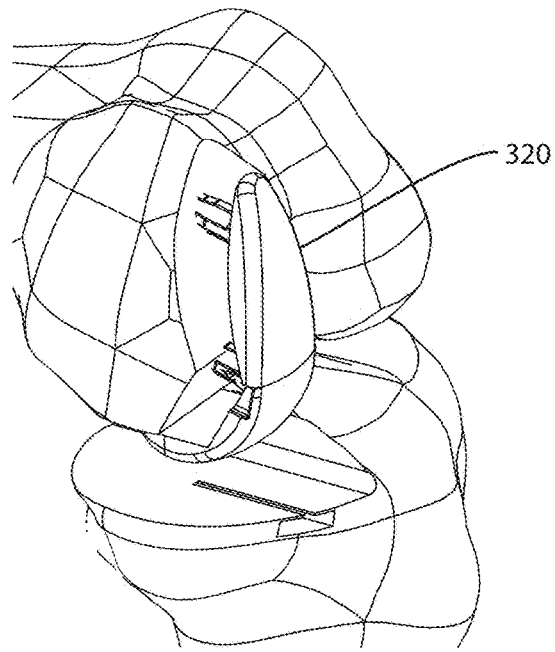
Figure 296:
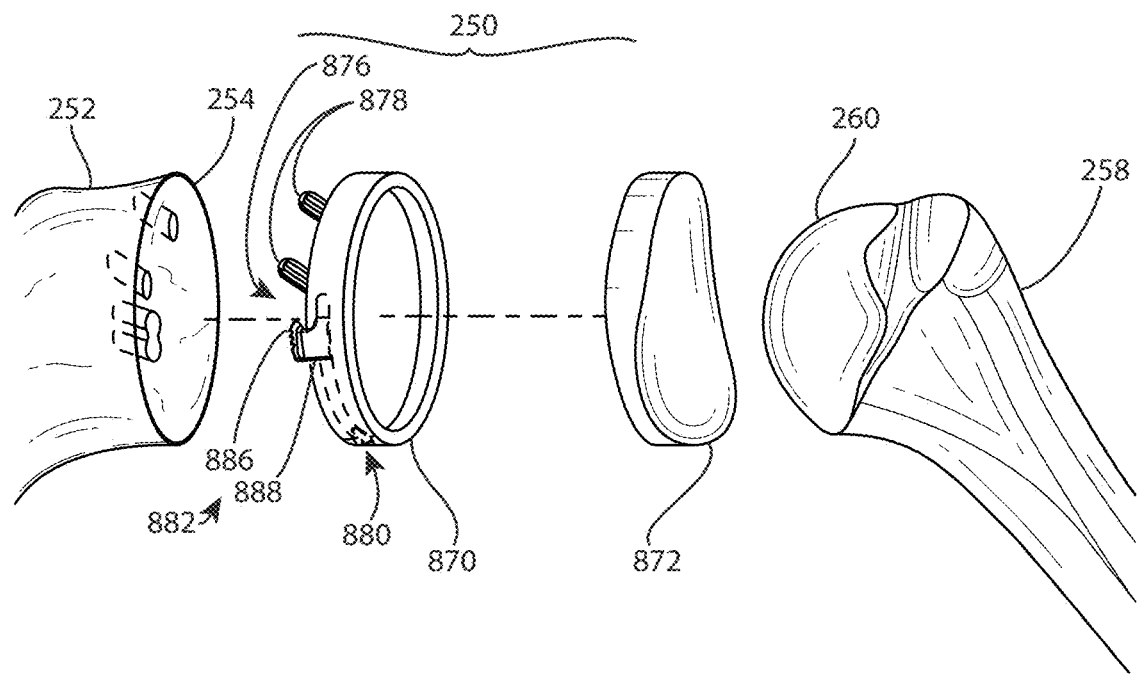
Figure 297:
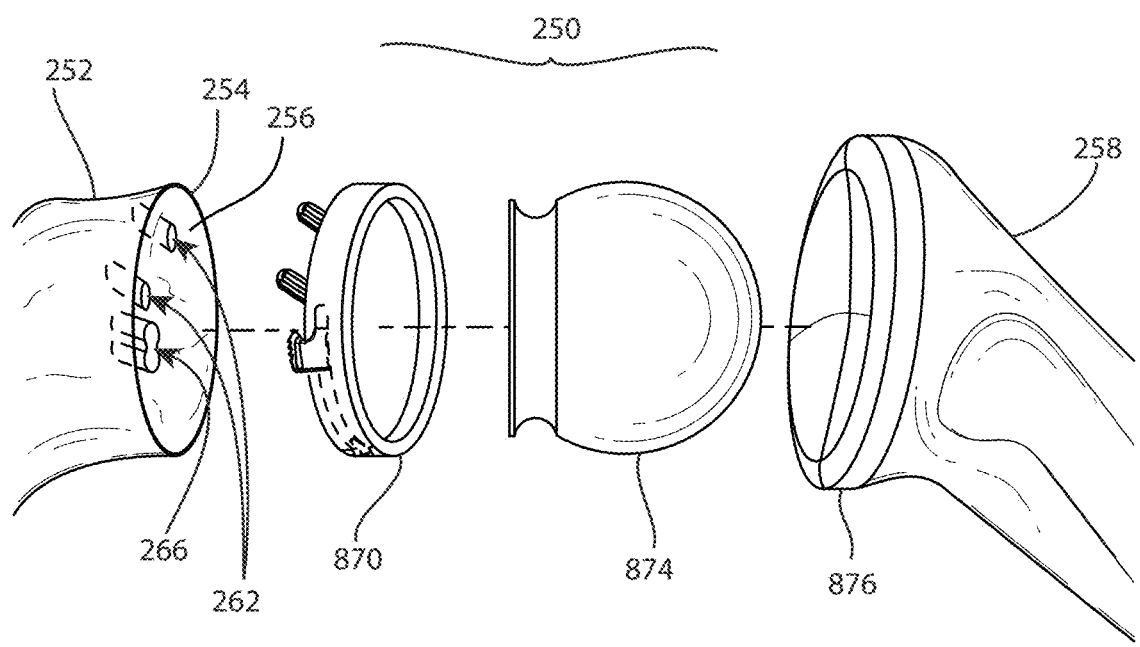
Figure 298:
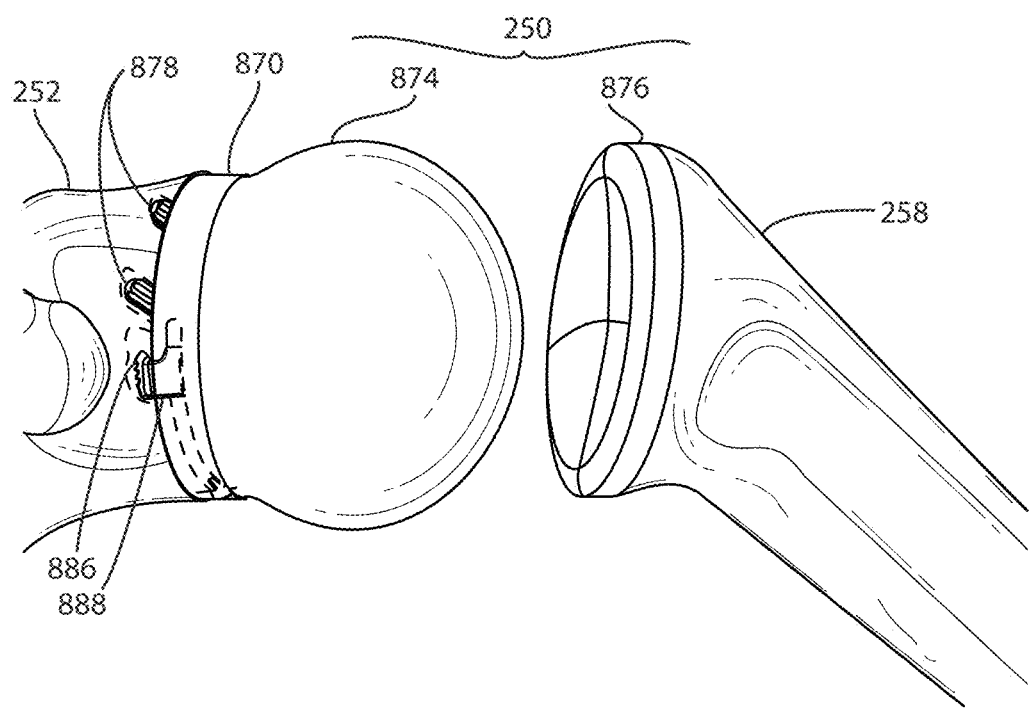
Figure 299:
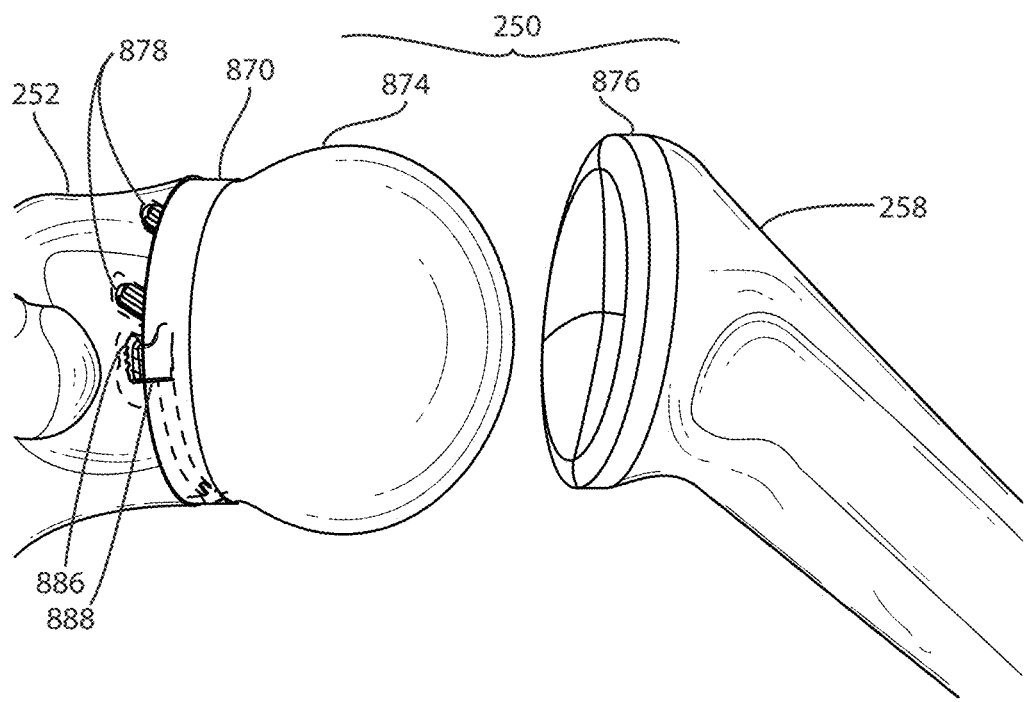
Figure 300:
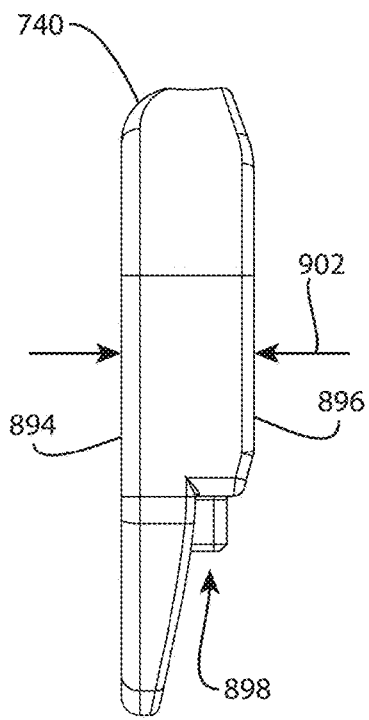
Figure 301:
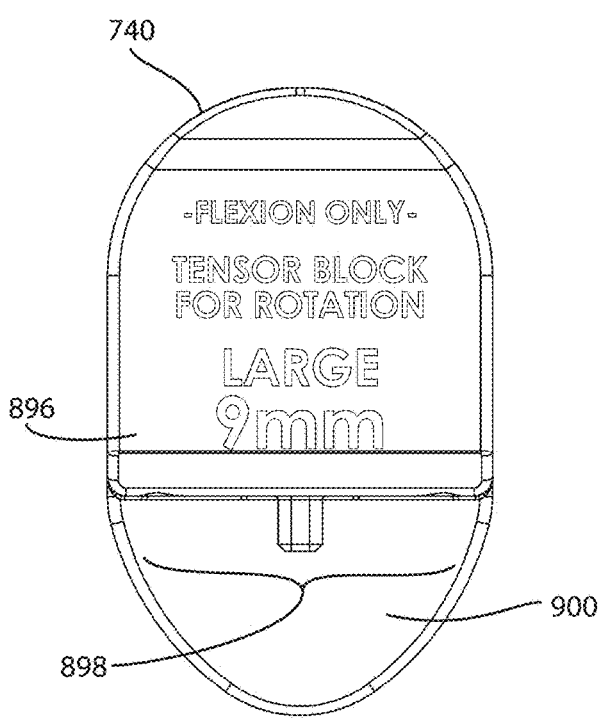
Figure 302:
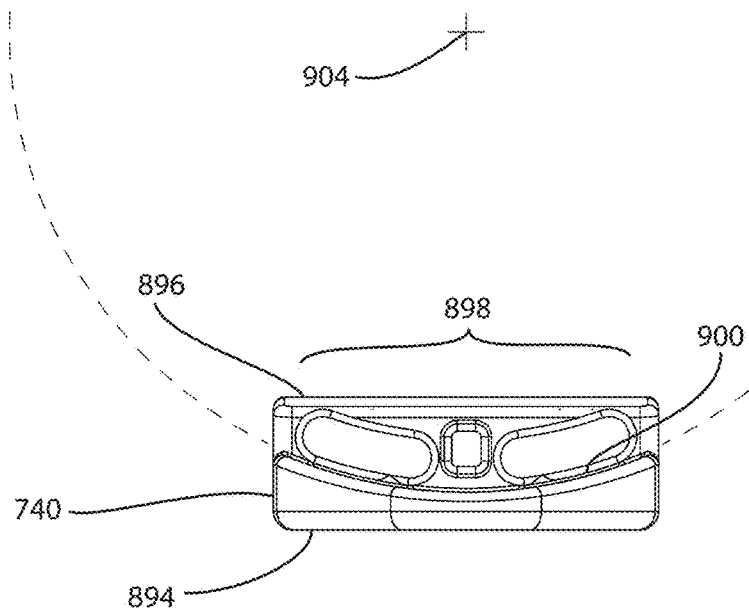
Figure 303:
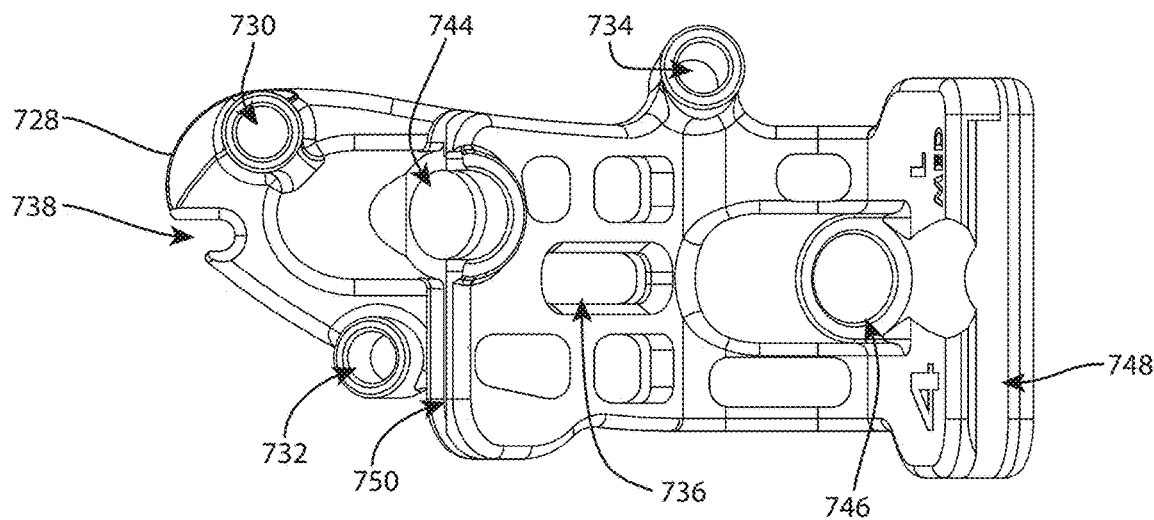
Figure 304:
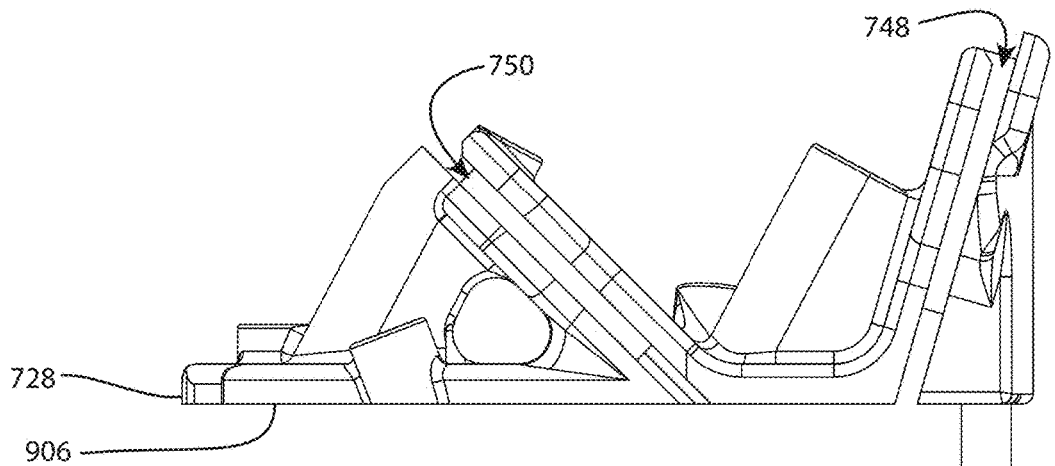
Figure 305:
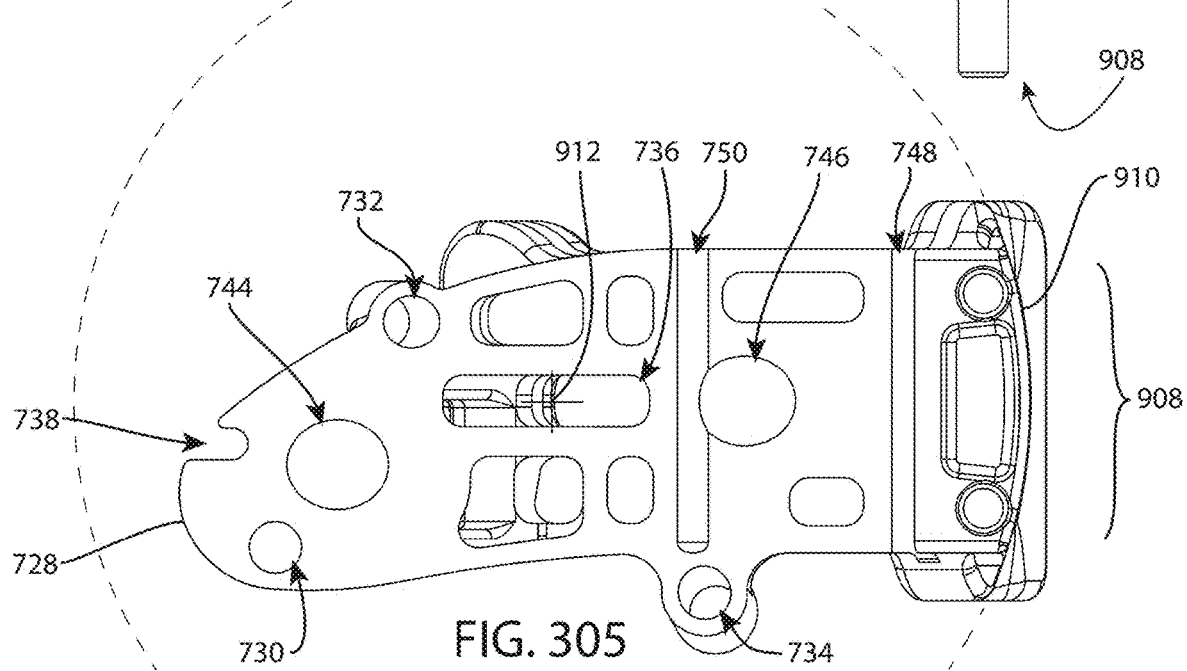

FIG. 131 is an oblique view of yet another fixation element;

FIG. 132 is another oblique view of the fixation element of FIG. 131 from a different direction;

FIG. 133 is a side view of the fixation element of FIG. 131;

FIG. 134 is a top view of the fixation element of FIG. 131;

FIG. 135 is an oblique view of yet another tibial tray coupled to yet another fixation element;

FIG. 136 is another oblique view of the tibial tray and fixation element of FIG. 135 from a different direction;

FIG. 137 is an oblique view of the tibial tray of FIG. 135;

FIG. 138 is another oblique view of the tibial tray of FIG. 137 from a different direction;

FIG. 139 is an oblique view of yet another fixation element;

FIG. 140 is another oblique view of the fixation element of FIG. 139 from a different direction;

FIG. 141 is a side view of the fixation element of FIG. 139;

FIG. 142 is a top view of the fixation element of FIG. 139;

FIG. 143 is an oblique view of yet another tibial tray;

FIG. 144 is another oblique view of the tibial tray of FIG. 143 from a different direction;

FIG. 145 is an oblique view of a slotted tibial tower showing a step of connecting the slotted tibial tower to a tibial resection guide rod;

FIG. 146 is an oblique view of a non-slotted tibial tower showing a step of connecting the non-slotted tibial tower to the tibial resection guide rod of FIG. 145;

FIG. 147 is an oblique view of the slotted tibial tower of FIG. 145 showing a step of connecting a slotted tibial cutting block to the slotted tibial tower;

FIG. 148 is another oblique view of the slotted tibial tower and slotted tibial cutting block of FIG. 147 from a different direction;

FIG. 149 is an oblique view of the slotted tibial tower and slotted tibial cutting block of FIG. 147 showing a step of using a screwdriver to lock the slotted tibial cutting block to the slotted tibial tower;

FIG. 150 is an oblique view of a distal femur and a proximal tibia of a knee joint showing a step of using a tibial AP sizer wand to measure the anterior-posterior dimension of the intact tibia;

FIG. 151 is an oblique view of the knee joint of FIG. 150 showing a step of using an angel wing in the transverse cutting slot to initially position the slotted tibial tower and slotted tibial cutting block of FIG. 149;

FIG. 152 is an oblique view of the knee joint, slotted tibial tower, slotted tibial cutting block, and angel wing of FIG. 151 showing a step of using the angel wing in the vertical cutting slot to initially position the slotted tibial tower and slotted tibial cutting block;

FIG. 153 is an oblique view of the knee joint of FIG. 150 showing a step of using the angel wing of FIG. 151 on the transverse cutting surface to initially position the non-slotted tibial tower of FIG. 146 and a non-slotted tibial cutting block;

FIG. 154 is an oblique view of the knee joint, non-slotted tibial tower, non-slotted tibial cutting block, and angel wing of FIG. 153 showing a step of using the angel wing on the vertical cutting surface to initially position the non-slotted tibial tower and non-slotted tibial cutting block;

FIG. 155 is an oblique view of the knee joint, slotted tibial tower, and slotted tibial cutting block of FIG. 151 showing a step of inserting a bone pin through a lateral pin hole of the guide rod;

FIG. 156 is an oblique view of the knee joint, slotted tibial tower, and slotted tibial cutting block of FIG. 155 showing a step of inserting a tibial stylus into the transverse cutting slot to contact the deepest point of the medial compartment of the tibial plateau;

FIG. 157 is a medial view of the knee joint, slotted tibial tower, slotted tibial cutting block, and tibial stylus of FIG. 156;

FIG. 158 is an oblique view of the knee joint, slotted tibial tower, and slotted tibial cutting block of FIG. 156 showing a step of inserting bone pins through medial and lateral holes of the slotted tibial tower;

FIG. 159 is an oblique view of the knee joint, non-slotted tibial tower, and non-slotted tibial cutting block of FIG. 153 showing a step of inserting bone pins through the lateral pin hole of the guide rod and a medial hole of the non-slotted tibial tower;

FIG. 160 is an oblique view of the knee joint, slotted tibial tower, slotted tibial cutting block, and bone pins of FIG. 158 showing a step of using a saw blade through the vertical cutting slot to make a sagittal resection;

FIG. 161 is an oblique view of the knee joint, slotted tibial tower, slotted tibial cutting block, bone pins, and saw blade of FIG. 160 showing a step of using the saw blade through the transverse cutting slot to make a transverse resection;

FIG. 162 is an oblique view of the knee joint, non-slotted tibial tower, non-slotted tibial cutting block, and bone pins of FIG. 159 showing a step of using a saw blade against the transverse cutting surface to make a transverse resection;

FIG. 163 is an oblique view of the knee joint, non-slotted tibial tower, non-slotted tibial cutting block, bone pins, and saw blade of FIG. 162 showing a step of using a second saw blade against the vertical cutting surface to make a sagittal resection;

FIG. 164 is another oblique view of the knee joint, non-slotted tibial tower, non-slotted tibial cutting block, bone pins, and saw blades of FIG. 163 from a different direction;

FIG. 165 is an oblique view of the knee joint of FIG. 161 showing a step of using a rasp to remove unresected bone;

FIG. 166 is an oblique view of the knee joint, slotted tibial tower, slotted tibial cutting block, and bone pins of FIG. 161 showing a step of using the screwdriver of FIG. 149 to unlock the slotted tibial cutting block from the slotted tibial tower;

FIG. 167 is an oblique view of the knee joint, slotted tibial tower, and bone pins of FIG. 166 after removing the slotted tibial cutting block;

FIG. 168 is an oblique view of the knee joint, slotted tibial tower, and bone pins of FIG. 167 showing a step of using an insert sizer to assess ligament tension;

FIG. 169 is an oblique view of the knee joint, slotted tibial tower, and bone pins of FIG. 168 showing a step of re-connecting the slotted tibial cutting block to the slotted tibial tower;

FIG. 170 is a medial view of the knee joint, slotted tibial tower, slotted tibial cutting block, and bone pins of FIG. 169;

FIG. 171 is an oblique view of the knee joint of FIG. 168 showing a step of attaching a re-cut block to the proximal tibia;

FIG. 172 is a medial view of the knee joint and re-cut block of FIG. 171;

FIG. 173 is an anterior view of the proximal tibia with a varus re-cut block attached;

FIG. 174 is an anterior view of the proximal tibia with a valgus re-cut block attached;

FIG. 175 is an oblique exploded view of a tensor block and tensor shim;

FIG. 176 is an oblique view of the tensor block and tensor shim of FIG. 175 connected together showing a step of connecting the tensor block and tensor shim to a quick-connect handle;

FIG. 177 is an oblique view of the knee joint of FIG. 168 and the tensor block, tensor shim, and quick-connect handle of FIG. 176 showing a step of inserting the tensor block and tensor shim into the medial compartment;

FIG. 178 is an oblique view of the knee joint, tensor block, tensor shim, and quick-connect handle of FIG. 177 showing the tensor block and tensor shim fully inserted into the medial compartment;

FIG. 179 is an oblique view of the knee joint, tensor block, and tensor shim of FIG. 178 after removing the quick-connect handle, showing a step of applying varus/valgus stress to the knee;

FIG. 180 is an oblique exploded view of the tensor block of FIG. 175 showing a step of replacing the tensor shim of FIG. 175 with a thicker tensor shim;

FIG. 181 is an oblique view of the knee joint, tensor block, and tensor shim of FIG. 179 showing a step of connecting a distal femoral cutting block to the tensor block and securing the distal femoral cutting block to the femur with bone pins;

FIG. 182 is an oblique view of the knee joint, tensor block, tensor shim, and distal femoral cutting block of FIG. 181 showing a step of securing the distal femoral cutting block to the femur with bone pins;

FIG. 183 is a medial view of the knee joint, tensor block, tensor shim, distal femoral cutting block, and bone pins of FIG. 182;

FIG. 184 is an anterior view of the knee joint, tensor block, tensor shim, distal femoral cutting block, and bone pins of FIG. 182 showing a step of using an extramedullary guide, extramedullary rod, and extramedullary rod with coupler to verify long limb alignment;

FIG. 185 is an oblique view of the knee joint, tensor block, tensor shim, distal femoral cutting block, bone pins, extramedullary guide, extramedullary rod, and extramedullary rod with coupler of FIG. 184;

FIG. 186 is an oblique view of the knee joint of FIG. 182 showing a step of inserting the insert sizer of FIG. 168 and a step of using the extramedullary rod and extramedullary rod with coupler of FIG. 184 to verify long limb alignment;

FIG. 187 is an anterior view of the knee joint, insert sizer, extramedullary guide, extramedullary rod, and extramedullary rod with coupler of FIG. 186;

FIG. 188 is an oblique view of the knee joint, tensor block, tensor shim, distal femoral cutting block, and bone pins of FIG. 185 showing a step of using a saw blade through the distal femoral cutting block to make a distal femoral resection;

FIG. 189 is an oblique view of the knee joint of FIG. 188 showing a step of using the insert sizer of FIG. 168 to confirm the distal femoral resection;

FIG. 190 is a medial view of the knee joint and insert sizer of FIG. 189;

FIG. 191 is an oblique view of the knee joint of FIG. 189 showing a step of using a tibial centerline marking guide to mark the transverse resection and the proximal anterior tibia;

FIG. 192 is another oblique view of the knee joint and tibial centerline marking guide of FIG. 191 from a different direction;

FIG. 193 is an oblique view of the knee joint of FIG. 191 showing a step of inserting the insert sizer of FIG. 168 and connecting a femoral marking tower to the insert sizer;

FIG. 194 is another oblique view of the knee joint, insert sizer, and femoral marking tower of FIG. 193 from a different direction;

FIG. 195 is an oblique view of the knee joint, insert sizer, and femoral marking tower of FIG. 193 showing a step of using the femoral marking tower to mark the distal femoral resection;

FIG. 196 is an oblique view of the knee joint and insert sizer of FIG. 195 showing a step of using the insert sizer to mark the distal anterior femur;

FIG. 197 is another oblique view of the knee joint and insert sizer of FIG. 196 from a different direction;

FIG. 198 is an oblique view of the knee joint of FIG. 196 showing a step of using a femoral sizer to measure the approximate femoral implant size;

FIG. 199 is a distal view of the femur and femoral sizer of FIG. 198;

FIG. 200 is an oblique view of the knee joint of FIG. 198 showing a step of connecting a tensor block and a posterior cutting block;

FIG. 201 is an oblique view of the knee joint, tensor block, and posterior cutting block of FIG. 200 showing the tensor block and posterior cutting block fully connected;

FIG. 202 is an oblique view of the knee joint, tensor block, and posterior cutting block of FIG. 201 showing a step of inserting the tensor block into the medial compartment;

FIG. 203 is an oblique view of the knee joint of FIG. 198 showing a step of connecting the tensor block of FIG. 200 to the quick-connect handle of FIG. 176;

FIG. 204 is an oblique view of the knee joint, tensor block, and quick-connect handle of FIG. 203 showing a step of inserting the tensor block into the medial compartment;

FIG. 205 is an oblique view of the knee joint and tensor block of FIG. 204 showing a step of connecting the posterior cutting block of FIG. 200 to the tensor block;

FIG. 206 is an oblique view of the knee joint, tensor block, and posterior cutting block of FIG. 205 showing the tensor block and posterior cutting block fully connected;

FIG. 207 is a medial view of the knee joint, tensor block, and posterior cutting block of FIG. 202;

FIG. 208 is a distal view of the femur, tensor block, and posterior cutting block of FIG. 202 showing a step of inserting bone pins through the posterior cutting block;

FIG. 209 is an oblique view of the knee, tensor block, posterior cutting block, and bone pins of FIG. 208;

FIG. 210 is an oblique view of the knee joint of FIG. 198 showing a step of connecting a rotation tensor block to the posterior cutting block of FIG. 200;

FIG. 211 is an oblique view of the knee joint, rotation tensor block, and posterior cutting block of FIG. 210 showing the rotation tensor block and posterior cutting block fully connected;

FIG. 212 is an oblique view of the knee joint, rotation tensor block, and posterior cutting block of FIG. 211 showing a step of inserting the rotation tensor block into the medial compartment and a step of inserting bone pins through the posterior cutting block;

FIG. 213 is a distal view of the femur, rotation tensor block, posterior cutting block, and bone pins of FIG. 212;

FIG. 214 is an oblique view of the knee joint, tensor block, posterior cutting block, and bone pins of FIG. 209 showing a step of using a drill to make a posterior peg hole in the femur;

FIG. 215 is an oblique view of the knee joint, tensor block, posterior cutting block, bone pins, and drill of FIG. 214 showing a step of using the drill to make an anterior peg hole in the femur;

FIG. 216 is an oblique view of the knee joint, tensor block, posterior cutting block, and bone pins of FIG. 215 showing a step of using a saw blade through a posterior saw slot of the posterior cutting block to make a posterior femoral resection;

FIG. 217 is an oblique view of the knee joint, tensor block, posterior cutting block, bone pins, and saw of FIG. 216 showing a step of using the saw through the posterior chamfer saw slot of the posterior cutting block to make a posterior chamfer resection;

FIG. 218 is an oblique view of the knee joint of FIG. 217 showing a step of using the insert sizer of FIG. 168 to check ligament tension with the knee in flexion;

FIG. 219 is an anterior view of the tibia and insert sizer of FIG. 218;

FIG. 220 is an oblique view of the knee joint and insert sizer of FIG. 218 showing a step of using the insert sizer to check ligament tension with the knee in extension;

FIG. 221 is an anterior view of the femur and insert sizer of FIG. 220;

FIG. 222 is a side view of multiple superimposed femoral implants of different sizes;

FIG. 223 is an oblique view of the knee joint of FIG. 218 showing a step of inserting a size 2-3/5-8 downsizing guide into the medial compartment;

FIG. 224 is an oblique view of the knee joint and 2-3/5-8 downsizing guide of FIG. 223 with the size 2-3/5-8 downsizing guide fully inserted in contact with the distal femoral resection and the posterior femoral resection and showing a step of inserting bone pins through the size 2-3/5-8 downsizing guide;

FIG. 225 is an oblique view of the knee joint, size 2-3/5-8 downsizing guide, and bone pins of FIG. 224 showing a step of using a saw blade through the cutting slot to cut a new posterior femoral resection;

FIG. 226 is an oblique view of the knee joint of FIG. 218 showing a step of inserting a size 4 downsizing guide into the medial compartment;

FIG. 227 is an oblique view of the knee joint and size 4 downsizing guide of FIG. 226 with the size 4 downsizing guide fully inserted in contact with the distal femoral resection and showing a step of inserting bone pins through the size 4 downsizing guide;

FIG. 228 is an oblique view of the knee joint, size 4 downsizing guide, and bone pins of FIG. 227 showing a step of using a drill to make a new anterior peg hole in the femur;

FIG. 229 is an oblique view of the knee joint, size 4 downsizing guide, and bone pins of FIG. 228 showing a step of using a saw blade through the cutting slot to cut a new posterior femoral resection;

FIG. 230 is an oblique view of the knee joint of FIG. 218 showing a step of using the tibial AP sizer wand of FIG. 150 to measure the anterior-posterior dimension of the resected tibia;

FIG. 231 is an anterior view of the femur and tibial AP sizer wand of FIG. 230;

FIG. 232 is an oblique view of the knee joint of FIG. 230 showing a step of using a tibial sizer to measure the tibia;

FIG. 233 is an anterior view of the femur and tibial sizer of FIG. 232;

FIG. 234 is an oblique view of the knee joint and tibial sizer of FIG. 232 showing a step of inserting a bone pin through the tibial sizer and a step of using the angel wing of FIG. 151 to verify posterior fit;

FIG. 235 is an oblique view of the knee joint, tibial sizer, and bone pin of FIG. 234 showing a step of using a drill to make a first peg hole;

FIG. 236 is an oblique view of the knee joint, tibial sizer, bone pin, and drill of FIG. 235 showing a step of using a second drill to make a second peg hole;

FIG. 237 is an oblique view of the knee joint of FIG. 236 showing a step of inserting a tibial tray trial into the medial compartment;

FIG. 238 is an oblique view of the knee joint and tibial tray trial of FIG. 237 showing a step of using a curved impactor to fully insert/seat the tibial tray trial;

FIG. 239 is an oblique view of the knee joint and tibial tray trial of FIG. 238 showing a step of using the angel wing of FIG. 151 to verify posterior fit;

FIG. 240 is an oblique view of the knee joint and tibial tray trial of FIG. 239 showing a step of using a femoral impactor to insert/seat a femoral trial;

FIG. 241 is an oblique view of the knee joint, tibial tray trial, and femoral trial of FIG. 240 showing a step of inserting an insert trial into the medial compartment;

FIG. 242 is an oblique view of the knee joint, tibial tray trial, femoral trial, and insert trial of FIG. 241 showing a step of using an insert impactor to fully insert/seat the insert trial;

FIG. 243 is an oblique view of the knee joint, tibial tray trial, femoral trial, and insert trial of FIG. 242 showing a step of manipulating the knee joint through a range of motion to assess joint stability and gap balancing;

FIG. 244 is an oblique view of the knee joint, tibial tray trial, femoral trial, and insert trial of FIG. 243 showing a step of using a removal hook to remove the insert trial;

FIG. 245 is a medial view of the knee joint, tibial tray trial, femoral trial, insert trial, and removal hook of FIG. 244;

FIG. 246 is an oblique view of the knee joint, tibial tray trial, femoral trial, and insert trial of FIG. 243 showing a step of connecting a slap hammer to the femoral trial;

FIG. 247 is an oblique view of the knee joint, tibial tray trial, femoral trial, insert trial, and slap hammer of FIG. 246 showing a step of locking the slap hammer to the femoral trial;

FIG. 248 is an oblique view of the knee joint and tibial tray trial of FIG. 247 showing a step of connecting the quick-connect handle of FIG. 176 to the tibial tray trial;

FIG. 249 is an oblique view of the knee joint of FIG. 248 showing a step of inserting a tibial tray implant into the medial compartment;

FIG. 250 is an oblique view of the knee joint and tibial tray implant of FIG. 249 showing a step of using the curved impactor to fully insert/seat the tibial tray implant;

FIG. 251 is an oblique view of the knee joint and tibial tray implant of FIG. 250 showing a step of using the angel wing of FIG. 151 to verify posterior fit;

FIG. 252 is an oblique view of the knee joint and tibial tray implant of FIG. 251 showing a step of inserting the insert trial of FIG. 241 into the tibial tray implant;

FIG. 253 is an oblique view of the knee joint, tibial tray implant, and insert trial of FIG. 252 showing a step of inserting a compression block between the insert trial and the distal femoral resection;

FIG. 254 is an oblique view of the knee joint, tibial tray implant, insert trial, and compression block of FIG. 253 showing a step of connecting an anchor guide to the tibial tray implant;

FIG. 255 is another oblique view of the knee joint, tibial tray implant, insert trial, compression block, and anchor guide of FIG. 254 from a different direction;

FIG. 256 is an oblique view of the knee joint, tibial tray implant, insert trial, compression block, and anchor guide of FIG. 255 showing a step of provisionally locking the anchor guide to the tibial tray implant;

FIG. 257 is an oblique view of the knee joint, tibial tray implant, insert trial, compression block, and anchor guide of FIG. 256 showing a step of using the screwdriver of FIG. 149 to fully lock the anchor guide to the tibial tray implant;

FIG. 258 is an oblique view of the knee joint, tibial tray implant, insert trial, compression block, and anchor guide of FIG. 257 showing a step of using a pilot cutter to cut a bone channel through the anterior tibial cortex;

FIG. 259 is an oblique view of the knee joint, tibial tray implant, insert trial, compression block, anchor guide, and pilot cutter of FIG. 258 showing the pilot cutter advancing into the anterior tibia;

FIG. 260 is an oblique view of the knee joint, tibial tray implant, insert trial, compression block, anchor guide, and pilot cutter of FIG. 259 showing the pilot cutter fully seated/advanced into the anterior tibia and showing a step of connecting the slap hammer of FIG. 246 to the pilot cutter;

FIG. 261 is an oblique view of the knee joint, tibial tray implant, insert trial, compression block, anchor guide, pilot cutter, and slap hammer of FIG. 260 showing the slap hammer locked to the pilot cutter;

FIG. 262 is an oblique view of the knee joint, tibial tray implant, insert trial, compression block, and anchor guide of FIG. 261 showing a step of inserting an anchor (fixation element) into the anchor guide;

FIG. 263 is an oblique view of the knee joint, tibial tray implant, insert trial, compression block, anchor guide, and anchor of FIG. 262 showing a step of using an anchor tamp to advance the anchor toward the anterior tibia and tibial tray implant;

FIG. 264 is an oblique view of the knee joint, tibial tray implant, insert trial, compression block, anchor guide, anchor, and anchor tamp of FIG. 263 showing the anchor and anchor tamp advancing into the anterior tibia and tibial tray implant;

FIG. 265 is a medial view of the knee joint, tibial tray implant, insert trial, compression block, anchor guide, anchor, and anchor tamp of FIG. 263 showing the anchor and anchor tamp fully seated/advanced into the anterior tibia and tibial tray implant;

FIG. 266 is a bottom view of the tibial tray implant and anchor of FIG. 265, the anchor blade omitted to show details of the anchor/tray locking mechanism;

FIG. 267 is an oblique view of the knee joint and tibial tray implant of FIG. 265 showing a step of inserting a femoral implant into the medial compartment;

FIG. 268 is an oblique view of the knee joint, tibial tray implant, and femoral implant of FIG. 267 showing a step of using the femoral impactor of FIG. 240 to fully seat the femoral implant against the distal femoral resection, the posterior femoral resection, and the posterior chamfer resection;

FIG. 269 is a medial view of the knee joint, tibial tray implant, and femoral implant of FIG. 268 showing the femoral implant fully seated against the distal femoral resection, the posterior femoral resection, and the posterior chamfer resection;

FIG. 270 is an oblique view of the knee joint, tibial tray implant, and femoral implant of FIG. 269 showing a step of using the insert impactor of FIG. 242 to insert an insert implant into the tibial tray implant and fully seat the insert implant;

FIG. 271 is an oblique view of the knee joint, tibial tray implant, anchor, femoral implant, and insert implant in a final implanted state;

FIG. 272 is another oblique view of the knee joint, tibial tray implant, anchor, femoral implant, and insert implant of FIG. 271 from a different direction;

FIG. 273 is an oblique view of the knee joint, tibial tray implant, anchor, femoral implant, and insert implant of FIG. 271 showing a step of connecting an anchor revision guide to the tibial tray implant;

FIG. 274 is an oblique view of the knee joint, tibial tray implant, anchor, femoral implant, insert implant, and anchor revision guide of FIG. 273 showing the anchor revision guide connected to the tibial tray implant;

FIG. 275 is an oblique view of the knee joint, tibial tray implant, anchor, femoral implant, insert implant, and anchor revision guide of FIG. 274 showing a step of using the screwdriver of FIG. 149 to lock the anchor revision guide to the tibial tray implant;

FIG. 276 is an oblique view of the knee joint, tibial tray implant, anchor, femoral implant, insert implant, and anchor revision guide of FIG. 275 showing a step of using an anchor removal chisel to create a pathway to the anchor and tibial tray implant;

FIG. 277 is an oblique view of the knee joint, tibial tray implant, anchor, femoral implant, insert implant, anchor revision guide, and anchor removal chisel of FIG. 276 showing the anchor removal chisel advancing toward the anchor and tibial tray implant;

FIG. 278 is an oblique view of the knee joint, tibial tray implant, anchor, femoral implant, insert implant, anchor revision guide, and anchor removal chisel of FIG. 277 showing the anchor removal chisel advancing toward the anchor and tibial tray implant;

FIG. 279 is an oblique view of the knee joint, tibial tray implant, anchor, femoral implant, insert implant, anchor revision guide, and anchor removal chisel of FIG. 278 showing the anchor removal chisel fully advanced toward the anchor and tibial tray implant;

FIG. 280 is an oblique view of the knee joint, tibial tray implant, anchor, femoral implant, insert implant, anchor revision guide, and anchor removal chisel of FIG. 279 showing a step of connecting the slap hammer of FIG. 246 to the anchor removal chisel;

FIG. 281 is an anterior view of the tibia, tibial tray implant, anchor, femoral implant, insert implant, and anchor revision guide of FIG. 280 showing the pathway created by the anchor removal chisel;

FIG. 282 is an oblique view of an anchor removal tool in a fully extended state;

FIG. 283 is an oblique view of the knee joint, tibial tray implant, anchor, femoral implant, insert implant, and anchor revision guide of FIG. 281 showing a step of advancing the anchor removal tool of FIG. 282 toward the anchor and tibial tray implant;

FIG. 284 is a proximal view of the tibia, tibial tray implant, anchor, femoral implant, insert implant, anchor revision guide, and anchor removal tool of FIG. 283 showing the anchor removal tool fully advanced/inserted;

FIG. 285 is an oblique view of the knee joint, tibial tray implant, anchor, femoral implant, insert implant, anchor revision guide, and anchor removal tool of FIG. 284;

FIG. 286 is a bottom view of the tibial tray implant, anchor, anchor revision guide, and anchor removal tool of FIG. 284, the anchor blade omitted for clarity;

FIG. 287 is a proximal view of the tibia, tibial tray implant, anchor, femoral implant, insert implant, anchor revision guide, and anchor removal tool of FIG. 284 showing the anchor removal tool fully advanced/inserted;

FIG. 288 is an oblique view of the knee joint, tibial tray implant, anchor, femoral implant, insert implant, anchor revision guide, and anchor removal tool of FIG. 287 showing a step of moving the anchor removal tool from an insertion position to an engaged position;

FIG. 289 is a bottom view of the tibial tray implant, anchor, anchor revision guide, and anchor removal tool of FIG. 288, the anchor blade omitted for clarity;

FIG. 290 is an oblique view of the knee joint, tibial tray implant, anchor, femoral implant, insert implant, anchor revision guide, and anchor removal tool of FIG. 288 showing a step of actuating the anchor removal tool to extract the anchor from the tibial tray implant;

FIG. 291 is another oblique view of the knee joint, tibial tray implant, anchor, femoral implant, insert implant, anchor revision guide, and anchor removal tool of FIG. 290 from a different direction;

FIG. 292 is a medial view of the knee joint, tibial tray implant, anchor, femoral implant, insert implant, anchor revision guide, and anchor removal tool of FIG. 290;

FIG. 293 is an oblique view of the knee joint, tibial tray implant, femoral implant, and insert implant of FIG. 290;

FIG. 294 is a medial view of the knee joint, tibial tray implant, femoral implant, and insert implant of FIG. 293;

FIG. 295 is an oblique view of the knee joint and femoral implant of FIG. 293 after removal of the tibial tray implant and insert implant, showing the femoral implant loosened from the femur for removal;

FIG. 296 is an exploded oblique view of a shoulder joint including a scapula/glenoid and proximal humerus with an anatomic shoulder arthroplasty system including a glenoid baseplate, anchor, and glenoid articular insert;

FIG. 297 is an exploded oblique view of the shoulder joint of FIG. 296 with a reverse shoulder arthroplasty system including a glenoid baseplate, anchor, glenosphere, and humeral socket;

FIG. 298 is an oblique view of the shoulder joint, glenoid baseplate, anchor, glenosphere, and humeral socket of FIG. 297 showing a step of placing the glenoid baseplate against a prepared glenoid socket and a step of connecting the glenosphere to the glenoid baseplate;

FIG. 299 is an oblique view of the shoulder joint, glenoid baseplate, anchor, glenosphere, and humeral socket of FIG. 298 showing a step of moving the anchor relative to the glenoid baseplate from an insertion position to a fixation position;

FIG. 300 is a side view of the rotation tensor block of FIG. 210;

FIG. 301 is a top view of the rotation tensor block of FIG. 210;

FIG. 302 is a front view of the rotation tensor block of FIG. 210;

FIG. 303 is a front view of the posterior cutting block of FIG. 200;

FIG. 304 is a side view of the posterior cutting block of FIG. 200;

FIG. 305 is a back view of the posterior cutting block of FIG. 200; and

Figures 54, 55:
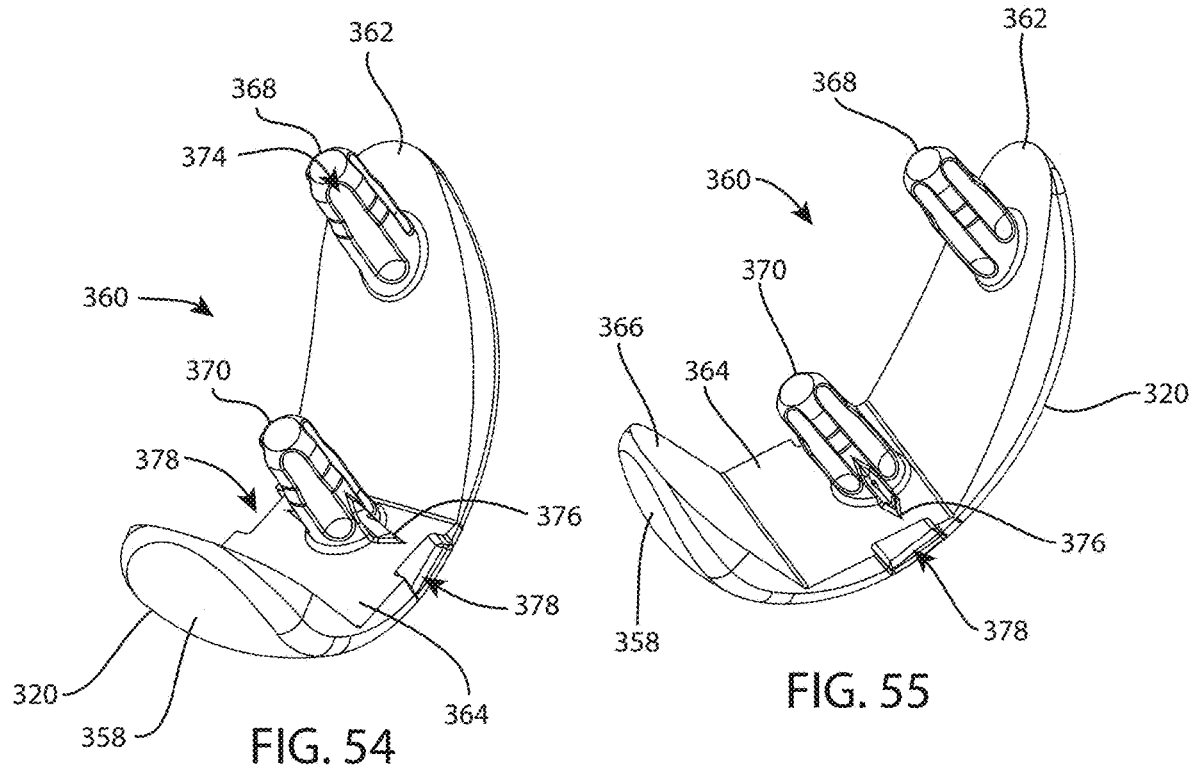
FIG. 54 is an oblique view of a femoral component of the unicompartmental implant construct of FIG. 52.
FIG. 55 is another oblique view of the femoral component of FIG. 54 from a different direction.
Figure 306:
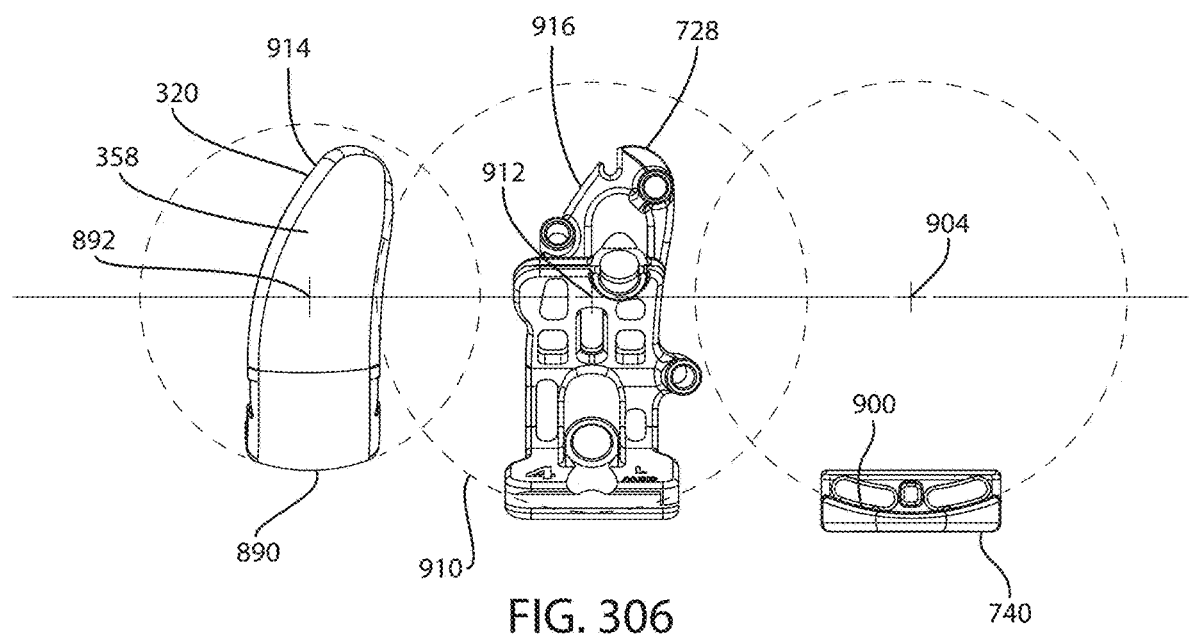

FIG. 306 is a distal view of the femoral implant of FIG. 54, the posterior cutting block of FIG. 200, and the rotation tensor block of FIG. 210 side by side.

DETAILED DESCRIPTION

Exemplary embodiments of the technology will be best understood by reference to the drawings, wherein like parts are designated by like numerals throughout. It will be readily understood that the components of the technology, as generally described and illustrated in the figures herein, could be arranged and designed in a wide variety of different configurations. Thus, the following more detailed description of the embodiments of the apparatus, system, and method is not intended to limit the scope of the invention, as claimed, but is merely representative of exemplary embodiments of the technology.

The phrases "connected to," "coupled to" and "in communication with" refer to any form of interaction between two or more entities, including mechanical, electrical, magnetic, electromagnetic, fluid, and thermal interaction. Two components may be functionally coupled to each other even though they are not in direct contact with each other. The term "abutting" refers to items that are in direct physical contact with each other, although the items may not necessarily be attached together. The phrase "fluid communication" refers to two features that are connected such that a fluid within one feature is able to pass into the other feature.

The word "exemplary" is used herein to mean "serving as an example, instance, or illustration." Any embodiment described herein as "exemplary" is not necessarily to be construed as preferred or advantageous over other embodiments. While the various aspects of the embodiments are presented in drawings, the drawings are not necessarily drawn to scale unless specifically indicated.

Standard medical planes of reference and descriptive terminology are employed in this specification. While these terms are commonly used to refer to the human body, certain terms are applicable to physical objects in general.

A standard system of three mutually perpendicular reference planes is employed. A sagittal plane divides a body into right and left portions. A coronal plane divides a body into anterior and posterior portions. A transverse plane divides a body into superior and inferior portions. A mid-sagittal, mid-coronal, or mid-transverse plane divides a body into equal portions, which may be bilaterally symmetric. The intersection of the sagittal and coronal planes defines a superior-inferior or cephalad-caudal axis. The intersection of the sagittal and transverse planes defines an anterior-posterior axis. The intersection of the coronal and transverse planes defines a medial-lateral axis. The superior-inferior or cephalad-caudal axis, the anterior-posterior axis, and the medial-lateral axis are mutually perpendicular.

Anterior means toward the front of a body. Posterior means toward the back of a body. Superior or cephalad means toward the head. Inferior or caudal means toward the feet or tail. Medial means toward the midline of a body, particularly toward a plane of bilateral symmetry of the body. Lateral means away from the midline of a body or away from a plane of bilateral symmetry of the body. Axial means toward a central axis of a body. Abaxial means away from a central axis of a body. Ipsilateral means on the same side of the body. Contralateral means on the opposite side of the body. Proximal means toward the trunk of the body. Proximal may also mean toward a user or operator. Distal means away from the trunk. Distal may also mean away from a user or operator. Dorsal means toward the top of the foot. Plantar means toward the sole of the foot.

Standard terminology related to knee arthroplasty is employed in this specification with the ordinary and customary meanings. Varus means deviation of the distal part of the leg below the knee inward, resulting in a bowlegged appearance. Valgus means deviation of the distal part of the leg below the knee outward, resulting in a knock-kneed appearance.

In this specification, "substantially" means ±5% on linear dimensions and ±5° on angular dimensions.

Figure 1:
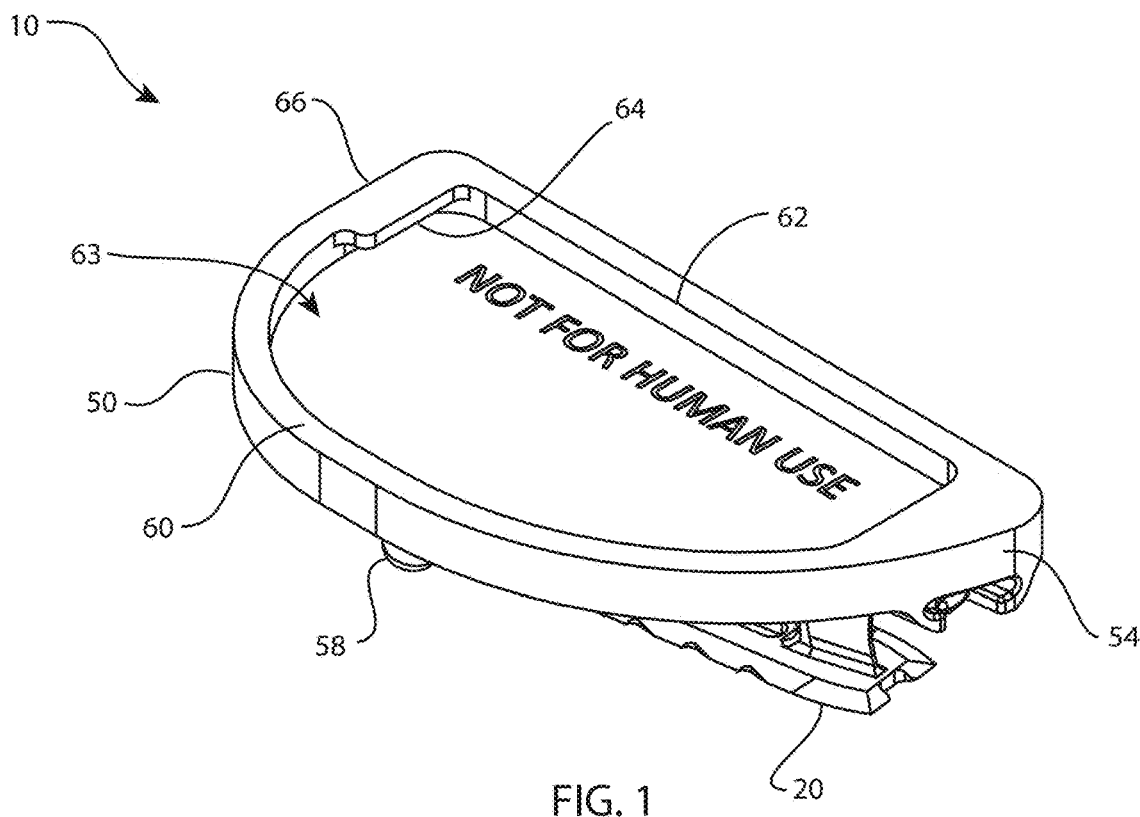
FIG. 1 is a perspective view of a unicompartmental tibial tray and a fixation element.
Figure 2:
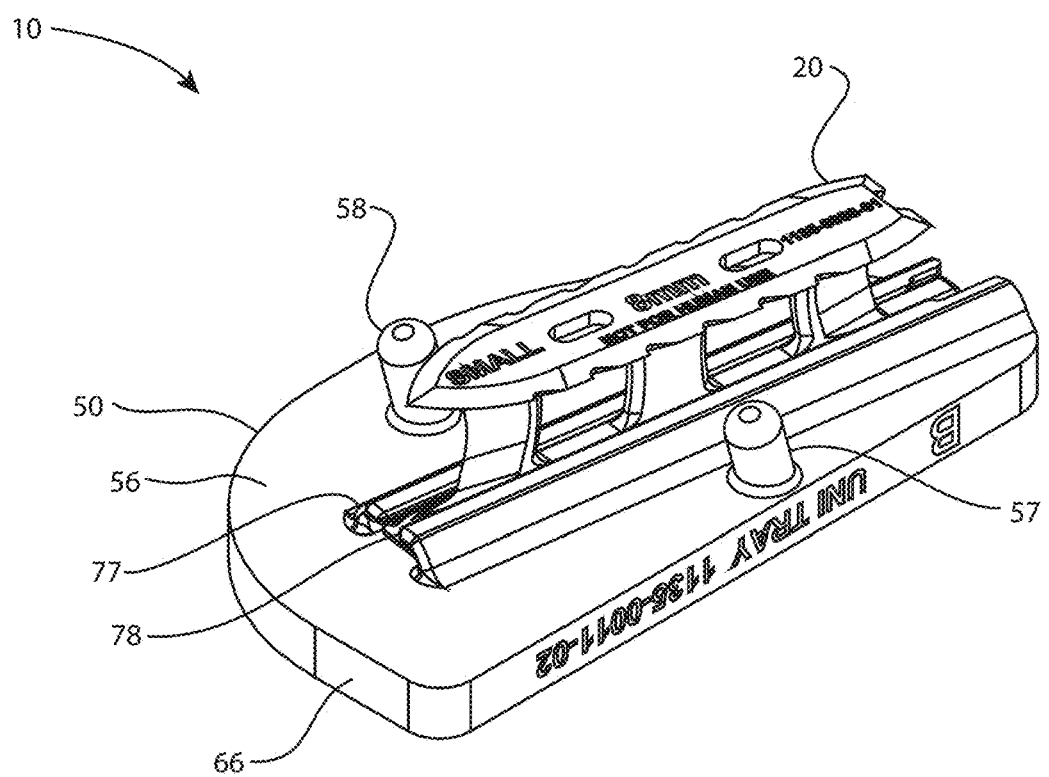
FIG. 2 is another perspective view of the tibial tray and fixation element of FIG. 1 from a different direction.
Figure 3:
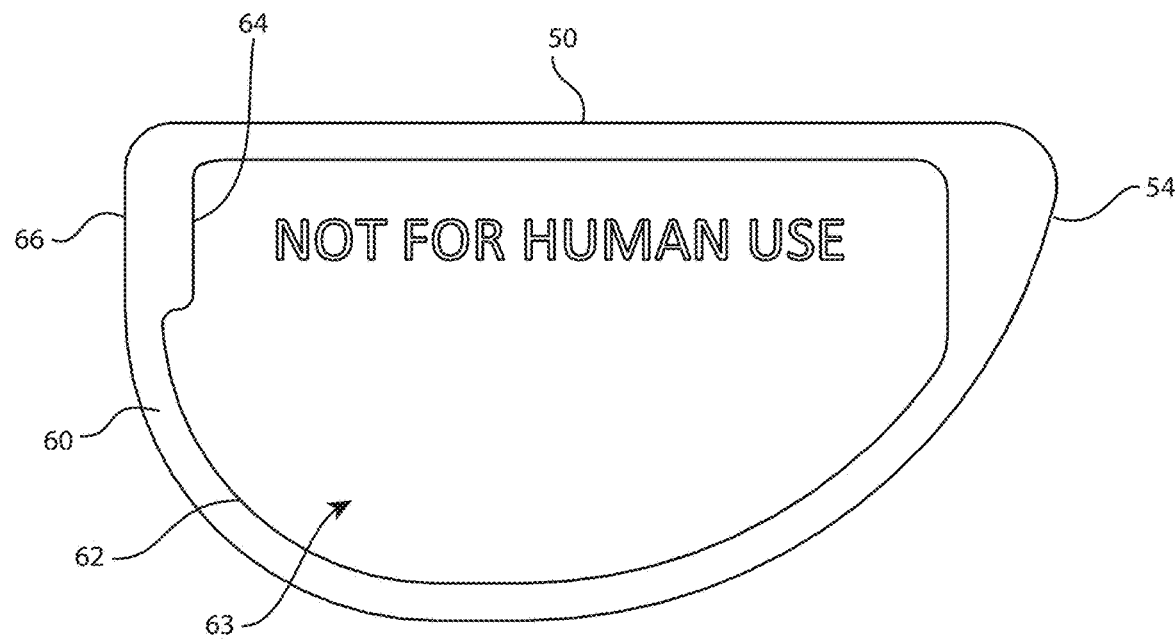
FIG. 3 is a top view of the tibial tray of FIG. 1.
Figure 18:
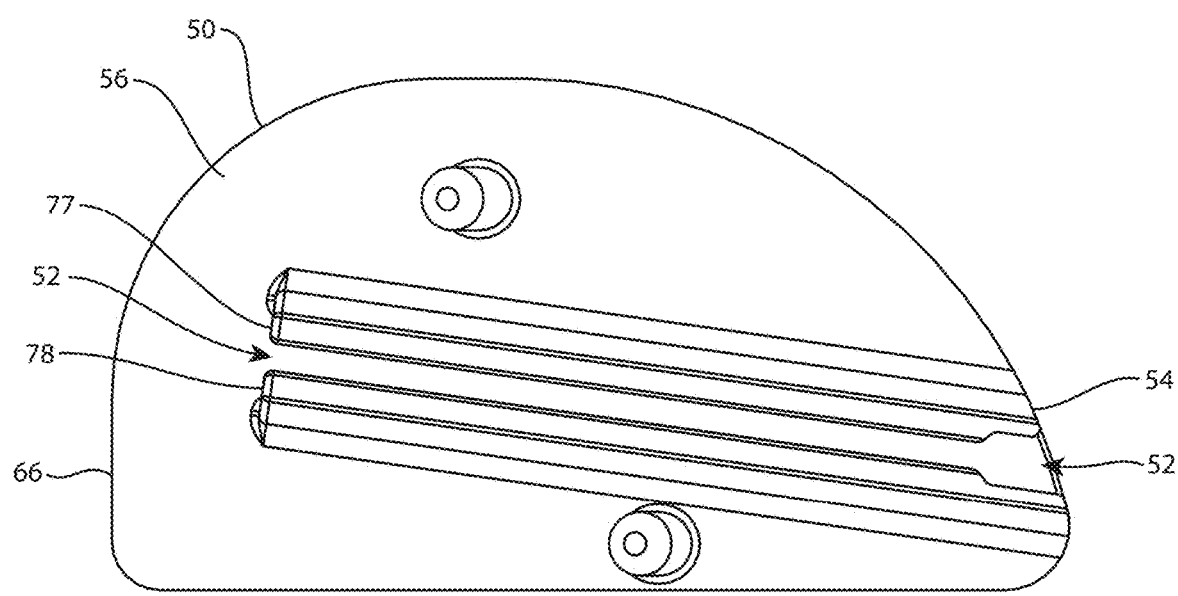
FIG. 18 is a bottom view of the tibial tray of FIG. 1.
Figure 19:
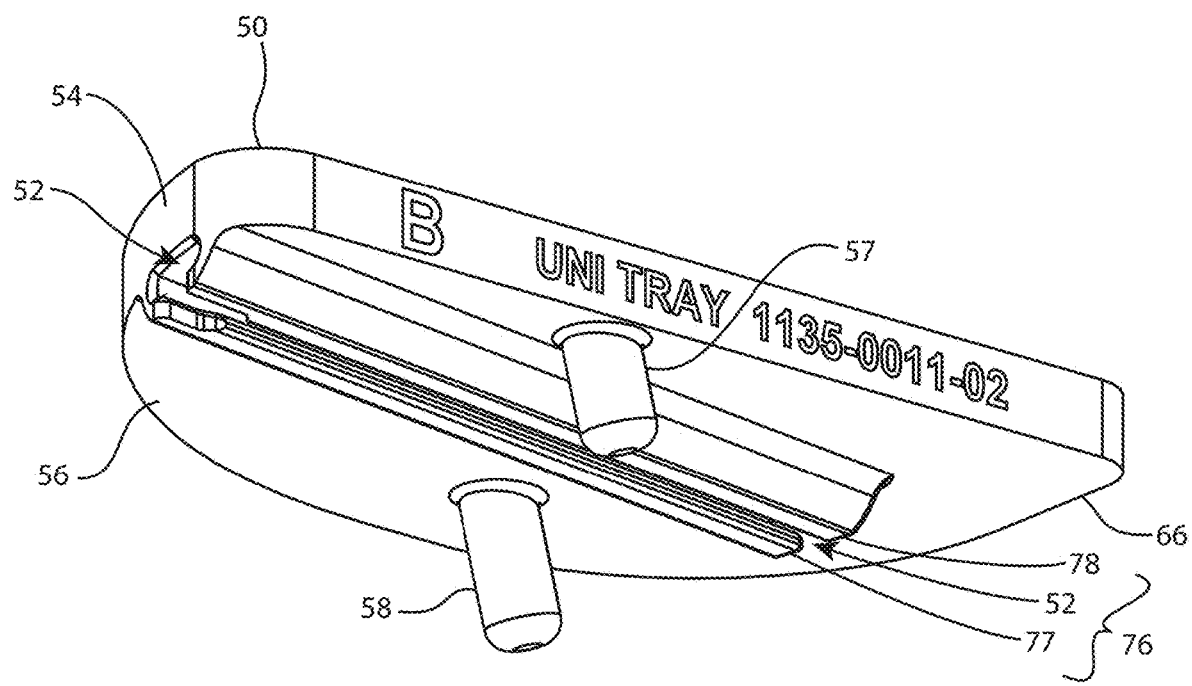
FIG. 19 is a perspective view of the tibial tray of FIG. 1.
Figure 20:
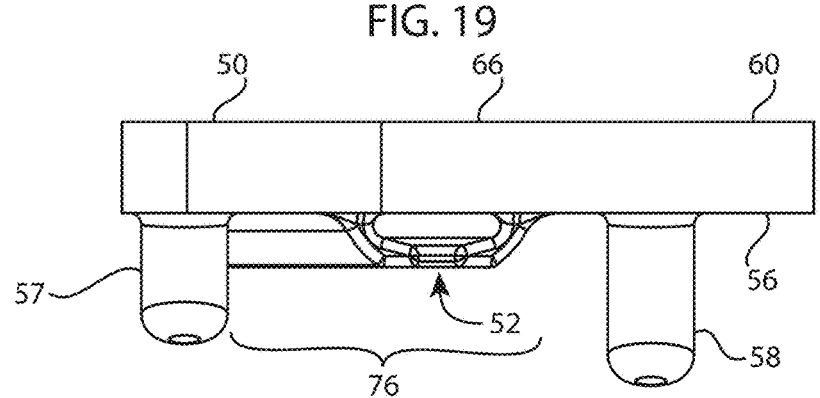
FIG. 20 is left view of the tibial tray of FIG. 1.
Figure 21:
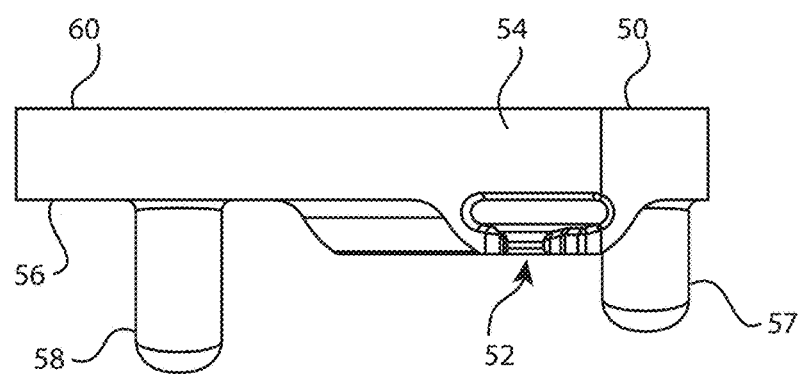
FIG. 21 is a right view of the tibial tray of FIG. 1.
Figure 22:
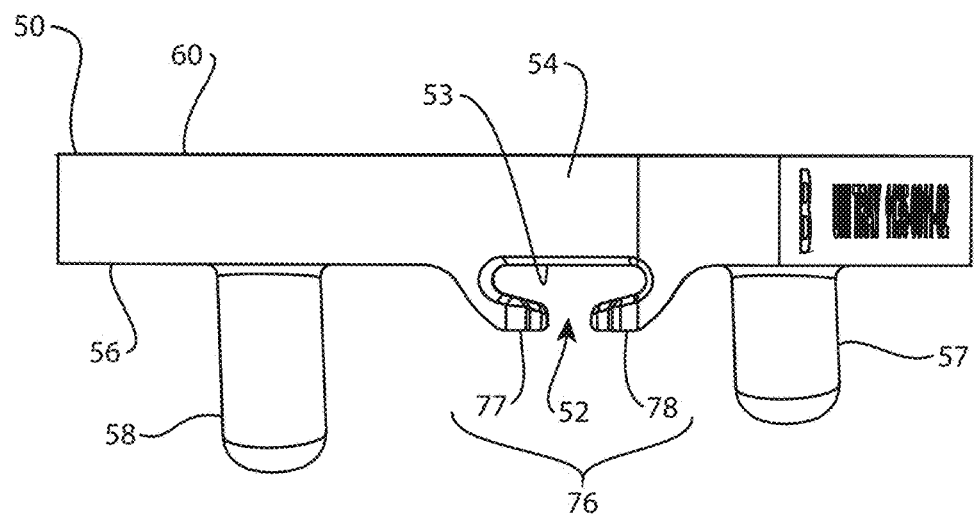
FIG. 22 is another auxiliary view of the tibial tray of FIG. 1 taken along line 10-10 of FIG. 9 parallel to the plane of symmetry of the fixation element.
Figure 23:
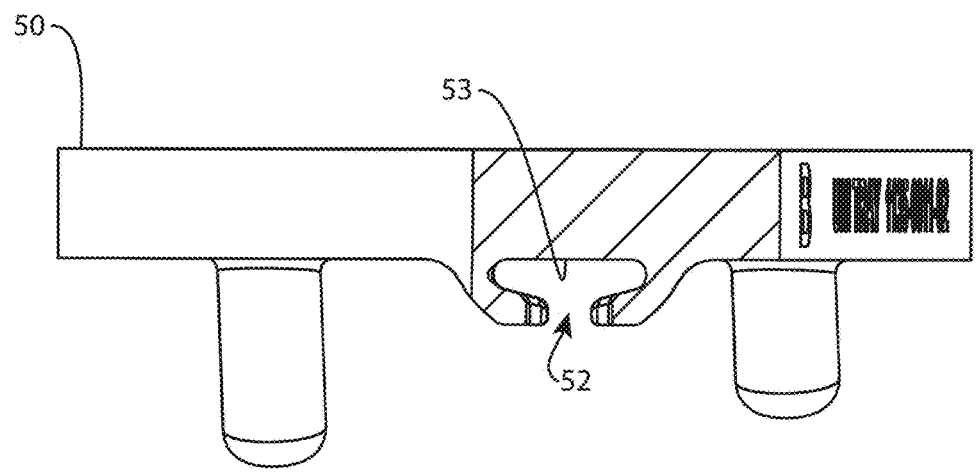
FIG. 23 is a cross-sectional view of the tibial tray of FIG. 1 taken along line 11-11 of FIG. 9.
Figure 24:
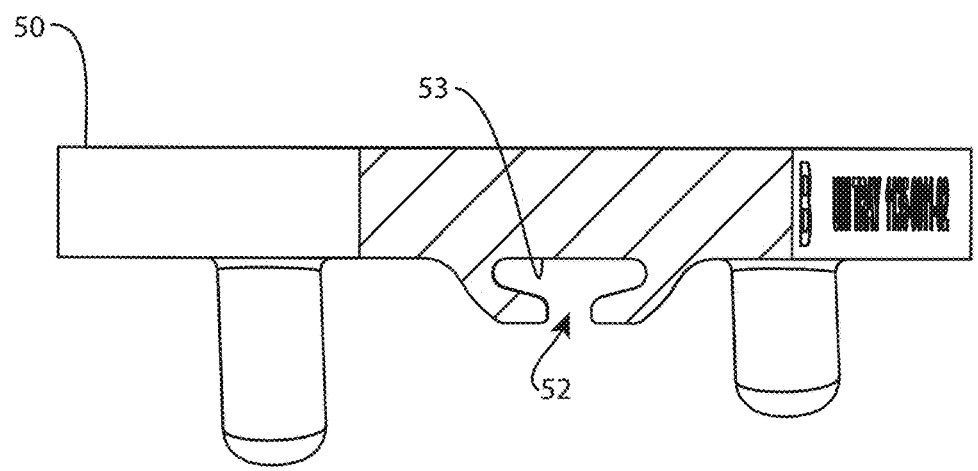
FIG. 24 is a cross-sectional view of the tibial tray of FIG. 1 taken along line 12-12 of FIG. 9.
Figure 25:
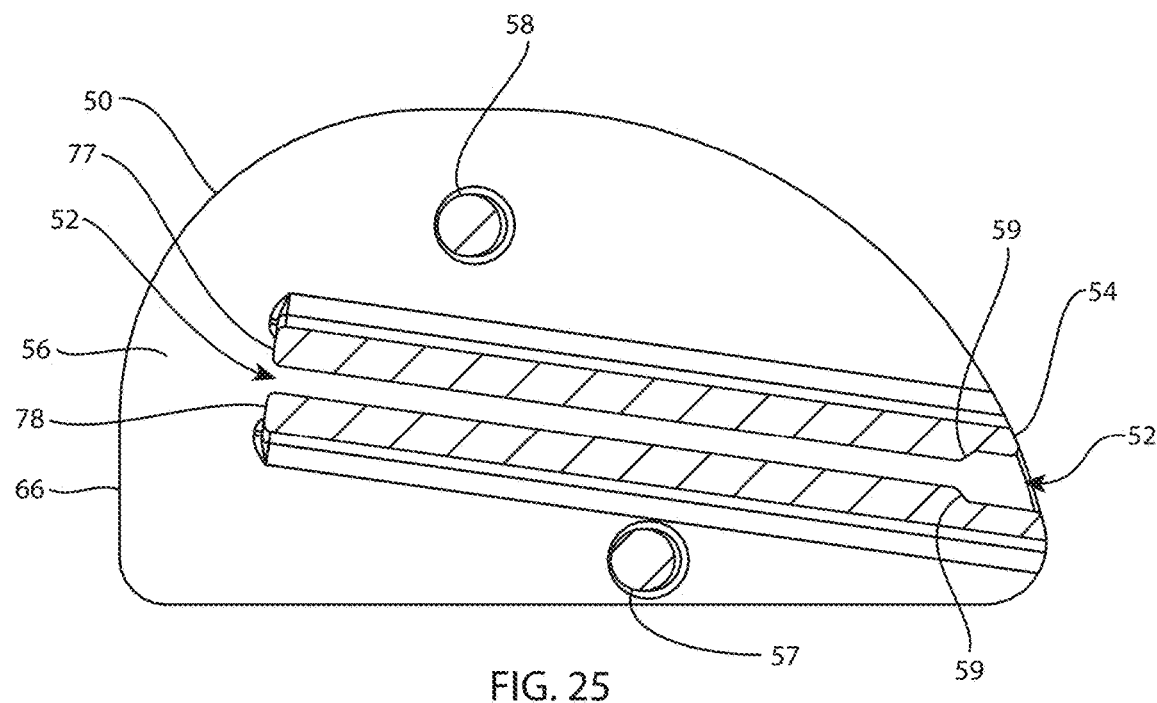
FIG. 25 is a cross-sectional view of the tibial tray of FIG. 1 taken along line 17-17 of FIG. 9.

Referring to FIGS. 1-36, a knee tibial prosthesis 10 includes a tibial component 50 and at least one fixation element 20. The tibial component 50 may be referred to as a tibial tray 50. The illustrated tibial component 50 is a unicompartmental tibial component. The tibial prosthesis 10 of FIG. 1 includes one fixation element 20, which may be referred to as an anchor 20. Multiple anchors may be present. The anchor 20 may be inserted from an anterior edge 54 of the tibial tray 50 and may be oriented roughly anterior-posterior, as shown. The anchor 20 may be parallel or angled relative to another anchor (if present) and/or the tray 50. The anchor may also be tilted with respect to the tray 50, for example, tilted medially or laterally. The anchor 20 is inserted into a channel 52 in the tibial tray 50 (FIG. 18). Multiple channels may be present. The channel may be dovetailed as shown; other undercut channel geometries are contemplated, such as T-slots. The channel 52 is shown extending between anterior and posterior edges 54, 66 of the tray 50. In some embodiments, the channel may only open at one of the anterior and posterior edges 54, 66, and may terminate in the main body of the tray 50. In other examples, the channel 52 may be oriented exactly anterior-posterior, exactly medial-lateral, generally medial-lateral, or in another orientation. A channel 52 may open through any perimeter edge of a bone-contacting side 56 of the tray 50.

The anchors in the present disclosure may share some or all of the features of the anchors disclosed in U.S. patent application Ser. No. 12/640,892 to Bae, et al. or U.S. patent application Ser. No. 13/328,592 to Bae, et al., which are incorporated by reference herein in their entirety.

Figure 26:
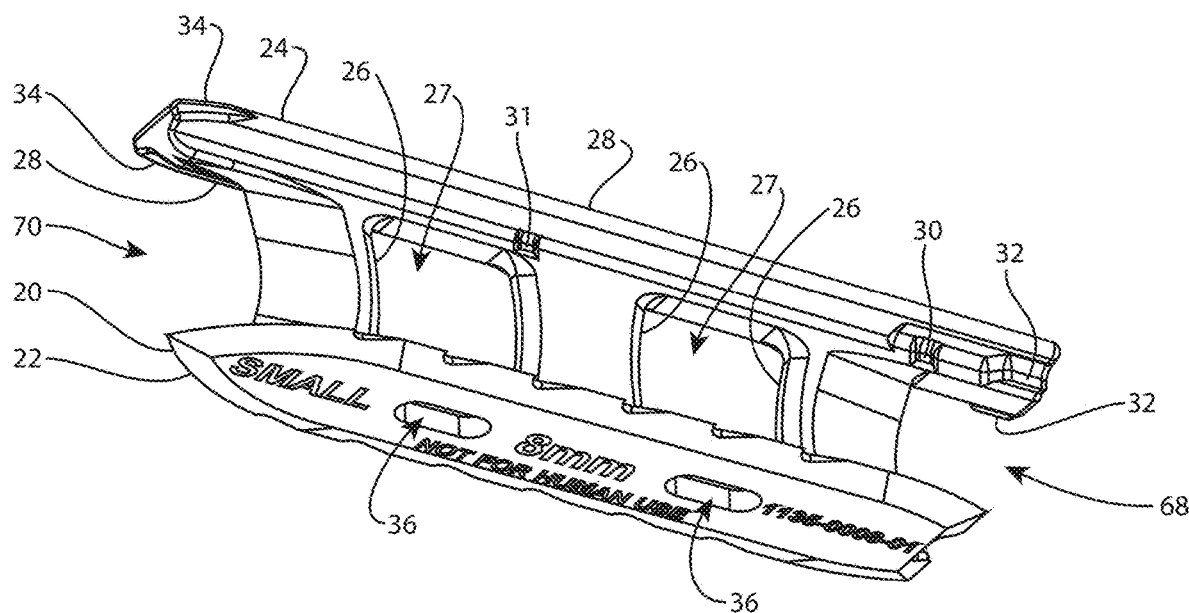
FIG. 26 is a perspective view of the fixation element of FIG. 1.

Referring mainly to FIGS. 26-36, each fixation element or anchor 20 comprises a blade 22 and a rail 24. The blade and rail extend between a leading end 70 and a trailing end 68 of the anchor. The leading end 70 may also be referred to as a distal end 70; the trailing end 68 may also be referred to as a proximal end 68. Supports 26 connect the blade 22 to the rail 24. FIG. 26 illustrates an anchor 20 with three supports 26, although other examples may include any number of supports. The supports 26 define apertures 27 through the anchor 20. In use, the blade 22 and at least a portion of the supports 26 may be inserted into bone which is adjacent to the bone-contacting side 56 of the tray 50. The blade 22 may be pointed, sharpened, and/or serrated, for ease of insertion into bone. The supports 26 may also be sharpened and/or obliquely profiled for ease of insertion into bone. The blade edges may be beveled. The blade 22 may be pierced by one or more apertures 36. Longitudinal edges 28 of the rail may be sized and shaped for complementary engagement with the dovetail channels 52 of the tray 50. In other examples, the rail may be of a complementary size and shape to engage another undercut channel geometry.

Figure 28:
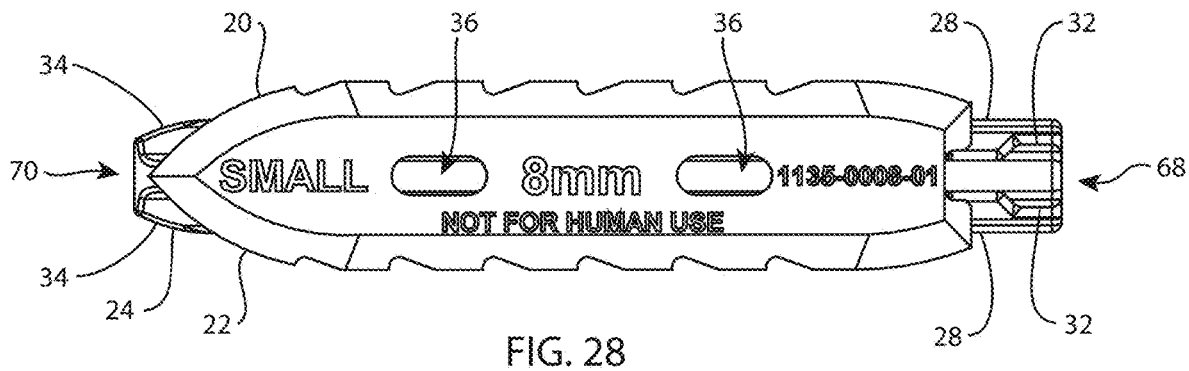
FIG. 28 is a bottom view of the fixation element of FIG. 1.
Figure 29:
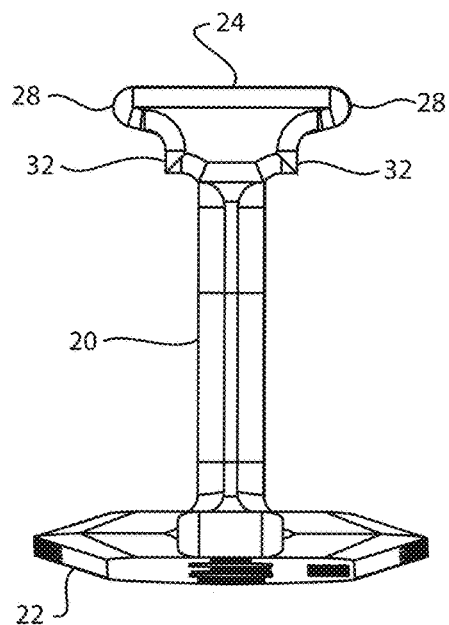
FIG. 29 is a right view of the fixation element of FIG. 1.
Figure 30:
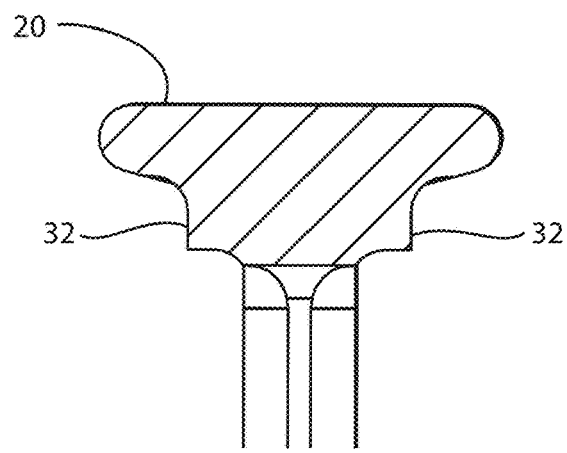
FIG. 30 is a cross-sectional view of the fixation element of FIG. 1 taken along line 11-11 of FIG. 9.
Figure 31:
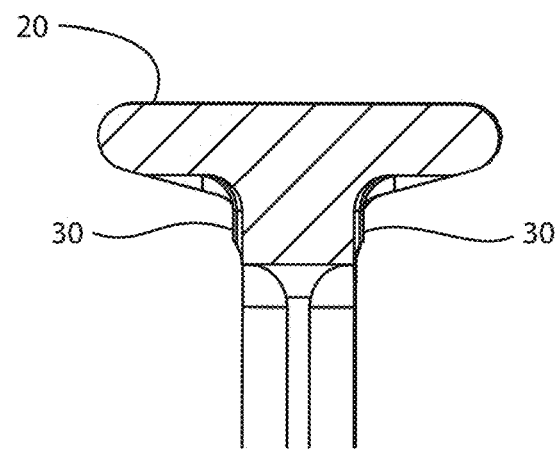
FIG. 31 is a cross-sectional view of the fixation element of FIG. 1 taken along line 12-12 of FIG. 9.
Figure 32:
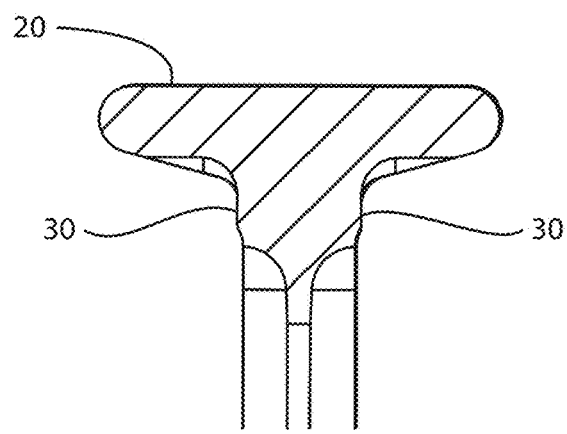
FIG. 32 is a cross-sectional view of the fixation element of FIG. 1 taken along line 13-13 of FIG. 9.
Figure 33:
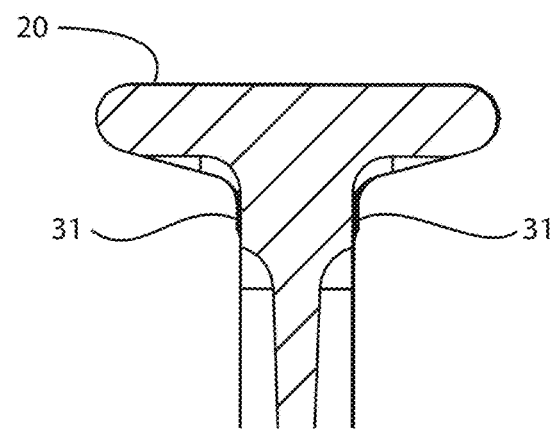
FIG. 33 is a cross-sectional view of the fixation element of FIG. 1 taken along line 14-14 of FIG. 9.
Figure 34:
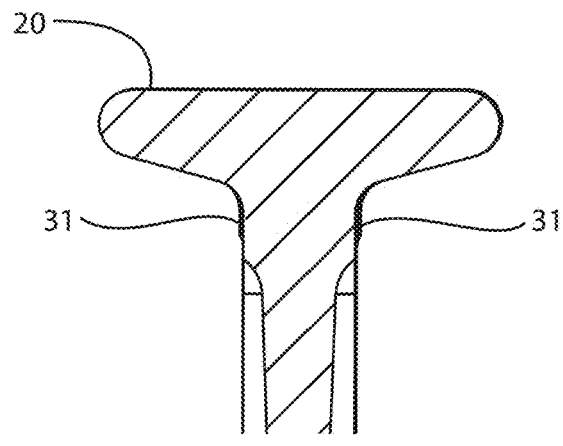
FIG. 34 is a cross-sectional view of the fixation element of FIG. 1 taken along line 15-15 of FIG. 9.
Figure 35:
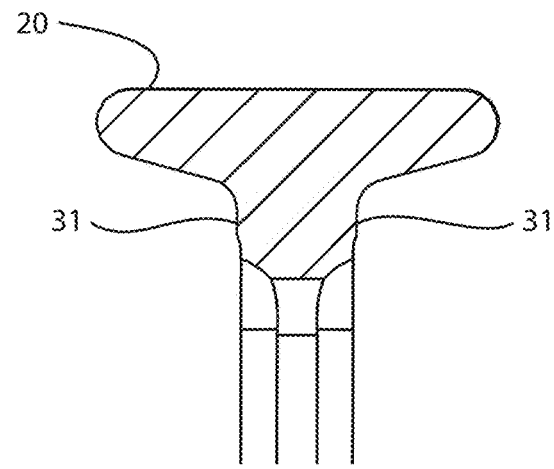
FIG. 35 is a cross-sectional view of the fixation element of FIG. 1 taken along line 16-16 of FIG. 9.
Figure 36:
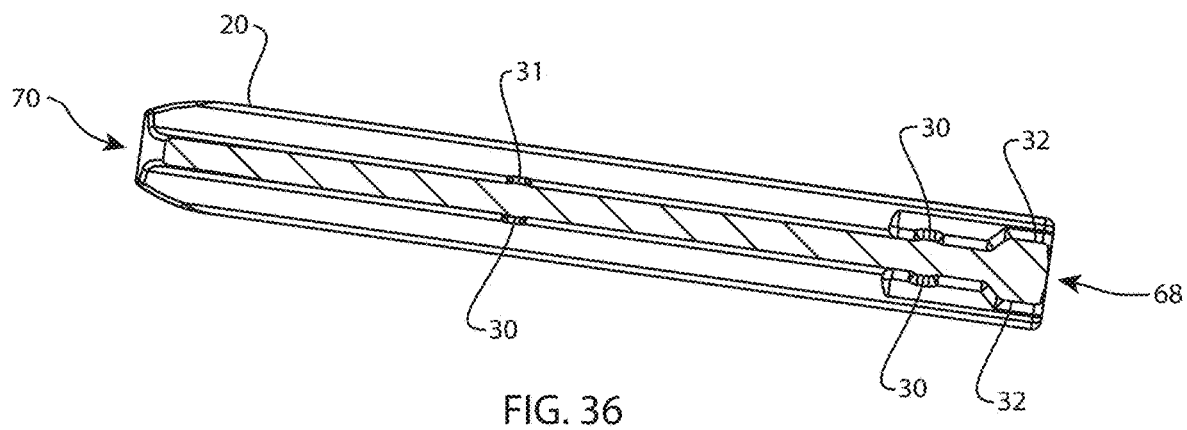
FIG. 36 is a cross-sectional view of the fixation element of FIG. 1 taken along line 17-17 of FIG. 9.
Figure 37:
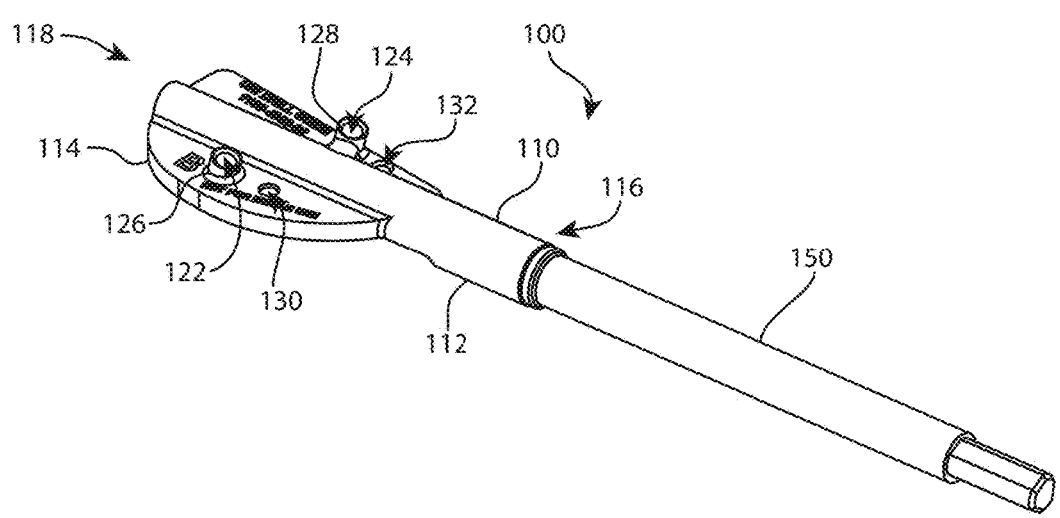
FIG. 37 is a perspective view of a unicondylar drill guide and a drill.
Figure 38:
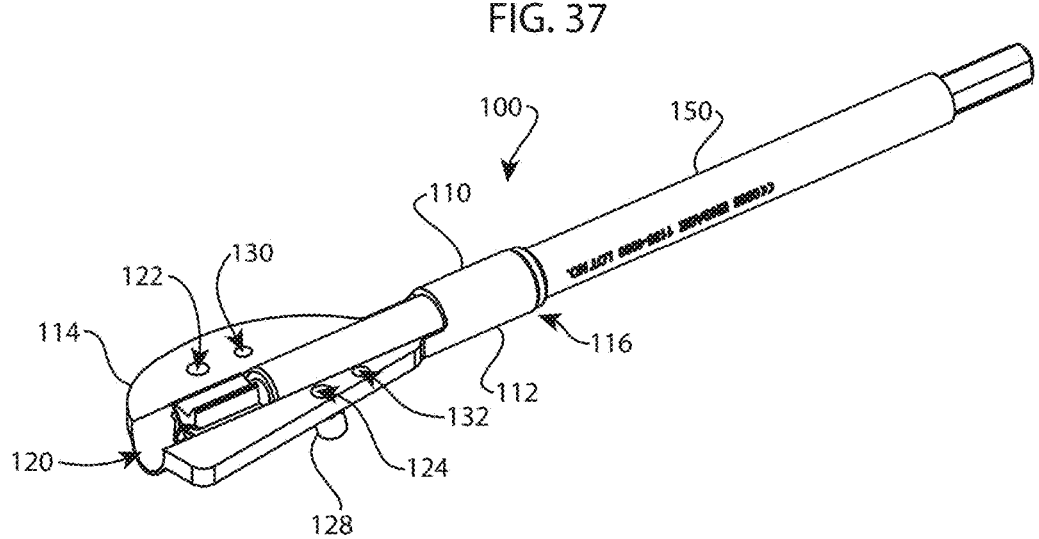
FIG. 38 is another perspective view of the drill guide and drill of FIG. 37.
Figure 39:
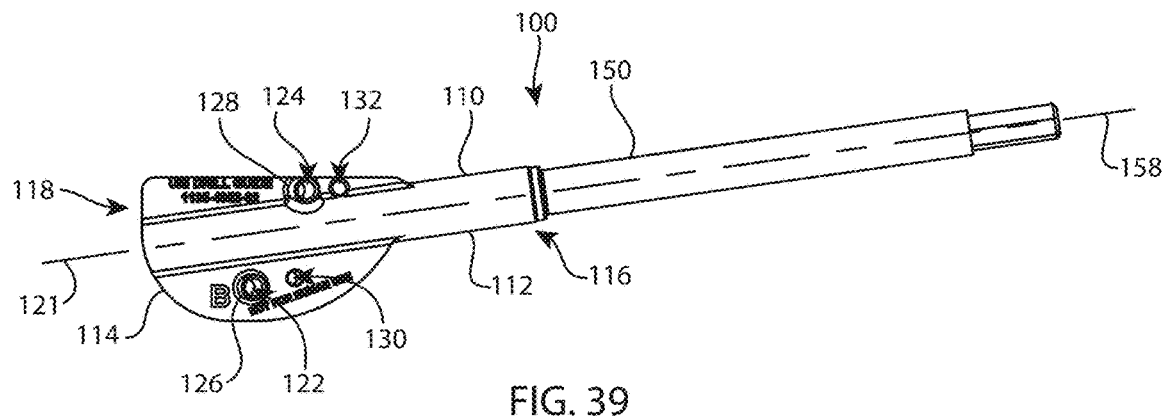
FIG. 39 is a top view of the drill guide and drill of FIG. 37.
Figure 40:
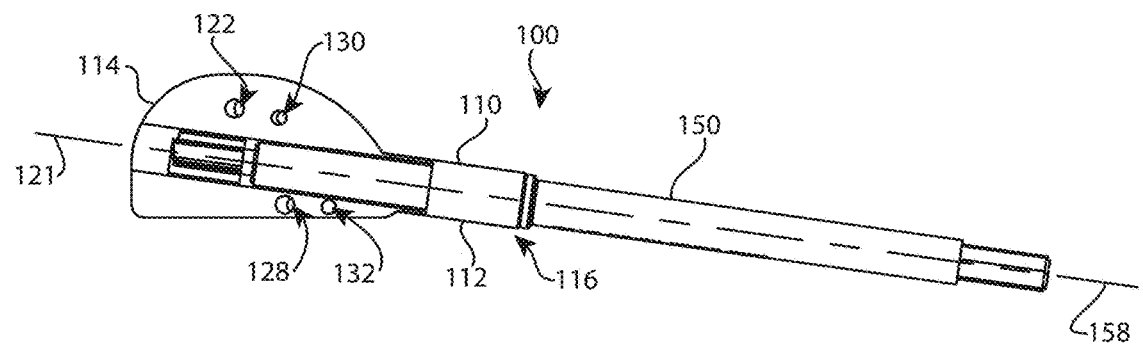
FIG. 40 is a bottom view of the drill guide and drill of FIG. 37.
Figure 41:
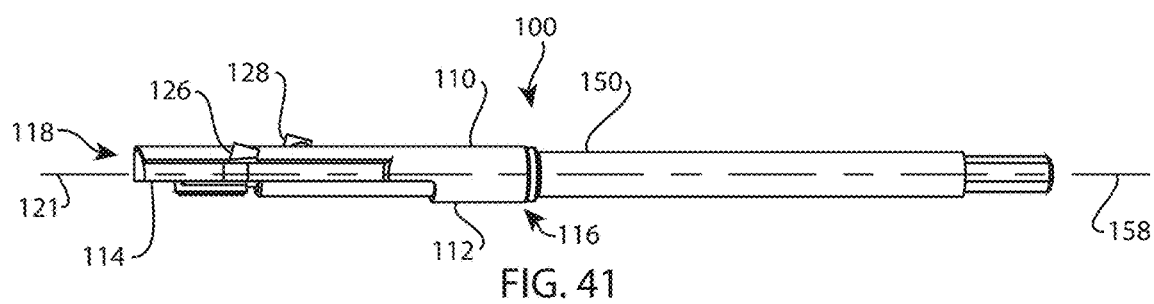
FIG. 41 is a front view of the drill guide and drill of FIG. 37.
Figure 42:
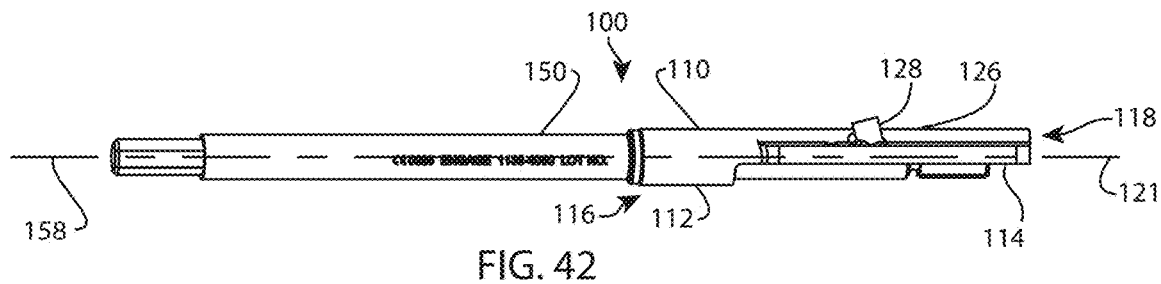
FIG. 42 is a back view of the drill guide and drill of FIG. 37.
Figure 43:
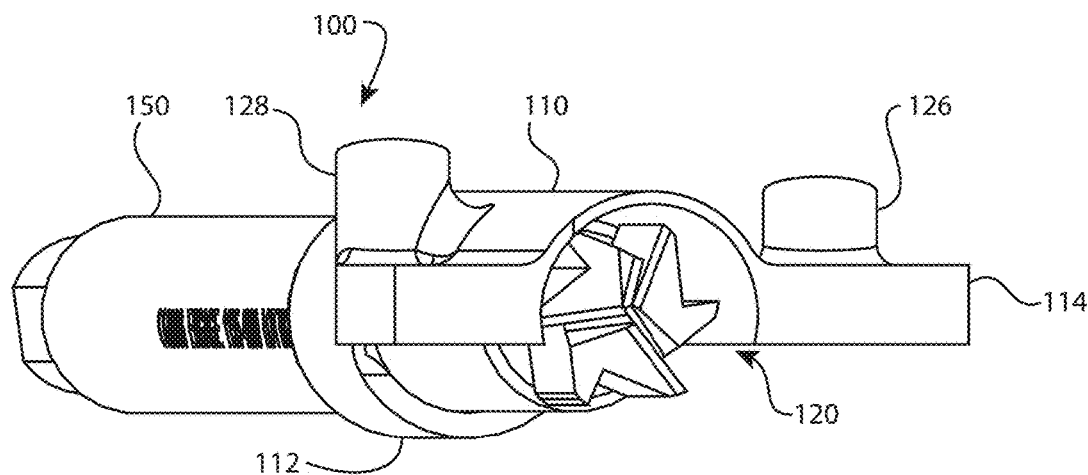
FIG. 43 is a left view of the drill guide and drill of FIG. 37.
Figure 44:
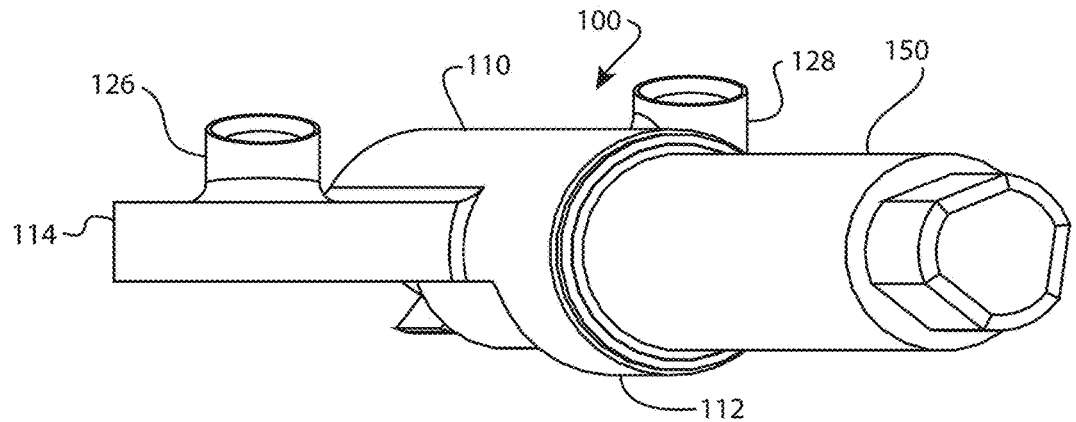
FIG. 44 is a right view of the drill guide and drill of FIG. 37.
Figure 45:
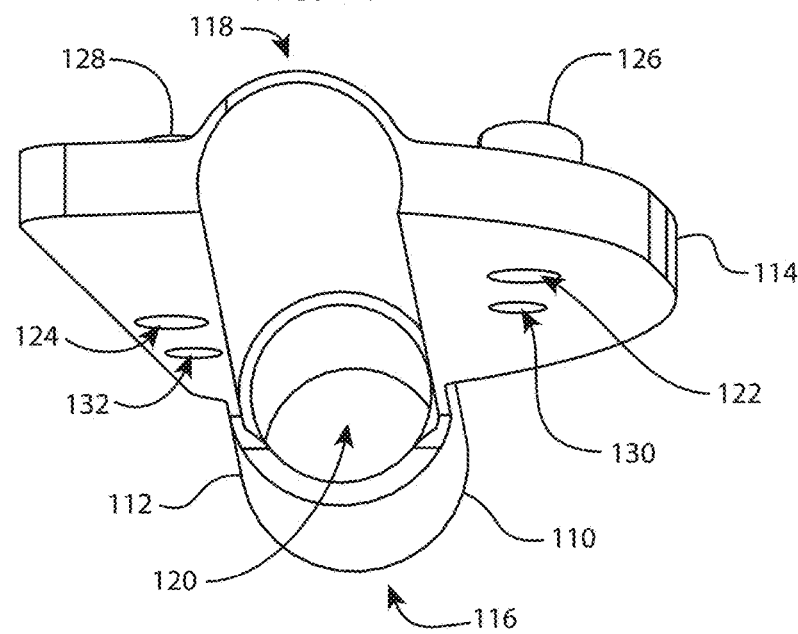
FIG. 45 is a perspective view of the drill guide of FIG. 37.

There may be a small tab 30 projecting from the rail 24. FIGS. 32 and 36 illustrate bilateral tabs. The tab may be said to protrude laterally or transversely from the rail 24. The tab deforms as the anchor is driven into the tibial tray 50, creating an interference fit. This material deformation serves to take up any relative motion between the anchor and the tibial tray as well as to lock the anchor 20 into the tray 50. The deformation may be characterized as plastic deformation, which may be at least partially irreversible. The deformation may cause galling, spot welding, and/or seizing to occur between the tab and the channel 52. Any of these adhesive phenomena may lock the anchor to the tray. There may be a physical stop 32 on the anchor to prevent overinsertion. FIGS. 28 and 29 illustrate bilateral stops. A distal tip 34 of the anchor rail may be tapered for ease of insertion into, and movement along, the channels 52. In FIGS. 26-36, physical stops 32 are located on each side of the rail 24 and extend distally from the proximal end 68. Tabs 30 are located on each side of the rail 24 near the proximal end 68, spaced apart distally from the physical stops 32. Another example may include a tab 30 on only one side of the rail. The illustrated example includes a second pair of bilateral interference tabs 31 located on each side of the rail 24 and spaced apart distally from the tabs 30. The tabs 31 are shown adjacent to a middle support 26, although they can be located anywhere along the rail 24 between the tabs 30 and the distal end 70. This arrangement may provide even greater fixation along the length of the anchor in the channel 52. Also, in other embodiments the length, height, or other dimensions of the anchor may vary.

To achieve optimal compression between the bone and the tibial tray, the anchor blade 22 may be angled divergent from the rail 24. At the leading, distal end 70 of the anchor 20, the blade 22 and the rail 24 may be farther apart than they are at the trailing, proximal end 68 of the anchor. The divergence angle 72 may be less than about 90 degrees. In some examples, the divergence angle may be less than about 15 degrees, less than about 5 degrees, or less than about 2 degrees. In the embodiment shown, the divergence angle between the blade 22 and the rail 24 is 1 degree. Divergence angles of less than 1 degree are also contemplated.

When the anchor rail 24 is inserted into the channel 52 of the tibial tray 50, the anchor blade 22 may diverge from an inferior or bone-contacting side 56 of the tray 50 at the same angle 72. Alternatively, the blade 22 may diverge from the inferior or bone-contacting side of the tray 50 at another angle, which may be greater than or less than the blade-to-rail divergence angle 72. Furthermore, the blade-to-tray divergence angle may open in the same or opposite direction as the blade-to-rail divergence angle 72.

The angle 72 between the blade 22 and the rail 24, and/or the angle between the blade and the bone-contacting side 56 may correlate to the mechanical properties of the bone into which the anchor 20 will be inserted, the desired amount of compression between the bone and the bone-contacting side, the compliance of the bone-contacting side, and/or other factors. For example, larger divergence angles may be appropriate for conditions such as: softer bone, greater compression, and/or a compliant bone-contacting side; smaller divergence angles may be appropriate for conditions such as harder or stiffer bone, less compression, and/or an unyielding bone-contacting side. The divergence angle may also correlate to the length of the anchor 20, with greater divergence angles possible with shorter anchors and smaller divergence angles suitable for longer anchors.

Figure 4:
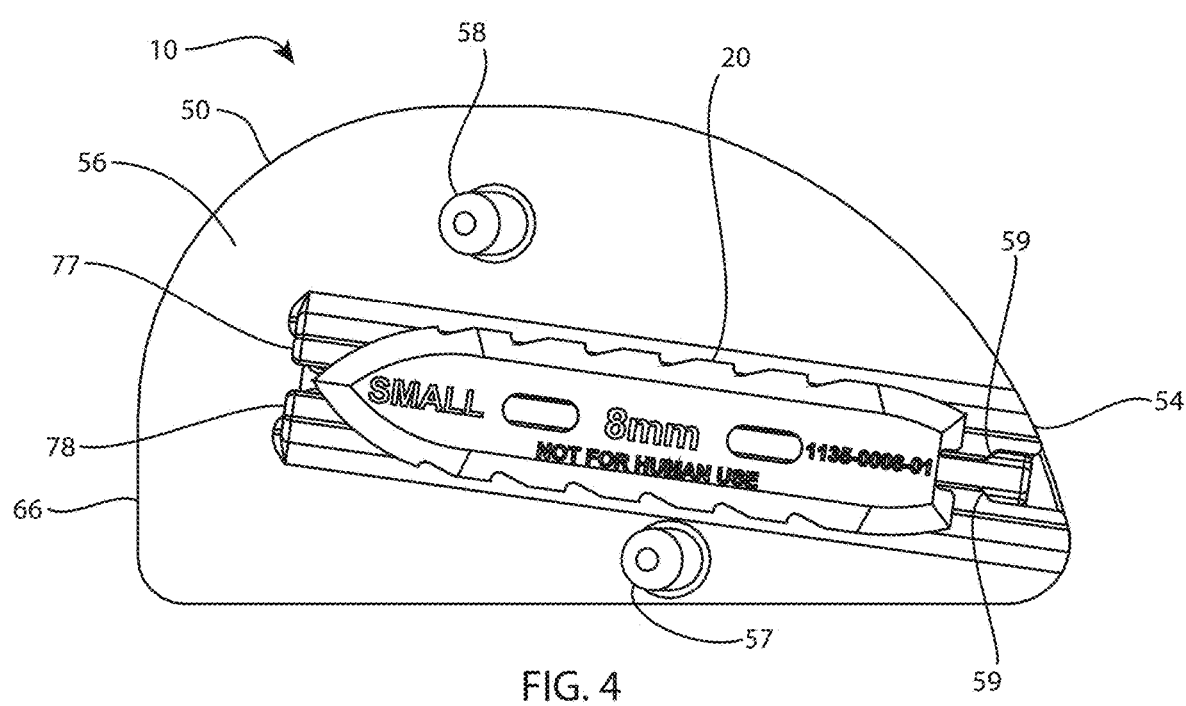
FIG. 4 is a bottom view of the tibial tray and fixation element of FIG. 1.
Figure 5:
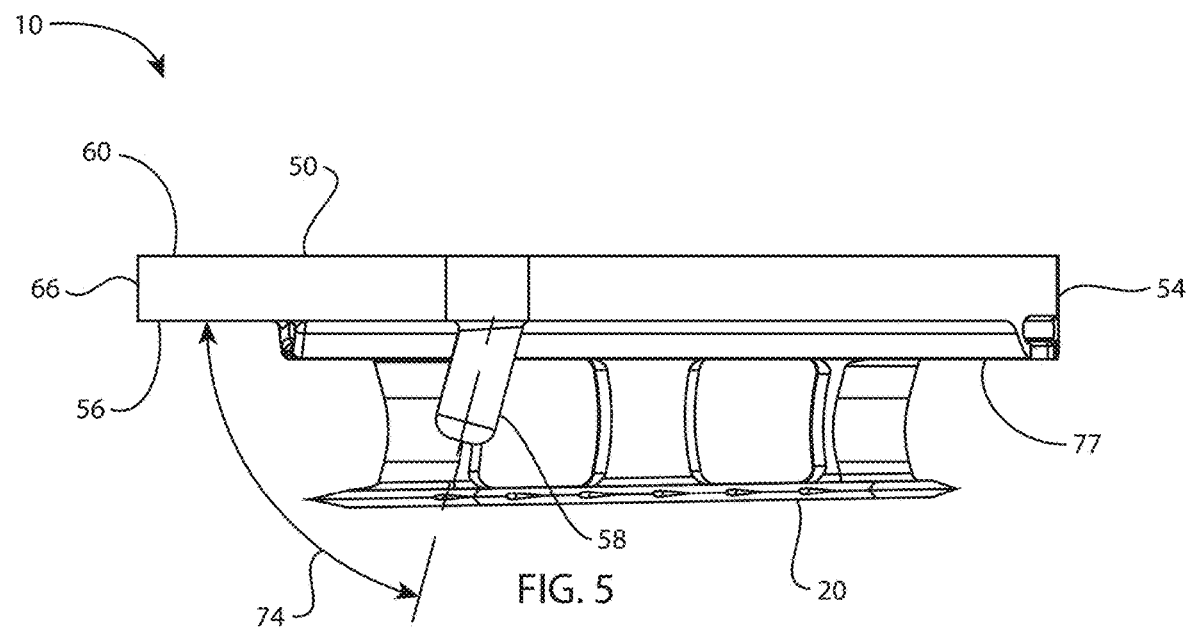
FIG. 5 is a front view of the tibial tray and fixation element of FIG. 1.
Figure 6:
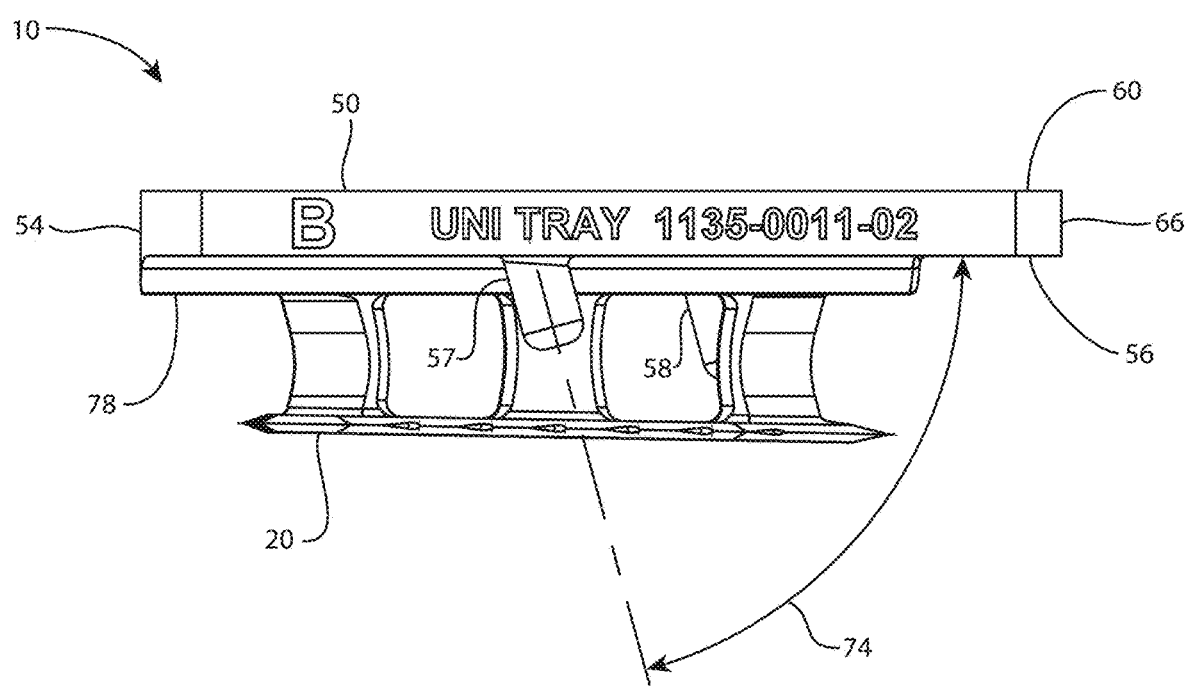
FIG. 6 is a back view of the tibial tray and fixation element of FIG. 1.
Figure 7:
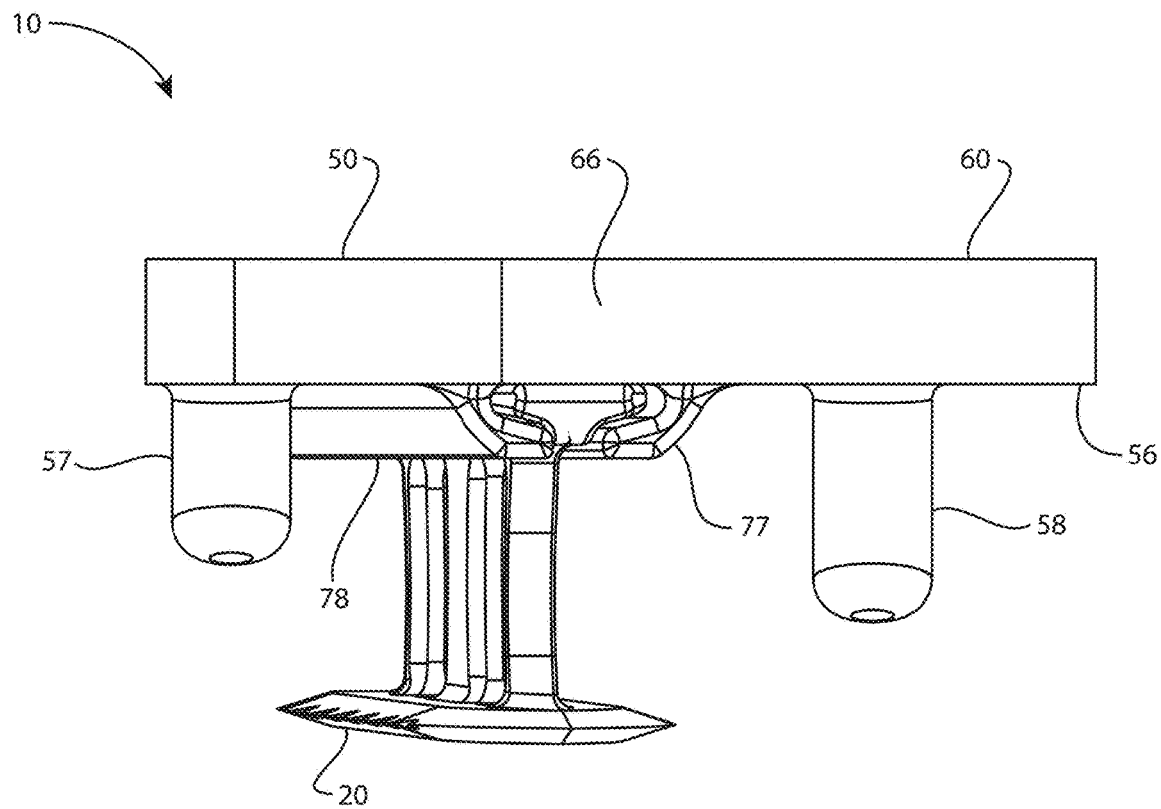
FIG. 7 is a left view of the tibial tray and fixation element of FIG. 1.
Figure 8:
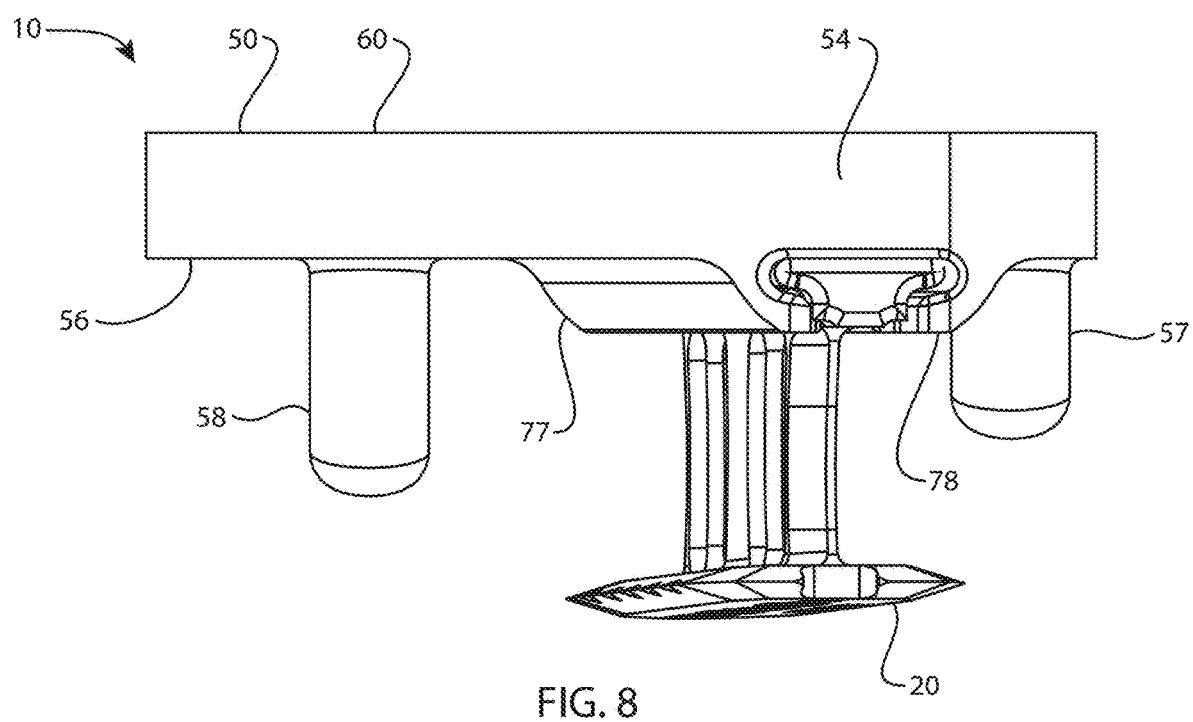
FIG. 8 is a right view of the tibial tray and fixation element of FIG. 1.
Figure 9:
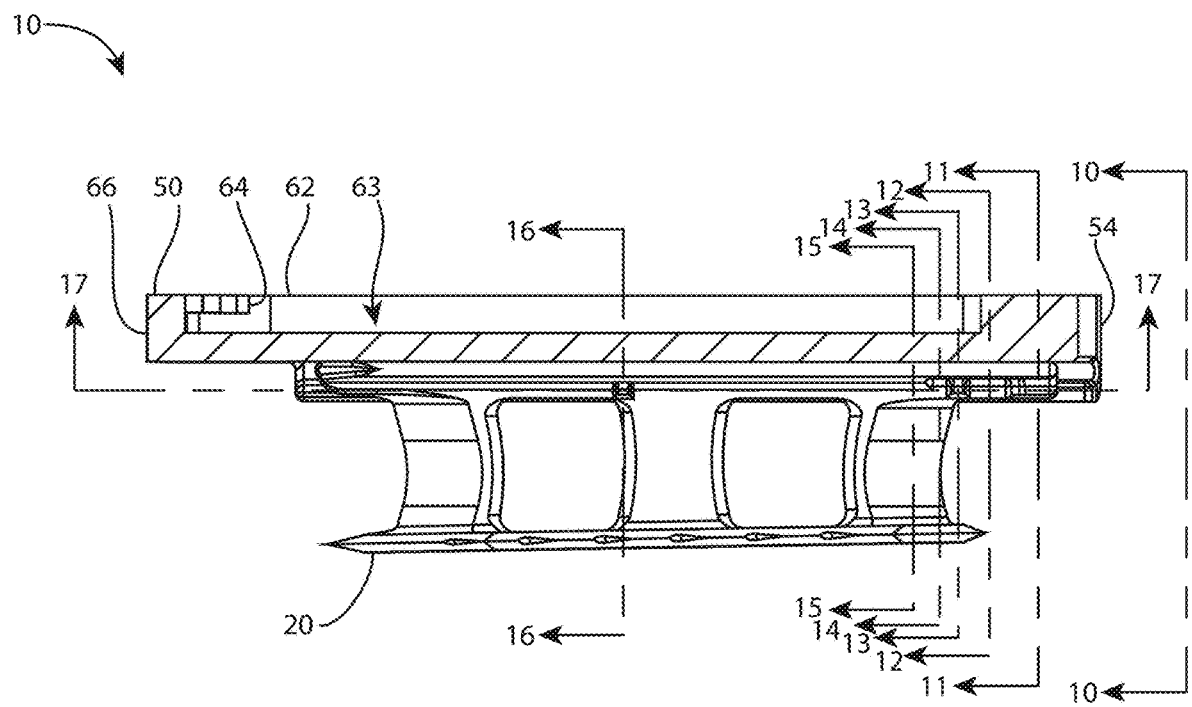
FIG. 9 is an auxiliary view of the tibial tray and fixation element of FIG. 1 perpendicular to a plane of symmetry along the length of the fixation element, the tibial tray shown in cross section taken through the plane of symmetry of the fixation element.
Figure 10:
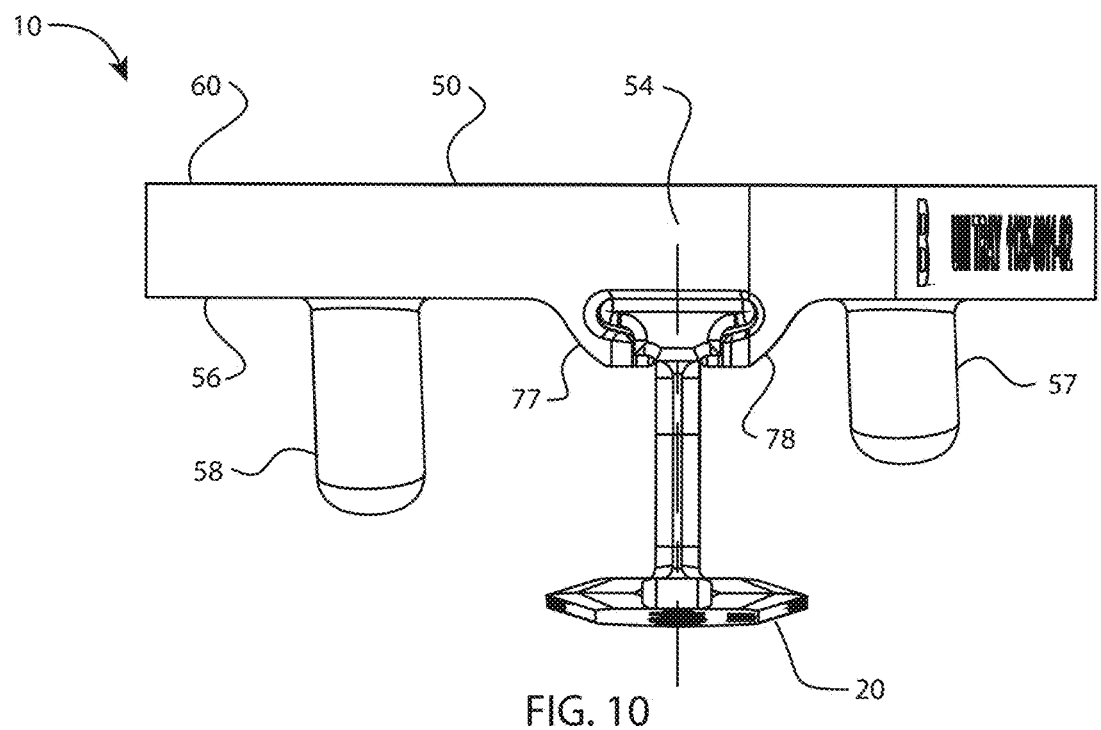
FIG. 10 is another auxiliary view of the tibial tray and fixation element of FIG. 1 taken along line 10-10 of FIG. 9 parallel to the plane of symmetry of the fixation element.
Figure 11:
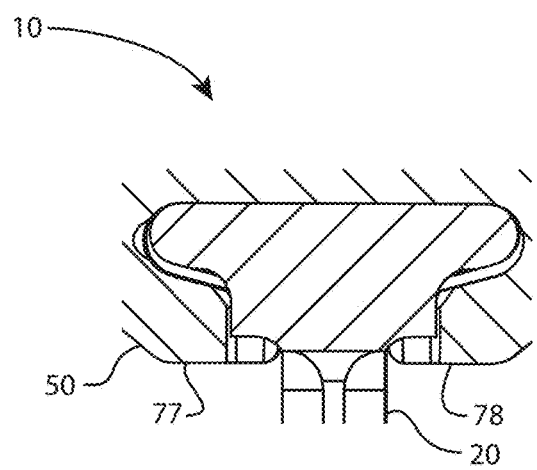
FIG. 11 is a cross-sectional view of the tibial tray and fixation element of FIG. 1 taken along line 11-11 of FIG. 9.
Figure 12:
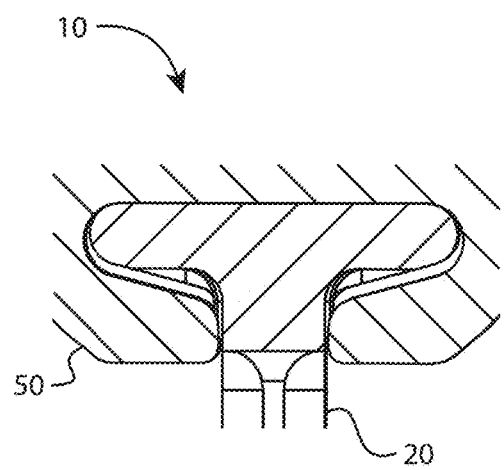
FIG. 12 is a cross-sectional view of the tibial tray and fixation element of FIG. 1 taken along line 12-12 of FIG. 9.
Figure 13:
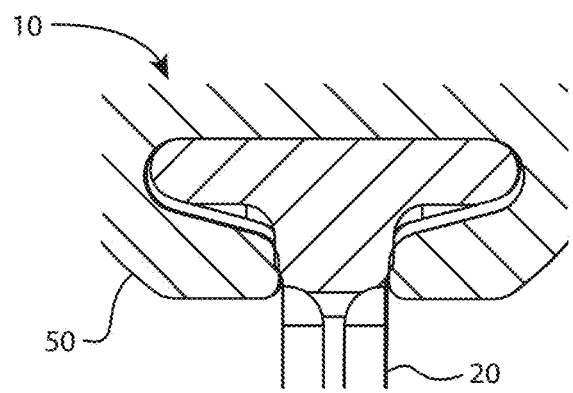
FIG. 13 is a cross-sectional view of the tibial tray and fixation element of FIG. 1 taken along line 13-13 of FIG. 9.
Figure 14:
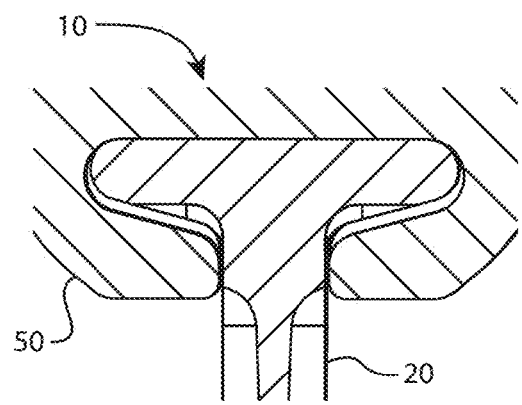
FIG. 14 is a cross-sectional view of the tibial tray and fixation element of FIG. 1 taken along line 14-14 of FIG. 9.
Figure 15:
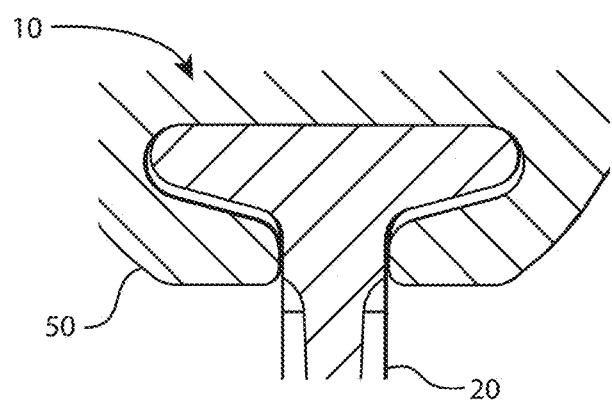
FIG. 15 is a cross-sectional view of the tibial tray and fixation element of FIG. 1 taken along line 15-15 of FIG. 9.
Figure 16:
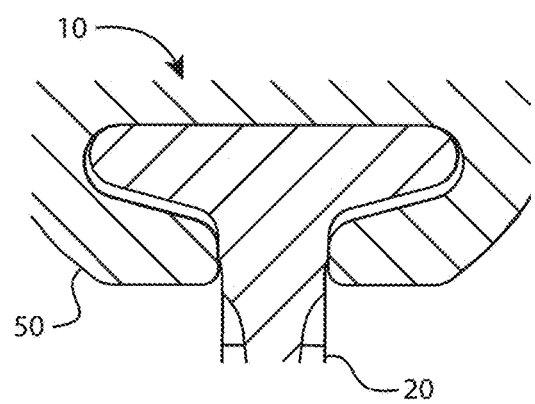
FIG. 16 is a cross-sectional view of the tibial tray and fixation element of FIG. 1 taken along line 16-16 of FIG. 9.
Figure 17:
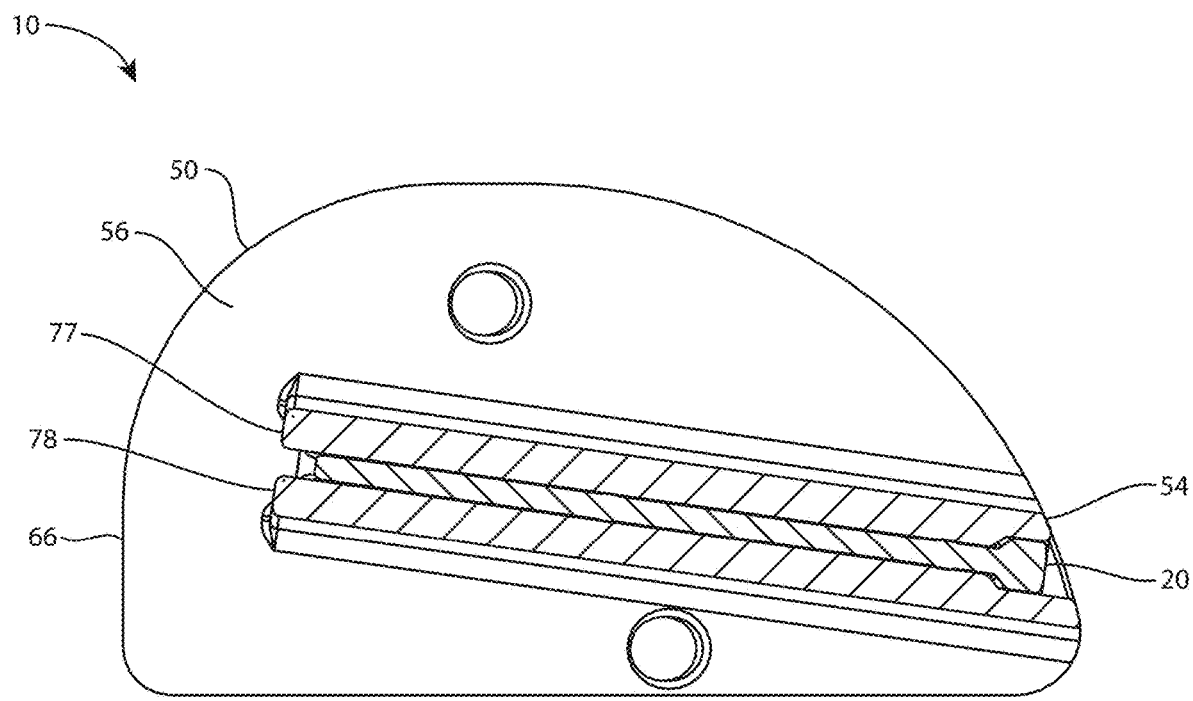
FIG. 17 is a cross-sectional view of the tibial tray and fixation element of FIG. 1 taken along line 17-17 of FIG. 9.

Referring mainly to FIGS. 1-8, 10 and 19-25, the tibial tray 50 includes a bone-contacting, or inferior side 56 across which the channel 52 extends. A ridge 76 extends across the bone-contacting side 56 to provide material within which to form the channel 52. In this example, the entire channel 52 is outside the main body of the tibial tray 50, as seen best in FIGS. 22-24. In other words, the most proximal surface 53 within the channel is flush with or distal to the inferior side 56. Surface 53 may be referred to as the bottom surface of the channel. The channel 52 is thus defined between first and second walls 77, 78. At one end of each channel 52, shoulders 59 are formed in the edges of the channels 52. The shoulders 59 are illustrated as being formed in interior edges of the channel near the anterior edge 54 of the tibial tray 50. As seen in FIG. 4, when the anchor rail 24 is inserted through the channel, the shoulders 59 deform the tabs 30 and engage with the stops 32 to provide the interference fit between the anchors 20 and the tray 50, and to properly position the anchors at the correct depth relative to the tray. A peg 58 or post provides further fixation of the tray 50 in the tibia. The illustrated example includes a second peg 57 or post; any number of pegs may be present. The pegs 57, 58 protrude from the bone-contacting side 56 and form an angle 74 with the bone-contacting side. The angle 74 may be up to 90 degrees; a 75 degree angle 74 is illustrated for both pegs 57, 58. The pegs extend in an inferior-posterior direction from the bone-contacting side 56, although the pegs may extend in other directions as a matter of design choice.

The tibial tray 50 further includes a joint-facing, or superior side 60 to which an articular insert (not shown) may be mounted, or the joint-facing side 60 may include a prosthetic articular surface integrally formed with the tibial tray 50. A raised rim 62 encompasses the superior side 60, and overhangs 64 are formed on a portion of the rim 62 for engagement with an articular insert and/or instruments. The rim 62 and overhangs 64 together define a recess 63 that may receive an articular insert, and may also engage an anchor guide instrument (not shown). The articular insert or instrument may engage under the overhangs 64 to be held rigidly in the tray 50, for example by a snap fit. Tibial tray 50 may be described as a unicondylar tibial component because it is adapted to extend across a single resected tibial condyle to replace the medial or lateral condyle.

In other embodiments, the features of the tibial tray 50 may vary. For example, the peg 58 or other fixation features may vary; the size and thickness of the tray 50 may vary, the outer peripheral size and shape may vary. Different connection features for engagement with an articular insert may be incorporated. Other features of tibial trays known in the art may be included as desired. The articular insert may carry the prosthetic articular surface.

Figures 48, 49:
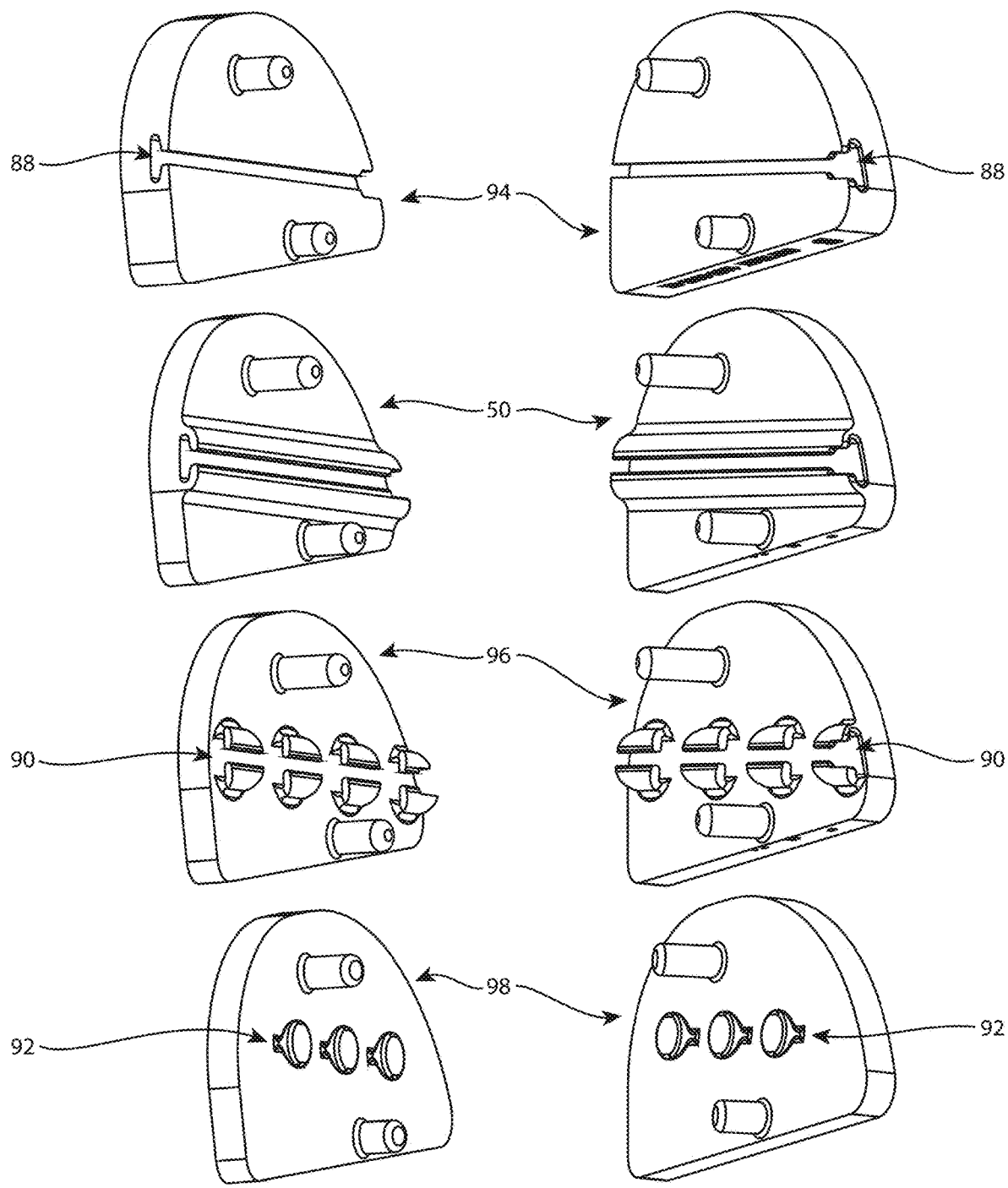
FIG. 48 is a left view of various embodiments of tibial trays.
FIG. 49 is a right view of various embodiments of tibial trays.

Referring to FIGS. 48-49, examples of other embodiments of the tray are shown with tibial tray 50. Tibial tray 94 includes a continuous channel 88 that is recessed entirely within the body of the tibial tray. Tibial tray 94 may share some or all of the features of the tibial tray 310 disclosed in U.S. patent application Ser. No. 13/328,592 to Bae, et al. Tibial tray 96 includes a channel 90 that includes a series of discrete channel elements within discrete ridges, or between discrete wall sections. A linear array of ridges or walls is shown. Channel 90 extends along the bone-contacting surface outside the main body of the tibial tray like channel 52. Tibial tray 98 is an example in which the negative feature of the channel is replaced by a positive connection feature 92 that includes a series of discrete connection elements, which may be referred to as posts or buttons. Not shown, the fixation element corresponding to tray 98 carries a negative feature, a channel, that is complementary to the positive connection feature 92. As in the other embodiments disclosed herein, the posts and channel may be complementary undercut shapes.

Referring to FIGS. 37-47, a guide and drill assembly 100 includes a tibial drill guide 110 and a reamer 150. The tibial drill guide 110 corresponds to the tibial tray 50. The reamer 150 is sized to correspond to the ridge 76.

Referring mainly to FIGS. 37-45, the tibial drill guide 110 includes a shaft 112 and a body 114. The shaft 112 extends between a proximal end 116 and a distal end 118 and includes a central longitudinal axis 121 and a central longitudinal hole 120 that extends entirely through the tibial drill guide 110. The body 114 corresponds to the main body of the tibial tray 50, and may be said to mimic or replicate the main body of the tibial tray 50, the perimeter of the main body, or the bone-contacting side 56. The body 114 is coupled to the distal end 118 of the shaft 112 so that the axis 121 and hole 120 are located to correspond to the height and width of the ridge 76 as viewed in FIG. 10. The body 114 includes holes 122, 124 which correspond to the pegs 58, 57, respectively, of the tibial tray 50. The holes 122, 124 may be defined by optional bosses 126, 128, respectively, to extend the length of the holes 122, 124 and/or to provide depth stops for greater accuracy in drilling holes for the pegs 58, 57. The holes 122, 124 receive a drill (not shown) sized according to the outer diameter of the pegs 58, 57. The body 114 also includes holes 130, 132 which receive bone pins (not shown) or other fasteners to secure the tibial drill guide 110 to the tibia in use.

Figure 46:
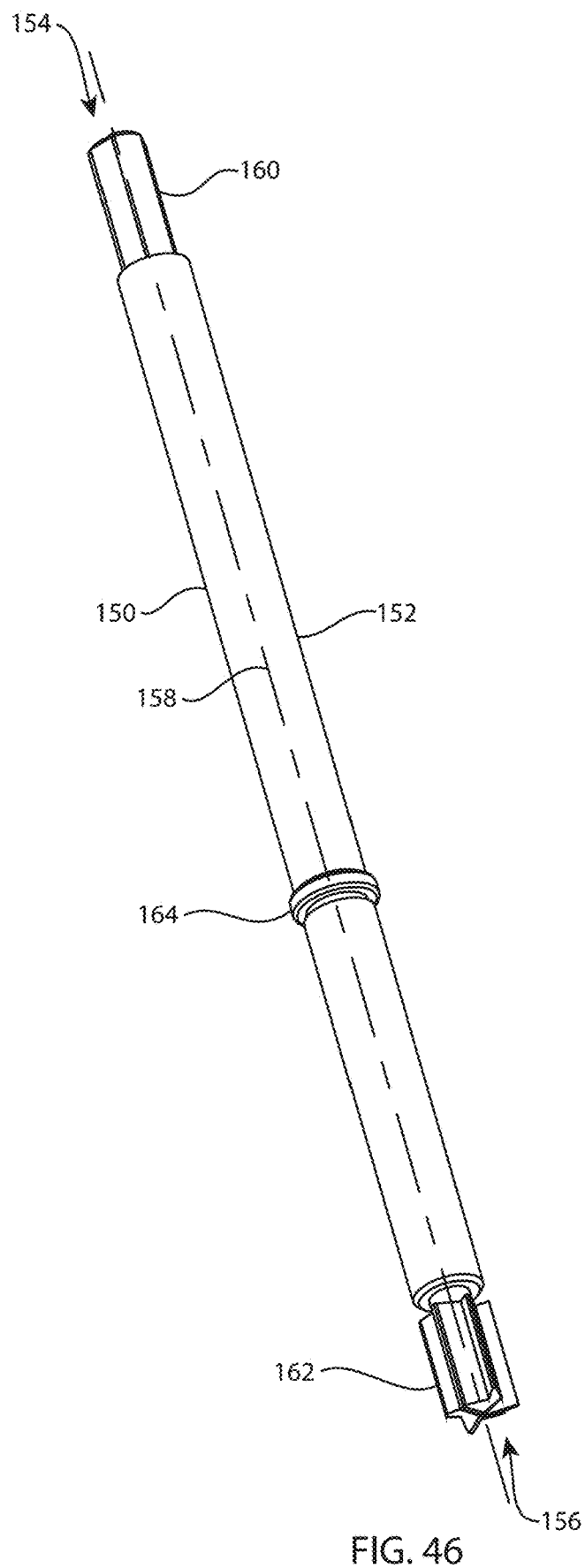
FIG. 46 is a perspective view of the drill of FIG. 37.
Figure 47:
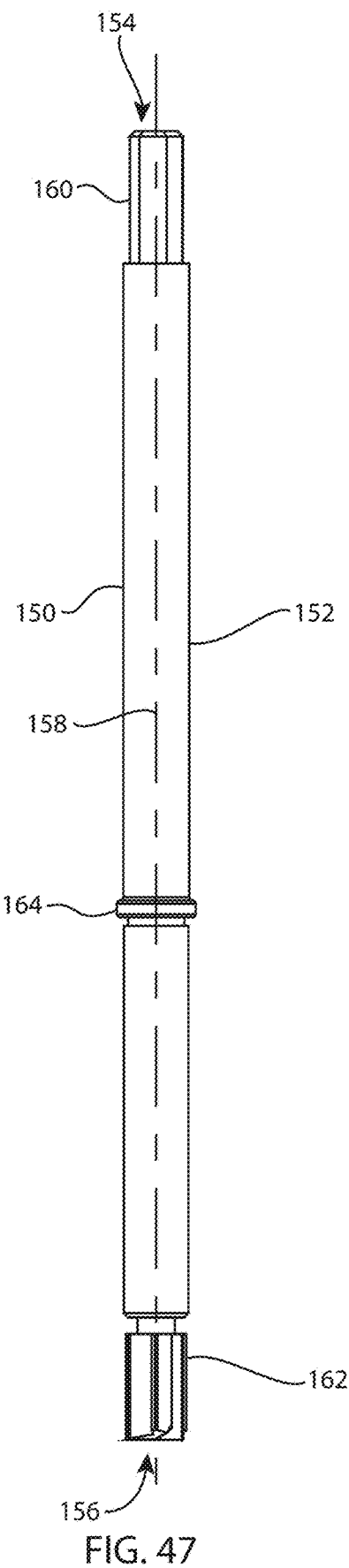
FIG. 47 is a top view of the drill of FIG. 37.

Referring mainly to FIGS. 46-47, the tibial reamer 150 includes a shaft 152 that extends between a proximal end 154 and a distal end 156 and includes a central longitudinal axis 158 about which the reamer 150 rotates in use. The proximal end 154 includes a torque drive feature 160, such as a hex key or three equilateral flats. The distal end 156 includes a cutting section 162 that may be side-cutting, end-cutting, or both. Between the torque drive feature 160 and the cutting section 162, an optional flange 164 encircles the shaft 152 to serve as a depth stop against the proximal end 116 of the shaft 112 of the tibial drill guide 110. The distance between the cutting section 162 and the flange 164 may be related to the overall length of the tibial drill guide along the axis 121 so that the cutting section 162 is prevented from extending distally across the body 114 past the end of the ridge 76. The outer diameter of the cutting section 162, as well as the outer diameter of the shaft 152 distal to the flange 164, are sized to fit in the hole 120 of the shaft 112 of the tibial drill guide 110. The outer diameter of the flange 164 is larger than the hole 120.

When the cutting section 162 is inserted into the hole 120 and advanced to be adjacent to the body 114, a portion of the cutting section 162 is exposed on the bone-contacting side of the body 114 and protrudes outwardly from the bone-contacting side of the body 114. When the bone-contacting side of the body 114 is placed against a resected bone surface, the reamer 150 is actuated (rotated about axis 158), and the reamer 150 is moved distally and proximally within the hole 120, the cutting section 162 cuts a groove across the resected bone surface that is deep enough, wide enough, and long enough to receive the ridge 76 of the tibial tray 50. The groove may receive the ridge 76 with clearance, with a line-to-line fit, or with interference (a press fit).

In a method of use, a tibia proximal end is prepared to receive the tibial tray 50. A transverse resection may be made to remove the medial or lateral proximal tibial articular cartilage. Recesses for a tray peg 58 and/or 57 may be reamed, drilled, broached, cut or otherwise prepared. The tibial tray 50 is fit onto the prepared tibia, and may be implanted with or without cement. An anchor 20 is inserted into the channel on the tray. The blade may cut into the bone as the anchor is inserted. As the anchor is inserted, the angled configuration of the anchor causes compression of the tray toward the tibia; i.e., the tray is pulled toward the tibia. The tabs, stops, and shoulders on the tray and the anchor cooperate to seat the anchor at the proper depth relative to the tray, and prevent unintentional withdrawal of the anchor. An articular insert (not shown) may be coupled to the superior surface of the tray 50, and may include an articular surface.

Figure 27:
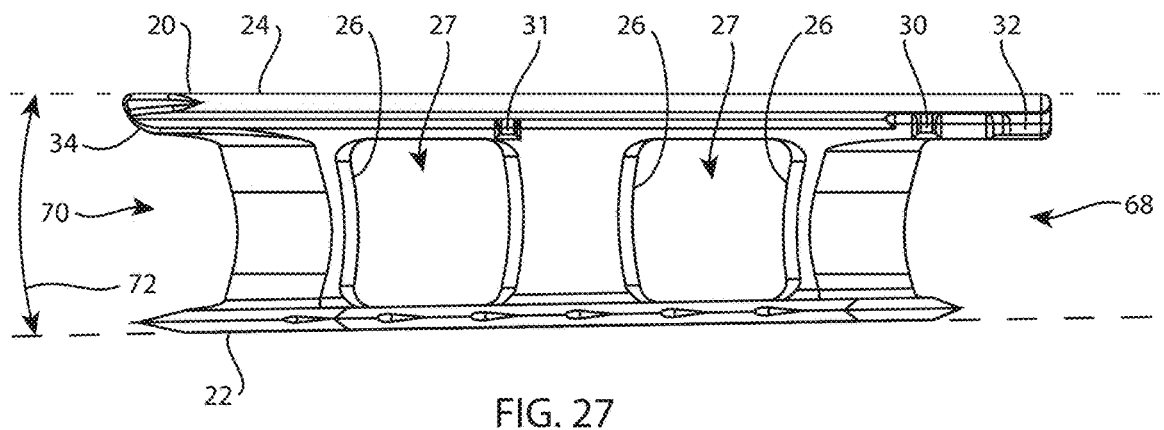
FIG. 27 is a front view of the fixation element of FIG. 1.

Referring to FIG. 27, it can be appreciated that the act of inserting anchor 20 into channel 52 and adjacent bone may be described as a sequence of events. The leading end 70 is configured so that the rail 24 and the blade 22 are the leading features, and are thus the first features to engage the channel or bone. The leading point of the blade 22 penetrates the bone. The leading support 26 is the next feature to engage, as it enters the channel and the bone. The support may be said to protrude through the bone-contacting surface, since the support extends through the open side of the channel. All leading edges of the support and blade are sharpened and obliquely oriented to reduce the effort necessary to cut through the bone.

Figure 50:
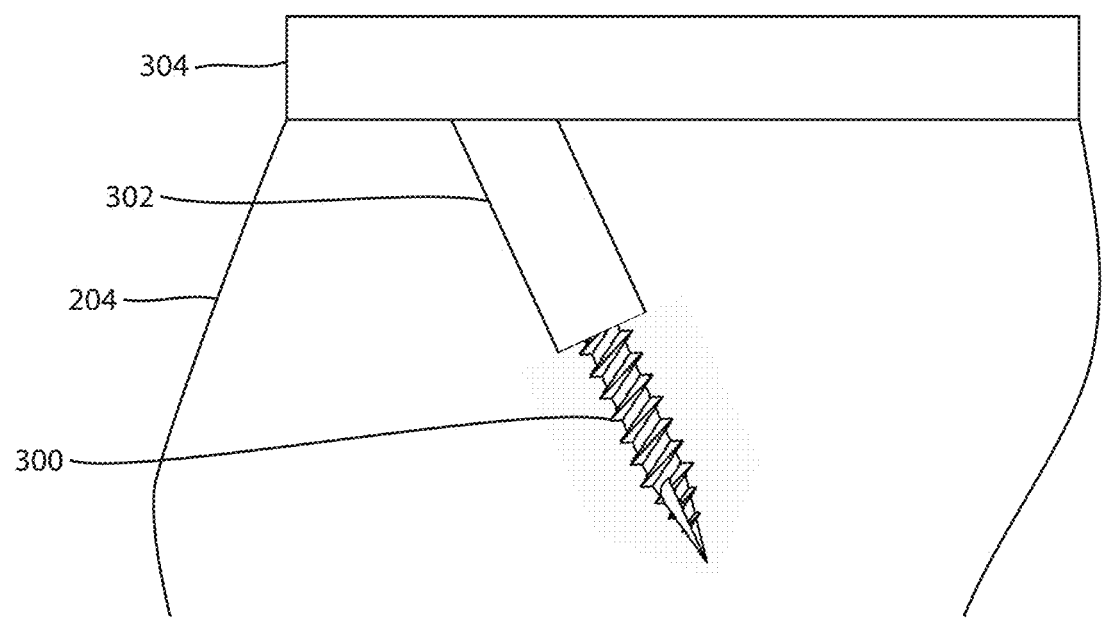
FIG. 50 is a side view of a tibial tray and bone screw implanted on a proximal tibia.

Referring to FIG. 50, a medial/lateral view of a proximal tibia 204 is shown. A bone screw 300 is shown extending through a peg 302 of a tibial tray 304 and into the proximal tibia 204.

Figure 51:
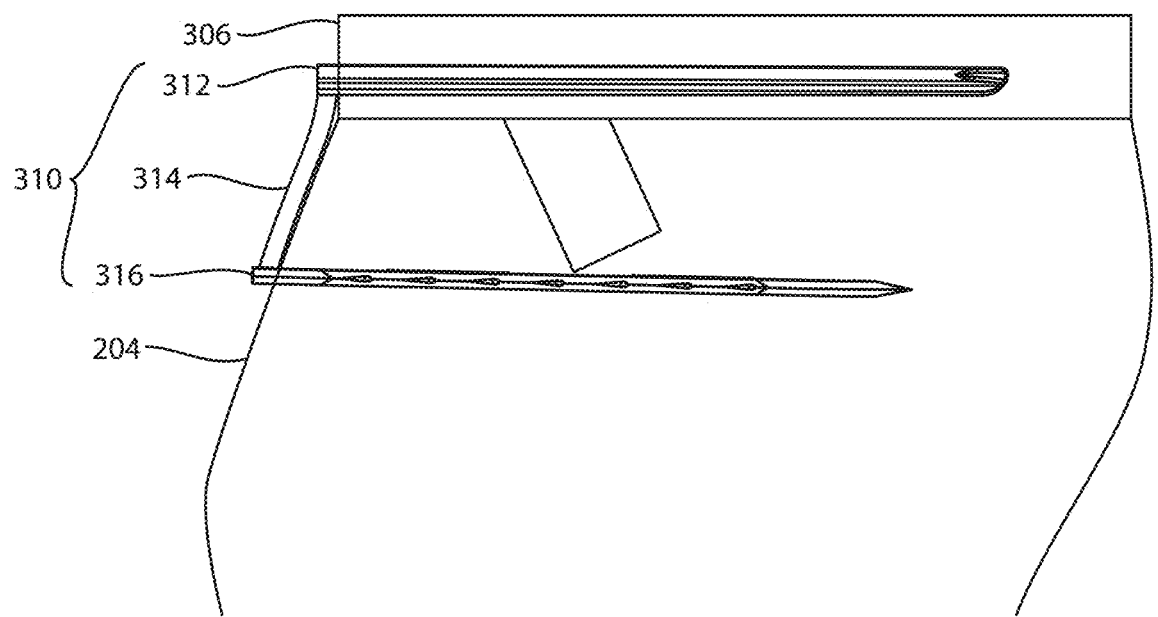
FIG. 51 is a side view of a tibial tray and fixation element implanted on a proximal tibia.

Referring to FIG. 51, a medial/lateral view of the proximal tibia 204 is shown. A tibial tray 306 with a peg 308 is shown implanted on the proximal end of the tibia 204. A fixation element 310 is connected to the tibial tray 306. The fixation element 310 includes a rail 312, a support 314, and a blade 316. The rail 312 engages an undercut channel of the tibial tray 306. The support 314 in this example is exterior to the tibia 204; the support may contact the tibia, but does not cut through the bone in the manner described for previous fixation elements. The blade 316 extends into the tibia 204 beside the tibial tray 306 in the manner described for previous fixation elements. The blade 316 may optionally engage the peg 308.

Referring to FIGS. 52-68, 77-96, and 112-144, a femoral implant 320, an insert implant 322 or tibial articular insert, five tibial trays 324, 326, 328, 330, 332, and eleven fixation elements 336-354 (even numbers) are disclosed. The femoral implant 320 and insert implant 322 may be used with any of the tibial trays and fixation elements. While the disclosed apparatus is adapted for unicondylar knee arthroplasty, it may be modified for bicondylar knee arthroplasty or arthroplasty of other joints.

Figure 52:
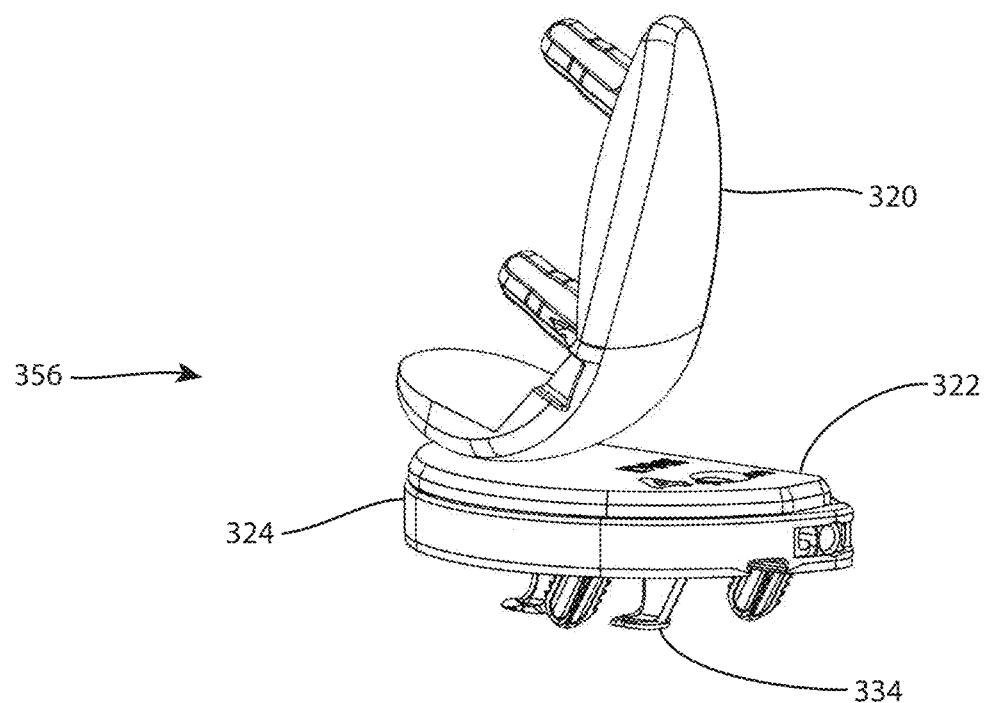
FIG. 52 is an oblique view of a unicompartmental implant construct.
Figure 53:
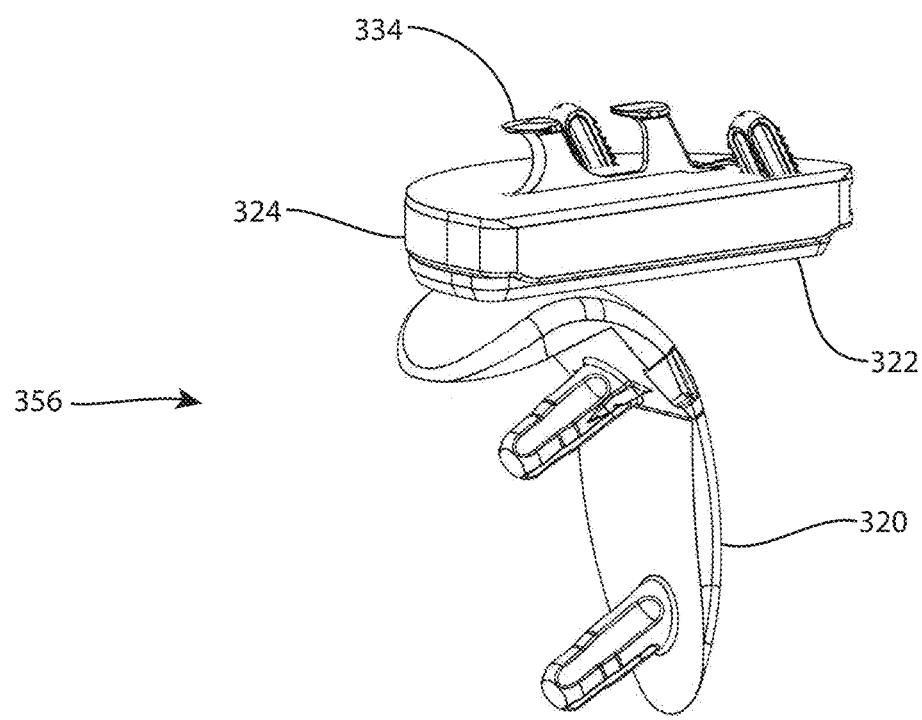
FIG. 53 is another oblique view of the unicompartmental implant construct of FIG. 52 from a different direction.

Referring to FIGS. 52-68, the femoral implant 320, insert implant 322, tibial tray 324, and fixation element 334 are shown arranged as if implanted in a knee joint in 90° of flexion. Any two of these components, taken together, may be referred to as a system 356 or prosthesis for arthroplasty. FIGS. 52-53 show the fixation element 334 in an implanted state.

Figure 56:
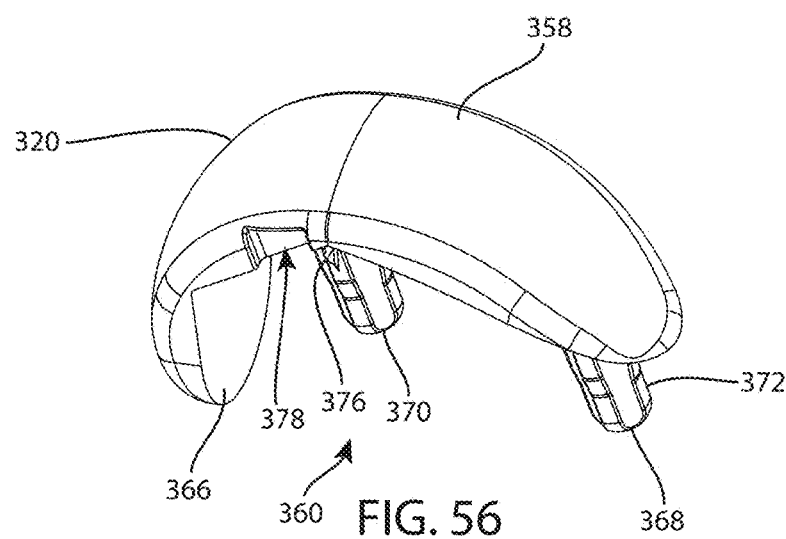
FIG. 56 is yet another oblique view of the femoral component of FIG. 54 from another different direction.
Figure 57:
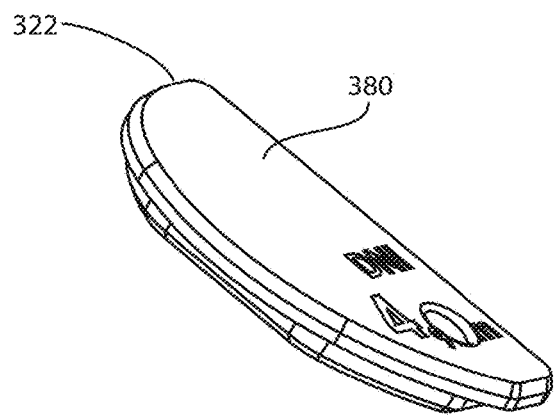
FIG. 57 is an oblique view of a tibial articular component of the unicompartmental implant construct of FIG. 52.
Figure 58:
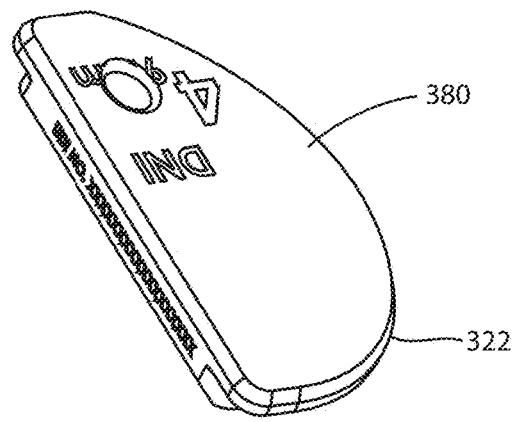
FIG. 58 is another oblique view of the tibial articular component of FIG. 57 from a different direction.
Figure 59:
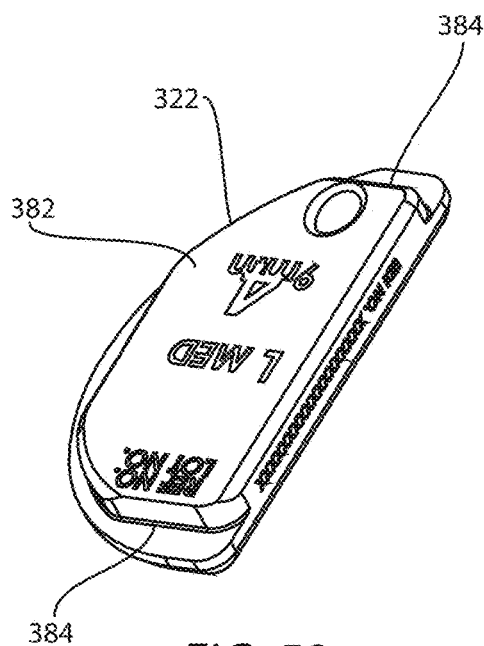
FIG. 59 is yet another oblique view of the tibial articular component of FIG. 57 from another different direction.
Figure 60:
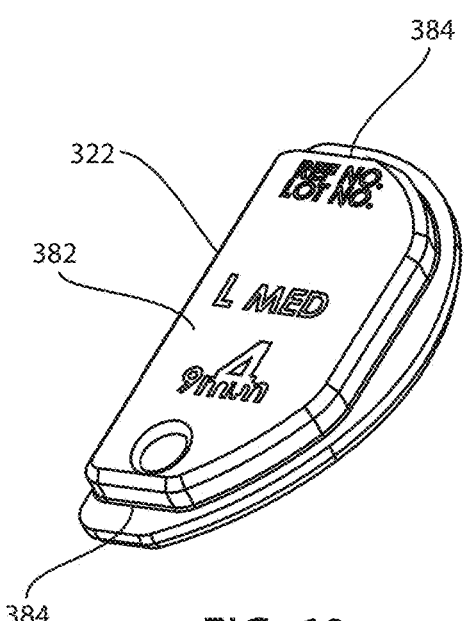
FIG. 60 is yet another oblique view of the tibial articular component of FIG. 57 from yet another different direction.
Figure 61:
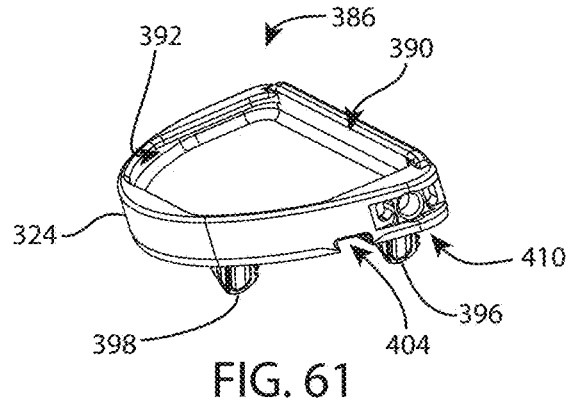
FIG. 61 is an oblique view of a tibial tray of the unicompartmental implant construct of FIG. 52.
Figure 62:
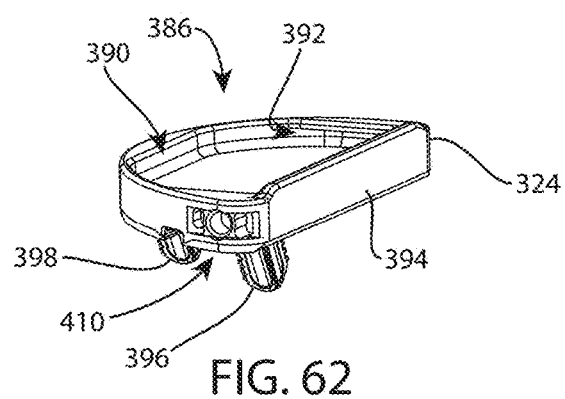
FIG. 62 is another oblique view of the tibial tray of FIG. 61 from a different direction.
Figure 63:
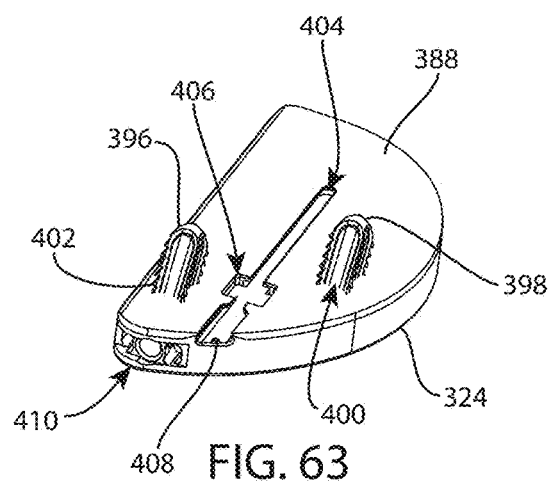
FIG. 63 is yet another oblique view of the tibial tray of FIG. 61 from another different direction.
Figure 64:
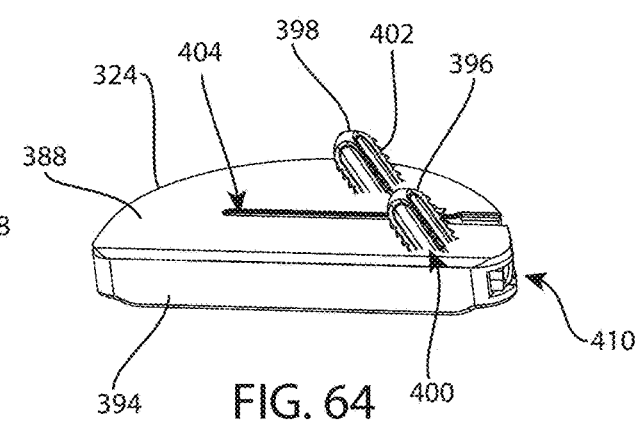
FIG. 64 is yet another oblique view of the tibial tray of FIG. 61 from yet another different direction.
Figure 65:
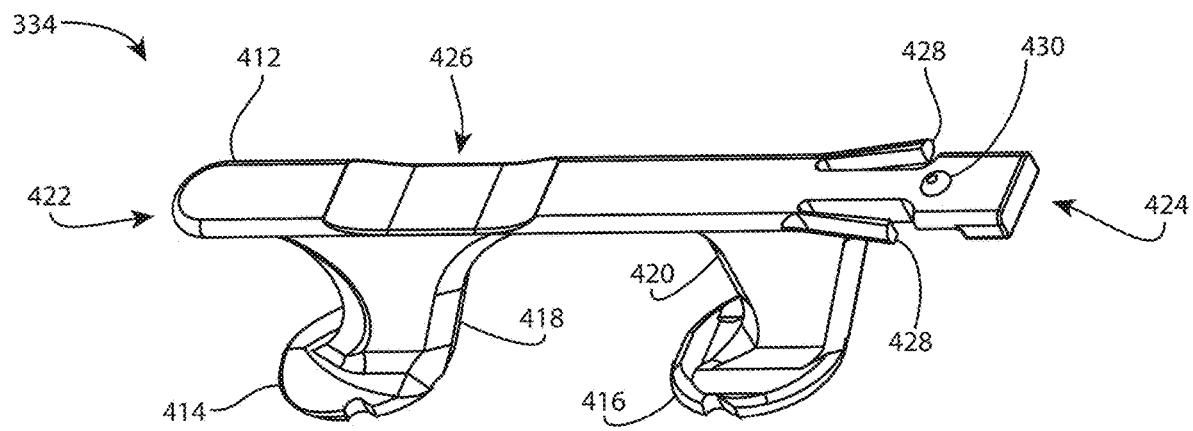
FIG. 65 is an oblique view of a fixation element of the unicompartmental implant construct of FIG. 52.
Figure 66:
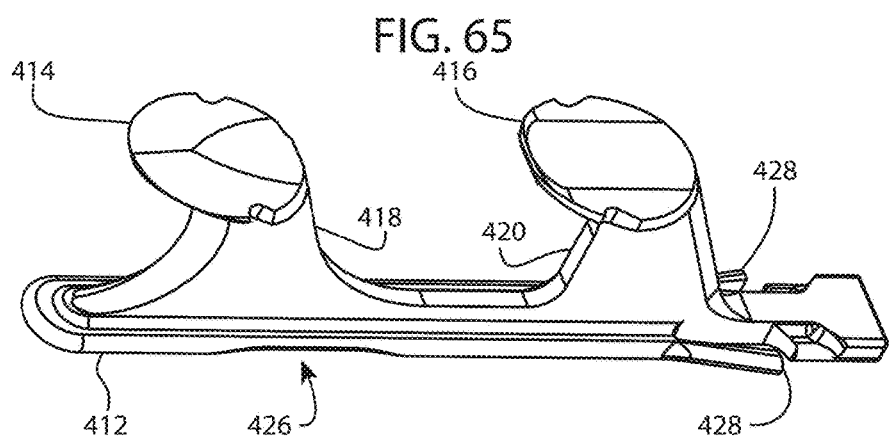
FIG. 66 is another oblique view of the fixation element of FIG. 65 from a different direction.
Figure 67:
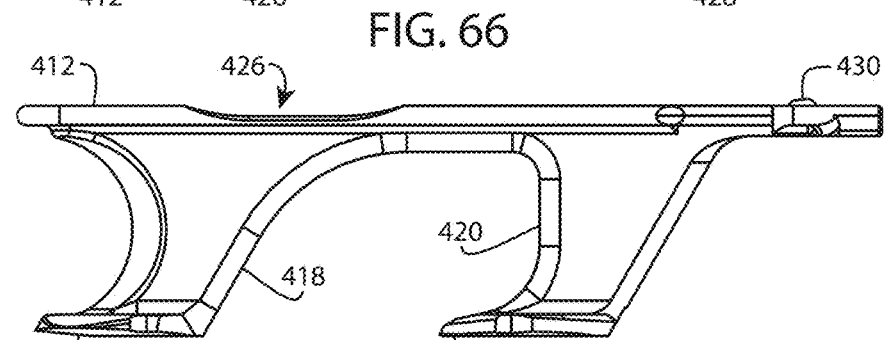
FIG. 67 is a side view of the fixation element of FIG. 65.
Figure 68:
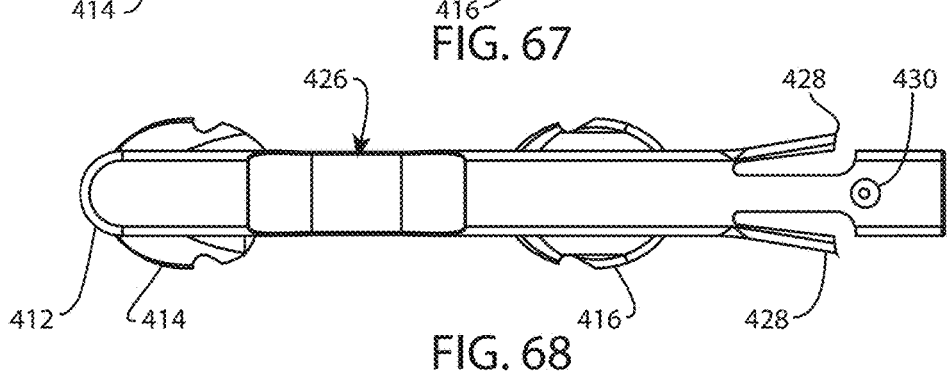
FIG. 68 is a top view of the fixation element of FIG. 65.

Referring to FIGS. 54-56, the femoral implant 320 includes an articular surface 358 and an opposite bone-facing side 360. The articular surface 358 is for articulation with the insert implant 322 or a natural articular surface of a proximal tibia. When the femoral implant 320 is oriented as if implanted in a knee joint in 90° of flexion, as shown in FIG. 52, and then viewed as if in a distal view of the femur, as shown in FIG. 306, the articular surface 358 has a medial-lateral curvature 890 which is an arc of a circle that has a center point 892. The femoral implant 320 can also be seen to have a profile 914, border, or outer perimeter in this view. The profile 914 is also seen in FIG. 281. The bone-facing side 360 may include a distal surface 362 for contacting a distal femoral resection, a posterior chamfer surface 364 for contacting a posterior chamfer resection, and a posterior surface 366 for contacting a posterior femoral resection. Referring to FIGS. 222, 269, 294, the femoral implant 320 has a thickness 918 perpendicular to the posterior surface 366 between the posterior surface 366 and the articular surface 358. The femoral implant 320 may have the same thickness perpendicular to the distal surface 362 between the distal surface 362 and the articular surface 358. Referring to FIG. 269, in a medial-lateral plane 920 that is perpendicular to the posterior surface 366, the articular surface 358 has the medial-lateral curvature 890 shown in FIG. 306. One or more pegs may project from the bone-facing side 360 for insertion into peg holes in the femur; first and second pegs 368, 370 are shown. The first peg 368 extends from the distal surface 362 and the second peg 370 extends from the posterior chamfer surface 364. The pegs 368, 370 may be parallel. Each peg may include a reduced-diameter tip portion 372, one or more longitudinal grooves 374, and/or optional longitudinal ribs 376 which may be sharpened and/or serrated. The second peg 370 is shown with a pair of triangular ribs 376 on opposite sides of the peg at its base, which merge with the posterior chamfer surface 364. The femoral implant 320 may include one or more instrument connection features 378, such as the pair of notches shown on opposite medial and lateral sides of the femoral implant.

Referring to FIGS. 57-60, the insert implant 322 may be referred to as a tibial articular insert, or simply an insert. The insert implant 322 includes an articular surface 380 and an opposite tray-facing side 382. The articular surface 380 is for articulation with the articular surface 358 of the femoral implant 320 or a natural articular surface of a distal femoral condyle. The tray-facing side 382 may include one or more connection features 384 for connection to the tibial tray 324, such as anterior and/or posterior tabs. The tray-facing side 382 may be referred to as a bone-facing side, since it faces the proximal tibia when implanted.

Referring to FIGS. 61-64, the tibial tray 324 includes an insert-facing side 386 and an opposite bone-facing side 388. The insert-facing side may include a pocket 390 or recess which receives the insert implant 322. The pocket 390 may include one or more connection features 392 for connection to the insert implant 322, such as anterior and/or posterior grooves. The bone-facing side 388 contacts a transverse proximal tibial resection when the tibial tray 324 is implanted, and may be referred to as a main or primary bone-facing side to differentiate it from a secondary bone-facing side 394 which faces or contacts a vertical proximal tibial resection. One or more pegs may project from the bone-facing side 388 for insertion into peg holes in the tibia; first and second pegs 396, 398 are shown. Each peg may include one or more longitudinal grooves 400 and/or longitudinal ribs 402 which may be sharpened or serrated. The pegs 396, 398 are shown extending obliquely posteriorly and inferiorly, in parallel. An undercut channel 404 extends through an anterior side of the tibial tray 324 and substantially posteriorly across the bone-facing side 388. The channel 404 may extend partially or entirely across the bone-facing side. The channel 404 may include a pocket 406 which may be located in a middle portion of the channel away from its ends. The channel 404 may include a retention feature 408, such as the dimple shown near its anterior end. The tibial tray 324 may include one or more instrument connection features 410, such as the group of three holes shown.

Referring to FIGS. 65-68, the fixation element 334 may be referred to as an anchor. The fixation element 334 includes a rail 412 for insertion into the channel 404 of the tibial tray 324, at least one blade 414 or bone engagement feature, and at least one support 418. The rail 412 extends between a leading end 422 and a trailing end 424, and has a cross-sectional shape which is complementary to the channel 404, such as a dovetail, a T-shape, or other undercut geometry for sliding interconnection. A rather wide, shallow transverse groove 426 extends across the tray-facing side of the rail 412. Close to the trailing end, the rail 412 may include one or more locking features 428, such as the pair of prongs or fingers shown. The prongs deflect elastically toward each other as the rail 412 is inserted into the channel 404, then spring outwardly within the pocket 406 to lock the rail in the channel. The rail 412 may include one or more retention features 430 such as the bump shown on the tray-facing side, which cooperates with the corresponding dimple 408 in the channel 404 of the tibial tray 324 to retain the rail in the channel with the prongs in an unlocked state not in the pocket 406. The fixation element 334 is shown with two blades 414, 416 and two supports 418, 420. The blades 414, 416 in this example are substantially circular, in other words, circular to the unaided eye. The leading edges of the blades 414, 416 and supports 418, 420 may be sharpened or serrated to more easily cut through bone. The blades 414, 416 may be angled relative to the rail 412 and/or the bone-facing side 388 of the tibial tray 324 to achieve compression, consistent with previous descriptions.

Figure 69:
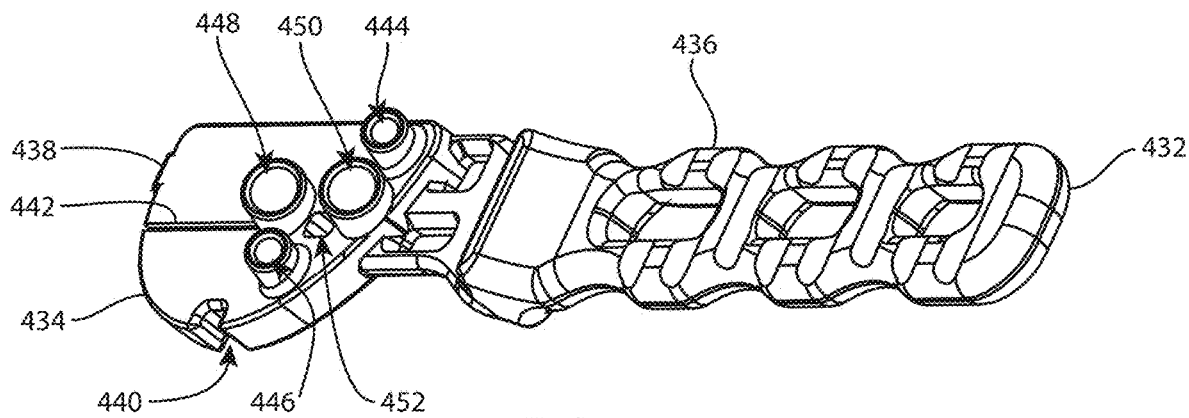
FIG. 69 is an oblique view of a tibial sizer.
Figure 70:
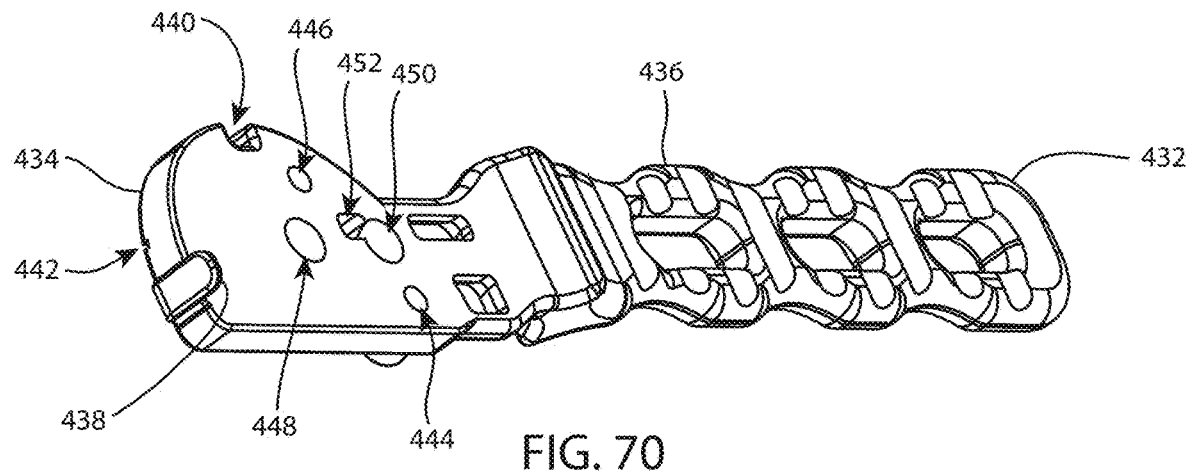
FIG. 70 is another oblique view of the tibial sizer of FIG. 69 from a different direction.

Referring to FIGS. 69-70, a tibial sizer 432 may be used to measure the size of a resected proximal tibia, and/or to prepare holes in the tibia to receive the pegs 396, 398 of the tibial tray 324 and/or the blades 414, 416 of the fixation element 334. The tibial sizer 432 may include a paddle 434 with a handle 436 extending from an anterior end of the paddle 434. The paddle 434 preferably closely or exactly matches the size and shape of the tibial tray 324. A hook 438 may extend distally from a posterior end of the paddle 434. A notch 440 may be present along a medial side of the paddle 434. A line 442 or groove may extend across a proximal side of the paddle 434 along an anterior-posterior direction. Preferably, the line 442 is centered in the medial-lateral width of the paddle. One or more holes may extend through the paddle 434 along a generally proximal-distal direction; five holes 444, 446, 448, 450, 452 are shown. The holes 444, 446 are for preparing bone holes to receive the pegs 396, 398. The holes 448, 450 are for preparing bone holes to receive the blades 414, 416 and/or supports 418, 420. The holes 444, 446, 448, 450 are all obliquely inclined and parallel; each hole may be surrounded by a boss or wall that protrudes outwardly from the proximal side of the paddle 434. The hole 452 is rectangular in shape, in line with the line 442, and extends perpendicularly through the paddle 434.

Figures 71, 72, 73, 74:
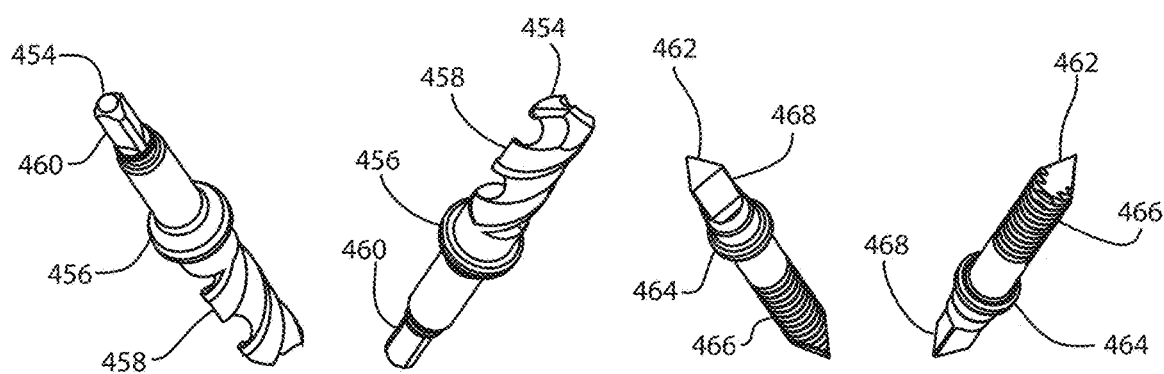
FIG. 71 is an oblique view of a drill.
FIG. 72 is another oblique view of the drill of FIG. 71 from a different direction.
FIG. 73 is an oblique view of a bone pin.
FIG. 74 is another oblique view of the bone pin of FIG. 73 from a different direction.

Referring to FIGS. 71-72, a drill 454 is sized for use in the holes 448, 450. The drill 454 includes a flange 456 which functions as a depth stop. The drill 454 includes a cutting portion 458 on one side of the flange 456, and a coupling 460 on the other side of the flange for connection to a torque source, such as a powered handpiece.

Referring to FIGS. 73-74, a bone pin 462 is sized for use in the holes 444, 446. The bone pin 462 includes a flange 464 which functions as a depth stop. The bone pin 462 includes an externally threaded portion 466 on one side of the flange 464, and a coupling 468 on the other side of the flange for connection to a torque source, such as a powered handpiece.

Figures 75, 76:
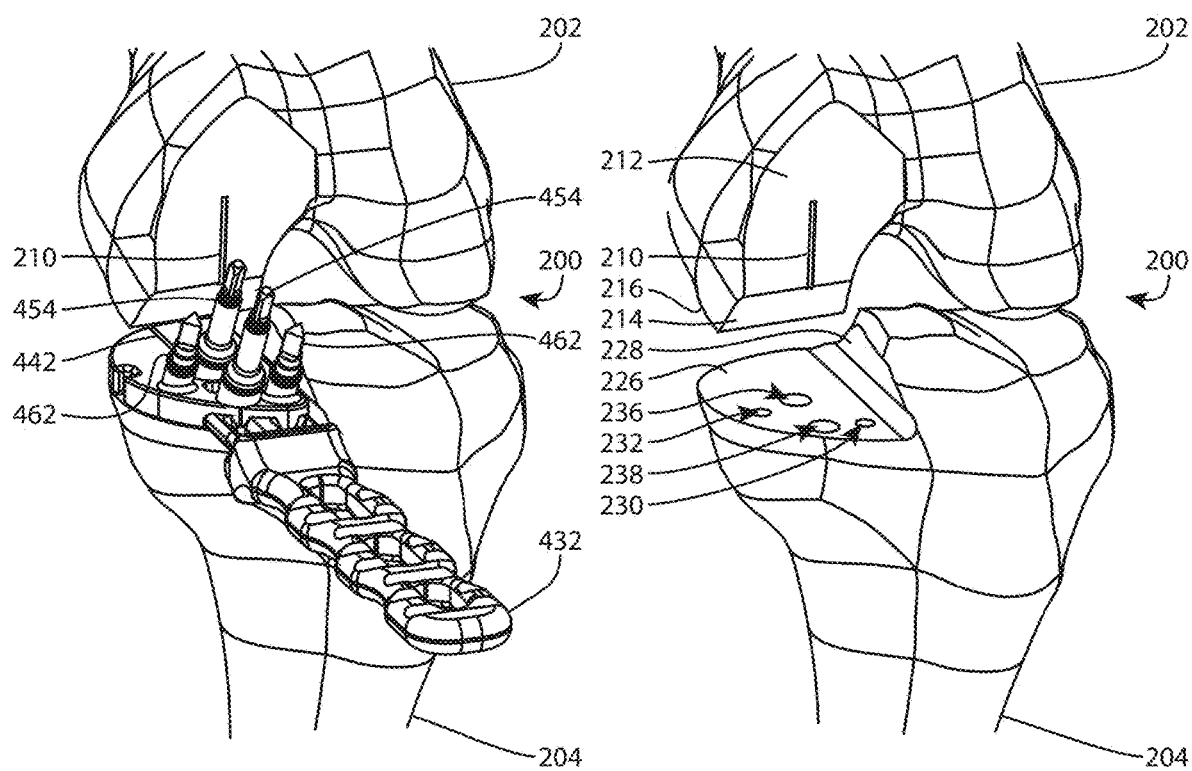
FIG. 75 is an oblique view of the tibial sizer of FIG. 69, the drill of FIG. 71, and the bone pin of FIG. 73 arranged in a knee joint.
FIG. 76 is an oblique view of the knee joint of FIG. 75 after bone preparation.

Referring to FIGS. 75-76, a knee joint 200 includes a femur 202 and a tibia 204. The femur 202 includes a distal femoral resection 212, a posterior chamfer resection 214, a posterior femoral resection 216, and a distal femoral mark 210. The tibia 204 includes a transverse resection 226 and a vertical resection 228. FIG. 75 shows steps of placing the paddle 434 of the tibial sizer 432 against the transverse resection 226, sliding the paddle 434 anteriorly until the hook 438 contacts a posterior side of the proximal tibia 204, inserting bone pins 462 through holes 444, 446 and into the proximal tibia 204, and inserting drills 454 through holes 448, 450 and into the proximal tibia 204. There may also be a step of aligning the line 442 with a corresponding distal femoral mark 210. FIG. 76 shows the knee joint 200 after removing the tibial sizer 432, drills 454, and bone pins 462. Holes 236, 238 were made by the drills 454 to receive the blades 414, 416 and/or supports 418, 420. Holes 230, 232 were made by the bone pins 462 to receive the pegs 396, 398.

The tibial tray 324 and fixation element 334 may be connected together for implantation by inserting the leading end 422 of the rail 412 into the anterior end of the channel 404 and moving the rail 412 from anterior to posterior until the locking features 428 enter the channel 404 and the retention features 408, 430 become engaged, while the locking features 428 remain outside of the pocket 406. The supports 418, 420 may enter the open side of the channel 404. This is referred to as an insertion state or an unlocked state of the fixation element 334. The tibial tray 324 and fixation element 334 in the insertion state may be implanted by inserting the pegs 396, 398 in the holes 230, 232, inserting the blades 414, 416 and/or supports 418, 420 in the holes 236, 238, placing the bone-facing side 388 against the transverse resection 226, and optionally placing the bone-facing side 394 against the vertical resection 228. The rail 412 may then be moved from anterior to posterior until the locking features 428 enter the pocket 406 of the channel 404 and spring outwardly to lock the fixation element 334 relative to the tibial tray 324. This is referred to as an implanted state or a locked state of the fixation element 334. At the same time, the blades 414, 416 and/or supports 418, 420 also move posteriorly to penetrate the posterior walls of the holes 236, 238 to achieve bone fixation. The fixation elements 334, 336, 338, 340, 342, 344, 348, 350, 352 all operate according to this principle.

Figure 77:
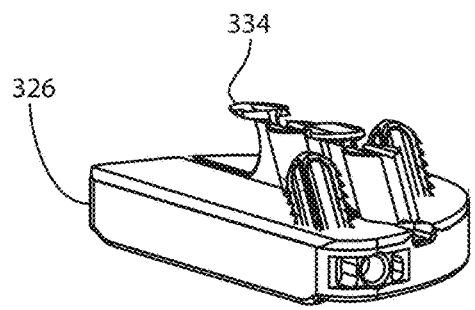
FIG. 77 is an oblique view of another tibial tray coupled to the fixation element of FIG. 65.
Figure 78:
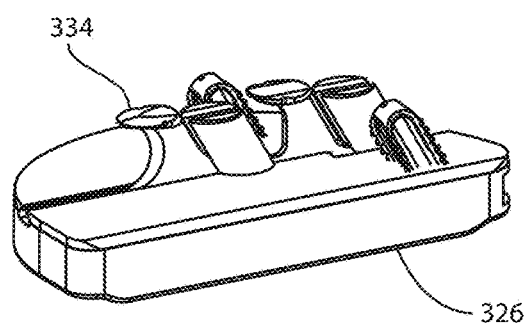
FIG. 78 is another oblique view of the tibial tray and fixation element of FIG. 77 from a different direction.
Figure 79:
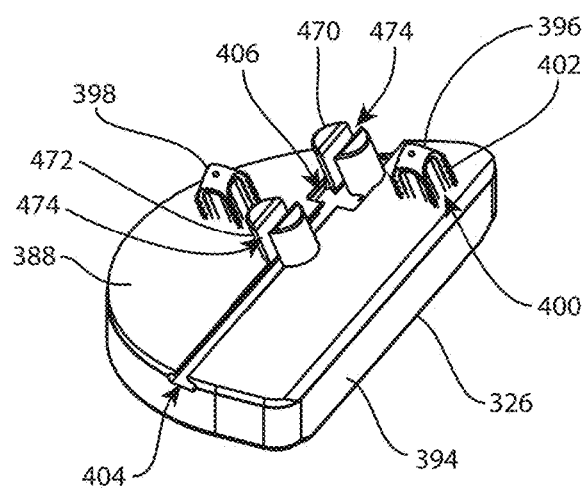
FIG. 79 is an oblique view of the tibial tray of FIG. 77.
Figure 80:
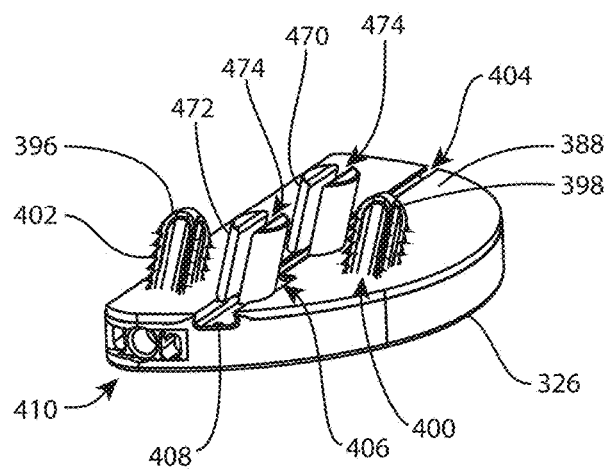
FIG. 80 is another oblique view of the tibial tray of FIG. 79 from a different direction.
Figure 81:
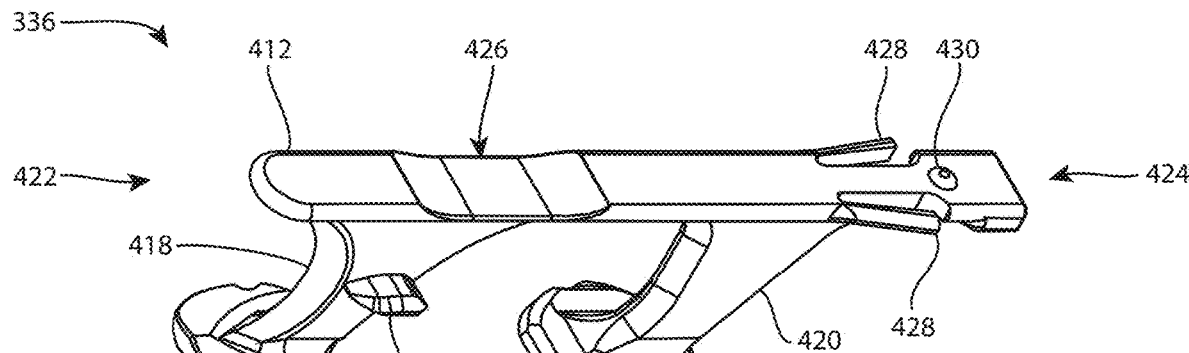
FIG. 81 is an oblique view of another fixation element.
Figure 82:
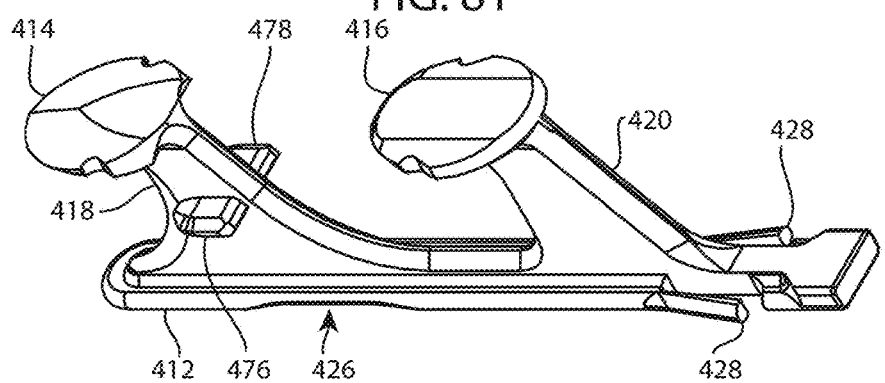
FIG. 82 is another oblique view of the fixation element of FIG. 81 from a different direction.
Figure 83:
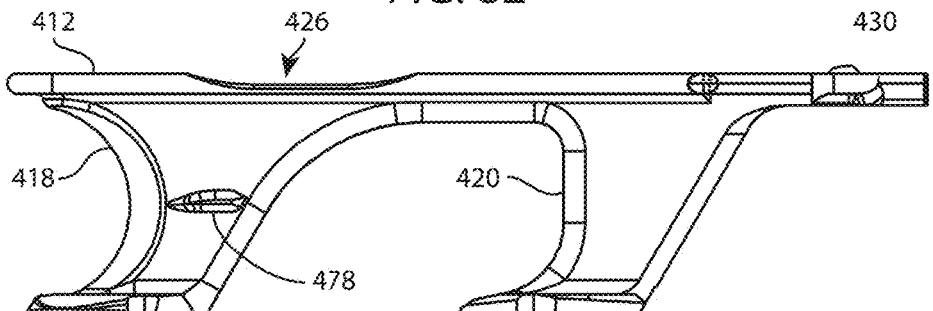
FIG. 83 is a side view of the fixation element of FIG. 81.

Referring to FIGS. 77-80, the tibial tray 326 may be used with the fixation element 334. FIG. 77 shows the tibial tray 326 with the fixation element 334 in the implanted state or locked state. The tibial tray 326 includes all of the features of tibial tray 324. The channel 404 is shown extending entirely across the bone-facing side 388. The tibial tray 326 includes first and second posts 470, 472 which are positioned along the channel 404 in locations corresponding to the blades 414, 416 and supports 418, 420 for the fixation element 334 in the insertion state or unlocked state. Each post 470, 472 is slotted 474 so that the supports 418, 420 may slide through the posts. In the insertion state, the blades 414, 416 are located over the free ends of the posts 470, 472 and the supports 418, 420 are located within the slots 474. In the implanted state, the blades 414, 416 and supports 418, 420 are posterior (beside) the posts 470, 472. Referring briefly to FIG. 76, the posts 470, 472 are received in the holes 236, 238. Thus, tibial trays 324, 326 may be implanted interchangeably after the bone preparation shown in FIGS. 75-75, and may be used, or adapted for use, with any fixation element suited to this bone preparation.

Figure 84:
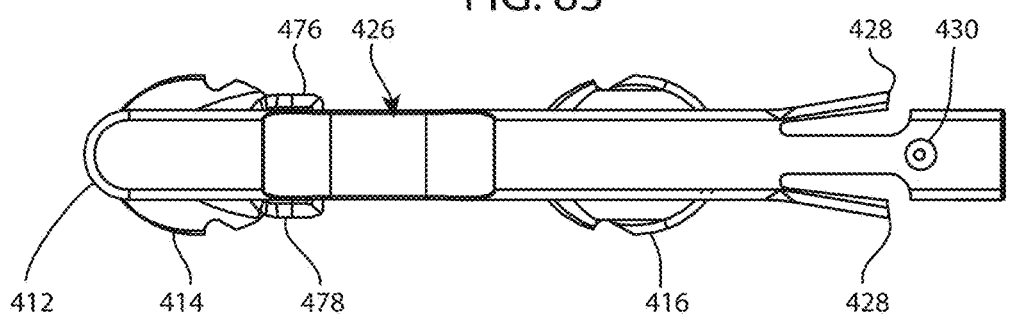
FIG. 84 is a top view of the fixation element of FIG. 81.
Figure 85:
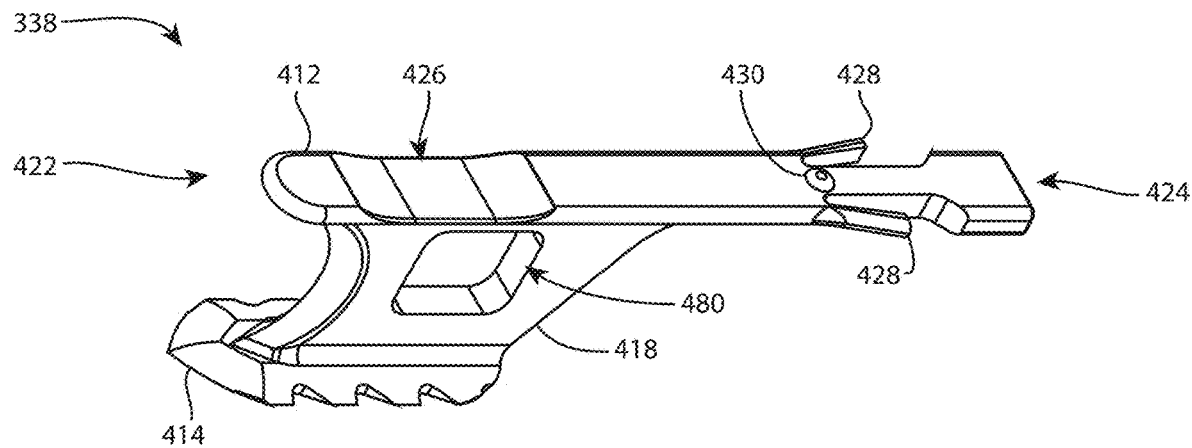
FIG. 85 is an oblique view of yet another fixation element.
Figure 86:
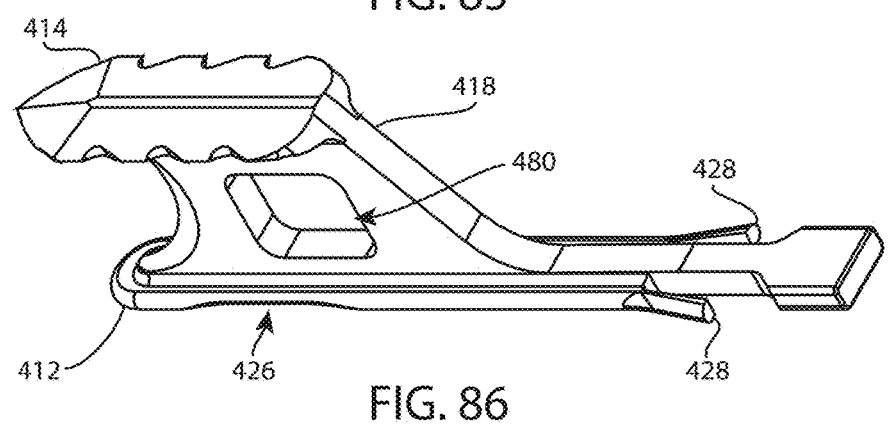
FIG. 86 is another oblique view of the fixation element of FIG. 85 from a different direction.
Figure 87:
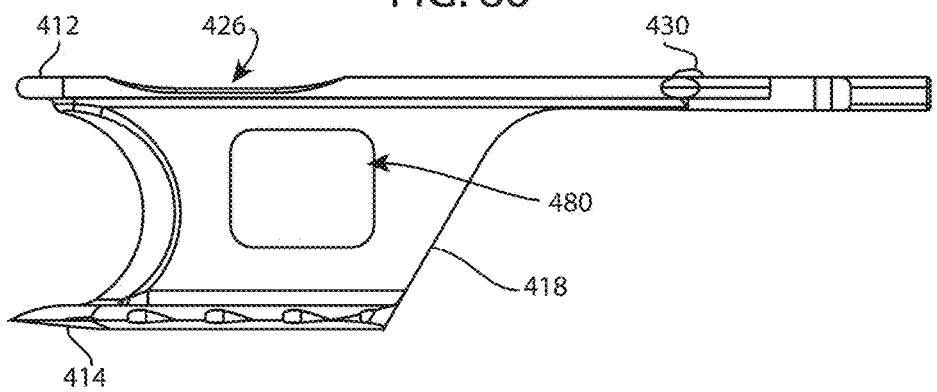
FIG. 87 is a side view of the fixation element of FIG. 85.
Figure 88:
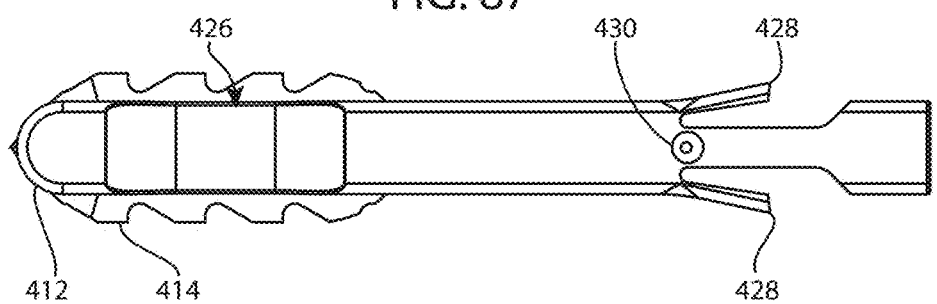
FIG. 88 is a top view of the fixation element of FIG. 85.
Figure 89:
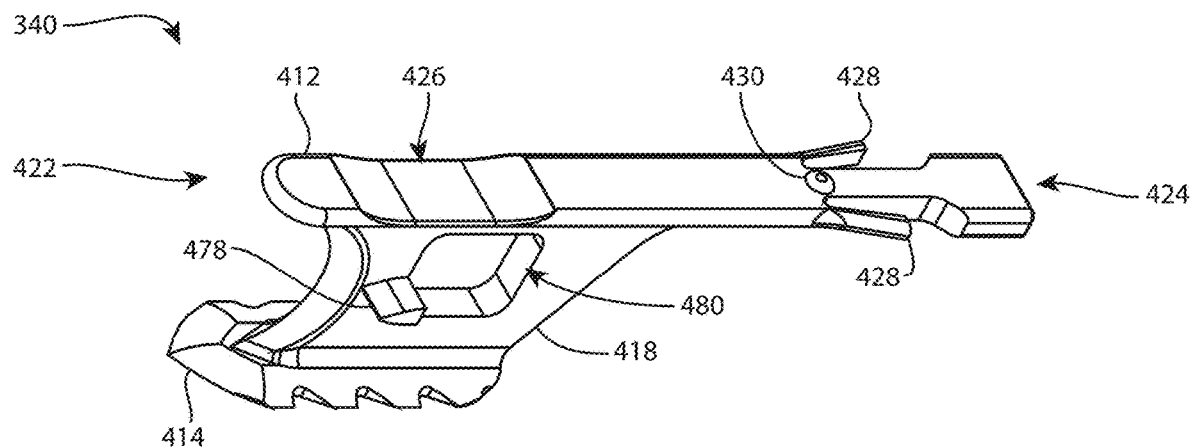
FIG. 89 is an oblique view of yet another fixation element.
Figure 90:
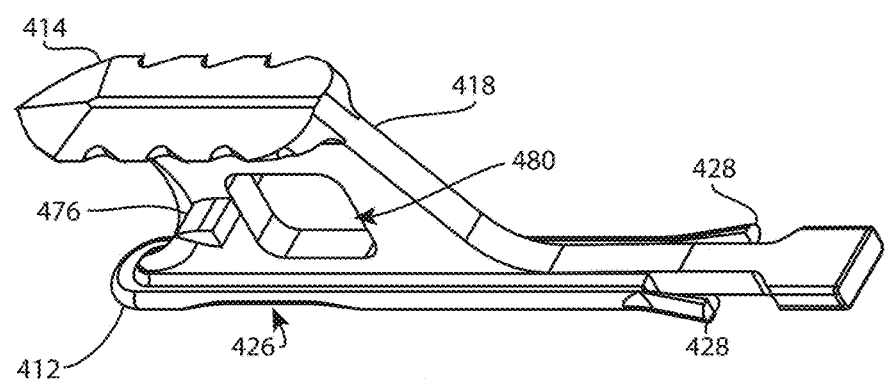
FIG. 90 is another oblique view of the fixation element of FIG. 89 from a different direction.
Figure 91:
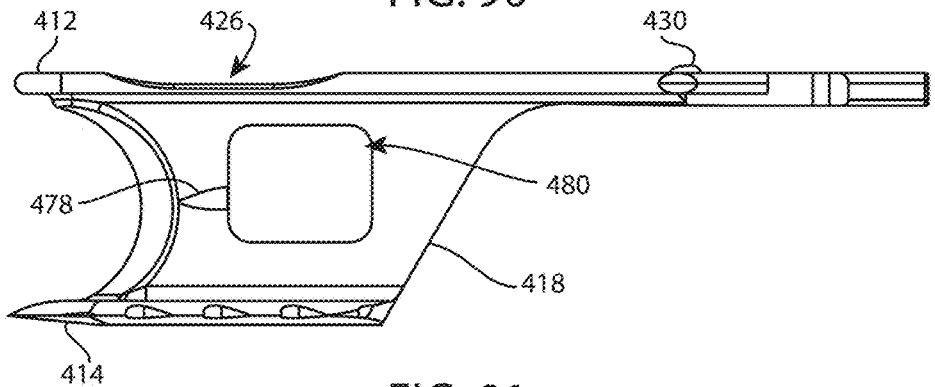
FIG. 91 is a side view of the fixation element of FIG. 89.
Figure 92:
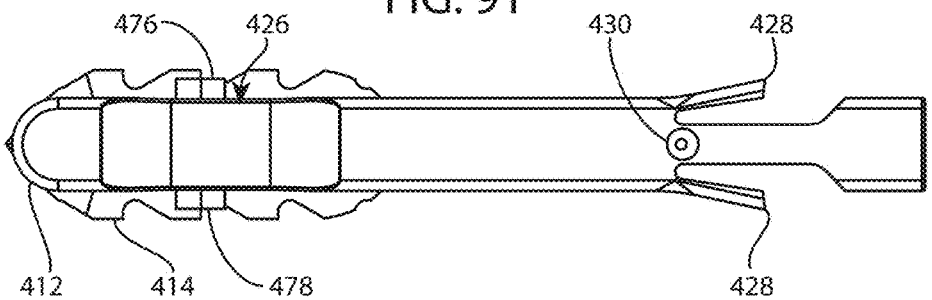
FIG. 92 is a top view of the fixation element of FIG. 89.
Figure 93:
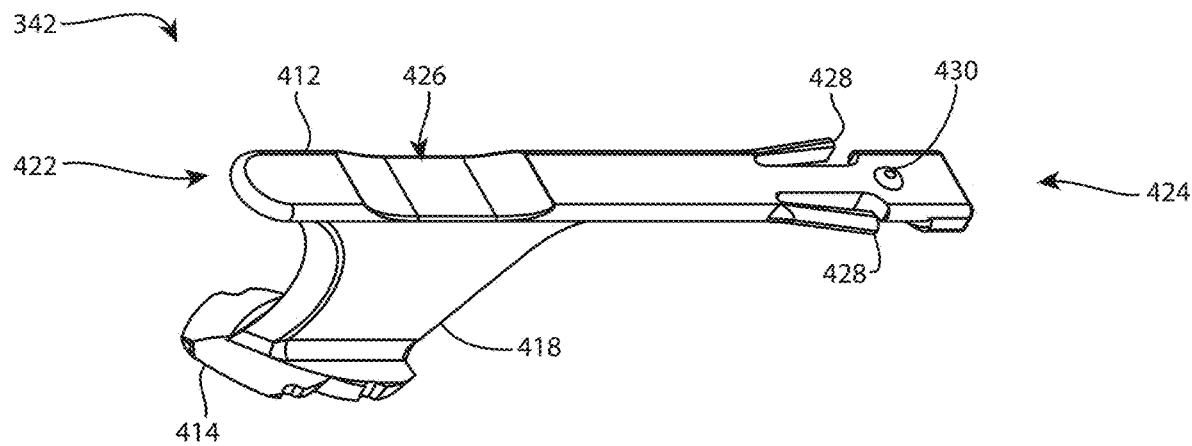
FIG. 93 is an oblique view of yet another fixation element.
Figure 94:
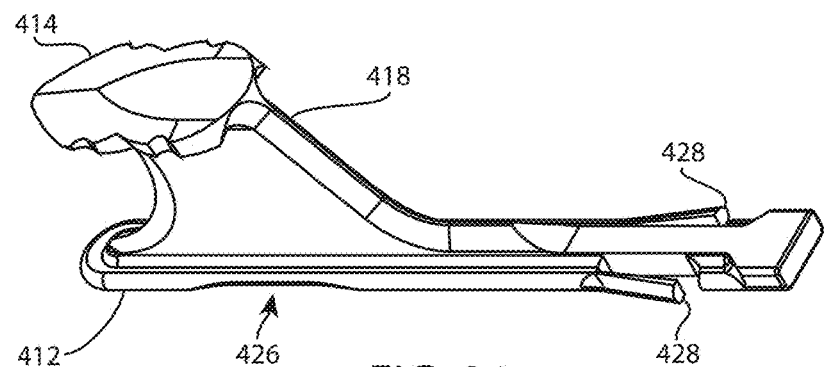
FIG. 94 is another oblique view of the fixation element of FIG. 93 from a different direction.
Figure 95:
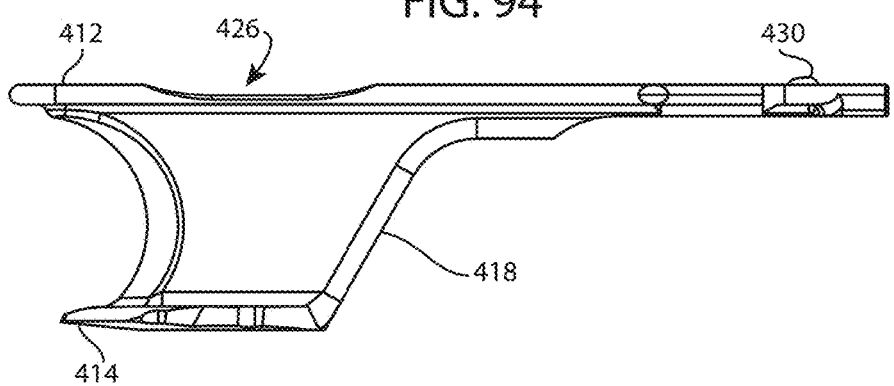
FIG. 95 is a side view of the fixation element of FIG. 93.
Figure 96:
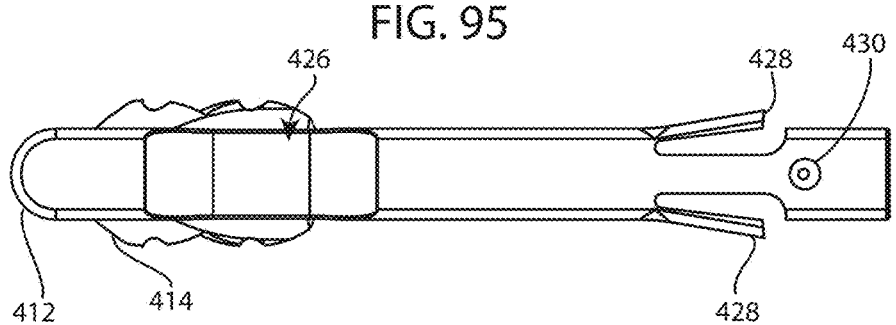
FIG. 96 is a top view of the fixation element of FIG. 93.

Referring to FIGS. 81-84, the fixation element 336 may be used with the tibial tray 324. The fixation element 336 includes all of the features of fixation element 334. The fixation element 336 includes a pair of blades 476, 478 protruding from either side of the support 418 between the rail 412 and the blade 414. The blades 476, 478 may be sharpened and/or serrated along their leading edges to more easily penetrate bone. Referring to FIG. 84, the blades 476, 478 taken together may be narrower than the blade 414, substantially the same width to the unaided eye, or wider than the blade. A second pair of blades 476, 478 may optionally be included on support 420. The fixation element 336 is used like fixation element 336, however the blades 476, 478 may increase bone fixation.

Referring to FIGS. 85-88, the fixation element 338 may be used with the tibial tray 324. The fixation element 338 includes the labeled features of fixation element 334, but lacks the blade 416 and support 420. The blade 414 is elongated, rectangular or oval with a pointed leading end. The retention feature 430 is located near the leading end of the locking features 428. The fixation element 338 includes a window 480 through the support 418; a rectangular window is shown. The fixation element 338 may be suited to the bone preparation shown in FIGS. 99-100.

Referring to FIGS. 89-92, the fixation element 340 may be used with the tibial tray 324. The fixation element 340 includes all of the features of fixation element 338, and the blades 476, 478 of fixation element 336. The fixation element 340 may be suited to the bone preparation shown in FIGS. 99-100.

Referring to FIGS. 93-96, the fixation element 342 may be used with the tibial tray 324. The fixation element 342 includes the labeled features of fixation element 334, but lacks the blade 416 and support 420. The blade 414 is elongated, rectangular or oval with a pointed leading end, although shorter than the blade 414 of fixation element 338. The blade 414 may be figure-8 shaped or hourglass shaped as seen best in FIG. 96. The fixation element 342 may be suited to the bone preparation shown in FIGS. 99-100.

Figure 97:
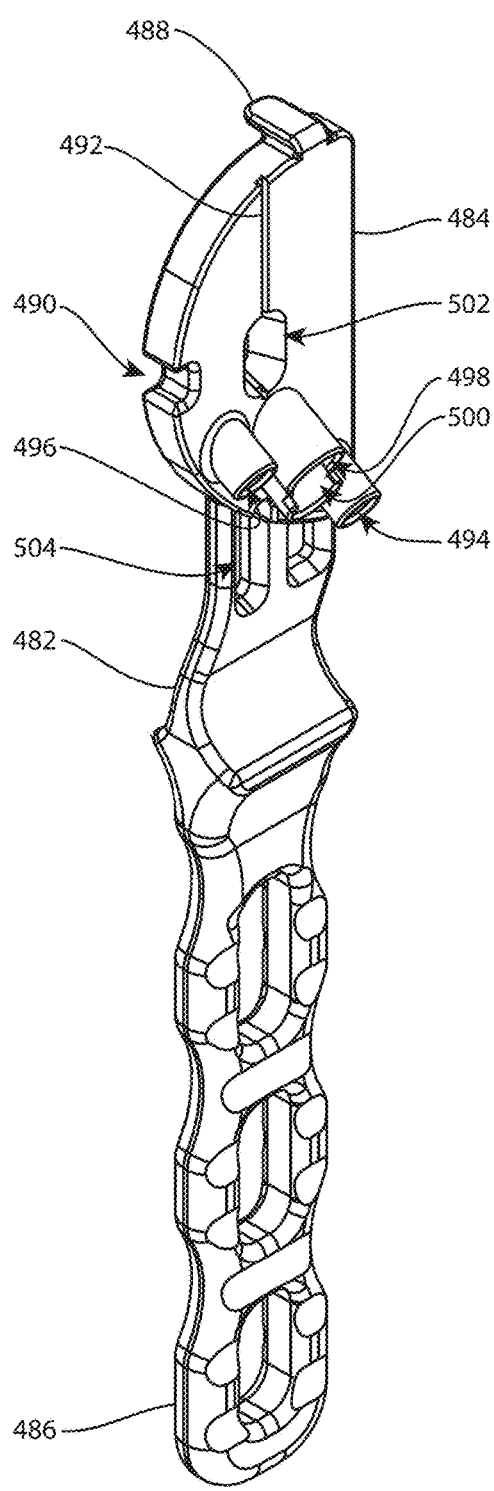
FIG. 97 is an oblique view of another tibial sizer.
Figure 98:
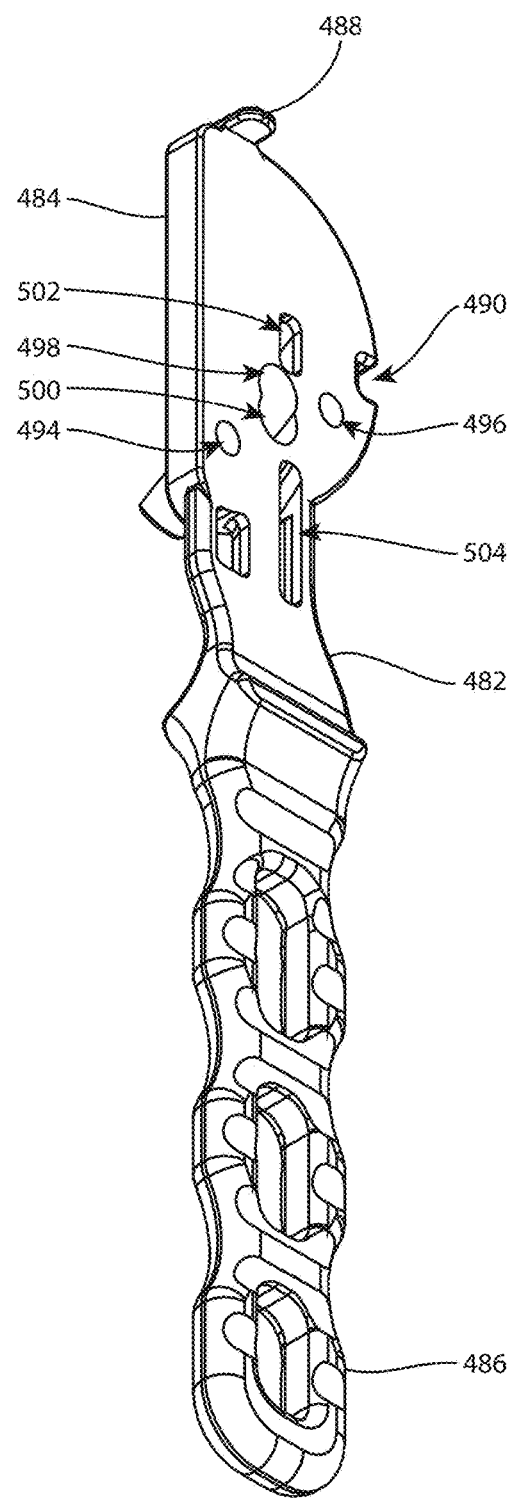
FIG. 98 is another oblique view of the tibial sizer of FIG. 97 from a different direction.

Referring to FIGS. 97-98, a tibial sizer 482 may be used to measure the size of a resected proximal tibia, and/or to prepare holes in the tibia to receive the pegs 396, 398 of the tibial tray 324 and/or the blade 414 of the fixation element 342. The tibial sizer 482 may include a paddle 484 with a handle 486 extending from an anterior end of the paddle 484. The paddle 484 preferably closely or exactly matches the size and shape of the tibial tray 324. A hook 488 may extend distally from a posterior end of the paddle 484. A notch 490 may be present along a medial side of the paddle 484. A line 492 or groove may extend across a proximal side of the paddle 484 along an anterior-posterior direction. Preferably, the line 492 is centered in the medial-lateral width of the paddle. One or more holes may extend through the paddle 484 along a generally proximal-distal direction; six holes 494, 496, 498, 500, 502, 504 are shown. The holes 494, 496 are for preparing bone holes to receive the pegs 396, 398. The overlapping holes 498, 500 are for preparing overlapping bone holes to receive the blade 414 and/or support 418 of the fixation element 342. The holes 494, 496, 498, 500 are all obliquely inclined and parallel; each hole may be surrounded by a boss or wall that protrudes outwardly from the proximal side of the paddle 484. The hole 502 is rectangular in shape, in line with the line 492, extends perpendicularly through the paddle 484, and is located posterior to the hole 498. The hole 504 is rectangular in shape, in line with the line 492, extends perpendicularly through the paddle 484, and is located anterior to the hole 500.

Figures 99, 100:
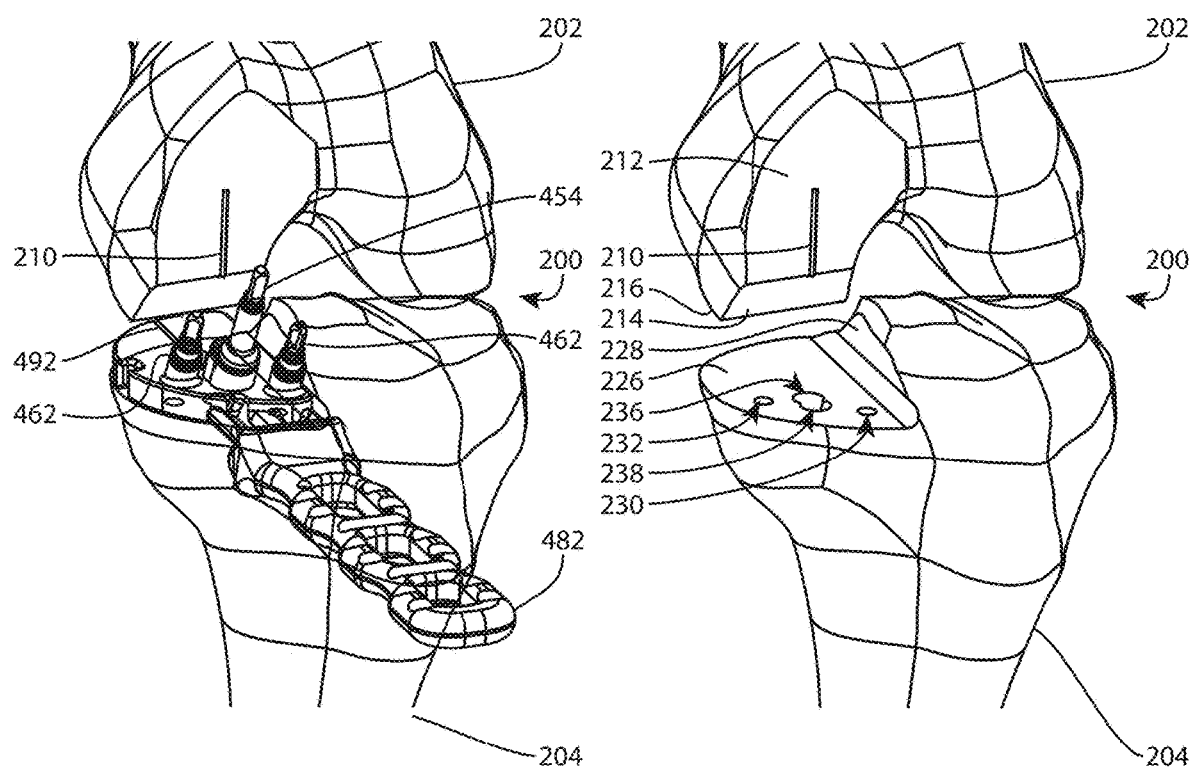
FIG. 99 is an oblique view of the tibial sizer of FIG. 97, the drill of FIG. 71, and the bone pin of FIG. 73 arranged in a knee joint.
FIG. 100 is an oblique view of the knee joint of FIG. 99 after bone preparation.
Figure 105:
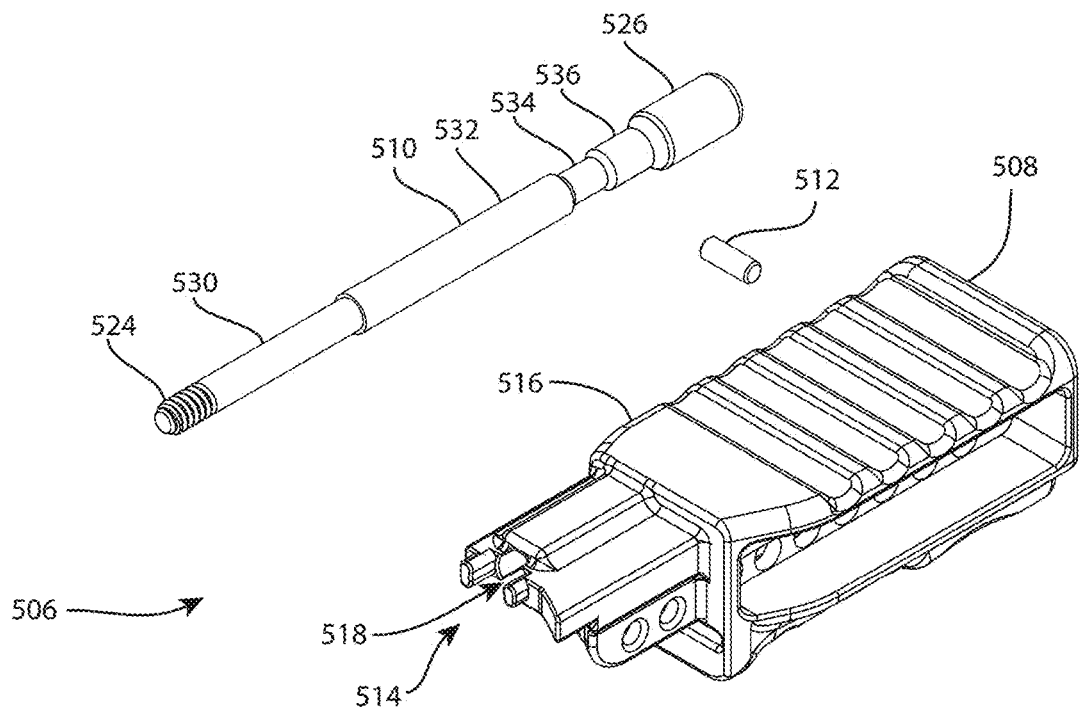
FIG. 105 is an oblique exploded view of the anchor guide of FIG. 101.
Figure 106:
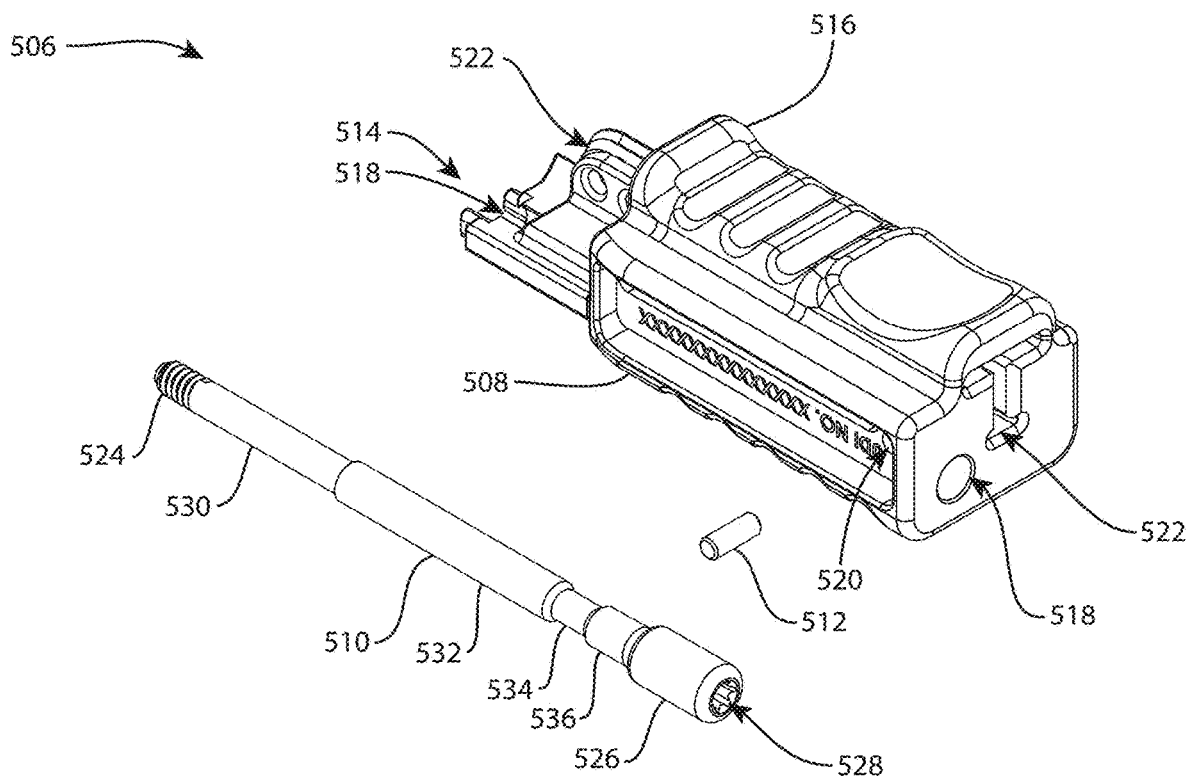
FIG. 106 is another oblique exploded view of the anchor guide of FIG. 101 from a different direction.
Figure 107:
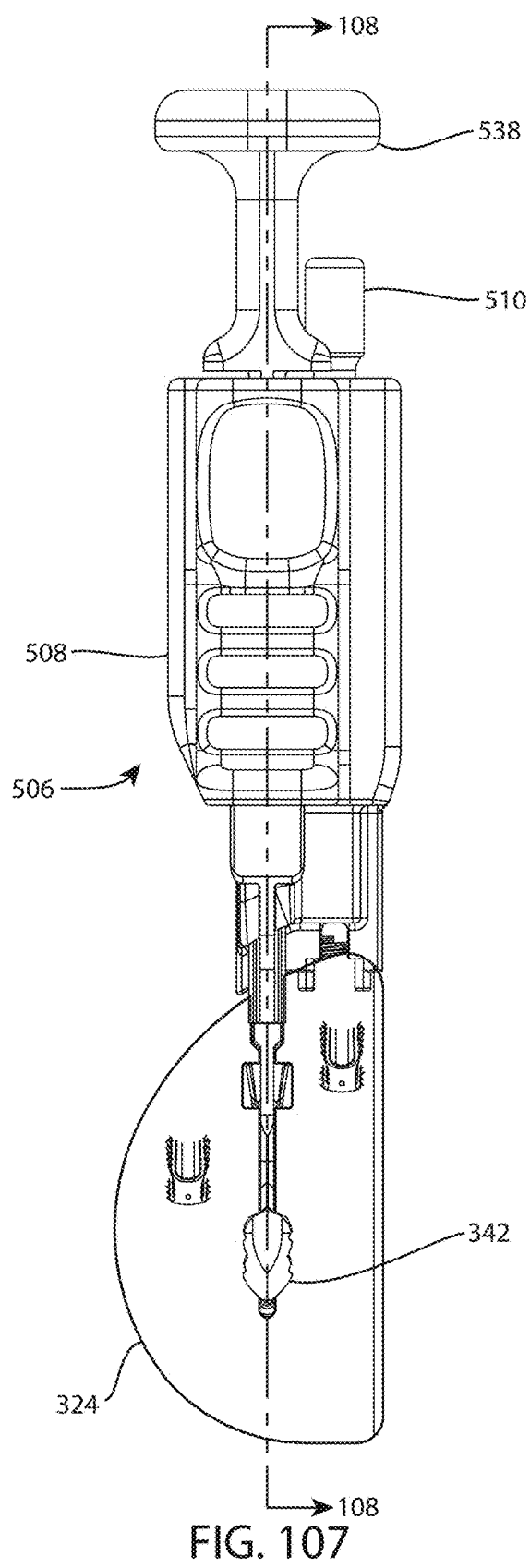
FIG. 107 is a bottom view of the anchor guide of FIG. 101, the tamp of FIG. 103, the tibial tray of FIG. 61, and the fixation element of FIG. 93 coupled together.
Figure 108:
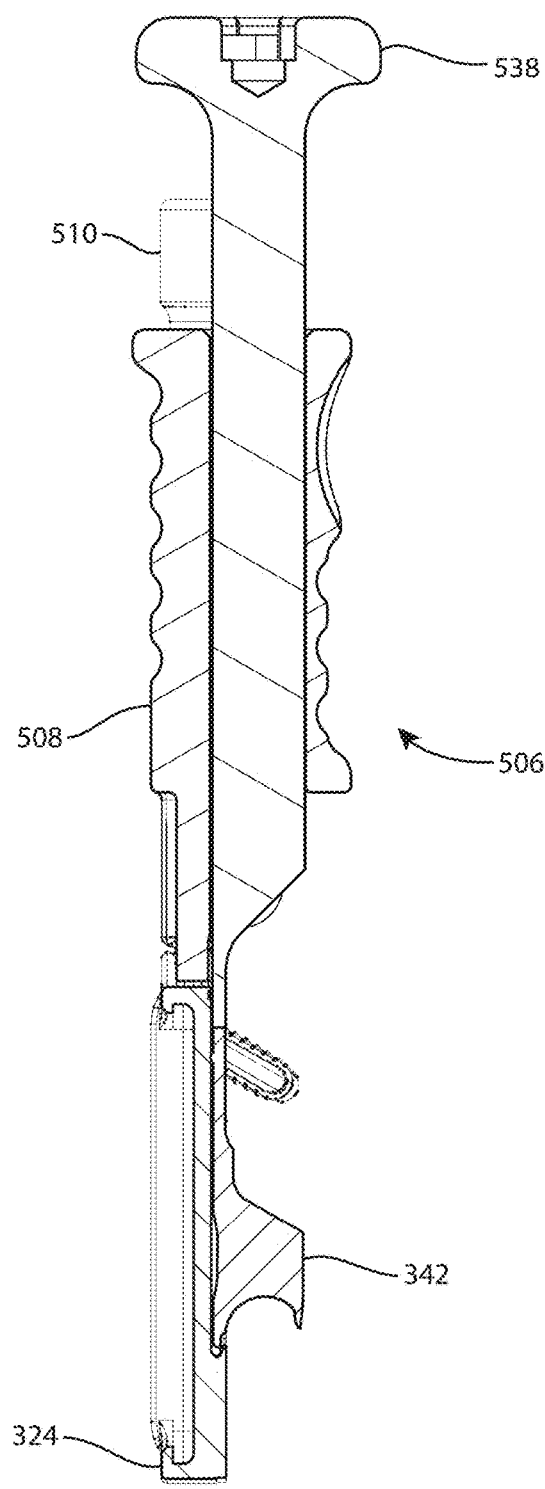
FIG. 108 is a cross-sectional view of the anchor guide, tamp, tibial tray, and fixation element of FIG. 107, taken along section line 108-108.
Figure 109:
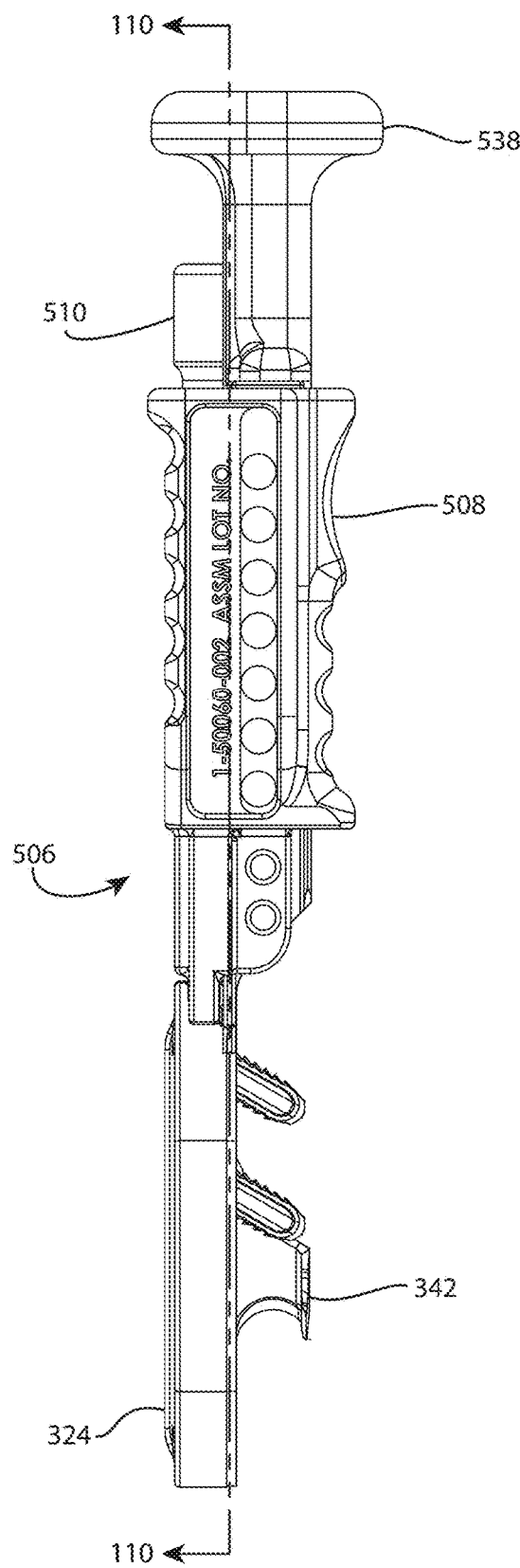
FIG. 109 is a side view of the anchor guide, tamp, tibial tray, and fixation element of FIG. 107.
Figure 110:
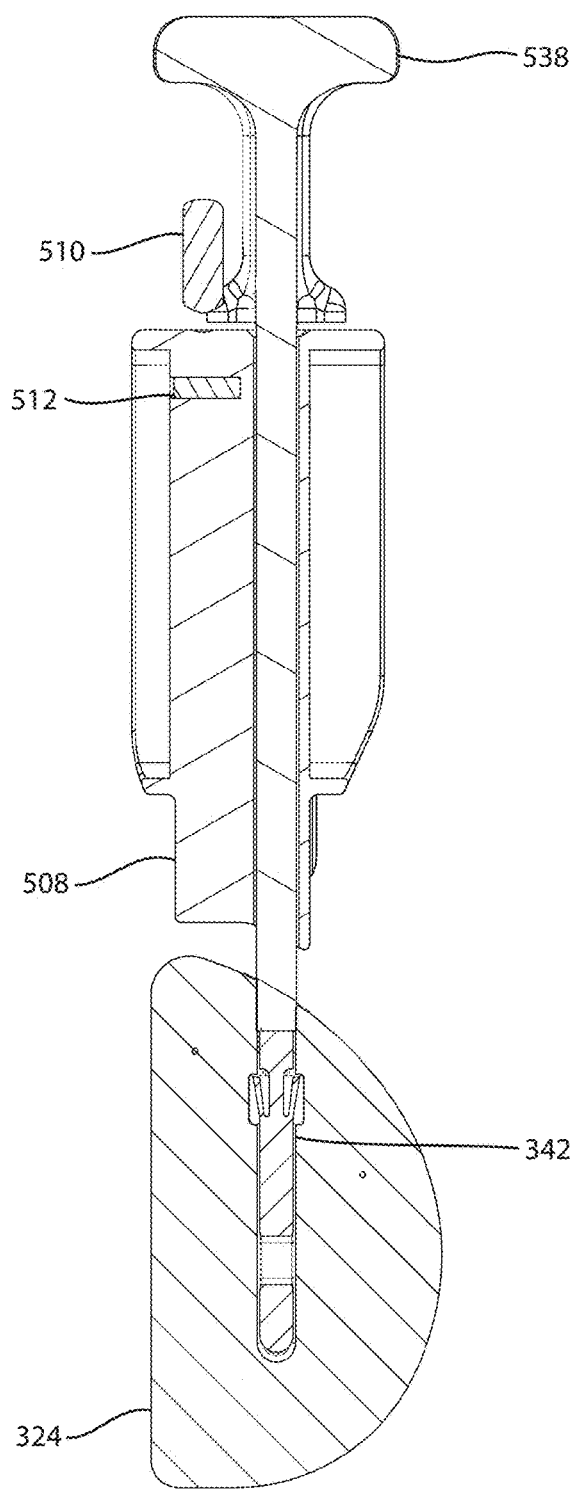
FIG. 110 is a cross-sectional view of the anchor guide, tamp, tibial tray, and fixation element of FIG. 109, taken along section line 110-110.

Referring to FIGS. 99-100, the knee joint 200, femur 202, and tibia 204 are shown. The femur 202 includes the distal femoral resection 212, the posterior chamfer resection 214, the posterior femoral resection 216, and the distal femoral mark 210. The tibia 204 includes the transverse resection 226 and the vertical resection 228. FIG. 99 shows steps of placing the paddle 434 of the tibial sizer 482 against the transverse resection 226, sliding the paddle 484 anteriorly until the hook 488 contacts a posterior side of the proximal tibia 204, inserting bone pins 462 through holes 494, 496 and into the proximal tibia 204, and inserting the drill 454 sequentially through holes 498, 500 and into the proximal tibia 204. There may also be a step of aligning the line 492 with the distal femoral mark 210. FIG. 100 shows the knee joint 200 after removing the tibial sizer 482, drill 454, and bone pins 462. Overlapping holes 236, 238 were made by the drill 454 to receive the blade 414 and/or support 418 of fixation element 342. Holes 230, 232 were made by the bone pins 462 to receive the pegs 396, 398.

Referring to FIGS. 101-102 and 105-106, a tibial anchor guide 506 may include a housing 508, a shaft 510, and a pin 512.

The housing 508 may include one or more tray connection features 514 that are complementary to the instrument connection features 410 of the tibial tray 324. Preferably, the connection features 410, 514 only go together in one orientation. The housing 508 may include a handle 516 that extends from the tray connection features 514. A longitudinal hole 518 may extend through the housing 508 to receive the shaft 510. The hole 518 may be located with the tray connection features 514. The hole 518 may have a smaller diameter at the tray connection features 514 and a larger diameter opposite the tray connection features 514. A transverse pin hole 520 may extend across the hole 518 at the end opposite the tray connection features 514 to receive the pin 512. A non-circular longitudinal hole 522 may extend through the housing 508 beside the hole 518 to receive the anchor tamp 538. The hole 522 may have a T-shape as seen best in FIG. 106, or another non-circular shape that is complementary to the cross-sectional shape of the anchor tamp 538.

The shaft 510 may include an externally threaded tip 524 at one end and a knob 526 at the other end. The knob 526 may include a torque input feature 528, such as the hexalobular socket shown, to receive torque from a tool such as a screwdriver. The shaft 510 may include one or more sections between the tip 524 and the knob 526; four sections 530, 532, 534, 536 are shown sequentially from the tip 524 to the knob 526. The outer diameter of the first section 530 may be equal to the outer diameter of the threads, and sized to be received in the smaller diameter portion of the hole 518 of the housing 508. The outer diameter of the second section 532 may be greater than the first section 530 and less than the knob 526, and sized to be received in the larger diameter portion of the hole 518. The outer diameter of the third section 534 may be less than the second section 532, and may also be less than the first section 530. The outer diameter of the fourth section may be equal to the second section 532.

The tibial anchor guide 506 may be assembled by performing some or all of the following steps in any order: inserting the shaft 510 in the hole 518 of the housing 508 so that the tip 524 protrudes from the end with the tray connection features 514; and inserting the pin 512 into the hole 520 and across the third section 534 to retain the shaft 510 in the hole 518 while permitting free rotation of the shaft in the hole.

When the tibial anchor guide 506 is operatively assembled, the shaft 510 is free to rotate clockwise and counterclockwise in the hole 518, and free to translate along the hole as permitted by the pin 512 beside the third section 534.

Referring to FIGS. 103-104, an anchor tamp 538 may be an elongated part that extends between an anchor-contacting tip 540 and an opposite platform 542 or knob. The tip 540 may be the leading end of a first rail 544 having the same cross-sectional shape and size as the rail 412 of the fixation element 342. The first rail 544 may extend longitudinally between the tip 540 and a depth stop feature 546 located between the tip 540 and the platform 542. The depth stop feature 546 is shown as a pair of tabs protruding from opposite sides of the anchor tamp 538. A second rail 548 may extend beside the first rail 544. The second rail 548 may stop short of the tip 540 as shown, and may include a much broader plate portion 550 at its leading end. The rails 544, 548 may be connected by a web 552 in an I-beam configuration. The platform 542 may include one or more connection features 554 for connection to a slap hammer or removal tool.

Referring to FIGS. 107-110, the tibial tray 324, fixation element 342, tibial anchor guide 506, and anchor tamp 538 may be connected by performing some or all of the following steps in any order: inserting the rail 412 of the fixation element 342 into the channel 404 of the tibial tray 324 and advancing the fixation element 342 to the insertion state; connecting the connection features 410, 514 of the tibial tray 324 and the housing 508 of the tibial anchor guide 506; turning the knob 526 of the shaft 510 to thread the tip 524 into a complementary internally threaded hole of the tibial tray 324 (which is one of the connection features 410) to lock the tibial tray 324 and tibial anchor guide 506 together; inserting the tip 540 of the anchor tamp 538 into the hole 522; and advancing the anchor tamp 538 so that the plate portion 550 enters the wide portion of the T-shaped hole 522.

Figure 111:
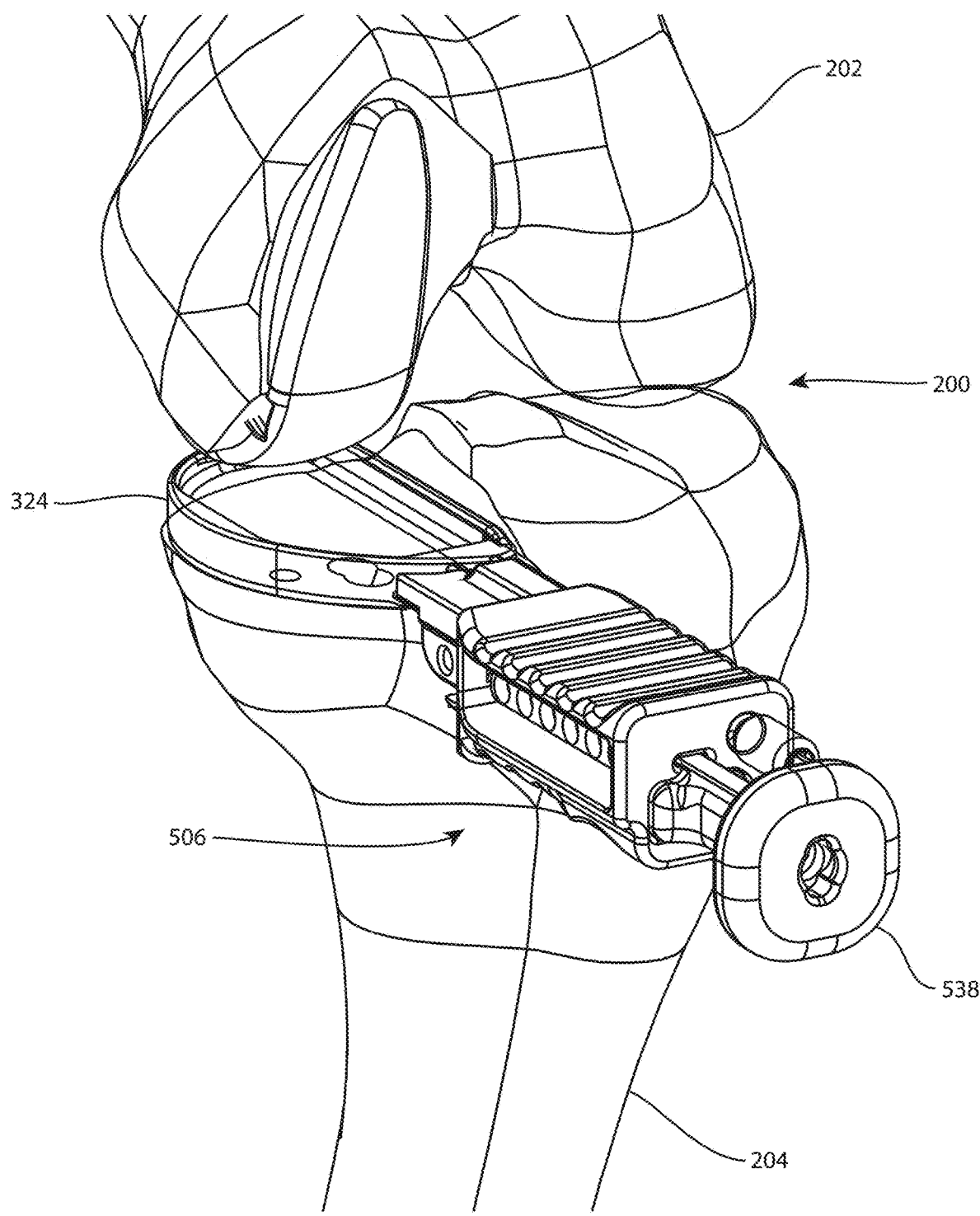
FIG. 111 is an oblique view of the anchor guide, tamp, tibial tray, and fixation element of FIG. 107 arranged in a knee joint.
Figure 112:
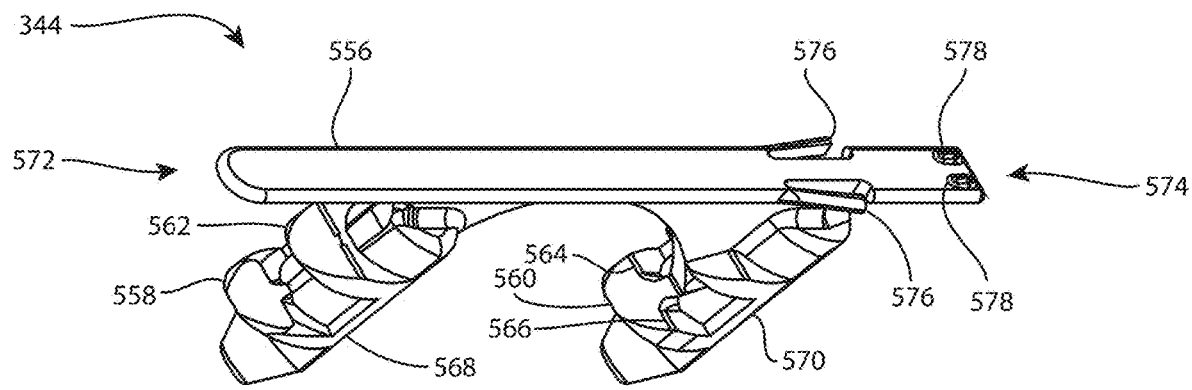
FIG. 112 is an oblique view of yet another fixation element.
Figure 113:
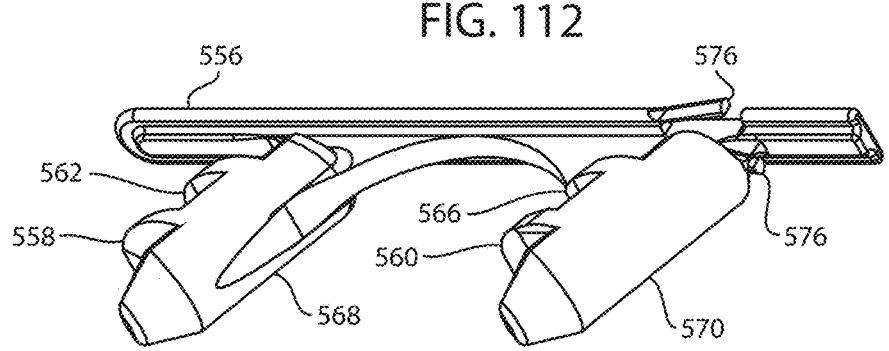
FIG. 113 is another oblique view of the fixation element of FIG. 112 from a different direction.
Figure 114:
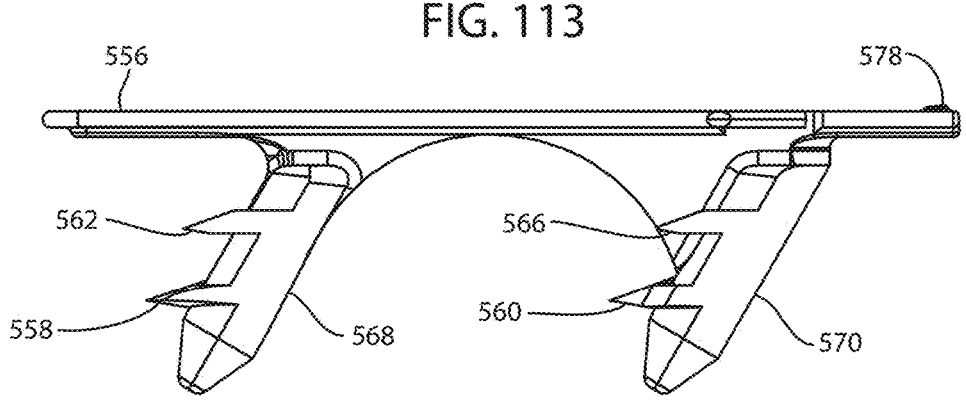
FIG. 114 is a side view of the fixation element of FIG. 112.
Figure 115:
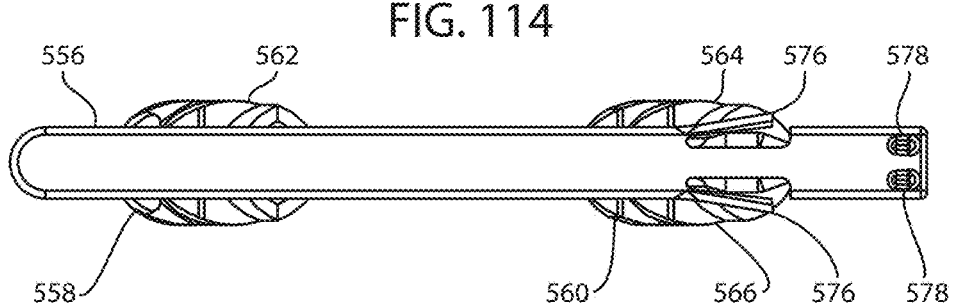
FIG. 115 is a top view of the fixation element of FIG. 112.

Referring to FIG. 111, the knee joint 200, femur 202, and tibia 204 are shown with the femoral implant 320 coupled to the femur, and the tibial tray 324 and fixation element 342 coupled to the tibia. A step of moving the fixation element 342 from the insertion state to the implanted state is shown. This step may be performed by advancing the anchor tamp 538 within the tibial anchor guide 506 until the depth stop feature 546 contacts the housing 508.

Referring to FIGS. 112-115, the fixation element 344 may be used with the tibial tray 324. The fixation element 344 includes a rail 556 for insertion into the channel 404 of the tibial tray 324, at least one blade 558 or bone engagement feature, and at least one support 568. The rail 556 extends between a leading end 572 and a trailing end 574, and has a cross-sectional shape which is complementary to the channel 404, such as a dovetail, a T-shape, or other undercut geometry for sliding interconnection. Close to the trailing end, the rail 556 may include one or more locking features 576, such as the pair of prongs or fingers shown. The prongs deflect elastically toward each other as the rail 556 is inserted into the channel 404, then spring outwardly within the pocket 406 to lock the rail in the channel. The rail 556 may include one or more retention features 578 such as the pair of bumps shown on the tray-facing side at the trailing end 574, which may cooperate with a corresponding pair of dimples 408 in the channel 404 of the tibial tray 324 to retain the rail in the channel with the prongs in an unlocked state not in the pocket 406. Alternatively, the bumps may drag against the channel 404. The fixation element 344 is shown with five blades 558, 560, 562, 564, 566 and two supports 568, 570. The blades 558, 560, 562, 564, 566 in this example are oval, elongated longitudinally. The leading edges of the blades may be sharpened or serrated to more easily cut through bone. The blades may be angled relative to the rail 556 and/or the bone-facing side 388 of the tibial tray 324 to achieve compression, consistent with previous descriptions. The supports 568, 570 in this example may be thicker and more rounded versus previously described supports.

Figure 116:
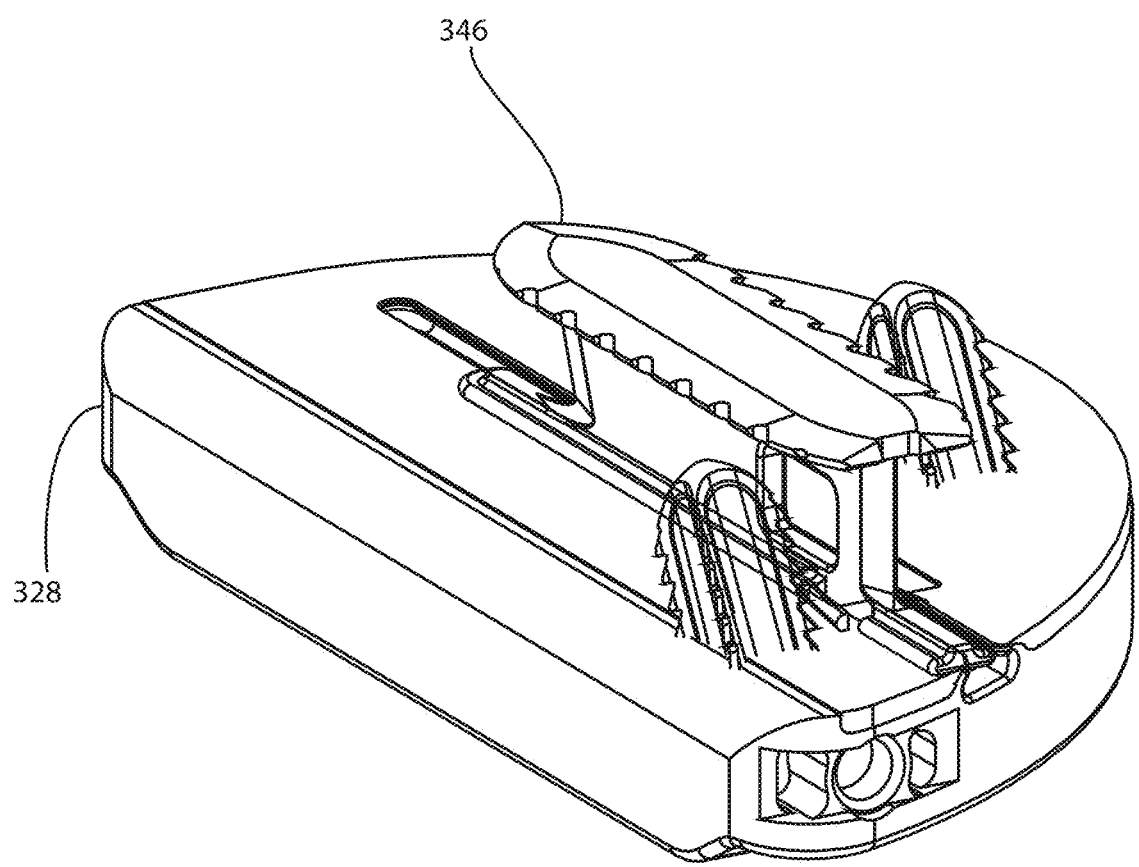
FIG. 116 is an oblique view of yet another tibial tray coupled to yet another fixation element.
Figure 117:
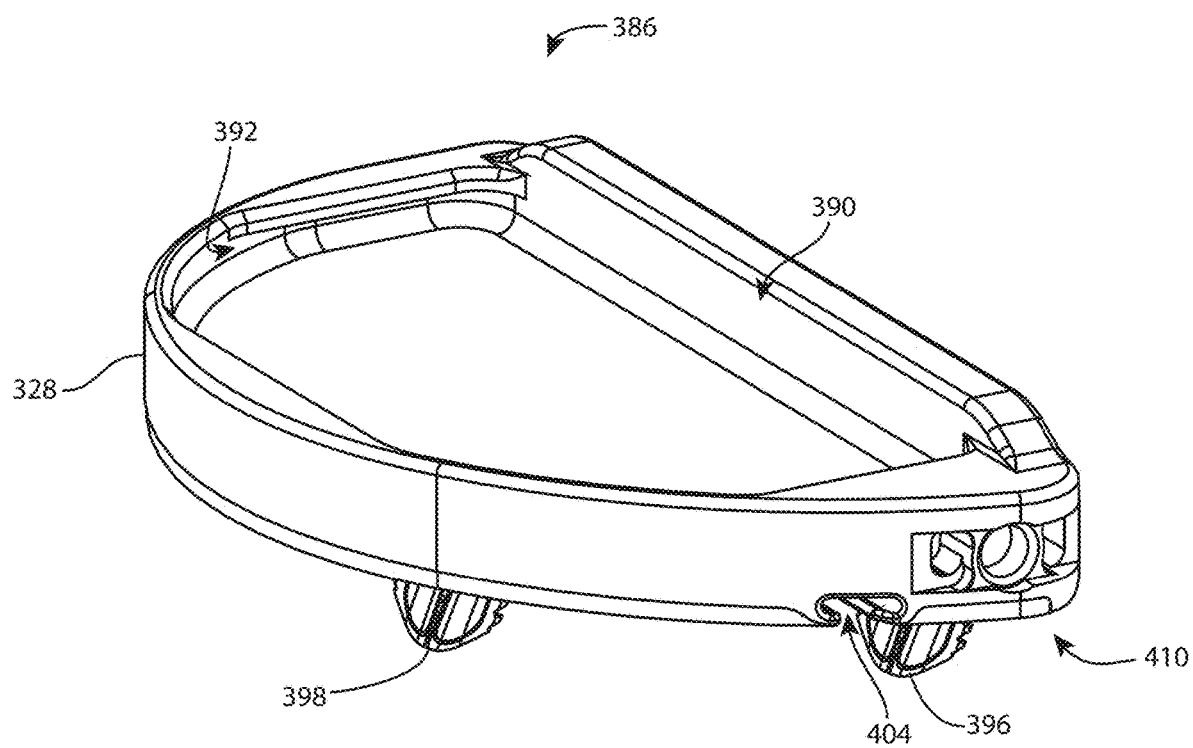
FIG. 117 is an oblique view of the tibial tray of FIG. 116.
Figure 118:
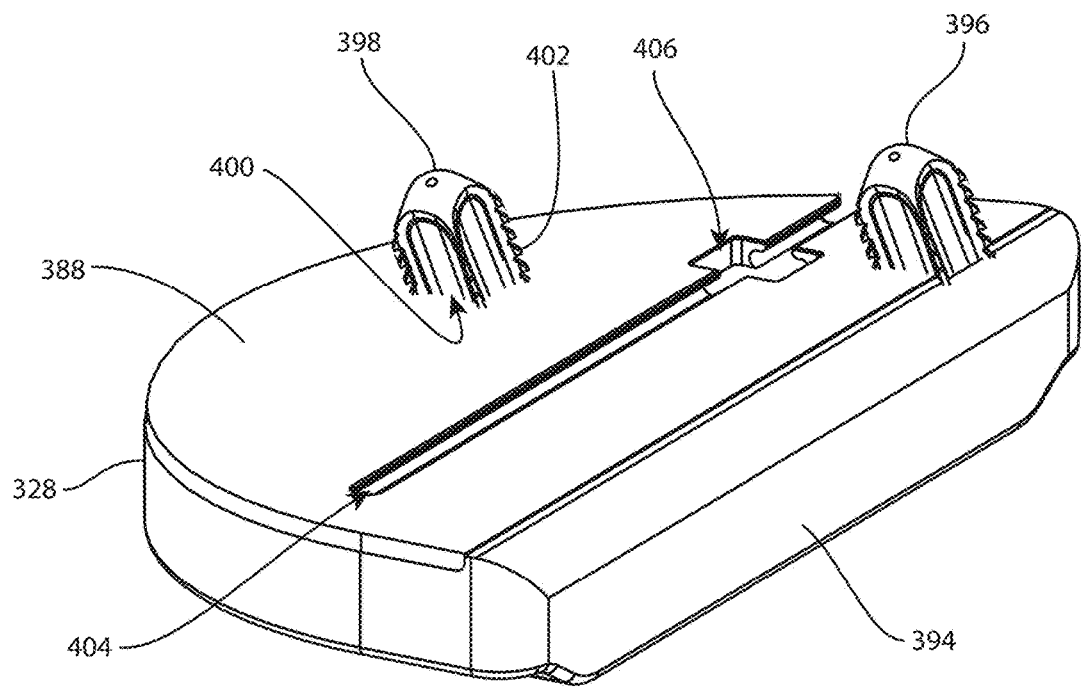
FIG. 118 is another oblique view of the tibial tray of FIG. 117 from a different direction.
Figure 119:
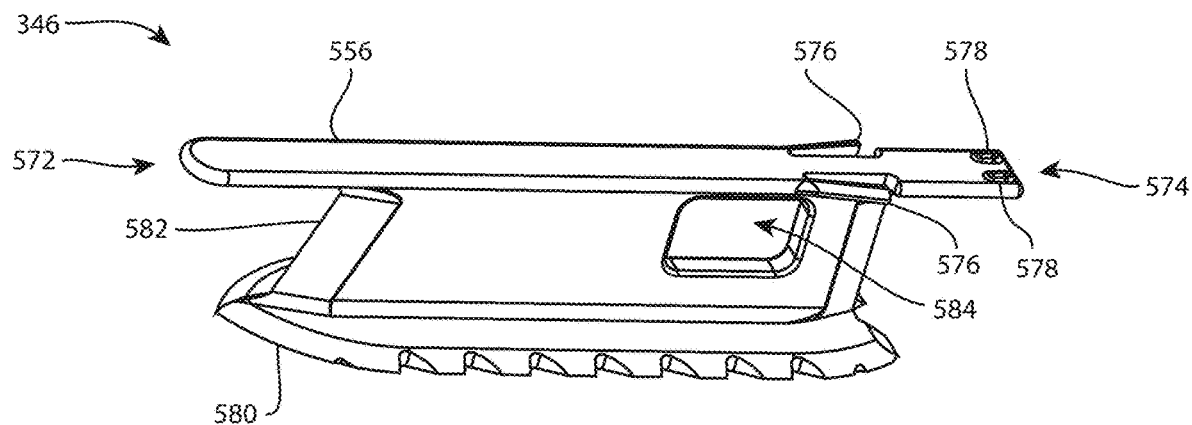
Figure 120:
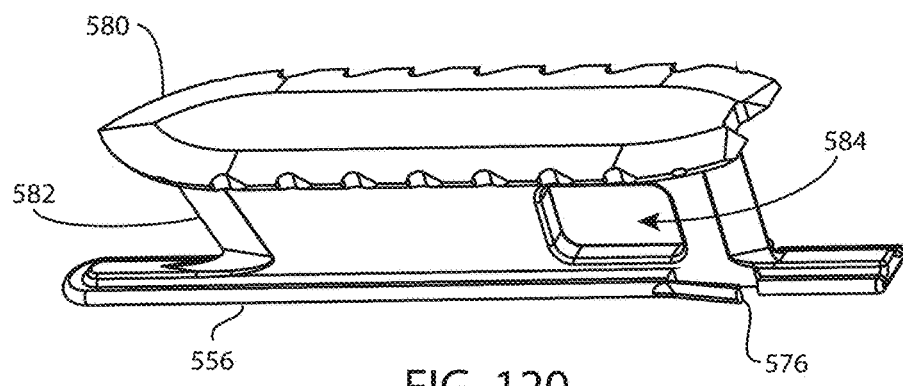
Figure 121:
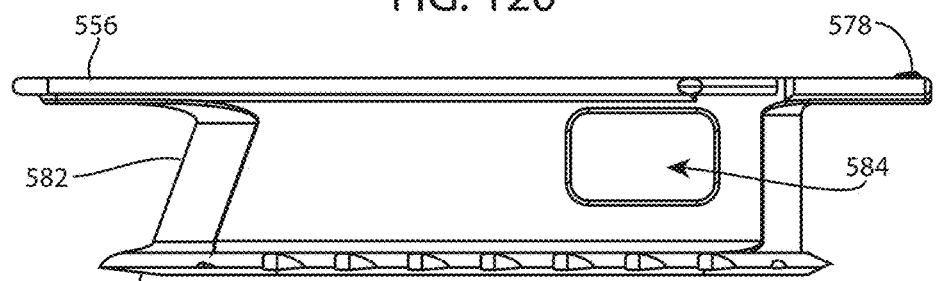
Figure 122:
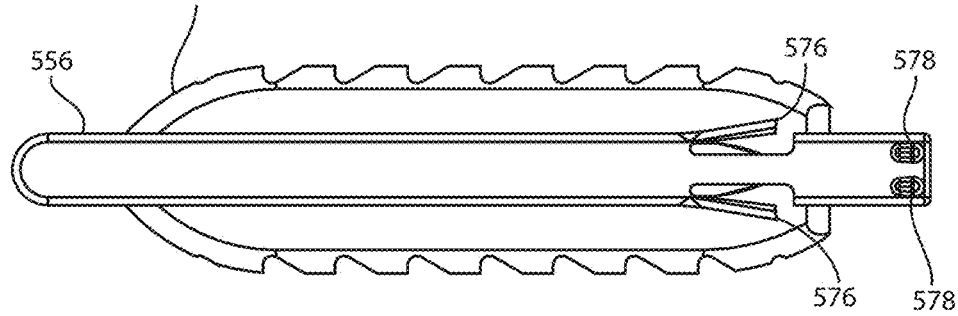
Figure 123:
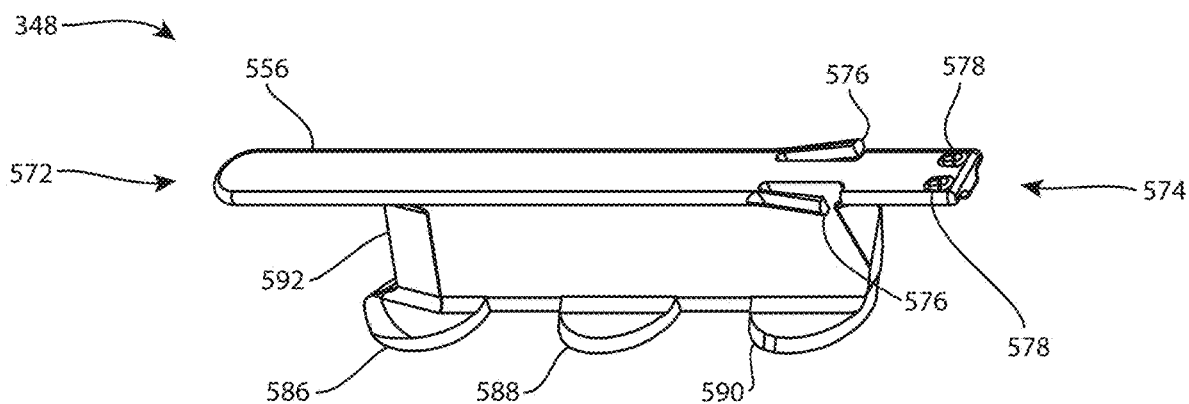
Figure 124:
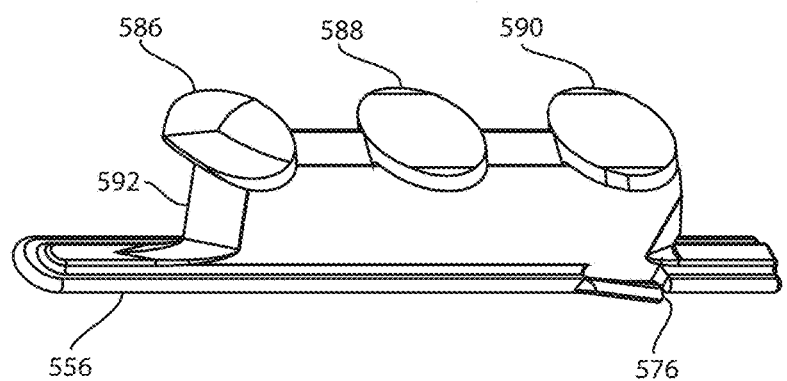
Figure 125:
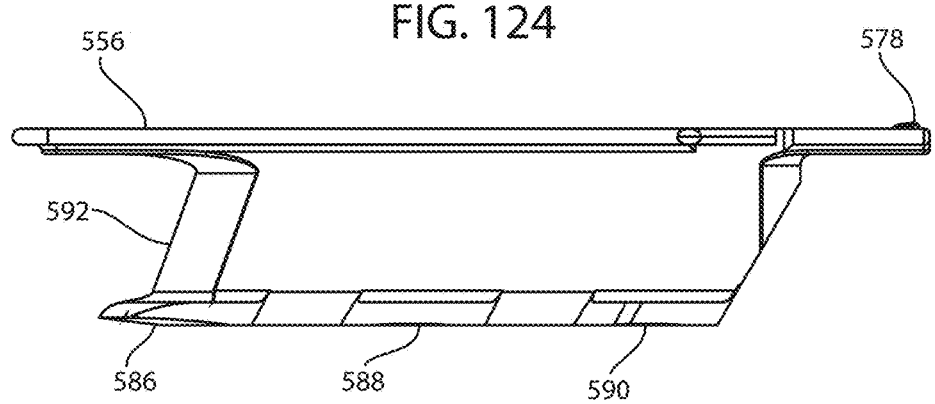
Figure 126:
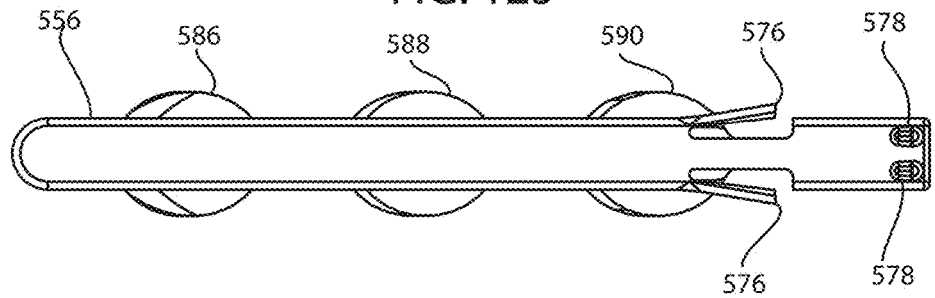
Figure 127:
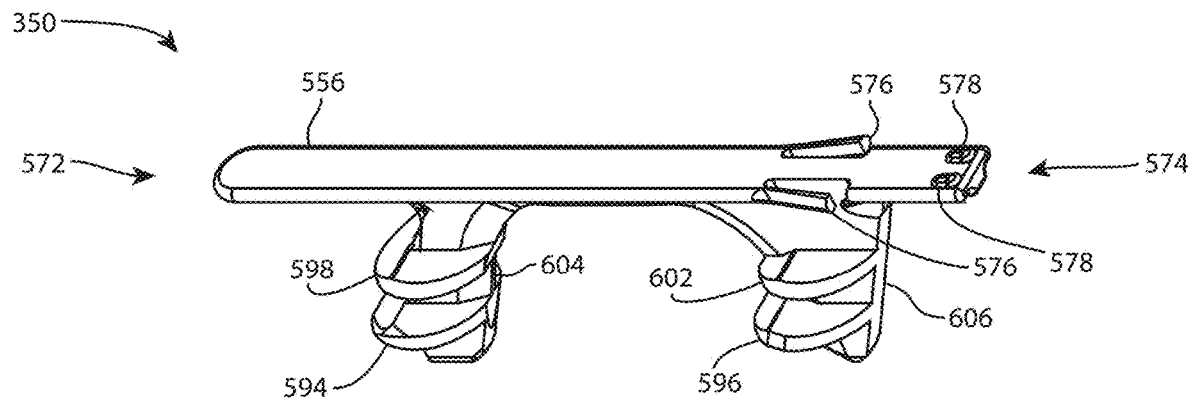
Figure 128:
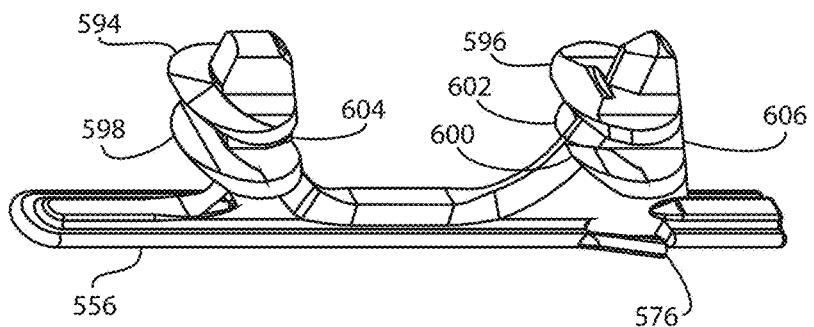
Figure 129:
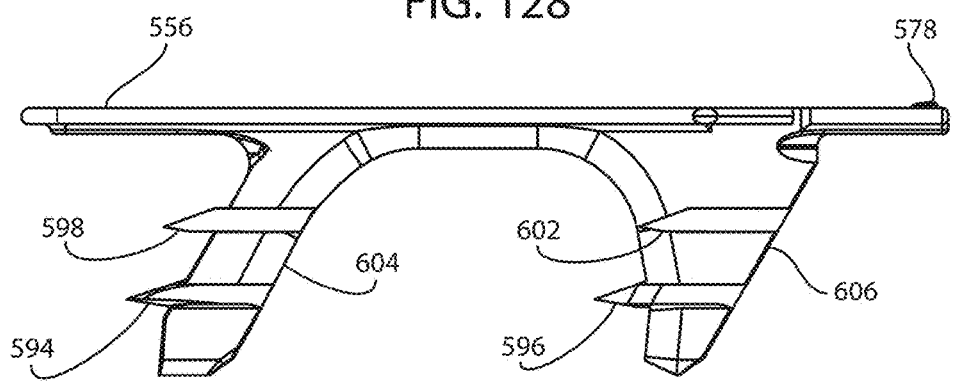
Figure 130:
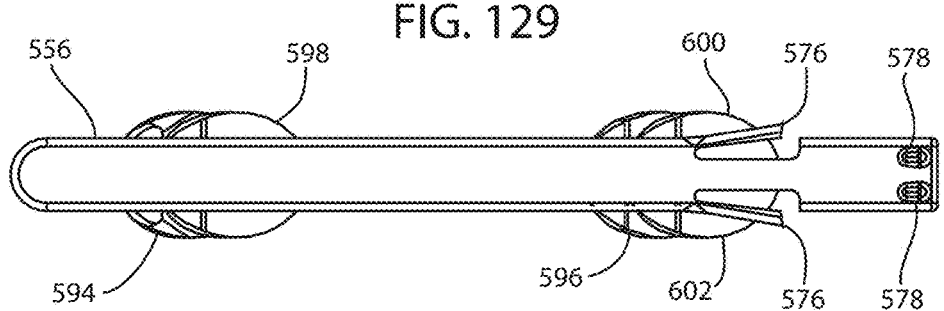

Referring to FIGS. 116-122, the tibial tray 328 may be used with the fixation element 346. FIG. 116 shows the tibial tray 328 with the fixation element 346 in the implanted state or locked state.

The tibial tray 328 includes all of the features of tibial tray 324, except it lacks the retention feature 408.

The fixation element 346 includes the rail 556, leading end 572, trailing end 574, locking features 576, and retention features 578 of fixation element 344. The fixation element 346 includes a blade 580 or bone engagement feature, and a support 582. The blade 580 in this example is elongated longitudinally with a pointed leading end. The leading edges of the blade 580 and/or the support 582 may be sharpened and/or serrated to more easily cut through bone. The blade 580 may be angled relative to the rail 556 and/or the bone-facing side 388 of the tibial tray 328 to achieve compression, consistent with previous descriptions. The fixation element 346 includes a window 584 through the support 582; a rectangular window is shown.

Referring to FIGS. 123-126, the fixation element 348 may be used with the tibial tray 328. The fixation element 348 includes the rail 556, leading end 572, trailing end 574, locking features 576, and retention features 578 of fixation element 344. The fixation element 348 includes three blades 586, 588, 590 all connected to a support 592. The blades are substantially circular to the unaided eye. The leading edges of the blades 586, 588, 590 and support 592 may be sharpened or serrated to more easily cut through bone. The blades 586, 588, 590 may be angled relative to the rail 556 and/or the bone-facing side 388 of the tibial tray 328 to achieve compression, consistent with previous descriptions.

Referring to FIGS. 127-130, the fixation element 350 may be used with the tibial tray 328. The fixation element 350 includes the rail 556, leading end 572, trailing end 574, locking features 576, and retention features 578 of fixation element 344. The fixation element 350 includes five blades 594, 596, 598, 600, 602 carried on two supports 604, 606, similar to fixation element 344. The blades 594, 596, 598, 600, 602 shown in this example are substantially circular to the unaided eye. The leading edges of the blades 594, 596, 598, 600, 602 and/or supports 604, 606 may be sharpened or serrated to more easily cut through bone. The blades 594, 596, 598, 600, 602 may be angled relative to the rail 556 and/or the bone-facing side 388 of the tibial tray 328 to achieve compression, consistent with previous descriptions.

Referring to FIGS. 131-134, the fixation element 352 may be used with the tibial tray 328. The fixation element 352 includes all of the features of fixation element 344 with additional blades and a third support.

Referring to FIGS. 135-142, the tibial tray 330 may be used with the fixation element 354. FIGS. 135-136 show the fixation element 354 in the implanted state.

The tibial tray 330 includes the insert-facing side 386, main bone-facing side 388, pocket 390, connection features 392, secondary bone-facing side 394, undercut channel 404, and pocket 406 of the tibial tray 324. In this example, a fin 608 protrudes from the bone-facing side 388. The fin 608 may be triangular as shown. The channel 404 and pocket 406 in this example extend through the anterior end of the tibial tray 330 and along a distal edge of the fin 608, so that the channel is oriented from proximal-anterior to distal-posterior.

The fixation element 354 includes the rail 556, leading end 572, trailing end 574, locking features 576, and retention features 578 of the fixation element 344, with the blade 580 of the fixation element 346. The fixation element 354 includes a support 610 which carries the blade 580 much closer to the rail 556 than in previous examples.

Referring to FIGS. 143-144, the tibial tray 332 includes an integral fixation element 612 which includes a blade 614 and support 616. The tibial tray 332 may include the insert-facing side 386, main bone-facing side 388, pocket 390, connection features 392, secondary bone-facing side 394, and/or other features of the tibial tray 324. The bone-facing side 388 is shown. The support 616 extends from the bone-facing side and the blade 614 extends along a distal side of the support 616. The leading edges of the blade 614 and/or support may be sharpened and/or serrated to more easily cut through bone. In this example, the blade 614 follows an arcuate path from proximal-anterior to distal-posterior. The tibial tray 332 may be rotated into position relative to the transverse tibial resection 226 along the arcuate path.

Referring to FIGS. 145-295, surgical methods and related instruments for unicondylar knee arthroplasty are disclosed, including bone preparation, implantation of implant components, and their removal. Surgical methods may include one or more of the disclosed steps, performed in any order. Some of the disclosed steps may be alternatives to other steps, or optional steps.

FIG. 145 shows a step of connecting a slotted tibial tower 620 to a tibial resection guide rod 618. FIG. 146 shows an alternative step of connecting a non-slotted tibial tower 622 to the tibial resection guide rod 618. These steps may include inserting an externally threaded shaft 624 of the tower into an internally threaded thumbscrew 626 of the tibial resection guide rod 618. The thumbscrew 626 may also be referred to as a vertical adjustment knob. After the threads of the shaft 624 and thumbscrew 626 are engaged, rotating the thumbscrew moves the tower up and down relative to the tibial resection guide rod 618.

FIGS. 147-148 show a step of connecting a modular slotted tibial cutting block 628 to the slotted tibial tower 620. This step may include sliding a rail 630 of the slotted tibial cutting block 628 into a complementary slot 632 of the slotted tibial tower 620. Sets of slotted and non-slotted tibial cutting blocks may be provided. Each set may include cutting blocks for 0 mm, +1 mm, +2 mm, and/or −2 mm cuts. Preferably, this step includes connecting a 0 mm slotted tibial cutting block 628 to the slotted tibial tower 620 so that the initial resection is made at a nominal level.

FIG. 149 shows a step of using a screwdriver 634 to lock the slotted tibial cutting block 628 to the slotted tibial tower 620 by tightening a locking screw 636 of the slotted tibial tower.

FIG. 150 shows the distal femur 202 and proximal tibia 204 of a knee joint 200 in a step of using a thin end 637 of a tibial AP sizer wand 638 to measure the anterior-posterior dimension of the intact tibia. This may be an optional step in preparation for using a blocker pin, discussed below. The measurement may be used to select an appropriate blocker pin length.

FIG. 151 shows a step of using an angel wing 640 in a transverse cutting slot 642 of the slotted tibial cutting block 628 to initially position the slotted tibial tower 620 and slotted tibial cutting block relative to the tibia 204. FIG. 152 shows a step of using the angel wing 640 in a vertical cutting slot 644 of the slotted tibial tower 620 to initially position the slotted tibial tower and slotted tibial cutting block 628 relative to the tibia 204.

FIG. 153 shows a step of using the angel wing 640 against a transverse cutting surface 646 of a non-slotted tibial cutting block 648 to initially position the non-slotted tibial tower 622 and the non-slotted tibial cutting block relative to the tibia 204. FIG. 154 shows a step of using the angel wing 640 vertically to initially position the non-slotted tibial tower 622 and non-slotted tibial cutting block 648 relative to the tibia 204.

FIG. 155 shows a step of inserting a bone pin 650 through a lateral pin hole 652 of a pin arm 654 of the tibial resection guide rod 618 to provide initial fixation to the tibia 204. The bone pin 650 may be a 3.2 mm threaded pin. Fine adjustments in the vertical and/or horizontal directions may be made using the thumbscrew 626 and/or a horizontal adjustment knob 656 of the tibial resection guide rod 618.

FIGS. 156-157 show a step of inserting a tibial stylus 658 into the transverse cutting slot 642 of the slotted tibial cutting block 628 and into the medial compartment to contact the deepest point of the medial compartment of the tibial plateau. This step may set the depth of the transverse tibial resection. The tibial stylus 656 may be double-ended so that one end sets a +2 mm resection depth and the other end sets a +4 mm resection depth. This step may include adjusting the resection depth up or down by turning the thumbscrew 626, and/or adjusting the resection medially or laterally by using the horizontal adjustment knob 656. Preferably, the resection should be adjacent to the medial attachment of the anterior cruciate ligament (ACL) in order to maximize tibial implant coverage; rotational alignment should be parallel to the anterior-posterior axis of the tibial plateau to properly establish the posterior slope.

FIG. 158 shows a step of inserting bone pins 660, 662 through medial and lateral holes 670, 672 of the slotted tibial tower 620. The bone pin 660 may be a 3.2 mm threaded pin. The bone pin 662 may be a 4 mm blocker pin. A set of blocker pins may be provided. The set may include 35 mm, 45 mm, and/or 60 mm lengths. The length of the bone pin 662 may be less than the measured anterior-posterior dimension of the intact tibia 204.

FIG. 159 shows a step of inserting bone pins 650, 660 through the lateral pin hole 652 of the tibial resection guide rod 618 and a medial hole 674 of the non-slotted tibial tower 622.

FIG. 160 shows a step of using a saw blade 676 through the vertical cutting slot 644 to make a vertical resection 228, also known as a sagittal resection. The saw blade 676 may be a blunt-tipped single-sided reciprocating saw blade. Preferably, the vertical resection 228 should be located just medial to the ACL insertion. This step may include contacting the bone pin 662 with the saw blade 676. The bone pin 662, also known as a blocker pin, blocks the saw blade from cutting below the level of the transverse resection 226.

FIG. 161 shows a step of using a saw blade 678 through the transverse cutting slot 642 to make a transverse resection 226. The saw blade 678 may be an oscillating saw blade, preferably a 1.27 mm×12.5/13 mm×90 mm oscillating saw blade. This saw blade thickness is advantageous to ensure that the transverse resection 226 is well-controlled through the transverse cutting slot 642.

FIG. 162 shows a step of using the saw blade 678 against the transverse cutting surface 646 to make the transverse resection 226. This step may include leaving the saw blade 676 in the deepest part of the tibial cut, which is preferably just lateral to the medial margin of the ACL.

FIGS. 163-164 show a step of using the saw blade 676 to make the vertical resection 228. This step may include contacting the saw blade 678 with the saw blade 676, which blocks the saw blade 676 from cutting below the level of the transverse resection 226.

FIG. 165 is an oblique view of the knee joint of FIG. 161 showing a step of using a rasp 680 to remove unresected bone, for example along the corner between the transverse and vertical resections 226, 228. The rasp 680 may be double-sided, with a coarse surface on one side and a fine surface on the other side. The rasp 680 may have bone removal surfaces along all four sides.

FIG. 166 shows a step of using the screwdriver 634 to unlock the slotted tibial cutting block 628 from the slotted tibial tower 620 by loosening the locking screw 636.

FIG. 167 shows the knee joint 200, slotted tibial tower 620, and bone pins 650, 660, 662 after removing the slotted tibial cutting block 628.

FIG. 168 shows a step of using an insert sizer 682 to assess ligament tension. The insert sizer 682 may include a thin end 683 and a thick end 685. The thin end 683 may match the thickness of the final tibial implant including a tibial tray implant and an articular insert implant. A set of implant sizers 682 may be provided. The set may include insert sizers having thin ends corresponding to articular insert implants that are 9 mm, 10 mm, 11 mm, and/or 13 mm thick. This step may include inserting the thin end 683 between the femur 202 and tibia 204, and may include using different sizes to achieve satisfactory ligament tension.

If the 9 mm sizer over-tensions the ligaments, or cannot be inserted, it may be necessary to re-cut the tibia at a lower level and re-assess ligament tension. FIGS. 169-170 show a step of re-connecting the slotted tibial cutting block 628 to the slotted tibial tower 620. This step may include the steps shown in FIGS. 147-149, and may be followed by one or more of the steps shown in FIGS. 160-161 and/or 165-168. This step may include connecting the 0 mm, +1 mm, or +2 mm slotted tibial cutting block 628 to the slotted tibial tower 620, where the "+" indicates a deeper resection than nominal. Re-cutting the tibia and re-assessing ligament tension may be performed repeatedly, starting with the 0 mm slotted tibial cutting block 628 and progressing to the +1 mm and +2 mm blocks if needed. If no slotted tibial cutting block 628 is connected to the slotted tibial tower 620, the top surface of the slotted tibial tower provides a +4 mm cutting surface. After satisfactory ligament tension is achieved, all apparatus may be removed from the tibia 204.

FIGS. 171-172 show a step of attaching a re-cut block 684 to the proximal tibia 204. This step may be performed if tibial re-cut is needed after removing the slotted tibial tower 620, non-slotted tibial tower 622, and/or tibial resection guide rod 618. A set of re-cut blocks 684 may be provided. The set may include +2 mm, 2° Posterior Slope, 2° Varus, and/or 2° Valgus re-cut blocks 684. The 2° Varus and 2° Valgus re-cut blocks change only the medial-lateral slope of the tibial resection, and may not be intended to adjust the overall alignment of the leg, also known as long limb alignment. The total thickness of the implanted construct or system, relative to the amount of resected bone, may govern long limb alignment.

FIG. 173 shows a 2° varus re-cut block 684 attached to the tibia 204. FIG. 174 shows a 2° valgus re-cut block 684 attached to the tibia 204.

FIG. 175 is an oblique exploded view of a tensor block 686 and tensor shim 688. The tensor block 686, alone or with an attached tensor shim 688, may be used to tension the ligaments during resection of the femoral condyle. The tensor blocks 686 may correspond to the thin end 683 of the insert sizer 682 and the total thickness of a tibial tray implant and articular insert implant. The tensor shims 688 may fill any excess space resulting from bone loss or defect that may be present on the distal femoral condyle. A set of tensor blocks 686 may be provided. The set may include tensor blocks in the same sizes as the insert sizer 682: 9 mm, 10 mm, 11 mm, and/or 13 mm. Preferably, a tensor block 686 the same size as the last insert sizer 682 should be used. A set of tensor shims 688 may be provided. The set may include tensor shims in 1 mm, 2 mm, 3 mm, 4 mm, and/or 5 mm thicknesses. One or more pegs 690 of the tensor shim 688 are received in corresponding holes 692 of the tensor block 686 to connect the parts together, for example with a snap fit.

FIG. 176 shows a step of connecting the tensor block 686 and tensor shim 688 to a quick-connect handle 694. FIG. 177 shows a step of inserting the tensor block 686 and tensor shim 688 between the femur 202 and tibia 204 with the knee joint 200 in extension. FIG. 178 shows the tensor block 686 and tensor shim 688 fully inserted between the femur 202 and tibia 204. The quick-connect handle 694 may be removed after this step. FIG. 179 shows a step of applying varus/valgus stress to the knee, indicated by the arrows. FIG. 180 shows a step of replacing the tensor shim 688 of FIG. 175 with a thicker tensor shim 688. The steps shown in FIGS. 176-180 may be repeated, using progressively thicker tensor shims 688, until satisfactory ligament tension is achieved in the step shown in FIG. 179, also known as ligament balancing or joint tension.

FIGS. 181-183 show a step of connecting a distal femoral cutting block 696 to the tensor block 686 and a step of securing the distal femoral cutting block 696 to the femur 202 with bone pins 650.

FIGS. 184-185 show a step of using an extramedullary guide 700, extramedullary rod 702, and extramedullary rod with coupler 704 to verify long limb alignment. This step may include inserting a tab 706 of the extramedullary guide 700 into a cutting slot 708 of the distal femoral cutting block 696, connecting the extramedullary rod 702 and the extramedullary rod with coupler 704, and connecting the extramedullary rod with coupler 704 to the extramedullary guide 700 by inserting the coupler 710 in a hole 712 of the extramedullary guide 700. This step may also include verifying that, in an anterior view of the leg, the proximal end of the extramedullary rod with coupler 704 passes over the center of the femoral head and the center of the distal tibia 204. Limb alignment may be adjusted by changing the thickness of the tensor shim 688, which may include one or more of the steps shown in FIGS. 176-185. A thinner tensor shim 688 results in a deeper distal femoral resection and shifts alignment toward varus; a thicker tensor shim would have the opposite effect, shifting alignment toward valgus. These steps may be repeated until satisfactory long limb alignment is achieved.

FIGS. 186-187 show a step of inserting the thin end 683 of the insert sizer 682 between the femur 202 and tibia 204 with the knee joint 200 in extension, and a step of using the extramedullary rod 702 and extramedullary rod with coupler 704 to verify long limb alignment. In this step, however, the extramedullary rod 702 and extramedullary rod with coupler 704 may be offset medial to the true mechanical axis of the leg. Limb alignment may be adjusted by changing the thickness of the tensor shim 688. A thinner tensor shim 688 shifts alignment toward varus, while a thicker tensor shim shifts alignment toward valgus.

FIG. 188 shows a step of using the saw blade 678 through the cutting slot 708 of the distal femoral cutting block 696 to make a distal femoral resection 212.

FIGS. 189-190 show a step of using the insert sizer 682 to confirm the distal femoral resection. This step may include placing the knee joint 200 in 5° of flexion (to match the posterior slope of the transverse resection 226), inserting the thick end 685 of the insert sizer 682 between the femur 202 and tibia 204, and applying slight varus/valgus stress to evaluate ligament tension. This step may include using various size insert sizers 682 to identify an appropriate thickness that achieves satisfactory ligament tension.

FIGS. 191-192 show a step of using a tibial centerline marking guide 710 to mark the transverse resection 226 and/or the proximal anterior tibia 204. This step may include positioning the knee joint 200 in flexion, positioning a paddle 712 of the tibial centerline marking guide 710 against the transverse resection 226, aligning the medial border of the paddle 712 with the medial border of the transverse resection 226, and aligning the tibial centerline marking guide 710 parallel with the sagittal plane. This step may include using a sterile marking pen or other tool through an aperture 714 of the paddle 712 to make a proximal tibial mark 224 on the transverse resection 226 along the centerline, and using the pen or other tool through an aperture 716 of the tibial centerline marking guide 710 to make an anterior tibial mark 222 on the anterior tibial cortex at or near the margin of the transverse resection 226 along the centerline. A set of tibial centerline marking guides 710 may be provided, having paddles 712 that correspond in shape and size to the various shapes and sizes of tibial tray implants.

FIGS. 193-194 show a step of inserting the insert sizer 682 between the femur 202 and tibial 204, and connecting a femoral marking tower 718 to the insert sizer. This step may include positioning the knee joint 200 in 95° of flexion, inserting the thin end 683 of the insert sizer 682 between the femur 202 and the tibia 204, visually aligning a central slot 720 of the insert sizer 682 with the anterior and/or proximal tibial marks 222, 224, coupling the femoral marking tower 718 to the central slot 720, and sliding the femoral marking tower 718 into contact with the distal femoral resection 212.

FIG. 195 shows a step of using the femoral marking tower 718 to mark the distal femoral resection 212. This step may include using a sterile marking pen or other tool through an aperture 722 of the femoral marking tower 718 to make a distal femoral mark 210 on the distal femoral resection 212 along the centerline.

FIGS. 196-197 show a step of using the insert sizer 682 to mark the distal anterior femur 202. This step may include placing the knee joint 200 in extension, inserting the thick end 685 of the insert sizer 682 between the femur 202 and the tibia 204, visually aligning a central hole 724 of the insert sizer 682 with the proximal tibial mark 224, and using the pen or tool to make an anterior femoral mark 208 on the anterior femoral cortex at or near the margin of the distal femoral resection 212. The anterior femoral mark 208 takes into account femorotibial rotation due to the screw-home mechanism.

FIGS. 198-199 show a step of using a femoral sizer 726 to measure the approximate femoral implant size. This step may include placing the femoral sizer against the distal femoral resection 212 and reading indicia 727 on the femoral sizer 726 to determine the approximate femoral implant size. The anterior margin of the distal femoral resection 212 may extend 2-3 mm above the appropriate size marking. Referring to FIG. 199, the appropriate femoral implant is size 4.

FIG. 200 shows a step of connecting a tensor block 686 and a posterior cutting block 728 together. FIG. 201 shows the tensor block 686 and posterior cutting block 728 fully connected. FIG. 202 shows a step of inserting the tensor block 686 between the femur 202 and the tibia 204 and placing the posterior cutting block 728 against the distal femoral resection 212. Preferably, these steps are performed without the use of a tensor shim 688, to ensure that the flexion and extension spaces are balanced.

FIG. 203 shows a step of connecting the tensor block 686 to the quick-connect handle 694. FIG. 204 shows a step of inserting the tensor block 686 between the femur 202 and the tibia 204 using the quick-connect handle 694. FIG. 205 shows a step of connecting the posterior cutting block 728 to the tensor block 686 after disconnecting the quick-connect handle 694. FIG. 206 shows the tensor block 686 and posterior cutting block 728 fully connected, with the posterior cutting block against the distal femoral resection 212.

FIG. 207 is a medial view of the knee joint 200, tensor block 686, and posterior cutting block 728. Preferably, the flexion angle of the knee joint 200 is set so that the posterior cutting block 728 is flush against the distal femoral resection 212 while the tensor block 686 is flush against the transverse resection 226. At this point, referring to FIG. 208, prior to inserting bone pins, the medial-lateral position of the posterior cutting block 728 may be assessed to ensure that the distal femoral mark 210 is visible in a window 736 of the posterior cutting block 728, that the anterior femoral mark 208 is visible in a notch 738 of the posterior cutting block, and/or that a rim of exposed bone is present anteriorly and medially relative to the posterior cutting block. FIG. 208 shows that the posterior cutting block 728 includes a profile 916, border, or outer perimeter in this view. The profile 916 is also seen in FIG. 306. The profile 916 matches the profile 914 of the femoral implant 320 so that the posterior cutting block 728 may be used to judge how the femoral implant 320 will cover the distal femoral resection 212. The posterior cutting block 728 may be repositioned, or a smaller size block selected if one or more of these criteria is not met.

FIGS. 208-209 show a step of inserting bone pins 650 through holes 730, 732, 734 of the posterior cutting block 728 and into the femur 202. Preferably, the bone pins 650 are inserted sequentially through holes 730, 732, 734.

FIG. 210 shows a step of coupling a rotation tensor block 740 to the posterior cutting block 728. This step may be performed when it would be beneficial to rotate the femoral implant slightly to match the shape of the resected femur 202, to achieve increased femoral coverage and/or improved femorotibial tracking throughout the range of motion of the knee joint 200. FIG. 211 shows the rotation tensor block 740 and posterior cutting block 728 fully coupled together. FIGS. 212-213 show a step of inserting the rotation tensor block 740 between the femur 202 and tibia 204, and a step of inserting bone pins 650 through the posterior cutting block 728. These steps may be identical to the steps shown in FIGS. 200-202 and 207-209, other than using the rotation tensor block 740 instead of the tensor block 686. Prior to inserting the bone pins 650, the medial-lateral position and external/internal rotation of the posterior cutting block 728 may be assessed to ensure that the distal femoral mark 210 is visible in a window 736 of the posterior cutting block 728, that the anterior femoral mark 208 is visible in a notch 738 of the posterior cutting block, and that a rim of exposed bone is present anteriorly and medially relative to the posterior cutting block.

Referring to FIGS. 300-302, the rotation tensor block 740 includes a first bone-facing side 894 for contacting the transverse resection 226, a second bone-facing side 896 for contacting an unresected posterior surface of the medial condyle of the femur 202, one or more connection features 898 for connection to other instruments and/or tools, and an interface surface 900 which articulates with the posterior cutting block 728 to enable the posterior cutting block to rotate relative to the rotation tensor block. The first and second bone-facing sides 894, 896 may be flat and parallel, separated by a thickness 902 which is the same as the thin end 683 of the insert sizer 682 and the thickness of the final tibial implant including a tibial tray implant and an articular insert implant. The connection features 898 in this example include a rounded rectangular post between mirror image o arcuate slots, as seen in FIGS. 210 and 302. The connection features 898 connect with the posterior cutting block 728, the quick-connect handle 694, and/or other instruments or tools. The interface surface 900 in this example is a concave cylindrical surface having a central longitudinal axis 904. FIG. 302 shows the interface surface 900 viewed on end. The axis 904 is shown as a center point of a dashed-line circle representing an extension or extrapolation of the cylindrical surface.

Referring to FIGS. 303-305, the posterior cutting block 728 includes a bone-facing side 906 for contacting the distal femoral resection 212, one or more connection features 908 for connection to the tensor block 686 or the rotation tensor block 740, and an interface surface 910 which articulates with the interface surface 900 of the rotation tensor block to enable the posterior cutting block to rotate relative to the rotation tensor block around the collinear central longitudinal axes 904, 912 of the interface surfaces 900, 910. The bone-facing side 906 may be flat. The connection features 908 in this example include a wide slot or pocket between protruding pegs. When the connection features 908 are connected to the connection features 898 of the rotation tensor block 740, they may limit the rotational range of motion of the posterior cutting block 728 relative to the rotation tensor block 740. In one embodiment, the posterior cutting block 728 may have 10° of rotational range of motion, in other words, 5° of external rotation and 5° of internal rotation; in other examples, the rotational range of motion may be 12°, 20° or more. The connection features 898, 908 may thus be referred to as rotation limiting features. The interface surface 910 in this example is a convex cylindrical surface having a central longitudinal axis 912. FIG. 305 shows the interface surface 910 viewed on end. The axis 912 is shown as a center point of a dashed-line circle representing an extension or extrapolation of the cylindrical surface.

Referring to FIG. 306, the relationship of the medial-lateral curvature 890 and center point 892 of the femoral implant 320, the interface surface 910 and central longitudinal axis 912 of the posterior cutting block 728, and the interface surface 900 and central longitudinal axis 904 of the rotation tensor block 740 is shown. The center point 892 and axes 912, 904 are all coincident, although the medial-lateral curvature 890 has a smaller radius than the interface surfaces 910, 900 (which are substantially the same radius). The axes 912, 904 may be described as collinear, coincident, or a common center longitudinal axis of the first and second interface surfaces 910, 900. FIG. 306 shows the coincident center point 892 and axes 912, 904 spaced apart along a line, only because the femoral implant 320, posterior cutting block 728, and rotation tensor block 740 are shown side by side for clarity instead of superimposed as in actual practice. The disclosed structure of the interface surfaces 900, 910 represents one design to provide rotation of the posterior cutting block 728 around the center longitudinal axes 912, 904 (and thus the center point 892). Other structure that provides the same rotational motion are contemplated, such as a pin or peg in a hole, an arcuate guide rail in a complementary slot, and the like. FIG. 306 also clearly shows that the profile 916 of the posterior cutting block 728 matches the profile 914 of the femoral implant 320.

FIG. 214 shows a step of using a femoral drill 742 through a hole 746 of the posterior cutting block 728 to make a peg hole 220 in the femur 202. FIG. 215 shows a step of using the drill 742 through a hole 744 of the posterior cutting block 728 to make a peg hole 218 in the femur 202.

FIG. 216 shows a step of using the saw blade 678 through a posterior saw slot 748 of the posterior cutting block 728 to make a posterior femoral resection 216. FIG. 217 shows a step of using the saw blade 678 through a posterior chamfer saw slot 750 of the posterior cutting block 728 to make a posterior chamfer resection 214.

FIGS. 214-217 show the tensor block 686 in use. The rotation tensor block 740 may be used instead for these steps.

FIGS. 218-219 show a step of using the insert sizer 682 to check ligament tension with the knee joint 200 in flexion. The knee joint 200 may be in about 110° of flexion for this step. This step may include inserting the thick end 685 of the insert sizer 682 between the transverse resection 226 and the posterior femoral resection 216 to verify posterior gap. Preferably, the thick end 685 should be flush against the transverse resection 226 and the posterior femoral resection 216. Slight varus/valgus stress may be applied to the knee joint 200 during this step to aid in determining the appropriate ligament tension.

FIGS. 220-221 show a step of using the insert sizer 682 to check ligament tension with the knee joint 200 in extension. The knee joint 200 may be in about 5° of flexion for this step. This step may include inserting the thick end 685 of the insert sizer 682 between the transverse resection 226 and the distal femoral resection 212 to verify distal gap. Preferably, the thick end 685 should be flush against the transverse resection 226 and the distal femoral resection 212. Slight varus/valgus stress may be applied to the knee joint 200 during this step to aid in determining the appropriate ligament tension.

If the ligament tension in flexion (FIGS. 218-219) is too tight, but the ligament tension in extension (FIGS. 220-221) is appropriate, the posterior femoral resection 216 may be re-cut deeper and a smaller size femoral implant used. With brief reference to FIGS. 54-56, FIG. 222 is a side view showing multiple superimposed femoral implants 320 of different sizes. The distal surfaces 362, posterior chamfer surfaces 364, and locations of the second pegs 370 are identical for all seven sizes shown. The locations of the first pegs 368 are identical for the three smallest femoral implants, and the locations of the first pegs 368 are identical for the four largest femoral implants, but different from the three smallest femoral implants. The posterior surfaces 366 are spaced 1.3 mm apart from one size to the next.

FIG. 223 shows a step of inserting a size 2-3/5-8 downsizing guide 752 between the femur 202 and the tibia 204.

FIG. 224 shows the size 2-3/5-8 downsizing guide 752 fully inserted in contact with the distal femoral resection 212 and the posterior femoral resection 216, and shows a step of inserting bone pins 650 through one or more of holes 754, 756, 758 of the size 2-3/5-8 downsizing guide 752. FIG. 225 shows a step of using the saw blade 678 through a cutting slot 760 of the size 2-3/5-8 downsizing guide 752 to cut a new posterior femoral resection 216.

FIG. 226 shows a step of inserting a size 4 downsizing guide 762 between the femur 202 and the tibia 204. This step may include inserting pegs 764, 766 of the size 4 downsizing guide 762 into the holes 218, 220 of the femur 202. FIG. 227 shows the size 4 downsizing guide 762 fully inserted in contact with the distal femoral resection 212, and shows a step of inserting bone pins 650 through one or more holes 768, 770, 772 of the size 4 downsizing guide 762. FIG. 228 shows a step of using the drill 742 to make a new peg hole 218 in the femur 202. FIG. 229 shows a step of using the saw blade 678 through a cutting slot 776 of the size 4 downsizing guide 762 to cut a new posterior femoral resection 216.

FIGS. 230-231 show a step of using a thick end 639 of the tibial AP sizer wand 638 to initially measure the anterior-posterior dimension of the resected tibia.

FIG. 232-233 show a step of using a tibial sizer 778 to measure the tibia. The tibial sizers 432, 482 may be used interchangeably with the tibial sizer 778, corresponding to a particular choice of tibial tray implant. This step may include initially placing a paddle 780 of the tibial sizer 778 against the transverse resection 226 in a relatively posterior location, sliding the paddle 780 anteriorly until a hook, like hook 438 of FIGS. 69-70 or hook 488 of FIGS. 97-98, contacts a posterior side of the proximal tibial 204 at a posterior margin of the transverse resection 226, aligning a medial side of the paddle 780 with a medial margin of the transverse resection, and aligning an anterior side of the paddle 780 with an anterior margin of the transverse resection. See FIG. 233 for illustration of the medial and anterior alignments. The paddle 780 preferably closely or exactly matches the size and shape of the tibial tray implant. This step may include viewing the anterior tibial mark 222 and/or proximal tibial mark 224 through corresponding elongated holes 784, 786 of the tibial sizer 778.

FIG. 234 shows a step of inserting a bone pin 788 through a hole 790 of the tibial sizer 778 and a step of using the angel wing 640 to verify posterior fit. The bone pin 788 may be a 3.2 mm short pin. The hole 790 may extend substantially perpendicularly through the paddle 780 of the tibial sizer 778.

FIG. 235 shows a step of using a tibial drill 792 through a hole 794 of the tibial sizer 778 to make a first peg hole 230 in the tibia 204. FIG. 236 shows a step of using the tibial drill 792 through a hole 796 of the tibial sizer 778 to make a second peg hole 232 in the tibia 204. Optionally, a second tibial drill 792 may be used in this step, leaving the first tibial drill 792 in the holes 794, 230 to further stabilize the tibial sizer 778.

FIG. 237 shows a step of inserting a tibial tray trial 800 between the femur 202 and the tibia 204. Preferably, the tibial tray trial 800 includes pegs that correspond to the tibial tray implant pegs, and which fit into the peg holes 230, 232 of the tibia 204. See for example FIGS. 61-64 showing tibial tray 324 with pegs 396, 398. Only one peg 802 of the tibial tray trial 800 is visible in FIG. 237. This step may include inserting pegs of the tibial tray trial 800 into the peg holes 230, 232 of the tibia 204 and placing a bone-facing side of the tibial tray trial 800 against the transverse resection 226. FIG. 238 shows a step of using a curved impactor 804 to fully insert/seat the tibial tray trial 800 in the peg holes 230, 232 and against the transverse resection 226. FIG. 239 shows a step of using the angel wing 640 to verify posterior fit.

FIG. 240 shows a step of using a femoral impactor 806 to insert/seat a femoral trial 808. Preferably, the femoral trial 808 includes pegs that correspond to the femoral implant pegs, and which fit into the peg holes 218, 220 of the femur 202. See for example FIGS. 54-56 showing femoral implant 320 with pegs 368, 370. This step may include inserting pegs of the femoral trial 808 into the peg holes 218, 220 and placing a bone-facing side of the femoral trial 808 against the distal femoral resection 212, the posterior chamfer resection 214, and the posterior femoral resection 216.

FIG. 241 shows a step of inserting an insert trial 810 between the femur 202 and the tibia 204. The insert trial 810 may be referred to as an articular insert trial. This step may include selecting an insert trial 810 size and thickness that matches the tibial tray trial 800 and the insert sizer 682 used in the steps shown in FIGS. 218-221. FIG. 242 shows a step of using an insert impactor 812 to fully insert/seat the insert trial 810.

FIG. 243 shows the tibial tray trial 800, femoral trial 808, and insert trial 810 fully inserted into the knee joint 200, and ready for a step of manipulating the knee joint 200 through a range of motion to assess joint stability and gap balancing.

FIGS. 244-245 show a step of using a removal hook 814 to remove the insert trial 810.

FIGS. 246-247 show a step of connecting and locking a slap hammer 816 to the femoral trial 808 to remove the femoral trial.

FIG. 248 shows a step of connecting the quick-connect handle 694 to the tibial tray trial 800 to remove the tibial tray trial.

FIG. 249 is an oblique view of the knee joint of FIG. 248 showing a step of inserting a tibial tray implant 818 between the femur 202 and tibia 204. FIG. 250 shows a step of using the curved impactor 804 to fully insert/seat the tibial tray implant 818. FIG. 251 shows a step of using the angel wing 640 to verify posterior fit. The tibial tray implant 818 may be the tibial tray implant 324 of FIGS. 61-64. These steps may include inserting pegs 820, 822 of the tibial tray implant 818 into the peg holes 230, 232 of the tibia 204 and placing a bone-facing side of the tibial tray implant 818 against the transverse resection 226.

FIG. 252 shows a step of inserting the insert trial 810 into the tibial tray implant 818.

FIG. 253 shows a step of inserting a compression block 824 between the insert trial 810 and the distal femoral resection 212. The compression block 824 enhances the stability of the tibial tray implant 818 during tibial anchor preparation and insertion by filling the medial compartment to reduce or eliminate laxity in the knee joint 200.

FIGS. 254-257 show a step of connecting and locking the anchor guide 506 to the tibial tray implant 818. FIG. 256 shows a step of provisionally locking the anchor guide 506 to the tibial tray implant 818 by turning the knob 526. FIG. 257 shows a step of using the screwdriver 634 to fully lock the anchor guide 506 to the tibial tray implant 818. These steps may be similar to the steps shown in FIGS. 107-111, with the inclusion of the compression block 824.

FIGS. 258-259 show a step of using a pilot cutter 826 to cut an anchor channel 234 through the anterior tibial cortex. The resulting anchor channel 235 may be complementary to those portions of an anchor, or fixation element, that will pass through the anterior tibial cortex, namely the blade and a portion of the support. More specifically, the anchor channel 235 may have a complementary cross-sectional shape to the blade and a portion of the support of the fixation element. FIG. 260 shows the pilot cutter 826 fully seated/advanced into the anterior tibia 204 and shows a step of connecting the slap hammer 816 to the pilot cutter 826. FIG. 261 shows the slap hammer 816 locked to the pilot cutter 826 to remove the pilot cutter.

FIG. 262-265 show a step of inserting a fixation element 830 (anchor) into the anchor guide 506. The fixation element 830 may be the fixation element 346 of FIGS. 119-122. A rail 832 of the fixation element 830 is received in the narrow proximal portion of the hole 522 of the housing 508 of the anchor guide 506, and a blade 834 of the fixation element 830 is received in the wider distal portion of the hole 522. FIGS. 263-264 show a step of using an anchor tamp 836 to advance the fixation element 830 toward the anterior tibia 204 and tibial tray implant 818. The anchor tamp 836 may be the anchor tamp 538. FIG. 265 shows the fixation element 830 and anchor tamp 836 fully seated/advanced into the anterior tibia 204 and tibial tray implant 818. After this step, the anchor guide 506 may be removed, followed by the compression block 824 and the insert trial 810.

FIG. 266 is a bottom view of the tibial tray implant 818 and fixation element 830, the blade 834 omitted to show details of the anchor/tray locking mechanism. The fixation element 830 is in the implanted state.

FIGS. 267-269 show a step of implanting the femoral implant 320. This step may include inserting pegs 368, 370 of the femoral implant 320 into peg holes 218, 220 of the femur 202. FIG. 268 shows a step of using the femoral impactor 806 to fully seat the femoral implant 320 against the distal femoral resection 212, the posterior chamfer resection 214, and the posterior femoral resection 216. FIG. 269 shows the femoral implant 320 fully seated against the distal femoral resection 212, the posterior chamfer resection 214, and the posterior femoral resection 216.

FIG. 270 shows a step of using the insert impactor 812 to insert an insert implant 838 into the tibial tray implant 818 and fully seat the insert implant 838.

FIGS. 271-272 show the knee joint 200, tibial tray implant 818, fixation element 830, femoral implant 320, and insert implant 838 in a final implanted state.

FIG. 273-275 show a step of connecting an anchor revision guide 840 to the tibial tray implant 818. FIG. 274 shows the anchor revision guide 840 connected to the tibial tray implant 818. FIG. 275 shows a step of using the screwdriver 634 to lock the anchor revision guide 840 to the tibial tray implant 818.

FIG. 276-279 show a step of using an anchor removal chisel 842 with the anchor revision guide 840 to create a pathway 844 to the fixation element 830 and tibial tray implant 818. This step may be similar to the steps shown in FIGS. 258-259 to create the anchor channel 234. The pathway 844 may be complementary to a working tip of an anchor removal tool, discussed below. FIG. 277-278 show the anchor removal chisel 842 advancing toward the fixation element 830 and tibial tray implant 818. FIG. 279 shows the anchor removal chisel 842 fully advanced toward the fixation element 830 and tibial tray implant 818.

FIG. 280 shows a step of connecting the slap hammer 816 to the anchor removal chisel 842 to remove the anchor removal chisel.

FIG. 281 shows the pathway 844 created by the anchor removal chisel 842.

FIG. 282 shows an anchor removal tool 846 in a fully extended state. Indicia 848, such as the arrowhead shown, may be visible in the fully extended state. The anchor removal tool 846 includes a working tip 850 terminating in a hook 852 for engaging the fixation element 830 for removal.

FIG. 283 shows a step of advancing the anchor removal tool 846 relative to the anchor revision guide 840 toward the fixation element 830 and tibial tray implant 818.

FIGS. 284-286 show the anchor removal tool 846 fully advanced/inserted, in a disengaged state relative to the fixation element 830. FIG. 285 shows indicia 854 of the anchor revision guide 840, which include right and left vertical lines, a numeral "1" to the left of the left line, and a numeral "2" to the right of the right line; and a line 856 on the anchor removal tool 846. The disengaged state is indicated when the line 856 is aligned with the left line of the anchor revision guide 840. The disengaged state is also indicated by the anchor removal tool 846 being slightly angled relative to the anchor revision guide 840. Referring to FIG. 286, in the disengaged state, the working tip 850 does not engage the fixation element 830, but is beside it instead.

FIG. 287 shows the anchor removal tool 846 fully advanced/inserted. A motion arrow 858 indicates a step of moving the anchor removal tool 846 to the right to an engaged state relative to the fixation element 830. FIG. 288 shows the anchor removal tool 846 in the engaged state. FIG. 288 shows that the engaged state is indicated when the line 856 is aligned with the right line of the anchor revision guide 840, and also by the anchor removal tool 846 being straight with the anchor revision guide 840. Referring to FIG. 289, in the engaged state, the hook 852 is engaged with the fixation element 830. More specifically, the hook 852 is hooked to a portion of a support of the fixation element 830.

FIG. 290-292 show a step of actuating the anchor removal tool 846 to extract the fixation element 830 from the tibial tray implant 818. This step may include rotating a T-handle 860 or knob of the anchor removal tool 846 to pull the fixation element 830 out of the channel of the tibial tray implant. This step may include permanently deforming, bending, cracking, or breaking the locking features of the fixation element 830 to unlock the fixation element from the tibial tray implant 818. FIG. 292 shows the fixation element 830 emerging from the proximal tibia 204 and tibial tray implant 818.

FIGS. 293-294 show the knee joint 200, tibial tray implant 818, femoral implant 320, and insert implant 838 after the fixation element 830 has been removed. The insert implant 838 may be unlocked from the tibial tray implant 818 using a small osteoeome (not shown) in an anterior notch of the insert implant to pry or impact the insert implant. The tibial tray implant 818, with or without attached insert implant 838, may be loosened from the proximal tibia with an osteotome or saw along the bone-facing side.

FIG. 295 shows the knee joint 200 and femoral implant 320 after removal of the tibial tray implant 818 and insert implant 838, showing the femoral implant 320 loosened from the femur 202 for removal.

Referring to FIGS. 296-299, the implants, instruments, and methods disclosed herein may be adapted to shoulder arthroplasty.

FIG. 296 shows an exploded view of a shoulder joint 250 including a scapula 252 with a glenoid socket 254 and a humerus 258 with a humeral head 260. A glenoid baseplate 870 is shown with a glenoid articular insert 872 for anatomic shoulder arthroplasty. The glenoid articular insert 872 may articulate against an intact natural humeral head 260, or an artificial articular surface of a humeral implant (not shown).

FIG. 297 shows a similar arrangement with implant components for reverse shoulder arthroplasty. The glenoid baseplate 870 is shown with a glenosphere 874 (glenoid articular component) for reverse shoulder arthroplasty. The glenosphere 874 articulates against a humeral socket implant 876.

The glenoid baseplate 870 of FIGS. 296-297 may be adapted in the manner disclosed above for any of the tibial tray implants, and may include a suitable fixation element. As one example, the illustrated glenoid baseplate 870 is adapted in the manner disclosed for tibial tray 324 of FIGS. 61-64. The glenoid baseplate 870 includes a bone-facing side 876 with pegs 878 and an undercut channel 880, shown in dashed lines. A fixation element 882 is shown connected to the glenoid baseplate 870 via the channel 880 and protruding from the bone-facing side 876. As an example, the illustrated fixation element 882 may be any one of the fixation elements 338, 340, 342 of FIGS. 85-96. A rail (not visible) is received in the channel 880, a support 888 protrudes from the channel 880 through the bone-facing side 876, and a blade 886 is carried by the support 888. While inserted in the channel 880, the fixation element 882 may be movable along the channel from an insertion state (unlocked) to an implanted state (locked).

FIGS. 296-297 show an example bone preparation in the glenoid socket 254, suitable for the illustrated glenoid baseplate 870 and fixation element 882. A reamed glenoid surface 256 may be prepared. Peg holes 262 may be drilled to receive the pegs 878. Overlapping anchor holes 266 may be drilled to receive the blade 886 and/or support 888 of the fixation element in the insertion state. An instrument like the tibial sizer 482 of FIGS. 97-98 may be adapted to guide the peg and anchor holes 262, 266 in surgical method steps similar to those shown in FIGS. 99-100.

FIG. 298 shows the glenoid baseplate 870 coupled to the prepared glenoid socket 254 with the pegs 878 in the peg holes 262 and the bone-facing side 876 against the reamed glenoid surface 256. The fixation element 882 is in the channel 880 in the insertion state. The blade 886 and support 888 are in the overlapping anchor holes 266. The glenosphere 874 is shown connected to the glenoid baseplate 870; this is optional at this point. The humeral socket implant 876 is coupled to a prepared proximal humerus 258.

FIG. 299 shows a step of moving the fixation element 882 from the insertion state to the implanted state. In the implanted state, the fixation element 882 is farther along the channel 880, its locking features (not visible) are engaged within the pocket (not visible) of the channel 880, and the blade 886 has penetrated the side wall of the overlapping anchor holes 266 to engage bone for fixation.

Any methods disclosed herein includes one or more steps or actions for performing the described method. The method steps and/or actions may be interchanged with one another. In other words, unless a specific order of steps or actions is required for proper operation of the embodiment, the order and/or use of specific steps and/or actions may be modified.

Reference throughout this specification to "an embodiment" or "the embodiment" means that a particular feature, structure or characteristic described in connection with that embodiment is included in at least one embodiment. Thus, the quoted phrases, or variations thereof, as recited throughout this specification are not necessarily all referring to the same embodiment.

Similarly, it should be appreciated that in the above description of embodiments, various features are sometimes grouped together in a single embodiment, Figure, or description thereof for the purpose of streamlining the disclosure. This method of disclosure, however, is not to be interpreted as reflecting an intention that any claim require more features than those expressly recited in that claim. Rather, as the following claims reflect, inventive aspects lie in a combination of fewer than all features of any single foregoing disclosed embodiment. Thus, the claims following this Detailed Description are hereby expressly incorporated into this Detailed Description, with each claim standing on its own as a separate embodiment. This disclosure includes all permutations of the independent claims with their dependent claims.

Recitation in the claims of the term "first" with respect to a feature or element does not necessarily imply the existence of a second or additional such feature or element. Elements recited in means-plus-function format are intended to be construed in accordance with 35 U.S.C. §112 Para. 6. It will be apparent to those having skill in the art that changes may be made to the details of the above-described embodiments without departing from the underlying principles of the technology.

While specific embodiments and applications of the present technology have been illustrated and described, it is to be understood that the technology is not limited to the precise configuration and components disclosed herein. Various modifications, changes, and variations which will be apparent to those skilled in the art may be made in the arrangement, operation, and details of the methods and systems of the present technology disclosed herein without departing from the spirit and scope of the technology.

The invention claimed is:

1. A system for unicompartmental knee arthroplasty of a knee joint comprising a femur and a tibia, comprising:
   a femoral implant comprising an articular surface and an opposite bone-facing side comprising a distal surface for contacting a distal resection of a condyle of the femur, and a posterior surface for contacting a posterior resection of the femoral condyle;
   an articular insert implant comprising an articular surface for articulation with the femoral implant articular surface and an opposite tray-facing side comprising a tray connection feature;
   a tibial tray implant comprising an insert-facing side and an opposite bone-facing side, wherein the insert-facing side comprises an insert connection feature for connection to the tray connection feature, wherein the bone-facing side is adapted for contacting a proximal resection of a proximal end of the tibia;
   a posterior cutting block comprising a bone-facing surface for contacting the distal resection, a first cutting slot for making the posterior resection, and a cylindrical first interface surface; and
   a rotation tensor block, comprising a first bone-facing side for contacting the proximal resection, an opposite second bone-facing side for contacting an unresected posterior surface of the femoral condyle, and a cylindrical second interface surface;
   wherein when the posterior cutting block is coupled to the rotation tensor block, the first interface surface articulates with the second interface surface so that the posterior cutting block rotates relative to the rotation tensor block around a center longitudinal axis that is common to the first and second interface surfaces, and the first cutting slot is separated from the first bone-facing side of the rotation tensor block by a distance that is substantially equal to the sum of a thickness of the femoral implant measured perpendicular to the posterior surface between the posterior surface and the articular surface of the femoral implant and a combined thickness of the articular insert implant and the tibial tray implant measured between the articular surface of the articular insert implant and the bone-facing side of the tibial tray implant.

2. The system of claim 1, wherein in a medial-lateral plane that is perpendicular to the posterior surface, the articular surface of the femoral implant comprises a medial-lateral curvature that is an arc of a circle, wherein the circle has a center point;
wherein the center longitudinal axis that is common to the first and second interface surfaces is coincident with the center point of the femoral implant.

3. The system of claim 1, wherein the femoral implant comprises an outer perimeter extending around the distal surface, wherein the posterior cutting block comprises an outer perimeter extending around the bone-facing surface of the posterior cutting block, wherein the outer perimeter of the posterior cutting block matches the outer perimeter of the femoral implant.

4. The system of claim 3, wherein the posterior cutting block comprises a window that extends through the bone-facing surface of the posterior cutting block and is centered in a medial-lateral width of the posterior cutting block.

5. The system of claim 1, wherein at least one of the posterior cutting block and the rotation tensor block comprises a rotation limiting feature, wherein when the posterior cutting block is coupled to the rotation tensor block, the rotation limiting feature limits a rotational range of motion of the posterior cutting block relative to the rotation tensor block around the center longitudinal axis of the first and second interface surfaces.

6. The system of claim 1, wherein the bone-facing side of the femoral implant comprises a posterior chamfer surface for contacting a posterior chamfer resection of the femoral condyle, wherein the posterior cutting block comprises a second cutting slot for making the posterior chamfer resection.

7. The system of claim 1, wherein the femoral implant comprises a peg protruding outwardly from the bone-facing side of the femoral implant, wherein the posterior cutting block comprises a drill guide hole for making a peg hole in the femoral condyle to receive the peg of the femoral implant.

8. A system for unicompartmental knee arthroplasty of a knee joint comprising a femur and a tibia, comprising:
a femoral implant comprising an articular surface and an opposite bone-facing side comprising a distal surface for contacting a distal resection of a condyle of the femur, and a posterior surface for contacting a posterior resection of the femoral condyle, wherein the femoral implant comprises a posterior thickness measured perpendicular to the posterior surface between the posterior surface and the articular surface of the femoral implant;
an articular insert implant comprising an articular surface for articulation with the femoral implant articular surface and an opposite tray-facing side comprising a tray connection feature;
a tibial tray implant comprising an insert-facing side and an opposite bone-facing side, wherein the insert-facing side comprises an insert connection feature for connection to the tray connection feature, wherein the bone-facing side is adapted for contacting a proximal resection of a proximal end of the tibia, wherein when the articular insert implant and the tibial tray implant are connected together, the connected articular insert implant and tibial tray implant comprise a combined thickness measured between the articular surface of the articular insert implant and the bone-facing side of the tibial tray implant;
a posterior cutting block comprising a bone-facing surface for contacting the distal resection, a first cutting slot for making the posterior resection, and a first interface feature; and
a rotation tensor block, comprising a first bone-facing side for contacting the proximal resection, an opposite second bone-facing side for contacting an unresected posterior surface of the femoral condyle, and a second interface feature;
wherein when the posterior cutting block is coupled to the rotation tensor block, the first interface feature articulates with the second interface feature so that the posterior cutting block rotates relative to the rotation tensor block around a center longitudinal axis of the first and second interface features, and the first cutting slot is separated from the first bone-facing side of the rotation tensor block by a distance that is substantially equal to the sum of the posterior thickness of the femoral implant and the combined thickness of the articular insert implant and the tibial tray implant.

9. The system of claim 8, wherein in a medial-lateral plane that is perpendicular to the posterior surface, the articular surface of the femoral implant comprises a medial-lateral curvature that is an arc of a circle, wherein the circle comprises a center point;
wherein the center longitudinal axis of the first and second interface features is coincident with the center point of the femoral implant.

10. The system of claim 8, wherein the femoral implant comprises an outer perimeter extending around the distal surface, wherein the posterior cutting block comprises an outer perimeter extending around the bone-facing surface of the posterior cutting block, wherein the outer perimeter of the posterior cutting block matches the outer perimeter of the femoral implant.

11. The system of claim 10, wherein the posterior cutting block comprises a window that extends through the bone-facing surface of the posterior cutting block and is centered in a medial-lateral width of the posterior cutting block.

12. The system of claim 8, wherein at least one of the posterior cutting block and the rotation tensor block comprises a rotation limiting feature, wherein when the posterior cutting block is coupled to the rotation tensor block, the rotation limiting feature limits a rotational range of motion of the posterior cutting block relative to the rotation tensor block around the center longitudinal axis of the first and second interface features.

13. The system of claim 8, wherein the bone-facing side of the femoral implant comprises a posterior chamfer surface for contacting a posterior chamfer resection of the femoral condyle, wherein the posterior cutting block comprises a second cutting slot for making the posterior chamfer resection.

14. The system of claim 8, wherein the femoral implant comprises a peg protruding outwardly from the bone-facing side of the femoral implant, wherein the posterior cutting block comprises a drill guide hole for making a peg hole in the femoral condyle to receive the peg of the femoral implant.

15. A system for unicompartmental knee arthroplasty of a knee joint comprising a femur and a tibia, comprising:
a femoral implant comprising an articular surface and an opposite bone-facing side comprising a distal surface for contacting a distal resection of a condyle of the femur, and a posterior surface for contacting a posterior resection of the femoral condyle, wherein the femoral implant comprises a posterior thickness measured perpendicular to the posterior surface between the posterior surface and the articular surface of the femoral implant, wherein in a medial-lateral plane that is perpendicular to the posterior surface, the articular surface comprises a medial-lateral curvature that is an arc of a circle that has a center point;

an articular insert implant comprising an articular surface for articulation with the femoral implant articular surface and an opposite tray-facing side comprising a tray connection feature;

a tibial tray implant comprising an insert-facing side and an opposite bone-facing side, wherein the insert-facing side comprises an insert connection feature for connection to the tray connection feature, wherein the bone-facing side is adapted for contacting a proximal resection of a proximal end of the tibia, wherein when the articular insert implant and the tibial tray implant are connected together, the connected articular insert implant and tibial tray implant comprise a combined thickness measured between the articular surface of the articular insert implant and the bone-facing side of the tibial tray implant;

a posterior cutting block comprising a bone-facing surface for contacting the distal resection and a first cutting slot for making the posterior resection; and a rotation tensor block, comprising a first bone-facing side for contacting the proximal resection and an opposite second bone-facing side for contacting an unresected posterior surface of the femoral condyle;

wherein the posterior cutting block rotates around an axis that is coincident with the center point of the femoral implant.

16. The system of claim 15, wherein the femoral implant comprises an outer perimeter extending around the distal surface, wherein the posterior cutting block comprises an outer perimeter extending around the bone-facing surface of the posterior cutting block, wherein the outer perimeter of the posterior cutting block matches the outer perimeter of the femoral implant.

17. The system of claim 16, wherein the posterior cutting block comprises a window that extends through the bone-facing surface of the posterior cutting block and is centered in a medial-lateral width of the posterior cutting block.

18. The system of claim 15, wherein when the posterior cutting block is coupled to the rotation tensor block, the posterior cutting block rotates relative to the rotation tensor block around the axis, and the first cutting slot is separated from the first bone-facing side of the rotation tensor block by a distance that is substantially equal to the sum of the posterior thickness of the femoral implant and the combined thickness of the articular insert implant and the tibial tray implant.

19. The system of claim 15, wherein the bone-facing side of the femoral implant comprises a posterior chamfer surface for contacting a posterior chamfer resection of the femoral condyle, wherein the posterior cutting block comprises a second cutting slot for making the posterior chamfer resection.

20. The system of claim 15, wherein the femoral implant comprises a peg protruding outwardly from the bone-facing side of the femoral implant, wherein the posterior cutting block comprises a drill guide hole for making a peg hole in the femoral condyle to receive the peg of the femoral implant.

* * * * *